(12) United States Patent
Dames et al.

(10) Patent No.: US 11,319,537 B2
(45) Date of Patent: May 3, 2022

(54) NUCLEIC ACIDS FOR INHIBITING EXPRESSION OF LPA IN A CELL

(71) Applicant: SILENCE THERAPEUTICS GMBH, Berlin (DE)

(72) Inventors: Sibylle Dames, Berlin (DE); Steffen Schubert, Berlin (DE); Stephan Tenbaum, Biberach An der Riss (DE); Christian Frauendorf, Berlin (DE); Lucas Bethge, Potsdam (DE); Judith Hauptmann, Berlin (DE); Adrien Weingärtner, Berlin (DE); David Anthony Rider, Berlin (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 0 days.

(21) Appl. No.: 16/763,458

(22) PCT Filed: Nov. 13, 2018

(86) PCT No.: PCT/EP2018/081106
§ 371 (c)(1),
(2) Date: May 12, 2020

(87) PCT Pub. No.: WO2019/092283
PCT Pub. Date: May 16, 2019

(65) Prior Publication Data
US 2021/0123048 A1 Apr. 29, 2021

(30) Foreign Application Priority Data

Nov. 13, 2017 (EP) .................................. 17201449
Jun. 21, 2018 (EP) .................................. 18179175
Sep. 28, 2018 (GB) .................................. 1815915

(51) Int. Cl.
C07H 21/02 (2006.01)
C07H 21/04 (2006.01)
C12N 15/113 (2010.01)

(52) U.S. Cl.
CPC ........ *C12N 15/113* (2013.01); *C12N 2310/14* (2013.01); *C12N 2310/315* (2013.01); *C12N 2310/344* (2013.01); *C12N 2310/351* (2013.01)

(58) Field of Classification Search
CPC .......................... C12N 15/113; C12N 2310/14
See application file for complete search history.

(56) References Cited

U.S. PATENT DOCUMENTS

| 5,885,968 A | 3/1999 | Biessen et al. |
| 2006/0160759 A1* | 7/2006 | Chen .................... A61K 9/5146 514/44 A |
| 2011/0110886 A1* | 5/2011 | Braddock ............... A61P 35/02 424/85.2 |

| 2019/0119676 A1 | 4/2019 | Frauendorf et al. |
| 2020/0095580 A1 | 3/2020 | Hauptmann et al. |
| 2021/0079397 A1 | 3/2021 | Frauendorf et al. |

FOREIGN PATENT DOCUMENTS

| WO | 2005/000201 A2 | 1/2005 | |
| WO | 2016/149020 A1 | 9/2016 | |
| WO | WO 2016/149020 A1 * | 9/2016 | ........... C12N 15/113 |
| WO | 2017/059223 A2 | 4/2017 | |
| WO | WO 2017/059223 A2 * | 4/2017 | ........... C12N 15/113 |
| WO | 2017/174657 A1 | 10/2017 | |
| WO | 2018/185241 A1 | 10/2018 | |
| WO | 2019/092282 A1 | 5/2019 | |
| WO | 2020/099476 A1 | 5/2020 | |

OTHER PUBLICATIONS

Elbashir et al. (The EMBO Journal, vol. 20, No. 23, pp. 6877-6888, 2001).*
Tadin-Strapps et al. (J of Cardiovasc Trans Res, 2015, 8, 44-53).*
Akinc et al., Targeted delivery of RNAi therapeutics with endogenous and exogenous ligand-based mechanisms, Mol. Ther., 18(7):1357-64 (2010).
Alonso et al., Lipoprotein(a) Levels in Familial Hypercholesterolemia: An Important Predictor of Cardiovascular Disease Independent of the Type of LDL Receptor Mutation, Journal of the American College of Cardiology, 63(19):1982-1989 (2014).
Biessen et al., Synthesis of cluster galactosides with high affinity for the hepatic asialoglycoprotein receptor, J. Med. Chem., 38(9):1538-46 (1995).
Dubber et al., Solid-phase synthesis of multivalent glycoconjugates on a DNA synthesizer, Bioconjug. Chem., 14(1):239-46 (2003).
Elbashir et al., Duplexes of 21-nucleotide RNAs mediate RNA interference in cultured mammalian cells, Nature, 411(6836):494-8 (2001).
Fire et al., Potent and specific genetic interference by double-stranded RNA in Caenorhabditis elegans, Nature, 391(6669):806-11 (1998).
Graham et al., Antisense inhibition of apolipoprotein (a) to lower plasma lipoprotein (a) levels in humans, J. Lipid. Res., 57(3):340-51 (2016).
Hoevelmann et al., LNA-enhanced DNA FIT-probes for multicolour RNA imaging, Chem. Sci., 7(1):128-135 (2016).
International Application No. PCT/EP18/081106, International Search Report and Written Opinion, dated Mar. 18, 2019.
International Application No. PCT/EP2018/081106, International Preliminary Report on Patentability, dated May 28, 2020.
Kurt et al., Lipoprotein(a)-clinical aspects and future challenges, Clin. Res. Cardiol., 10(Suppl 1):26-32 (2015).

(Continued)

*Primary Examiner* — Amy H Bowman
(74) *Attorney, Agent, or Firm* — Marshall, Gerstein & Borun LLP

(57) ABSTRACT

The present invention relates to products and compositions and their uses. In particular the invention relates to nucleic acid products that interfere with the LPA gene expression or inhibit its expression for use as treatment, prevention or reduction of risk of suffering cardiovascular disease such as coronary heart disease or aortic stenosis or stroke or any other disorder, pathology or syndrome linked to elevated of Lp(a)-containing particles.

15 Claims, 44 Drawing Sheets
Specification includes a Sequence Listing.

(56) References Cited

OTHER PUBLICATIONS

Ishibashi et al., Asialoglycoprotein receptor deficiency in mice lacking the minor receptor subunit, J. Biol. Chem., 269(45):27803-6 (1994).

Nair et al., Multivalent N-acetylgalactosamine-conjugated siRNA localizes in hepatocytes and elicits robust RNAi-mediated gene silencing, J. Am. Chem. Soc., 136(49):16958-16961 (2014).

Saeedi et al., Lipoprotein (a), an independent cardiovascular risk marker, Clinical Diabetes and Endocrinology, 2:7 (2016).

Schmidt et al., Structure, function, and genetics of lipoprotein (a), J. Lipid Res., 57(8):1339-59 (2016).

Tadin-Strapps et al., Development of lipoprotein(a) siRNAs for mechanism of action studies in non-human primate models of atherosclerosis, Journal of Cardiovascular Translational Research, 8:44-53 (2015).

Takei et al., 5'-,3'-inverted thymidine-modified antisense oligodeoxynucleotide targeting midkine. Its design and application for cancer therapy, J. Biol. Chem., 277(26):23800-06 (2002).

Watts et al., Silencing disease genes in the laboratory and the clinic, Journal of Pathology, 226(2):365-379 (2012).

Weigel et al., Glycans as endocytosis signals: the cases of the asialoglycoprotein and hyaluronan/chondroitin sulfate receptors, Biochim. Biophys. Acta., 1572(2-3):341-63(2002).

Witztum et al., Lipoprotein (a): Coming of Age at Last, J. Lipid Res., 57(3):336-9 (2016).

Elbashir et al., Functional anatomy of siRNAs for mediating efficient RNAi in *Drosophila melanogaster* embryo lysate, The EMBO Journal, 20(23):6877-6888 (2001).

International Application No. PCT/EP2019/081158, International Search Report and Written Opinion, dated Mar. 19, 2020.

Livak et al., Analysis of relative gene expression data using real-time quantitative PCR and the 2(-Delta Delta C(T)) Method, Methods, 25(4):402-8 (2001).

Schmittgen et al., Analyzing real-time PCR data by the comparative C(T) method, Nat. Protoc., 3(6):1101-8 (2008).

* cited by examiner

SEQUENCE LISTING

<160> NUMBER OF SEQ ID NOS: 162

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
ucguauaaca auaagggc                                           19

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
gccccuuauu guuauacga                                          19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
gauaacucug uccauuacc                                          19

<210> SEQ ID NO 4
<211> LENGTH: 19
<212> TYPE: RNA
<213> ORGANISM: Artificial Sequence
<220> FEATURE:
<223> OTHER INFORMATION: siRNA

<400> SEQUENCE: 4
gguaauggac agaguuauc                                          19

<210> SEQ ID NO 5
<211> LENGTH: 19
<212> TYPE: RNA
<213> ORGANISM: Artificial Sequence
<220> FEATURE:
<223> OTHER INFORMATION: siRNA

<400> SEQUENCE: 5
auaacucugu ccauuacca                                          19

-continued

```
<210> SEQ ID NO 6
<211> LENGTH: 19
<212> TYPE: RNA
<213> ORGANISM: Artificial Sequence
<220> FEATURE:
<223> OTHER INFORMATION: siRNA

<400> SEQUENCE: 6
ugguaaugga cagaguuau                                                  19

<210> SEQ ID NO 7
<211> LENGTH: 19
<212> TYPE: RNA
<213> ORGANISM: Artificial Sequence
<220> FEATURE:
<223> OTHER INFORMATION: siRNA

<400> SEQUENCE: 7
uaacucuguc cauuaccgu                                                  19

<210> SEQ ID NO 8
<211> LENGTH: 19
<212> TYPE: RNA
<213> ORGANISM: Artificial Sequence
<220> FEATURE:
<223> OTHER INFORMATION: siRNA

<400> SEQUENCE: 8
acgguaaugg acagaguua                                                  19

<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
auaacucugu ccauuaccg                                                  19

<210> SEQ ID NO 10
<211> LENGTH: 19
<212> TYPE: RNA
<213> ORGANISM: Artificial Sequence
<220> FEATURE:
<223> OTHER INFORMATION: siRNA

<400> SEQUENCE: 10
cgguaaugga cagaguuau                                                  19

<210> SEQ ID NO 11
<211> LENGTH: 19
<212> TYPE: RNA
<213> ORGANISM: Artificial Sequence
<220> FEATURE:
<223> OTHER INFORMATION: siRNA

<400> SEQUENCE: 11
agaaugugcc ucgauaacu                                                  19

<210> SEQ ID NO 12
<211> LENGTH: 19
<212> TYPE: RNA
<213> ORGANISM: Artificial Sequence
<220> FEATURE:
<223> OTHER INFORMATION: siRNA
```

```
<400> SEQUENCE: 12
aguuaucgag gcacauucu                                                    19

<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
auaacucugu ccaucacca                                                    19

<210> SEQ ID NO 14
<211> LENGTH: 19
<212> TYPE: RNA
<213> ORGANISM: Artificial Sequence
<220> FEATURE:
<223> OTHER INFORMATION: siRNA

<400> SEQUENCE: 14
uggugaugga cagaguuau                                                    19

<210> SEQ ID NO 15
<211> LENGTH: 19
<212> TYPE: RNA
<213> ORGANISM: Artificial Sequence
<220> FEATURE:
<223> OTHER INFORMATION: siRNA

<400> SEQUENCE: 15
auaacucugu ccaucaccu                                                    19

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
aggugaugga cagaguuau                                                    19

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
uaacucuguc cauuaccau                                                    19

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
augguaaugg acagaguua                                                    19
```

```
<210> SEQ ID NO 19
<211> LENGTH: 19
<212> TYPE: RNA
<213> ORGANISM: Artificial Sequence
<220> FEATURE:
<223> OTHER INFORMATION: siRNA

<400> SEQUENCE: 19
augugccuug auaacucug                                                    19

<210> SEQ ID NO 20
<211> LENGTH: 19
<212> TYPE: RNA
<213> ORGANISM: Artificial Sequence
<220> FEATURE:
<223> OTHER INFORMATION: siRNA

<400> SEQUENCE: 20
cagaguuauc aaggcacau                                                    19

<210> SEQ ID NO 21
<211> LENGTH: 19
<212> TYPE: RNA
<213> ORGANISM: Artificial Sequence
<220> FEATURE:
<223> OTHER INFORMATION: siRNA

<400> SEQUENCE: 21
aguuggugcu gcuucagaa                                                    19

<210> SEQ ID NO 22
<211> LENGTH: 19
<212> TYPE: RNA
<213> ORGANISM: Artificial Sequence
<220> FEATURE:
<223> OTHER INFORMATION: siRNA

<400> SEQUENCE: 22
uucugaagca gcaccaacu                                                    19

<210> SEQ ID NO 23
<211> LENGTH: 19
<212> TYPE: RNA
<213> ORGANISM: Artificial Sequence
<220> FEATURE:
<223> OTHER INFORMATION: siRNA

<400> SEQUENCE: 23
aauaaggggc ugccacagg                                                    19

<210> SEQ ID NO 24
<211> LENGTH: 19
<212> TYPE: RNA
<213> ORGANISM: Artificial Sequence
<220> FEATURE:
<223> OTHER INFORMATION: siRNA

<400> SEQUENCE: 24
ccuguggcag ccccuuauu                                                    19

<210> SEQ ID NO 25
<211> LENGTH: 19
<212> TYPE: RNA
<213> ORGANISM: Artificial Sequence
<220> FEATURE:
<223> OTHER INFORMATION: siRNA
```

```
<400> SEQUENCE: 25
uaacucuguc caucaccau                                                    19

<210> SEQ ID NO 26
<211> LENGTH: 19
<212> TYPE: RNA
<213> ORGANISM: Artificial Sequence
<220> FEATURE:
<223> OTHER INFORMATION: siRNA

<400> SEQUENCE: 26
auggugaugg acagaguua                                                    19

<210> SEQ ID NO 27
<211> LENGTH: 19
<212> TYPE: RNA
<213> ORGANISM: Artificial Sequence
<220> FEATURE:
<223> OTHER INFORMATION: siRNA

<400> SEQUENCE: 27
augagccucg auaacucug                                                    19

<210> SEQ ID NO 28
<211> LENGTH: 19
<212> TYPE: RNA
<213> ORGANISM: Artificial Sequence
<220> FEATURE:
<223> OTHER INFORMATION: siRNA

<400> SEQUENCE: 28
cagaguuauc gaggcucau                                                    19

<210> SEQ ID NO 29
<211> LENGTH: 19
<212> TYPE: RNA
<213> ORGANISM: Artificial Sequence
<220> FEATURE:
<223> OTHER INFORMATION: siRNA

<400> SEQUENCE: 29
aaugagccuc gauaacucu                                                    19

<210> SEQ ID NO 30
<211> LENGTH: 19
<212> TYPE: RNA
<213> ORGANISM: Artificial Sequence
<220> FEATURE:
<223> OTHER INFORMATION: siRNA

<400> SEQUENCE: 30
agaguuaucg aggcucauu                                                    19

<210> SEQ ID NO 31
<211> LENGTH: 19
<212> TYPE: RNA
<213> ORGANISM: Artificial Sequence
<220> FEATURE:
<223> OTHER INFORMATION: siRNA

<400> SEQUENCE: 31
aaugcuucca ggacauuuc                                                    19
```

```
<210> SEQ ID NO 32
<211> LENGTH: 19
<212> TYPE: RNA
<213> ORGANISM: Artificial Sequence
<220> FEATURE:
<223> OTHER INFORMATION: siRNA

<400> SEQUENCE: 32
gaaauguccu ggaagcauu                                                    19

<210> SEQ ID NO 33
<211> LENGTH: 19
<212> TYPE: RNA
<213> ORGANISM: Artificial Sequence
<220> FEATURE:
<223> OTHER INFORMATION: siRNA

<400> SEQUENCE: 33
acaguggugg agaaugugc                                                    19

<210> SEQ ID NO 34
<211> LENGTH: 19
<212> TYPE: RNA
<213> ORGANISM: Artificial Sequence
<220> FEATURE:
<223> OTHER INFORMATION: siRNA

<400> SEQUENCE: 34
gcacauucuc caccacugu                                                    19

<210> SEQ ID NO 35
<211> LENGTH: 19
<212> TYPE: RNA
<213> ORGANISM: Artificial Sequence
<220> FEATURE:
<223> OTHER INFORMATION: siRNA

<400> SEQUENCE: 35
guaugugccu cgauaacuc                                                    19

<210> SEQ ID NO 36
<211> LENGTH: 19
<212> TYPE: RNA
<213> ORGANISM: Artificial Sequence
<220> FEATURE:
<223> OTHER INFORMATION: siRNA

<400> SEQUENCE: 36
gaguuaucga ggcacauac                                                    19

<210> SEQ ID NO 37
<211> LENGTH: 19
<212> TYPE: RNA
<213> ORGANISM: Artificial Sequence
<220> FEATURE:
<223> OTHER INFORMATION: siRNA

<400> SEQUENCE: 37
ucgauaacuc uguccauca                                                    19

<210> SEQ ID NO 38
<211> LENGTH: 19
<212> TYPE: RNA
<213> ORGANISM: Artificial Sequence
<220> FEATURE:
<223> OTHER INFORMATION: siRNA
```

```
<400> SEQUENCE: 38
ugauggacag aguuaucga                                              19

<210> SEQ ID NO 39
<211> LENGTH: 19
<212> TYPE: RNA
<213> ORGANISM: Artificial Sequence
<220> FEATURE:
<223> OTHER INFORMATION: siRNA

<400> SEQUENCE: 39
ugucacugga cauuguguc                                              19

<210> SEQ ID NO 40
<211> LENGTH: 19
<212> TYPE: RNA
<213> ORGANISM: Artificial Sequence
<220> FEATURE:
<223> OTHER INFORMATION: siRNA

<400> SEQUENCE: 40
gacacaaugu ccagugaca                                              19

<210> SEQ ID NO 41
<211> LENGTH: 19
<212> TYPE: RNA
<213> ORGANISM: Artificial Sequence
<220> FEATURE:
<223> OTHER INFORMATION: siRNA

<400> SEQUENCE: 41
cugggaucca ugguguaac                                              19

<210> SEQ ID NO 42
<211> LENGTH: 19
<212> TYPE: RNA
<213> ORGANISM: Artificial Sequence
<220> FEATURE:
<223> OTHER INFORMATION: siRNA

<400> SEQUENCE: 42
guuacaccau ggaucccag                                              19

<210> SEQ ID NO 43
<211> LENGTH: 19
<212> TYPE: RNA
<213> ORGANISM: Artificial Sequence
<220> FEATURE:
<223> OTHER INFORMATION: siRNA

<400> SEQUENCE: 43
agaugaccaa gcuuggcag                                              19

<210> SEQ ID NO 44
<211> LENGTH: 19
<212> TYPE: RNA
<213> ORGANISM: Artificial Sequence
<220> FEATURE:
<223> OTHER INFORMATION: siRNA

<400> SEQUENCE: 44
cugccaagcu uggucaucu                                              19
```

```
<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
aagtgtcctt gcgacgtcc                                                19

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
cctggactgt ggggcttt                                                 18

<210> SEQ ID NO 47
<211> LENGTH: 27
<212> TYPE: DNA
<213> ORGANISM: Artificial Sequence
<220> FEATURE:
<223> OTHER INFORMATION: Probe

<400> SEQUENCE: 47
ctgtttctga acaagcacca acggagc                                       27

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
gtgtcctcgc aacgtcca                                                 18

<210> SEQ ID NO 49
<211> LENGTH: 15
<212> TYPE: DNA
<213> ORGANISM: Artificial Sequence
<220> FEATURE:
<223> OTHER INFORMATION: Primer

<400> SEQUENCE: 49
gaccccgggg ctttg                                                    15

<210> SEQ ID NO 50
<211> LENGTH: 27
<212> TYPE: DNA
<213> ORGANISM: Artificial Sequence
<220> FEATURE:
<223> OTHER INFORMATION: Probe

<400> SEQUENCE: 50
tggctgtttc tgaacaagca ccaatgg                                       27

<210> SEQ ID NO 51
<211> LENGTH: 22
<212> TYPE: DNA
<213> ORGANISM: Artificial Sequence
<220> FEATURE:
<223> OTHER INFORMATION: Primer
```

<400> SEQUENCE: 51
tcattccttc cccaaagaga cc                                          22

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
cacctccgtt ttggtggtag ag                                          22

<210> SEQ ID NO 53
<211> LENGTH: 28
<212> TYPE: DNA
<213> ORGANISM: Artificial Sequence
<220> FEATURE:
<223> OTHER INFORMATION: Probe

<400> SEQUENCE: 53
caagctgctc agtggaggca acacatta                                    28

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
gcatgggtca gaaggattcc tat                                         23

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
tgtagaaggt gtggtgccag att                                         23

<210> SEQ ID NO 56
<211> LENGTH: 22
<212> TYPE: DNA
<213> ORGANISM: Artificial Sequence
<220> FEATURE:
<223> OTHER INFORMATION: Probe

<400> SEQUENCE: 56
tcgagcacgg catcgtcacc aa                                          22

<210> SEQ ID NO 57
<211> LENGTH: 18
<212> TYPE: DNA
<213> ORGANISM: Artificial Sequence
<220> FEATURE:
<223> OTHER INFORMATION: Primer

<400> SEQUENCE: 57
aaggccaacc gcgagaag                                               18

```
<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
agaggcgtac agggacagca                                                    20

<210> SEQ ID NO 59
<211> LENGTH: 28
<212> TYPE: DNA
<213> ORGANISM: Artificial Sequence
<220> FEATURE:
<223> OTHER INFORMATION: Probe

<400> SEQUENCE: 59
tgagaccttc aacacccag ccatgtac                                            28

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
agatgtaggc cgggtgatct tt                                                 22

<210> SEQ ID NO 61
<211> LENGTH: 24
<212> TYPE: DNA
<213> ORGANISM: Artificial Sequence
<220> FEATURE:
<223> OTHER INFORMATION: Primer

<400> SEQUENCE: 61
gtagccaaat cctttctctc ctgt                                               24

<210> SEQ ID NO 62
<211> LENGTH: 31
<212> TYPE: DNA
<213> ORGANISM: Artificial Sequence
<220> FEATURE:
<223> OTHER INFORMATION: Probe

<400> SEQUENCE: 62
tgttccaaaa acagtggata attttgtggc c                                       31

<210> SEQ ID NO 63
<211> LENGTH: 19
<212> TYPE: RNA
<213> ORGANISM: Artificial Sequence
<220> FEATURE:
<223> OTHER INFORMATION: siRNA

<400> SEQUENCE: 63
uuaacucugu ccauuaccg                                                     19

<210> SEQ ID NO 64
<211> LENGTH: 19
<212> TYPE: RNA
<213> ORGANISM: Artificial Sequence
<220> FEATURE:
<223> OTHER INFORMATION: siRNA
```

```
<400> SEQUENCE: 64
cgguaaugga cagaguuaa                                              19

<210> SEQ ID NO 65
<211> LENGTH: 19
<212> TYPE: RNA
<213> ORGANISM: Artificial Sequence
<220> FEATURE:
<223> OTHER INFORMATION: siRNA

<400> SEQUENCE: 65
uuaacucugu ccauuaccc                                              19

<210> SEQ ID NO 66
<211> LENGTH: 19
<212> TYPE: RNA
<213> ORGANISM: Artificial Sequence
<220> FEATURE:
<223> OTHER INFORMATION: siRNA

<400> SEQUENCE: 66
ggguaaugga cagaguuaa                                              19

<210> SEQ ID NO 67
<211> LENGTH: 19
<212> TYPE: RNA
<213> ORGANISM: Artificial Sequence
<220> FEATURE:
<223> OTHER INFORMATION: siRNA

<400> SEQUENCE: 67
uuaacucugu ccauuaccu                                              19

<210> SEQ ID NO 68
<211> LENGTH: 19
<212> TYPE: RNA
<213> ORGANISM: Artificial Sequence
<220> FEATURE:
<223> OTHER INFORMATION: siRNA

<400> SEQUENCE: 68
agguaaugga cagaguuaa                                              19

<210> SEQ ID NO 69
<211> LENGTH: 19
<212> TYPE: RNA
<213> ORGANISM: Artificial Sequence
<220> FEATURE:
<223> OTHER INFORMATION: siRNA

<400> SEQUENCE: 69
auaacucugu ccauuaccc                                              19

<210> SEQ ID NO 70
<211> LENGTH: 19
<212> TYPE: RNA
<213> ORGANISM: Artificial Sequence
<220> FEATURE:
<223> OTHER INFORMATION: siRNA

<400> SEQUENCE: 70
ggguaaugga cagaguuau                                              19
```

```
<210> SEQ ID NO 71
<211> LENGTH: 19
<212> TYPE: RNA
<213> ORGANISM: Artificial Sequence
<220> FEATURE:
<223> OTHER INFORMATION: siRNA

<400> SEQUENCE: 71
auaacucugu ccauuaccu                                                 19

<210> SEQ ID NO 72
<211> LENGTH: 19
<212> TYPE: RNA
<213> ORGANISM: Artificial Sequence
<220> FEATURE:
<223> OTHER INFORMATION: siRNA

<400> SEQUENCE: 72
agguaaugga cagaguuau                                                 19

<210> SEQ ID NO 73
<211> LENGTH: 19
<212> TYPE: RNA
<213> ORGANISM: Artificial Sequence
<220> FEATURE:
<223> OTHER INFORMATION: siRNA

<400> SEQUENCE: 73
uuaacucugu ccauuacca                                                 19

<210> SEQ ID NO 74
<211> LENGTH: 19
<212> TYPE: RNA
<213> ORGANISM: Artificial Sequence
<220> FEATURE:
<223> OTHER INFORMATION: siRNA

<400> SEQUENCE: 74
ugguaaugga cagaguuaa                                                 19

<210> SEQ ID NO 75
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 75
ucguauaaca auaaggggc                                                 19

<210> SEQ ID NO 76
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 76
gccccuuauu guuauacga                                                 19

<210> SEQ ID NO 77
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 77
gauaacucug uccauuacc                                                   19

<210> SEQ ID NO 78
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 78
gguaauggac agaguuauc                                                   19

<210> SEQ ID NO 79
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 79
auaacucugu ccauuacca                                                   19

<210> SEQ ID NO 80
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 80
ugguaaugga cagaguuau                                                   19

<210> SEQ ID NO 81
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 81
uaacucuguc cauuaccgu                                                   19

<210> SEQ ID NO 82
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 82
acgguaaugg acagaguua                                                   19

<210> SEQ ID NO 83
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 83
auaacucugu ccauuaccg                                                 19

<210> SEQ ID NO 84
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 84
cgguaaugga cagaguuau                                                 19

<210> SEQ ID NO 85
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 85
agaaugugcc ucgauaacu                                                 19

<210> SEQ ID NO 86
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 86
aguuaucgag gcacauucu                                                 19

<210> SEQ ID NO 87
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 87
auaacucugu ccaucacca                                                 19

<210> SEQ ID NO 88
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 88
uggugaugga cagaguuau                                                 19

<210> SEQ ID NO 89
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 89
auaacucugu ccaucaccu                                                    19

<210> SEQ ID NO 90
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 90
aggugaugga cagaguuau                                                    19

<210> SEQ ID NO 91
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 91
uaacucuguc cauuaccau                                                    19

<210> SEQ ID NO 92
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 92
augguaaugg acagaguua                                                    19

<210> SEQ ID NO 93
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 93
augugccuug auaacucug                                                    19

<210> SEQ ID NO 94
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 94
cagaguuauc aaggcacau                                                    19

<210> SEQ ID NO 95
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 95
aguuggugcu gcuucagaa                                                    19

<210> SEQ ID NO 96
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 96
uucugaagca gcaccaacu                                                    19

<210> SEQ ID NO 97
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 97
aauaaggggc ugccacagg                                                    19

<210> SEQ ID NO 98
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 98
ccuguggcag ccccuuauu                                                    19

<210> SEQ ID NO 99
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 99
uaacucuguc caucaccau                                                    19

<210> SEQ ID NO 100
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 100
auggugaugg acagaguua                                                    19

<210> SEQ ID NO 101
<211> LENGTH: 19
<212> TYPE: RNA
<213> ORGANISM: Artificial Sequence
```

<220> FEATURE:
<223> OTHER INFORMATION: siRNA - modified_base, modified as per summary
      sequence table at the end of the description

<400> SEQUENCE: 101
augagccucg auaacucug                                                19

<210> SEQ ID NO 102
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 102
cagaguuauc gaggcucau                                                19

<210> SEQ ID NO 103
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 103
aaugagccuc gauaacucu                                                19

<210> SEQ ID NO 104
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 104
agaguuaucg aggcucauu                                                19

<210> SEQ ID NO 105
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 105
aaugcuucca ggacauuuc                                                19

<210> SEQ ID NO 106
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 106
gaaauguccu ggaagcauu                                                19

<210> SEQ ID NO 107
<211> LENGTH: 19
<212> TYPE: RNA
<213> ORGANISM: Artificial Sequence

```
<220> FEATURE:
<223> OTHER INFORMATION: siRNA - modified_base, modified as per summary
      sequence table at the end of the description

<400> SEQUENCE: 107
acaguggugg agaaugugc                                                19

<210> SEQ ID NO 108
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 108
gcacauucuc caccacugu                                                19

<210> SEQ ID NO 109
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 109
guaugugccu cgauaacuc                                                19

<210> SEQ ID NO 110
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 110
gaguuaucga ggcacauac                                                19

<210> SEQ ID NO 111
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 111
ucgauaacuc uguccauca                                                19

<210> SEQ ID NO 112
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 112
ugauggacag aguuaucga                                                19

<210> SEQ ID NO 113
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 113
ugucacugga cauuguguc                                                        19

<210> SEQ ID NO 114
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 114
gacacaaugu ccagugaca                                                        19

<210> SEQ ID NO 115
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 115
cugggaucca ugguguaac                                                        19

<210> SEQ ID NO 116
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 116
guuacaccau ggaucccag                                                        19

<210> SEQ ID NO 117
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 117
agaugaccaa gcuuggcag                                                        19

<210> SEQ ID NO 118
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 118
cugccaagcu uggucaucu                                                        19

<210> SEQ ID NO 119
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 119
auaacucugu ccauuacca                                                  19

<210> SEQ ID NO 120
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 120
ugguaaugga cagaguuau                                                  19

<210> SEQ ID NO 121
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 121
auaacucugu ccauuacca                                                  19

<210> SEQ ID NO 122
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 122
ugguaaugga cagaguuau                                                  19

<210> SEQ ID NO 123
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 123
auaacucugu ccauuaccg                                                  19

<210> SEQ ID NO 124
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 124
cgguaaugga cagaguuau                                                  19

<210> SEQ ID NO 125
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 125
auaacucugu ccauuaccg                                                   19

<210> SEQ ID NO 126
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 126
cgguaaugga cagaguuau                                                   19

<210> SEQ ID NO 127
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 127
uuauagagca agaacacugu u                                                21

<210> SEQ ID NO 128
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 128
aacaguguuc uugcucuaua a                                                21

<210> SEQ ID NO 129
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 129
uuauagagca agaacacugu u                                                21

<210> SEQ ID NO 130
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 130
aacaguguuc uugcucuaua a                                                21

<210> SEQ ID NO 131
<211> LENGTH: 21
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 131
aacaguguuc uugcucuaua a                                               21

<210> SEQ ID NO 132
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 132
ucgaaguauu ccgcguacg                                                  19

<210> SEQ ID NO 133
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 133
cguacgcgga auacuucga                                                  19

<210> SEQ ID NO 134
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 134
aacaguguuc uugcucuaua a                                               21

<210> SEQ ID NO 135
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 135
auaacucugu ccauuaccg                                                  19

<210> SEQ ID NO 136
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 136
cgguaaugga cagaguuau                                                  19

<210> SEQ ID NO 137
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 137
cgguaaugga cagaguuau                                                19

<210> SEQ ID NO 138
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 138
cuuacucucg cccaagcga                                                19

<210> SEQ ID NO 139
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 139
ucgcuugggc gagaguaag                                                19

<210> SEQ ID NO 140
<211> LENGTH: 27
<212> TYPE: DNA
<213> ORGANISM: Artificial Sequence
<220> FEATURE:
<223> OTHER INFORMATION: probe - modified_base, modified as per summary
      sequence table at the end of the description

<400> SEQUENCE: 140
tggctgtttc tgaacaagca ccaatgg                                       27

<210> SEQ ID NO 141
<211> LENGTH: 22
<212> TYPE: DNA
<213> ORGANISM: Artificial Sequence
<220> FEATURE:
<223> OTHER INFORMATION: probe - modified_base, modified as per summary
      sequence table at the end of the description

<400> SEQUENCE: 141
tcgagcacgg catcgtcacc aa                                            22

<210> SEQ ID NO 142
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 142
aacaguguuc uugcucuaua a                                             21

<210> SEQ ID NO 143
<211> LENGTH: 21
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 143
aacaguguuc uugcucuaua a                                                  21

<210> SEQ ID NO 144
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 144
aacaguguuc uugcucuaua a                                                  21

<210> SEQ ID NO 145
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 145
aacaguguuc uugcucuaua a                                                  21

<210> SEQ ID NO 146
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 146
aacaguguuc uugcucuaua a                                                  21

<210> SEQ ID NO 147
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 147
aacaguguuc uugcucuaua a                                                  21

<210> SEQ ID NO 148
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 148
aacaguguuc uugcucuaua a                                                  21

<210> SEQ ID NO 149
<211> LENGTH: 21
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 149
aacaguguuc uugcucuaua a                                             21

<210> SEQ ID NO 150
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 150
aacaguguuc uugcucuaua a                                             21

<210> SEQ ID NO 151
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 151
ucuucuuaaa cugaguuuc                                                19

<210> SEQ ID NO 152
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 152
gaaacucagu uuaagaaga                                                19

<210> SEQ ID NO 153
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 153
auguagccga ggaucuucu                                                19

<210> SEQ ID NO 154
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 154
agaagauccu cggcuacau                                                19

<210> SEQ ID NO 155
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 155
aaccagaaga agcagguga                                                      19

<210> SEQ ID NO 156
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 156
ucaccugcuu cuucugguu                                                      19

<210> SEQ ID NO 157
<211> LENGTH: 21
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 157
aacaguguuc uugcucuaua a                                                   21

<210> SEQ ID NO 158
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 158
gaaacucagu uuaagaaga                                                      19

<210> SEQ ID NO 159
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 159
agaagauccu cggcuacau                                                      19

<210> SEQ ID NO 160
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 160
uaccagaaga agcagguga                                                      19

<210> SEQ ID NO 161
<211> LENGTH: 19
<212> TYPE: RNA
<213> ORGANISM: Artificial Sequence
```

```
<220> FEATURE:
<223> OTHER INFORMATION: siRNA - modified_base, modified as per summary
      sequence table at the end of the description

<400> SEQUENCE: 161
ucaccugcuu cuucuggua                                              19

<210> SEQ ID NO 162
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 162
cgguaaugga cagaguuau                                              19
```

NUCLEIC ACIDS FOR INHIBITING EXPRESSION OF LPA IN A CELL

CROSS-REFERENCE TO RELATED APPLICATIONS

This application is a 35 U.S.C. § 371 National Stage of International Patent Application No. PCT/EP2018/081106, filed Nov. 13, 2018, which itself claims the benefit of and priority to European Patent Application No. 1815915.2, filed Sep. 28, 2018, European Patent Application No. 18179175.7, filed Jun. 21, 2018, and European Patent Application No. 17201449.0, filed Nov. 13, 2017, the content of each of which is incorporated by reference herein in its entirety and for all purposes.

The present invention relates to products and compositions and their uses. In particular the invention relates to nucleic acid products that interfere with the LPA gene expression or inhibit its expression. Such therapeutic Lp(a) lowering therapy serves to prevent and reduce the risk of suffering stroke, atherosclerosis, thrombosis and cardiovascular diseases such as coronary heart disease and aortic stenosis or any other disorder, pathology or syndrome linked to elevated levels of Lp(a)-containing particles.

BACKGROUND

Double-stranded RNA (dsRNA) able to complementarily bind expressed mRNA has been shown to be able to block gene expression (Fire et al., 1998, Nature. 1998 Feb. 19; 391(6669):806-11 and Elbashir et al., 2001, Nature. 2001 May 24; 411(6836):494-8) by a mechanism that has been termed RNA interference (RNAi). Short dsRNAs direct gene-specific, post-transcriptional silencing in many organisms, including vertebrates, and have become a useful tool for studying gene function. RNAi is mediated by the RNA-induced silencing complex (RISC), a sequence-specific, multi-component nuclease that degrades messenger RNAs homologous to the silencing trigger loaded into the RISC complex. Interfering RNA (termed herein iRNA) such as siRNAs, antisecond strand RNA, and micro-RNA are oligonucleotides that prevent the formation of proteins by gene-silencing i.e. inhibiting gene translation of the protein through degradation of mRNA molecules. Gene-silencing agents are becoming increasingly important for therapeutic applications in medicine.

According to Watts and Corey in the Journal of Pathology (2012; Vol 226, p 365-379) there are algorithms that can be used to design nucleic acid silencing triggers, but all of these have severe limitations. It may take various experimental methods to identify potent iRNAs, as algorithms do not take into account factors such as tertiary structure of the target mRNA or the involvement of RNA binding proteins. Therefore, the discovery of a potent nucleic acid silencing trigger with minimal off-target effects is a complex process. For the pharmaceutical development of these highly charged molecules it is necessary that they can be synthesised economically, distributed to target tissues, enter cells and function within acceptable limits of toxicity.

Lp(a) is a heterogeneous low-density lipoprotein particle expressed predominantly in the liver (Witztum and Ginsberg, J Lipid Res. 2016 March; 57(3):336-9). It is composed of Apolipoprotein(a) (Apo(a) encoded by the LPA gene) linked to LDL via ApoB poly-peptide. Genetically defined high Lp(a) serum levels are unaffected by diet and exercise and are associated to increased risk to suffer from cardiovascular disease through the associated atherosclerotic potential (Alonso et al., Journal of the American College of Cardiology Vol. 63, No. 19, 2014). In terms of diagnostics and preventive medicine the patient's serum level of Lp(a) is a highly prevalent, independent, genetic risk factor for coronary heart disease and aortic stenosis (Saeedi and Frohlich Clinical Diabetes and Endocrinology (2016) 2:7). There is no current approved specific Lp(a) reduction therapy beyond indirect standard general LDL-lowering measures. Accordingly, methods for effective treatment, prevention and reduction of risk of suffering from disorders such as and associated with stroke, atherosclerosis, thrombosis and cardiovascular diseases such as coronary heart disease, aortic stenosis and other yet unidentified associated disorders, pathologies or syndromes are currently needed. The present invention addresses this unmet medical need:

A first aspect of the invention relates to a nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of a RNA transcribed from the LPA gene, wherein said first strand comprises a nucleotide sequence selected from the following sequences: SEQ ID NOs: 1, 3, 5, 7, 9, 11, 13, 15, 17, 19, 21, 23, 25, 27, 29, 31, 33, 35, 37, 39, 41, 43, 63, 65, 67, 69, 71 or 73.

In one embodiment, the nucleic acid comprises in the first strand a sequence of at least 15, preferably at least 16, more preferably at least 17, yet more preferably at least 18 and most preferably at least 19 nucleotides of any one of the reference sequences SEQ ID NOs: 1, 3, 5, 7, 9, 11, 13, 15, 17, 19, 21, 23, 25, 27, 29, 31, 33, 35, 37, 39, 41, 43, 63, 65, 67, 69, 71 or 73.

In one embodiment, the number of single nucleotide mismatches in the first strand sequence relative to the portion of the reference sequence that is comprised in the first strand sequence is at most three, preferably at most two, more preferably at most one and most preferably zero.

The second strand may comprise a nucleotide sequence of SEQ ID NO: 2, 4, 6, 8, 10, 12, 14, 16, 18, 20, 22, 24, 26, 28, 30, 32, 34, 38, 40, 42, 44, 64, 66, 68, 70, 72 or 74.

The first strand may comprise the nucleotide sequence of SEQ ID NO:5 and SEQ ID NO:9 and/or the second strand may comprise the nucleotide sequence of SEQ ID NO:6 and SEQ ID NO:10.

The first strand and/or the second strand may each be from 17-35 nucleotides in length and at least one duplex region may be from 10-25 nucleotides in length. The duplex may comprise two separate strands or it may comprise a single strand which comprises the first strand and the second strand.

The nucleic acid may: a) be blunt ended at both ends; b) have an overhang at one end and a blunt end at the other; or c) have an overhang at both ends.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more odd nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be modified by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first strand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with a second different modification.

The nucleic acid of the invention may have the modified nucleotides of the first strand shifted by at least one nucleotide relative to the unmodified or differently modified nucleotides of the second strand.

The modification and/or modifications may each and individually be selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide. At least one modification may be 2'-O-methyl and/or at least one modification may be 2'-F.

The invention further provides, as a second aspect, a nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of an RNA transcribed from the LPA gene, wherein said first strand comprises a nucleotide sequence selected from the following sequences: SEQ ID NOs: 1, 3, 5, 7, 9, 11, 13, 15, 17, 19, 21, 23, 25, 27, 29, 31, 33, 35, 37, 39, 41, 43, 63, 65, 67, 69, 71 or 73, wherein the nucleotides of first strand are modified by a first modification on the odd numbered nucleotides, and modified by a second modification on the even numbered nucleotides, and nucleotides of the second strand are modified by a third modification on the even numbered nucleotides and modified by a fourth modification on the odd numbered nucleotides, wherein at least the first modification is different to the second modification and the third modification is different to the fourth modification. The second strand may comprise a nucleotide sequence of SEQ ID NO: 2, 4, 6, 8, 10, 12, 14, 16, 18, 20, 22, 24, 26, 28 30, 32, 34, 36, 38, 40, 42, 44, 64, 66, 68, 70, 72 or 74. The third modification and the first modification may be the same and/or the second modification and the fourth modification may be the same.

The first modification may be 2'OMe and the second modification may be 2'F.

In the nucleic acid of the second aspect, the first strand may comprise the nucleotide sequence of SEQ ID NO: 5 and SEQ ID NO:9 and the second strand may comprise the nucleotide sequence of SEQ ID NO: 6 and SEQ ID NO:10.

The sequence and modifications may be as shown in the Table below; which shows preferred sequences based on an extract of Table 1 as provided herein:

SEQ ID 5' auaacucuguccauuacca 3'6162717181736152736
NO: 5

SEQ ID 5' ugguaauggacagaguuau 3'1845261846364645161
NO: 6

SEQ ID 5' auaacucuguccauuaccg 3'6162717181736152738
NO: 9

SEQ ID 5' cgguaauggacagaguuau 3'38452618463646145161
NO: 10 wherein the specific modifications are depicted by the following numbers
1=2'F-dU,
2=2'F-dA,
3=2'F-dC,
4=2'F-dG,
5=2'-OMe-rU;
6=2'-OMe-rA;
7=2'-OMe-rC;
8=2'-OMe-rG.

A nucleic acid of the invention may comprise a phosphorothioate linkage between the terminal one, two or three 3' nucleotides and/or one, two or three 5' nucleotides of the first and/or the second strand. It may comprise two phosphorothioate linkages between each of the three terminal 3' and between each of the three terminal 5' nucleotides on the first strand, and two phosphorothioate linkages between the three terminal nucleotides of the 3' end of the second strand.

Such a nucleic acid may be conjugated to a ligand.

The invention further provides, as a third aspect, a nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of a RNA transcribed from the LPA gene, wherein said first strand comprises a nucleotide sequence selected from the following sequences: SEQ ID NOs: 1, 3, 5, 7, 9, 11, 13, 15, 17, 19, 21, 23, 25, 27, 29, 31, 33, 35, 37, 39, 41, 43, 63, 65, 67, 69, 71 or 73 and wherein the nucleic acid is conjugated to a ligand.

The ligand may comprise (i) one or more N-acetyl galactosamine (GalNAc) moieties and derivatives thereof, and (ii) a linker, wherein the linker conjugates the GalNAc moieties to a sequence as defined in any preceding aspects. The linker may be a bivalent or trivalent or tetravalent branched structure. The nucleotides may be modified as defined herein.

The ligand may comprise the formula I:

$$[S-X^1-P-X^2]_3-A-X^3-\qquad(I)$$

wherein:
S represents a saccharide, wherein the saccharide is N-acetyl galactosamine;
$X^1$ represents $C_3-C_6$ alkylene or $(-CH_2-CH_2-O)_m(-CH_2)_2-$ wherein m is 1, 2, or 3;
P is a phosphate or modified phosphate (preferably a thiophosphate);
$X^2$ is alkylene or an alkylene ether of the formula $(-CH_2)_n-O-CH_2-$ where n=1-6;
A is a branching unit;
$X^3$ represents a bridging unit;
wherein a nucleic acid according to the present invention is conjugated to $X^3$ via a phosphate or modified phosphate (preferably a thiophosphate).

The present invention therefore additionally provides a conjugated nucleic acid having one of the following structures

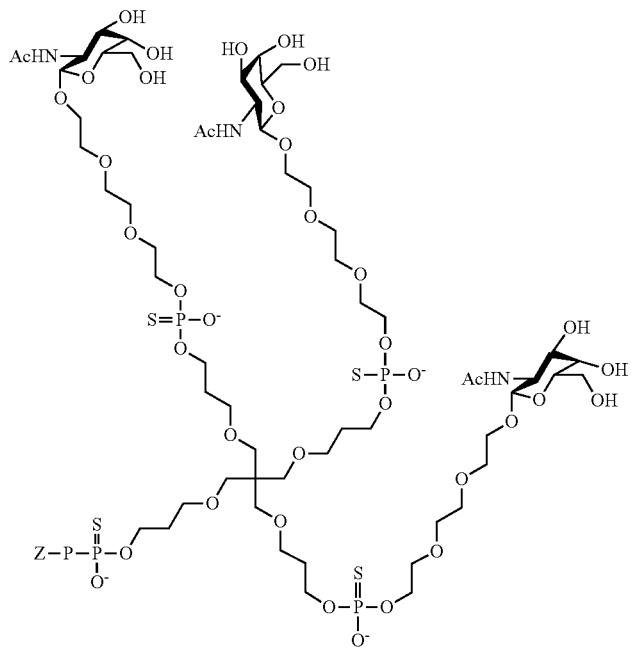

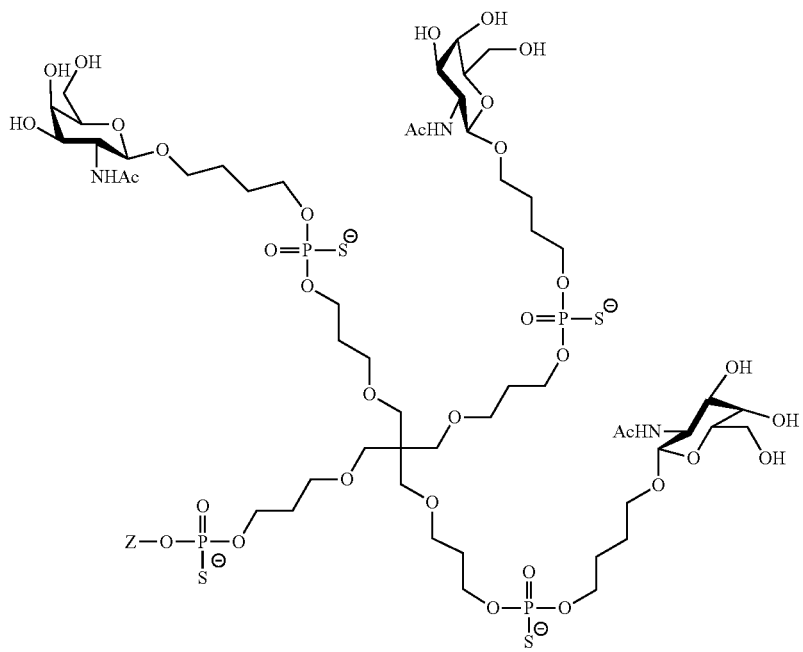

-continued
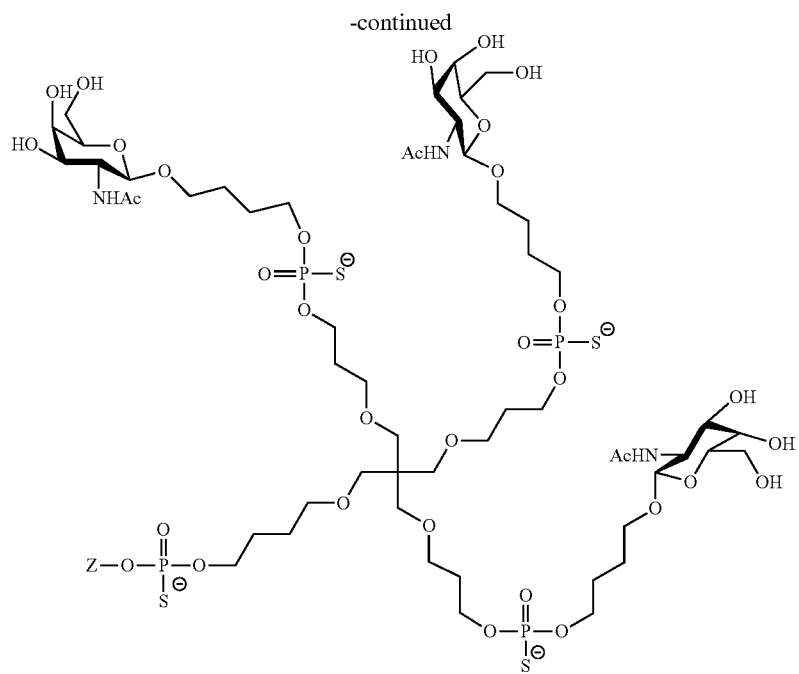
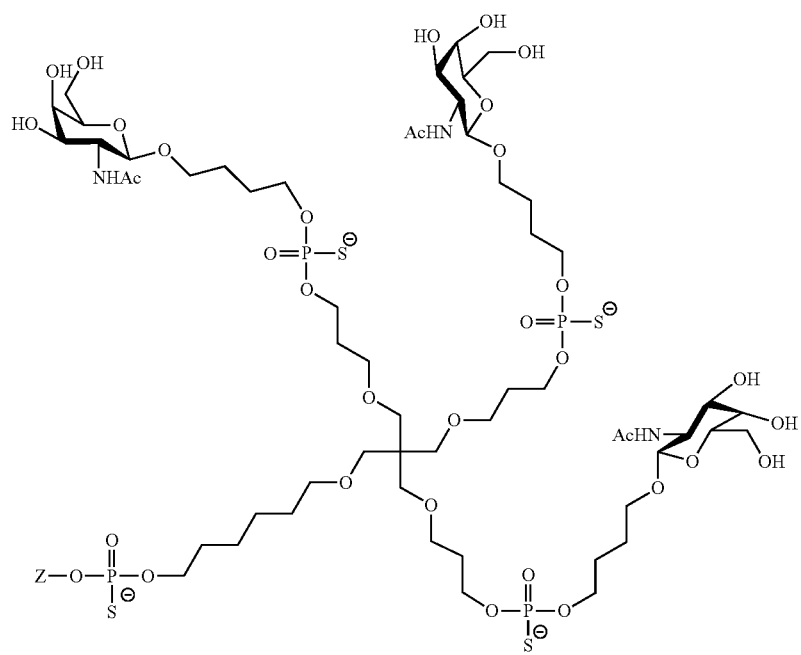

-continued
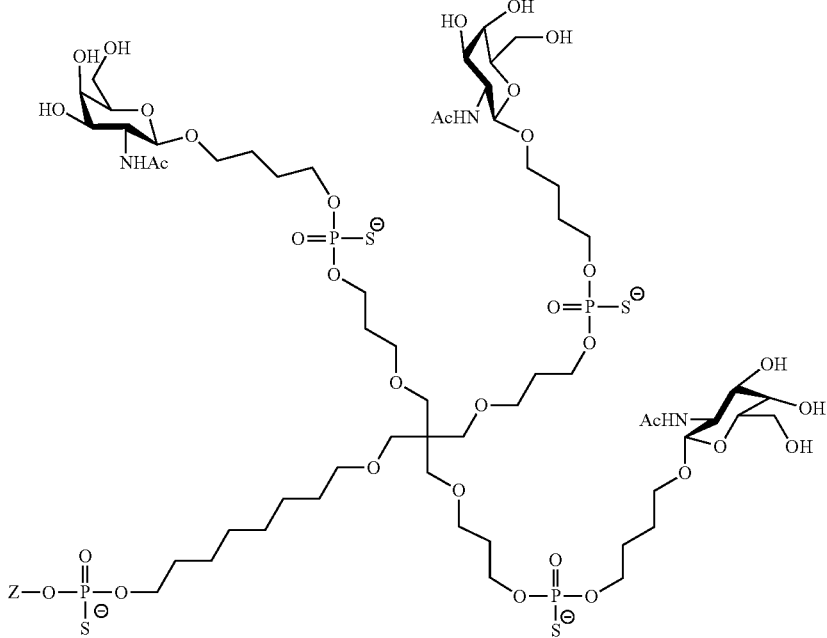
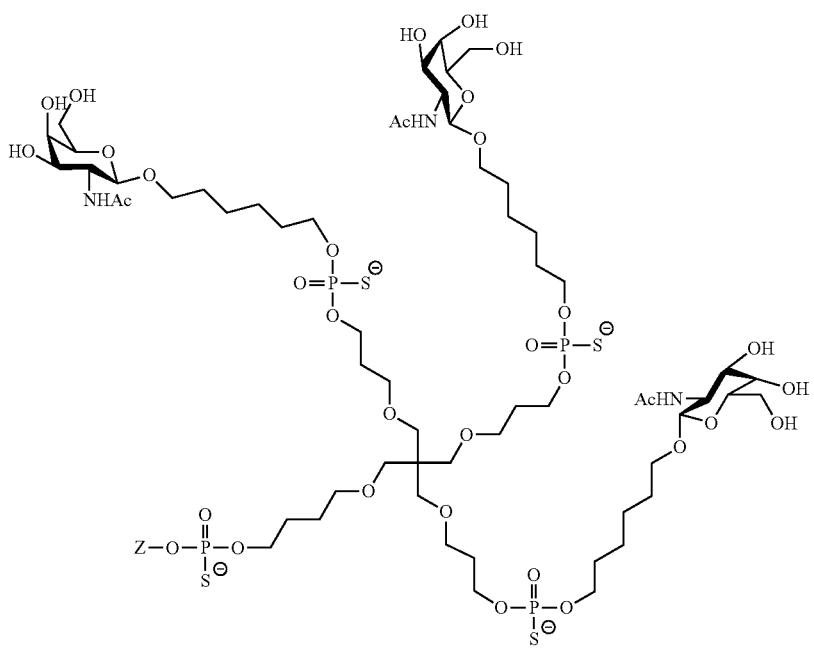

-continued
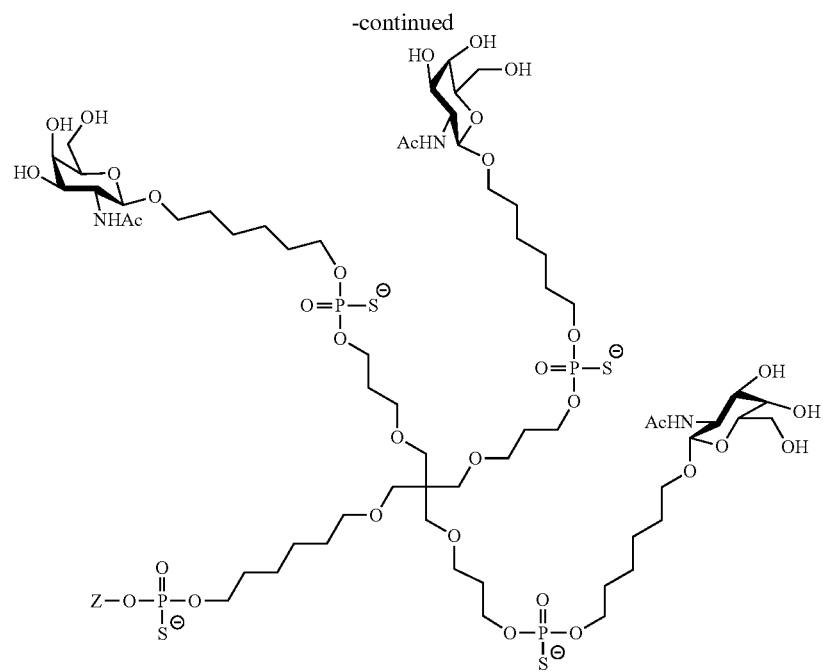
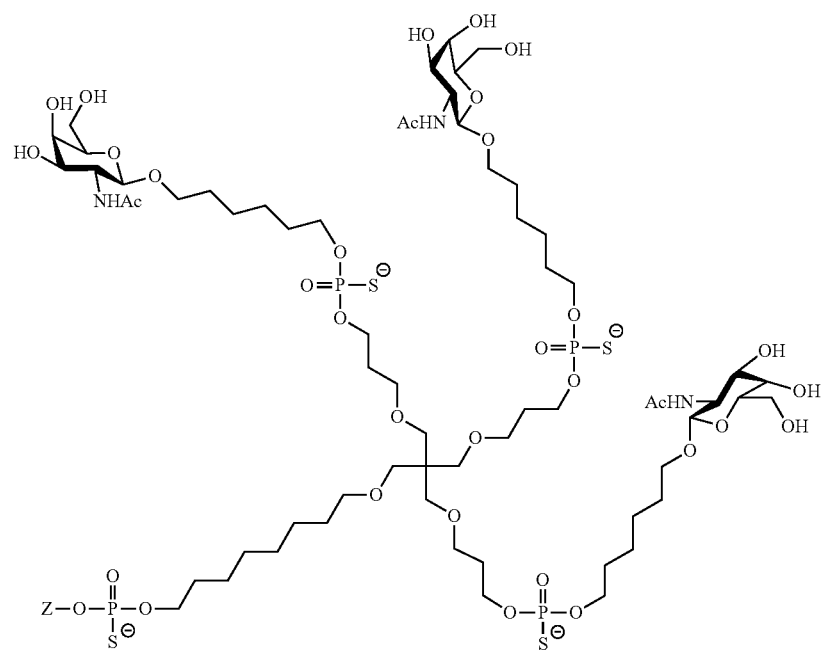
wherein Z represents a nucleic acid as defined herein before.

Alternatively, a nucleic acid according to the present invention may be conjugated to a ligand of the following structure

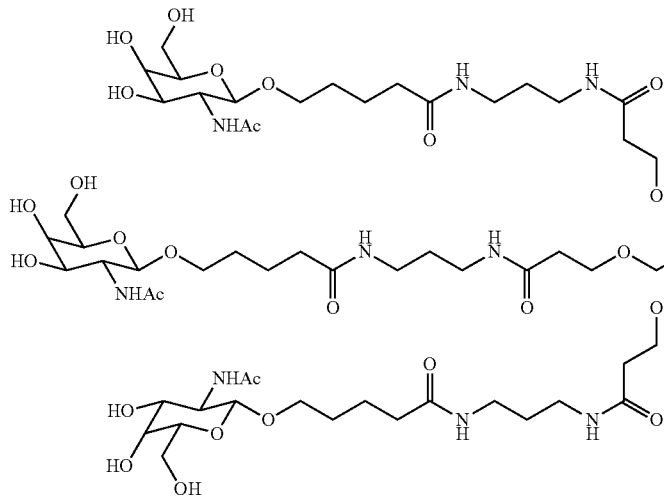 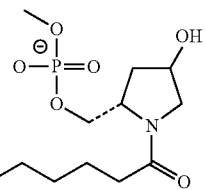

The present invention also relates to a conjugate for inhibiting expression of a LPA gene in a cell, said conjugate comprising a nucleic acid portion, comprising the nucleic acid of any aspect of the invention, and ligand portions, said nucleic acid portion comprising at least one duplex region that comprises at least a portion of a first RNA strand and at least a portion of a second RNA strand that is at least partially complementary to the first strand, wherein said first strand is at least partially complementary to at least a portion of RNA transcribed from said LPA gene, said ligand portions comprising a linker moiety, preferably a serinol-derived linker moiety, and a targeting ligand for in vivo targeting of cells and being conjugated exclusively to the 3' and/or 5' ends of one or both RNA strands, wherein the 5' end of the first RNA strand is not conjugated, wherein:
 (i) the second RNA strand is conjugated at the 5' end to the targeting ligand, and wherein (a) the second RNA strand is also conjugated at the 3' end to the targeting ligand and the 3' end of the first RNA strand is not conjugated; or (b) the first RNA strand is conjugated at the 3' end to the targeting ligand and the 3' end of the second RNA strand is not conjugated; or (c) both the second RNA strand and the first RNA strand are also conjugated at the 3' ends to the targeting ligand; or
 (ii) both the second RNA strand and the first RNA strand are conjugated at the 3' ends to the targeting ligand and the 5' end of the second RNA strand is not conjugated,
or
the present invention relates to a conjugate for inhibiting expression of a LPA gene in a cell, said conjugate comprising a nucleic acid portion and ligand portions, said nucleic acid portion comprising at least one duplex region that comprises at least a portion of a first RNA strand and at least a portion of a second RNA strand that is at least partially complementary to the first strand, wherein said first strand is at least partially complementary to at least a portion of RNA transcribed from said LPA gene, said ligand portions comprising a linker moiety and a targeting ligand for in vivo targeting of cells and being conjugated exclusively to the 3' and/or 5' ends of one or both RNA strands, wherein the 5' end of the first RNA strand is not conjugated, wherein:
 (i) the second RNA strand is conjugated at the 5' end to the targeting ligand, and wherein (a) the second RNA strand is also conjugated at the 3' end to the targeting ligand and the 3' end of the first RNA strand is not conjugated; or (b) the first RNA strand is conjugated at the 3' end to the targeting ligand and the 3' end of the second RNA strand is not conjugated; or (c) both the second RNA strand and the first RNA strand are also conjugated at the 3' ends to the targeting ligand; or
 (ii) both the second RNA strand and the first RNA strand are conjugated at the 3' ends to the targeting ligand and the 5' end of the second RNA strand is not conjugated.

The linker moiety may for example be a serinol-derived linker moiety or one of the other linker types described herein.

The invention also provides a composition comprising the nucleic acid or conjugated nucleic acid of any aspect of the invention, and a physiologically acceptable excipient.

Also provided is a nucleic acid or conjugated nucleic acid according to any aspect of the invention for use in the treatment of a disease, disorder or syndrome and/or in the manufacture of a medicament for treating a disease, disorder, or syndrome.

The invention provides a method of treating or preventing a disease, disorder or syndrome comprising administration of a composition comprising a nucleic acid or conjugated nucleic acid according to any aspect of the invention to an individual in need of treatment. The nucleic acid or conjugated nucleic acid may be administered to the subject subcutaneously, intravenously or using any other application routes such as oral, rectal or intraperitoneal.

After subcutaneous application, the invention may be delivered in a tissue specific manner to liver (hepatocytes) and target specifically LPA, in order to reduce unwanted side effects and achieve a lower therapeutic dose necessary to achieve the desired effect.

The invention or the pharmaceutical composition comprising the nucleic acid or conjugated nucleic acid of the invention may be used in the treatment of a disease, disorder or syndrome. The treatment may be to prevent and reduce risk to suffer from stroke, atherosclerosis, thrombosis or cardiovascular diseases such as coronary heart disease or aortic stenosis and any other disease or pathology associated to elevated levels Lp(a)-containing particles.

A method of making the nucleic acid or conjugated nucleic acid according to the invention is also included.

DETAILED DESCRIPTION OF INVENTION

The present invention relates to a nucleic acid which is double stranded and directed to an expressed RNA transcript of LPA and compositions thereof. These nucleic acids or conjugated nucleic acids can be used in the treatment and prevention of a variety of diseases, disorders and syndromes where reduced expression of LPA gene product is desirable.

A first aspect of the invention relates to a nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of a RNA transcribed from the LPA gene, wherein said first strand comprises a nucleotide sequence selected from the following sequences: SEQ ID NOs: 1, 3, 5, 7, 9, 11, 13, 15, 17, 19, 21, 23, 25, 27, 29, 31, 33, 35, 37, 39, 41, 43, 63, 65, 67, 69, 71 or 73.

The nucleic acid may comprise a first strand that comprises a nucleotide sequence of SEQ ID NO: 9, and optionally wherein the second strand comprises a nucleotide sequence of SEQ ID NO: 10; or a first strand that comprises a nucleotide sequence of SEQ ID NO: 5, and optionally wherein the second strand comprises a nucleotide sequence of SEQ ID NO: 6; or a first strand that comprises a nucleotide sequence of SEQ ID NO: 1, and optionally wherein the second strand comprises a nucleotide sequence of SEQ ID NO: 2; or a first strand that comprises a nucleotide sequence of SEQ ID NO:4, and optionally wherein the second strand comprises a nucleotide sequence of SEQ ID NO: 4; or a first strand that comprises a nucleotide sequence of SEQ ID NO: 7, and optionally wherein the second strand comprises a nucleotide sequence of SEQ ID NO: 8; or a first strand that comprises a nucleotide sequence of SEQ ID NO: 11, and optionally wherein the second strand comprises a nucleotide sequence of SEQ ID NO: 12; or a first strand that comprises a nucleotide sequence of SEQ ID NO: 13, and optionally wherein the second strand comprises a nucleotide sequence of SEQ ID NO: 14; or a first strand that comprises a nucleotide sequence of SEQ ID NO: 15, and optionally wherein the second strand comprises a nucleotide sequence of SEQ ID NO: 16; or a first strand that comprises a nucleotide sequence of SEQ ID NO: 17, and optionally wherein the second strand comprises a nucleotide sequence of SEQ ID NO: 18; or a first strand that comprises a nucleotide sequence of SEQ ID NO: 19, and optionally wherein the second strand comprises a nucleotide sequence of SEQ ID NO: 20; or a first strand that comprises a nucleotide sequence of SEQ ID NO: 21, and optionally wherein the second strand comprises a nucleotide sequence of SEQ ID NO: 22; or a first strand that comprises a nucleotide sequence of SEQ ID NO:23, and optionally wherein the second strand comprises a nucleotide sequence of SEQ ID NO: 24; or a first strand that comprises a nucleotide sequence of SEQ ID NO:25, and optionally wherein the second strand comprises a nucleotide sequence of SEQ ID NO: 26; or a first strand that comprises a nucleotide sequence of SEQ ID NO: 27, and optionally wherein the second strand comprises a nucleotide sequence of SEQ ID NO: 28; or a first strand that comprises a nucleotide sequence of SEQ ID NO: 29, and optionally wherein the second strand comprises a nucleotide sequence of SEQ ID NO: 30; or a first strand that comprises a nucleotide sequence of SEQ ID NO: 31, and optionally wherein the second strand comprises a nucleotide sequence of SEQ ID NO: 32; or a first strand that comprises a nucleotide sequence of SEQ ID NO: 33, and optionally wherein the second strand comprises a nucleotide sequence of SEQ ID NO: 34; or a first strand that comprises a nucleotide sequence of SEQ ID NO: 35, and optionally wherein the second strand comprises a nucleotide sequence of SEQ ID NO: 36; or a first strand that comprises a nucleotide sequence of SEQ ID NO: 37, and optionally wherein the second strand comprises a nucleotide sequence of SEQ ID NO: 38; or a first strand that comprises a nucleotide sequence of SEQ ID NO: 39, and optionally wherein the second strand comprises a nucleotide sequence of SEQ ID NO: 40; or a first strand that comprises a nucleotide sequence of SEQ ID NO: 41, and optionally wherein the second strand comprises a nucleotide sequence of SEQ ID NO: 42; or a first strand that comprises a nucleotide sequence of SEQ ID NO: 43, and optionally wherein the second strand comprises a nucleotide sequence of SEQ ID NO: 44; or a first strand that comprises a nucleotide sequence of SEQ ID NO: 63, and optionally wherein the second strand comprises a nucleotide sequence of SEQ ID NO: 64; or a first strand that comprises a nucleotide sequence of SEQ ID NO: 65, and optionally wherein the second strand comprises a nucleotide sequence of SEQ ID NO: 66; or a first strand that comprises a nucleotide sequence of SEQ ID NO: 67, and optionally wherein the second strand comprises a nucleotide sequence of SEQ ID NO: 68; or a first strand that comprises a nucleotide sequence of SEQ ID NO: 69, and optionally wherein the second strand comprises a nucleotide sequence of SEQ ID NO: 70; or a first strand that comprises a nucleotide sequence of SEQ ID NO: 71, and optionally wherein the second strand comprises a nucleotide sequence of SEQ ID NO: 72; or a first strand that comprises a nucleotide sequence of SEQ ID NO: 73, and optionally wherein the second strand comprises a nucleotide sequence of SEQ ID NO: 74.

The LPA gene comprises highly repetitive sequences. First strand nucleic acids with very similar sequences can therefore have perfect sequence complementarity to very different target regions of the mRNA.

A related aspect of the invention is a nucleic acid for inhibiting expression of LPA in a cell, wherein the nucleic acid comprises at least one duplex region that comprises: a first strand; and a second strand, wherein said second strand is at least partially complementary to the first strand, wherein said first strand comprises a sequence of at least 15, preferably at least 16, more preferably at least 17, yet more preferably at least 18 and most preferably at least 19 nucleotides of any one of the reference sequences SEQ ID NO: 9, 5, 1, 3, 7, 11, 13, 15, 17, 19, 21, 23, 25, 27, 29, 31, 33, 35, 37, 39, 41, 43, 63, 65, 67, 69, 71 or 73, and wherein the number of single nucleotide mismatches and/or deletions and/or insertions in the first strand sequence relative to the portion of the reference sequence that is comprised in the first strand sequence is at most three, preferably at most two, more preferably at most one and most preferably zero.

In one aspect, the first strand of the nucleic acid comprises a sequence of at least 18 nucleotides of any one of the reference sequences, preferably of any one of the reference sequences SEQ ID NO: 9 and 5, and wherein the number of single-nucleotide mismatches and/or deletions and/or insertions in the first strand sequence relative to the portion of the reference sequence that is comprised in the first strand sequence is at most one, and preferably zero.

In one aspect, the first strand of the nucleic acid comprises a sequence of at least 19 nucleotides of any of the reference sequences SEQ ID NO: 9 and 5.

A certain number of mismatches, deletions or insertions between the first (antisense) strand and the target sequence, or between the first strand and the second (sense) strand can be tolerated in the context of siRNA and even have the potential in certain cases to increase activity.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide molecule that is self-complementary which 'folds' back to form a double stranded molecule. The nucleic acid may be an siRNA molecule.

The nucleic acid may comprise ribonucleotides, modified ribonucleotides, deoxynucleotides, deoxyribonucleotides, or nucleotide analogues non-nucleotides that are able to mimic nucleotides such that they may 'pair' with the corresponding base on the target sequence or complementary strand. The nucleic acid may further comprise a double-stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region it is meant the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single stranded regions. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another.

The portion of the first strand and second strand that form at least one duplex region may be fully complementary and is at least partially complementary to each other. Depending on the length of a nucleic acid, a perfect match in terms of base complementarity between the first strand and the second strand is not necessarily required. However, the first and second strands must be able to hybridise under physiological conditions.

The complementarity between the first strand and second strand in the at least one duplex region may be perfect in that there are no nucleotide mismatches or additional/deleted nucleotides in either strand. Alternatively, the complementarity may not be perfect. The complementarity may be from about 70% to about 100%. More specifically, the complementarity may be at least 70%, 75%, 80%, 85%, 90% or 95% and intermediate values.

In the context of this invention, "a portion of" as for example in "one duplex region that comprises at least a portion of a first strand" should be understood to mean that the duplex region comprises at least 10, preferably at least 12, more preferably at least 14, yet more preferably at least 16, even more preferably at least 18 and most preferably all of the nucleotides of a given reference strand sequence. The portion of the reference sequence in the dublex region is at least 70%, preferably at least 80%, more preferably at least 90%, yet more preferably at least 95% and most preferably 100% identical to the corresponding portion of the reference sequence. Alternatively, the number of single nucleotide mismatches relative to the portion of the reference sequence is at most three, preferably at most two, more preferably at most one and most preferably zero.

The first strand and the second strand may each comprise a region of complementarity which comprises at least 15 contiguous nucleotides differing by no more than 3 nucleotides from any one of the sequences listed in Table 1.

The nucleic acid may comprise a second sequence comprising a nucleotide sequence of SEQ ID NO: 2, 4, 6, 8, 10, 12, 14, 16, 18, 20, 22, 24, 26, 28 30, 32, 34, 36, 38, 40, 42, 44, 64, 66, 68, 70, 72 or 74.

Use of a nucleic acid according to the present invention involves the formation of a duplex region between all or a portion of the first strand and a portion of a target nucleic acid. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence; however, the first strand must be able to form a duplex structure with both the second strand and the target sequence, at least under physiological conditions.

The complementarity between the first strand and the target sequence may be perfect (no nucleotide mismatches or additional/deleted nucleotides in either nucleic acid).

The complementarity between the first strand and the target sequence may not be perfect. The complementarity may be from about 70% to about 100%. More specifically, the complementarity may be at least 70%, 80%, 85%, 90% or 95% and intermediate values.

The identity between the first strand and the complementary sequence of the target sequence may range from about 75% to about 100%. More specifically, the complementarity may be at least 75%, 80%, 85%, 90% or 95% and intermediate values, provided a nucleic acid is capable of reducing or inhibiting the expression of LPA.

A nucleic acid having less than 100% complementarity between the first strand and the target sequence may be able to reduce the expression of LPA to the same level as a nucleic acid having perfect complementarity between the first strand and target sequence. Alternatively, it may be able to reduce expression of LPA to a level that is 15%-100% of the level of reduction achieved by the nucleic acid with perfect complementarity.

The nucleic acid may comprise a first strand and a second strand that are each from 19-25 nucleotides in length. The first strand and the second strand may be of different lengths.

The nucleic acid may be 15-25 nucleotide pairs in length. The nucleic acid may be 17-23 nucleotide pairs in length. The nucleic acid may be 17-25 nucleotide pairs in length. The nucleic acid may be 23-24 nucleotide pairs in length. The nucleic acid may be 19-21 nucleotide pairs in length. The nucleic acid may be 21-23 nucleotide pairs in length.

The nucleic acid may comprise a duplex region that consists of 19-25 nucleotide base pairs. The duplex region may consist of 17, 18, 19, 20, 21, 22, 23, 24 or 25 base pairs, which may be contiguous.

The nucleic acid may comprise a first strand sequence of SEQ ID NO: 5 or SEQ ID NO:9. The nucleic acid may comprise a second strand sequence of SEQ ID NO:6 or SEQ ID NO:10.

Preferably, the nucleic acid mediates RNA interference.

In one embodiment, the nucleic acid for inhibiting expression of LPA in a cell, comprises at least one duplex region that comprises a first strand and a second strand that is at least partially complementary to the first strand, wherein said first strand comprises a sequence of at least 15, preferably at least 16, more preferably at least 17, yet more preferably at least 18 and most preferably at least 19 nucleotides with a sequence identity of at least 70%, preferably at least 80%, more preferably at least 90%, yet more preferably at least 95% and most preferably 100% of any of sequences SEQ ID NOs: 9, 5, 1, 3, 7, 11, 13, 15, 17, 19, 21, 23, 25, 27, 29, 31, 33, 35, 37, 39, 41, 43, 63, 65, 67, 69, 71 or 73.

In a further aspect the nucleic acid or conjugated nucleic acid as described may reduce the expression of LPA by at least 15% compared to the expression observed in the absence of the nucleic acid or conjugated nucleic acid. All preferred features of any of the previous aspects also apply to this aspect. In particular, the expression of LPA may be reduced to at least the following given % or less than 90%, 80%, 70%, 60%, 50%, 40%, 30%, 20%, 15% or less, and intermediate values, than that observed in the absence of the nucleic acid or conjugated nucleic acid or in the presence of a non-silencing control.

The nucleic acid may be blunt ended at both ends; have an overhang at one end and a blunt end at the other end; or have an overhang at both ends.

An "overhang" as used herein has its normal and customary meaning in the art, i.e. a single stranded portion of a nucleic acid that extends beyond the terminal nucleotide of a complementary strand in a double strand nucleic acid. The term "blunt end" includes double stranded nucleic acid whereby both strands terminate at the same position, regardless of whether the terminal nucleotide(s) are base-paired. The terminal nucleotide of a first strand and a second strand at a blunt end may be base paired. The terminal nucleotide of a first strand and a second strand at a blunt end may not be paired. The terminal two nucleotides of a first strand and a second strand at a blunt end may be base-paired. The terminal two nucleotides of a first strand and a second strand at a blunt end may not be paired.

The nucleic acid may have an overhang at one end and a blunt end at the other. The nucleic acid may have an overhang at both ends. The nucleic acid may be blunt ended at both ends. The nucleic acid may be blunt ended at the end with the 5'-end of the first strand and the 3'-end of the second strand or at the 3'-end of the first strand and the 5'-end of the second strand.

The nucleic acid may comprise an overhang at a 3'- or 5'-end. The nucleic acid may have a 3'-overhang on the first strand. The nucleic acid may have a 3'-overhang on the second strand. The nucleic acid may have a 5'-overhang on the first strand. The nucleic acid may have a 5'-overhang on the second strand. The nucleic acid may have an overhang at both the 5'-end and 3'-end of the first strand. The nucleic acid may have an overhang at both the 5'-end and 3'-end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand.

An overhang at the 3'-end or 5' end of the second strand or the first strand may be selected from consisting of 1, 2, 3, 4 and 5 nucleotides in length. Optionally, an overhang may consist of 1 or 2 nucleotides, which may or may not be modified.

Unmodified polynucleotides, particularly ribonucleotides, may be prone to degradation by cellular nucleases, and, as such, modifications/modified nucleotides may be included in the nucleic acid of the invention. Such modifications may help to stabilise the nucleic acid by making them more resistant against nucleases. This improved resistance allows nucleic acids to be active in mediating RNA interference for longer time periods and is especially desirable when the nucleic acids are to be used for treatment.

One or more nucleotides on the second and/or first strand of the nucleic acid of the invention may be modified.

Modifications of the nucleic acid of the present invention generally provide a powerful tool in overcoming potential limitations including, but not limited to, in vitro and in vivo stability and bioavailability inherent to native RNA molecules. The nucleic acid according to the invention may be modified by chemical modifications. Modified nucleic acid can also minimise the possibility of inducing interferon activity in humans. Modification can further enhance the functional delivery of a nucleic acid to a target cell. The modified nucleic acid of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution or insertion with analogues of nucleic acids or bases.

One or more nucleotides of a nucleic acid of the present invention may be modified. The nucleic acid may comprise at least one modified nucleotide. The modified nucleotide may be in the first strand. The modified nucleotide may be in the second strand. The modified nucleotide may be in the duplex region. The modified nucleotide may be outside the duplex region, i.e., in a single stranded region. The modified nucleotide may be on the first strand and may be outside the duplex region. The modified nucleotide may be on the second strand and may be outside the duplex region. The 3'-terminal nucleotide of the first strand may be a modified nucleotide. The 3'-terminal nucleotide of the second strand may be a modified nucleotide. The 5'-terminal nucleotide of the first strand may be a modified nucleotide. The 5'-terminal nucleotide of the second strand may be a modified nucleotide.

A nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, 24-26 modified nucleotides or about 26-28 modified nucleotides. In each case the nucleic acid comprising said modified nucleotides retains at least 50% of its activity as compared to the same nucleic acid but without said modified nucleotides or vice versa. The nucleic acid may retain 55%, 60%, 65%, 70%, 75%, 80%, 85%, 90%, 95% or 100% and intermediate values of its activity as compared to the same nucleic acid but without said modified nucleotides, or may have more than 100% of the activity of the same nucleic acid without said modified nucleotides.

The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 3'-terminal deoxy-thymine (dT) nucleotide, a 2'-O-methyl modified nucleotide, a 2' modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified nucleotide, wherein the base is selected from 2-aminoadenosine, 2,6-diaminopurine, inosine, pyridin-4-one, pyridin-2-one, phenyl, pseudouracil, 2,4,6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Nucleic acids discussed herein include unmodified RNA as well as RNA which has been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. Modified nucleotide as used herein refers to a nucleotide in which one or more of the components of the nucleotides, namely sugars, bases, and phosphate moieties, are different from those which occur in nature. While they are referred to as modified nucleotides they will of course, because of the modification, the term also includes molecules which are not nucleotides, for example a polynucleotide molecule in which the ribophosphate backbone is replaced with a non-ribophosphate construct that allows hybridisation between strands i.e. the modified nucleotides mimic the ribophosphate backbone.

Many of the modifications described below that occur within a nucleic acid will be repeated within a polynucleotide molecule, such as a modification of a base, or a phosphate moiety, or a non-linking O of a phosphate moiety. In some cases the modification will occur at all of the possible positions/nucleotides in the polynucleotide but in many cases it will not. A modification may only occur at a 3' or 5' terminal position, may only occur in a terminal regions, such as at a position on a terminal nucleotide or in the last 2, 3, 4, 5, or 10 nucleotides of a strand. A modification may occur in a double strand region, a single strand region, or in both. A modification may occur only in the double strand region of a nucleic acid of the invention or may only occur in a single strand region of a nucleic acid of the invention. A phosphorothioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single strand regions, particularly at termini. The 5' end or 3' ends may be phosphorylated.

Stability of a nucleic acid of the invention may be increased by including particular bases in overhangs, or to include modified nucleotides, in single strand overhangs, e.g., in a 5' or 3' overhang, or in both. Purine nucleotides may be included in overhangs. All or some of the bases in a 3' or 5' overhang may be modified. Modifications can include the use of modifications at the 2'OH group of the ribose sugar, the use of deoxyribonucleotides, instead of ribonucleotides, and modifications in the phosphate group, such as phosphorothioate modifications. Overhangs need not be homologous with the target sequence.

Nucleases can hydrolyse nucleic acid phosphodiester bonds. However, chemical modifications to nucleic acids can confer improved properties, and, can render oligoribonucleotides more stable to nucleases.

Modified nucleic acids, as used herein, can include one or more of:
(i) alteration, e.g., replacement, of one or both of the non-linking phosphate oxygens and/or of one or more of the linking phosphate oxygens (referred to as linking even if at the 5' and 3' terminus of the nucleic acid of the invention);
(ii) alteration, e.g., replacement, of a constituent of the ribose sugar, e.g., of the 2' hydroxyl on the ribose sugar;
(iii) replacement of the phosphate moiety with "dephospho" linkers;
(iv) modification or replacement of a naturally occurring base;
(v) replacement or modification of the ribose-phosphate backbone;
(vi) modification of the 3' end or 5' end of the RNA, e.g., removal, modification or replacement of a terminal phosphate group or conjugation of a moiety, e.g., a fluorescently labelled moiety, to either the 3' or 5' end of RNA.

The terms replacement, modification, alteration, indicate a difference from a naturally occurring molecule.

Specific modifications are discussed in more detail below.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

A modified nucleotide can include modification of the sugar groups. The 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH2CH2O)nCH2CH2OR; "locked" nucleic acids (LNA) in which the 2' hydroxyl is connected, e.g., by a methylene bridge, to the 4' carbon of the same ribose sugar; O-AMINE (AMINE=NH2; alkylamino, dialkylamino, heterocyclyl, arylamino, diaryl amino, heteroaryl amino, or diheteroaryl amino, ethylene diamine, polyamino) and aminoalkoxy, O(CH2)nAMINE, (e.g., AMINE=NH2; alkylamino, dialkylamino, heterocyclyl, arylamino, diaryl amino, heteroaryl amino, or diheteroaryl amino, ethylene diamine, polyamino).

"Deoxy" modifications include hydrogen, halogen, amino (e.g., NH2; alkylamino, dialkylamino, heterocyclyl, arylamino, diaryl amino, heteroaryl amino, diheteroaryl amino, or amino acid); NH(CH2CH2NH)nCH2CH2-AMINE (AMINE=NH2; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substitutents of certain embodiments include 2'-methoxyethyl, 2'-OCH3,2'-O-allyl, 2'-C-allyl, and 2'-fluoro. The sugar group can also contain one or more carbons that possess the opposite stereochemical configuration than that of the corresponding carbon in ribose. Thus, a modified nucleotides may contain a sugar such as arabinose.

Modified nucleotides can also include "abasic" sugars, which lack a nucleobase at C-1'. These abasic sugars can further contain modifications at one or more of the constituent sugar atoms.

The 2' modifications may be used in combination with one or more phosphate linker modifications (e.g., phosphorothioate).

The phosphate groups can individually be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

The phosphate linker and ribose sugar may be replaced by nuclease resistant nucleotides.

Examples include the morpholino, cyclobutyl, pyrrolidine and peptide nucleic acid (PNA) nucleoside surrogates. In certain embodiments, PNA surrogates may be used.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labelling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5'O, N, S or C group of the sugar. Alternatively, the linker can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, —(CH$_2$CH$_2$O)$_n$CH$_2$CH$_2$O— (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases, EDTA, lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including to modulate activity or to modulate resistance to degradation. Terminal modifications useful for modulating activity include modification of the 5' end with phosphate or phosphate analogues. Nucleic acids of the invention, on the first or second strand, may be 5' phosphorylated or include a phosphoryl analogue at the 5' prime terminus. 5'-phosphate modifications include those which are compatible with RISC mediated gene silencing.

Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g., RP(OH)(O)—O-5'-, (OH)$_2$(O)P-5'-CH$_2$—), 5' vinylphosphonate, 5'-alkyletherphosphonates (R=alkylether=methoxymethyl (MeOCH$_2$—), ethoxymethyl, etc., e.g., RP(OH)(O)—O-5'-).

The nucleic acid of the present invention may include one or more phosphorothioate modifications on one or more of the terminal ends of the first and/or the second strand. Optionally, each or either end of the first strand may comprise one or two or three phosphorothioate modified nucleotides. Optionally, each or either end of the second strand may comprise one or two or three phosphorothioate modified nucleotides.

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Adenine, guanine, cytosine and uracil are the most common bases found in RNA. These bases can be modified or replaced to provide RNAs having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogues of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyluracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N<4>-acetyl cytosine, 2-thiocytosine, N6-methyladenine, N6-isopentyladenine, 2-methylthio-N6-isopentenyladenine, N-methylguanines, or O-alkylated bases.

As used herein, the terms "non-pairing nucleotide analogue" means a nucleotide analogue which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analogue is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

Certain moieties may be linked to the 5' terminus of the first strand or the second strand. These include abasic ribose moiety, abasic deoxyribose moiety, modifications abasic ribose and abasic deoxyribose moieties including 2'O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogues including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non-bridging methylphosphonate and 5'-mercapto moieties.

The nucleic acids of the invention may include one or more inverted nucleotides, for example inverted thymidine or inverted adenine (for example see Takei, et al., 2002. JBC 277 (26):23800-06).

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits, is reduced below that observed in the absence of the nucleic acid or conjugated nucleic acid of the invention or in reference to an siRNA molecule with no known homology to human transcripts (herein termed non-silencing control). Such control may be conjugated and modified in an analogous manner to the molecule of the invention and delivered into the target cell by the same route; for example the expression may be reduced to 90%, 80%, 70%, 60%, 50%, 40%, 30%, 20%, 15%, or to intermediate values, or less than that observed in the absence of the nucleic acid or conjugated nucleic acid or in the presence of a non-silencing control.

The nucleic acid of the present invention may comprise an abasic nucleotide. The term "abasic" as used herein, refers to moieties lacking a base or having other chemical groups in place of a base at the 1' position, for example a 3',3'-linked or 5',5'-linked deoxyabasic ribose derivative.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

One or more of the odd numbered nucleotides of the first strand of the nucleic acid of the invention may be modified wherein the first strand is numbered 5' to 3', the 5'-most nucleotide being nucleotide number 1 of the first strand. The term "odd numbered" as described herein means a number not divisible by two. Examples of odd numbers are 1, 3, 5, 7, 9, 11 and so on. One or more of the even numbered nucleotides of the first strand of the nucleic acid of the invention may be modified, wherein the first strand is numbered 5' to 3'. The term "even numbered" as described herein means a number which is evenly divisible by two. Examples of even numbers are 2, 4, 6, 8, 10, 12, 14 and so on. One or more of the odd numbered nucleotides of the second strand of the nucleic acid of the invention may be modified wherein the second strand is numbered 3' to 5', the 3'-most nucleotide being nucleotide number 1 of the second strand. One or more of the even numbered nucleotides of the second strand of the nucleic acid of the invention may be modified, wherein the second strand is numbered 3' to 5'.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more odd nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be modified by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first stand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with the second modification.

The nucleic acid of the invention may have the modified nucleotides of the first strand shifted by at least one nucleotide relative to the unmodified or differently modified nucleotides of the second strand.

One or more or each of the odd numbered nucleotides may be modified in the first strand and one or more or each of the even numbered nucleotides may be modified in the second strand. One or more or each of the alternating nucleotides on either or both strands may be modified by a second modification. One or more or each of the even numbered nucleotides may be modified in the first strand and one or more or each of the even numbered nucleotides may be modified in the second strand. One or more or each of the alternating nucleotides on either or both strands may be modified by a second modification. One or more or each of the odd numbered nucleotides may be modified in the first strand and one or more of the odd numbered nucleotides may be modified in the second strand by a common modification. One or more or each of the alternating nucleotides on either or both strands may be modified by a second modification. One or more or each of the even numbered nucleotides may be modified in the first strand and one or more or each of the odd numbered nucleotides may be modified in the second strand by a common modification. One or more or each of the alternating nucleotides on either or both strands may be modified by a second modification.

The nucleic acid of the invention may comprise single or double stranded constructs that comprise at least two regions of alternating modifications in one or both of the strands. These alternating regions can comprise up to about 12 nucleotides but preferably comprise from about 3 to about 10 nucleotides. The regions of alternating nucleotides may be located at the termini of one or both strands of the nucleic acid of the invention. The nucleic acid may comprise from 4 to about 10 nucleotides of alternating nucleotides at each termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd numbered nucleotides of the first strand. One or more nucleotides of second strand may also be modified with the second modification. One or more nucleotides with the second modification may be adjacent to each other and to nucleotides having a modification that is the same as the modification of the odd numbered nucleotides of the first strand. The first strand may also comprise phosphorothioate linkages between the two nucleotides at the 3' end and at the 5' end. The second strand may comprise a phosphorothioate linkage between the two nucleotides at 5' end. The second strand may also be conjugated to a ligand at the 5' end.

The nucleic acid of the invention may comprise a first strand comprising adjacent nucleotides that are modified with a common modification. One or more of such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of second strand may also be modified with the second modification. One or more nucleotides with the second modification may be adjacent. The first strand may also comprise phosphorothioate linkages between the two nucleotides at the 5' end and at the 3' end. The second strand may comprise a phosphorothioate linkage between the two nucleotides at the 3' end. The second strand may also be conjugated to a ligand at the 5' end.

The nucleotides numbered from 5' to 3' on the first strand and 3' to 5' on the second strand, 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand. Nucleotides are numbered for the sake of the nucleic acid of the present invention from 5' to 3' on the first strand and 3' to 5' on the second strand The nucleotides numbered 2, 4, 6, 8, 10, 12, 14, 16, 18, 20, 22 and 24 may be modified by a modification on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter than 25 nucleotides in length, such as 19 nucleotides in length, there are no nucleotides numbered 20, 21, 22, 23, 24 and 25 to be modified. The skilled person understands the description above to apply to shorter strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

The modification and/or modifications may each and individually be selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-O-methyl and/or at least one modification may be 2'-F. Further modifications as described herein may be present on the first and/or second strand.

The nucleic acid of the invention may comprise an inverted RNA nucleotide at one or several of the strand ends. Such inverted nucleotides provide stability to the nucleic acid. Preferably, the nucleic acid comprises at least an inverted nucleotide at one or several of the 3' end of at least one of the strands and/or at the 5' end of the second strand. More preferably, the nucleic acid comprises an inverted nucleotide at the 3' end of the second strand. Most preferably, the nucleic acid comprises an inverted RNA nucleotide at the 3' end of the second strand and this nucleotide is preferably an inverted A. The inverted nucleotide is preferably present at an end of a strand not as an overhang but opposite a corresponding nucleotide in the other strand. A nucleic acid with such a modification is stable and easy to synthesise.

Throughout the description of the invention, "same or common modification" means the same modification to any nucleotide, be that A, G, C or U modified with a group such as a methyl group or a fluoro group. Is it not taken to mean the same addition on the same nucleotide. For example, 2'F-dU, 2'F-dA, 2'F-dC, 2'F-dG are all considered to be the same or common modification, as are 2'-OMe-rU, 2'-OMe-rA; 2'-OMe-rC; 2'-OMe-rG. A 2'F modification is a different modification to a 2'OMe modification.

Some representative modified nucleic acid sequences of the present invention are shown in the examples. These examples are meant to be representative and not limiting.

Preferably, the nucleic acid may comprise a modification and a second or further modification which are each and individually selected from the group comprising 2'-O-methyl modification and 2'-F modification. The nucleic acid may comprise a modification that is 2'-O-methyl (2'OMe) that may be a first modification, and a second modification that is 2'-F. The nucleic acid of the invention may also include a phosphorothioate modification and/or a deoxy modification which may be present in or between the terminal 1, 2 or 3 nucleotides of each or any end of each or both strands.

The invention provides as a further aspect, a nucleic acid for inhibiting expression of LPA in a cell, comprising a nucleotide sequence of SEQ ID NO: 1, 3, 5, 7, 9, 11, 13, 15, 17, 19, 21, 23, 25, 27, 29, 31, 33, 35, 37, 39, 41, 43, 63, 65, 67, 69, 71 or 73, wherein the nucleotides of first strand are modified by a first modification on the odd numbered nucleotides, and modified by a second modification on the even numbered nucleotides, and nucleotides of the second strand are modified by a third modification on the even numbered nucleotides and modified by a fourth modification the odd numbered nucleotides, wherein at least the first modification is different to the second modification and the third modification is different to the fourth modification. The third and first modifications may be the same or different, the second and fourth modifications may be the same or different. The first and second modifications may be different to each other and the third and fourth modifications may be different to each other.

The second strand may comprise a nucleotide sequence of SEQ ID NO: 2, 4, 6, 8, 10, 12, 14, 16, 18, 20, 22, 24, 26, 28, 30, 32, 34, 36, 38, 40, 42, 44, 64, 66, 68, 70, 72 or 74. The nucleotides of the first strand may be modified by a first modification on the odd numbered nucleotides, and modified with a second modification on the even numbered nucleotides, and the second strand may be modified on the odd numbered nucleotides with the second modification and modified with the first modification on the even numbered nucleotides. The first modification may be 2'OMe and the second modification may be 2' F. The first strand may comprise the nucleotide sequence of SEQ ID NO: 5 or SEQ ID NO: 9 and/or the second strand may comprise the nucleotide sequence of SEQ ID NO: 6, or SEQ ID NO:10. The modifications may be those as set out in Table 1.

The nucleic acid of the invention may be conjugated to a ligand. Efficient delivery of oligonucleotides, in particular double stranded nucleic acids of the invention, to cells in vivo is important and requires specific targeting and substantial protection from the extracellular environment, particularly serum proteins. One method of achieving specific targeting is to conjugate a ligand to the nucleic acid. The ligand helps in targeting the nucleic acid to the required target site. There is a need to conjugate appropriate ligands for the desired receptor molecules in order for the conjugated molecules to be taken up by the target cells by mechanisms such as different receptor-mediated endocytosis pathways or functionally analogous processes.

One example is the asialoglycoprotein receptor complex (ASGP-R) composed by varying ratios of multimers of membrane ASGR1 and ASGR2 receptors, which is highly abundant on hepatocytes and has high affinity for the here described GalNAc moiety. One of the first disclosures of the use of triantennary cluster glycosides as conjugated ligands was in U.S. Pat. No. 5,885,968. Conjugates having three GalNAc ligands and comprising phosphate groups are known and are described in Dubber et al. (Bioconjug. Chem. 2003 January-February; 14(1):239-46). The ASGP-R complex shows a 50-fold higher affinity for N-Acetyl-D-Galactosylamine (GalNAc) than D-Gal.

The asialoglycoprotein receptor complex (ASGP-R), which recognizes specifically terminal β-galactosyl subunits of glycosylated proteins or other oligosaccharides (Weigel, P. H. et. al., Biochim. Biophys. Acta. 2002 Sep. 19; 1572 (2-3):341-63) can be used for delivering a drug to the liver's hepatocytes expressing the receptor complex by covalent coupling of galactose or galactosamine to the drug substance (Ishibashi, S.; et. al., J Biol. Chem. 1994 Nov. 11; 269(45): 27803-6). Furthermore the binding affinity can be significantly increased by the multi-valency effect, which is achieved by the repetition of the targeting moiety (Biessen E A, et al., J Med Chem. 1995 Apr. 28; 38(9):1538-46).

The ASGP-R complex is a mediator for an active uptake of terminal β-galactosyl containing glycoproteins to the cell's endosomes. Thus, the ASGPR is highly suitable for targeted delivery of drug candidates conjugated to such ligands like, e.g., nucleic acids into receptor-expressing cells (Akinc et al., Mol Ther. 2010 July; 18(7):1357-64).

More generally the ligand can comprise a saccharide that is selected to have an affinity for at least one type of receptor on a target cell. In particular, the receptor is on the surface of a mammalian liver cell, for example, the hepatic asialoglycoprotein receptor complex described before (ASGP-R).

The saccharide may be selected from N-acetyl galactosamine, mannose, galactose, glucose, glucosamine and fucose. The saccharide may be N-acetyl galactosamine (GalNAc).

A ligand for use in the present invention may therefore comprise (i) one or more N-acetyl galactosamine (GalNAc) moieties and derivatives thereof, and (ii) a linker, wherein the linker conjugates the GalNAc moieties to a sequence as defined in any preceding aspects. The linker may be a bivalent or trivalent or tetravalent branched structure. The nucleotides may be modified as defined herein.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. Both the β-form: 2-(Acetylarnino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylarnino)-2-deoxy-3-D-galactopyranose.

The ligand may therefore comprise GalNAc.

The ligand may comprise a compound of formula I:

$$[S-X^1-P-X^2]_3-A-X^3- \quad (I)$$

wherein:
S represents a saccharide, wherein the saccharide is N-acetyl galactosamine;
$X^1$ represents $C_3$-$C_6$ alkylene or $(-CH_2-CH_2-O)_m(-CH_2)_2-$ wherein m is 1, 2, or 3;
P is a phosphate or modified phosphate (preferably a thiophosphate);
$X^2$ is alkylene or an alkylene ether of the formula $(-CH_2)_n-O-CH_2-$ where n=1-6;
A is a branching unit;
$X^3$ represents a bridging unit;
wherein a nucleic acid according to the present invention is conjugated to $X^3$ via a phosphate or modified phosphate (preferably a thiophosphate).

In formula I, branching unit "A" branches into three in order to accommodate the three saccharide ligands. The branching unit is covalently attached to the remaining tethered portions of the ligand and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

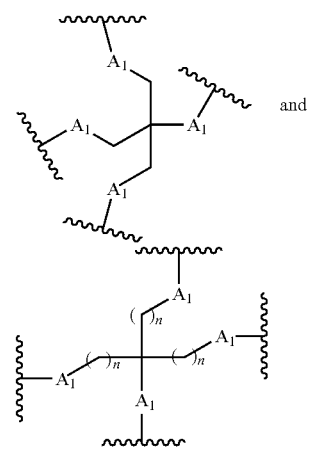

and wherein each $A_1$ independently represents O, S, C=O or NH; and
each n independently represents an integer from 1 to 20.

The branching unit may have a structure selected from:

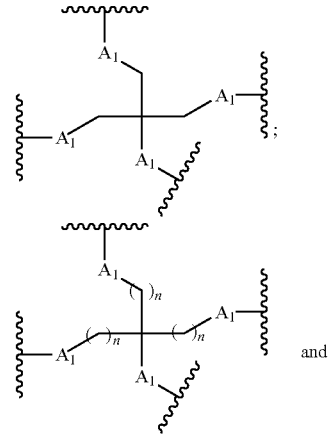

and

-continued

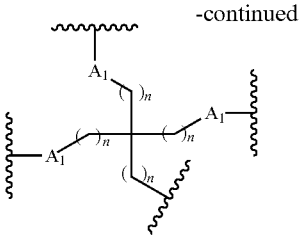

wherein each $A_1$ independently represents O, S, C=O or NH; and
each n independently represents an integer from 1 to 20.
The branching unit may have a structure selected from:

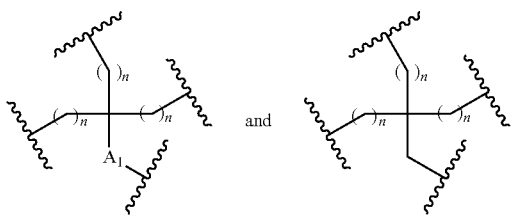

wherein $A_1$ is O, S, C=O or NH; and
each n independently represents an integer from 1 to 20.
The branching unit may have the structure:

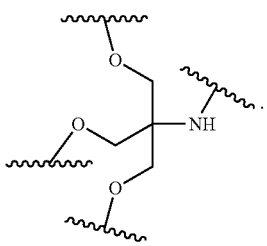 [SMILES: *NC(CO*)(CO*)CO*]

The branching unit may have the structure:

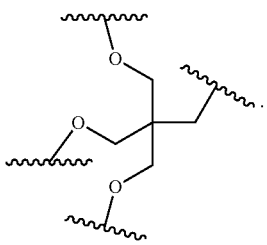 [SMILES: *CC(CO*)(CO*)CO*]

The branching unit may have the structure:

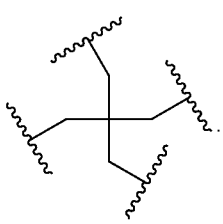 [SMILES: *CC(C*)(C*)C*]

Optionally, the branching unit consists of only a carbon atom.

The "$X^3$" portion is a bridging unit. The bridging unit is linear and is covalently bound to the branching unit and the nucleic acid.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula —($C_1$-$C_{20}$ alkylene)-O—($C_1$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

The ligand may comprise a compound of formula (II):

$$[S—X^1—P—X^2]_3\text{-}A\text{-}X^3— \qquad (II)$$

wherein:
S represents a saccharide;
$X^1$ represents $C_3$-$C_6$ alkylene or (—$CH_2$—$CH_2$—O)$_m$(—$CH_2$)$_2$— wherein m is 1, 2, or 3;
P is a phosphate or modified phosphate (preferably a thiophosphate);
$X^2$ is $C_1$-$C_8$ alkylene;
A is a branching unit selected from:

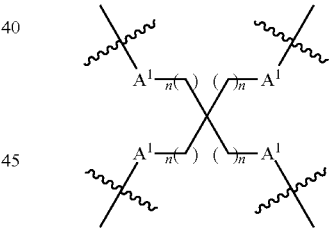

$A^1$ = O, NH
n = 1 to 4

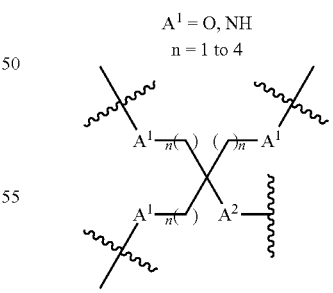

$A^1$ = O, NH
$A^2$ = NH, $CH_2$, O
n = 1 to 4

$X^3$ is a bridging unit;
wherein a nucleic acid according to the present invention is conjugated to $X^3$ via a phosphate or modified phosphate (preferably a thiophosphate)

Branching unit A may have the structure:

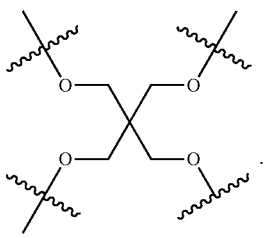 [SMILES: *OCC(CO*)(CO*)CO*]

Branching unit A may have the structure:

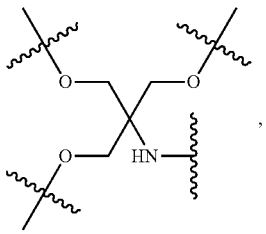

wherein $X^3$ is attached to the nitrogen atom.

$X^3$ may be $C_1$-$C_{20}$ alkylene. Preferably, $X^3$ is selected from the group consisting of —$C_3H_6$—, —$C_4H_8$—, —$C_6H_{12}$— and —$C_8H_{16}$—, especially —$C_4H_8$—, —$C_6H_{12}$— and —$C_8H_{16}$—.

The ligand may comprise a compound of formula (III):

$$[S-X^1-P-X^2]_3-A-X^3-  \qquad (III)$$

wherein:
S represents a saccharide;
$X^1$ represents $C_3$-$C_6$ alkylene or (—$CH_2$—$CH_2$—O)$_m$(—$CH_2$)$_2$— wherein m is 1, 2, or 3;
P is a phosphate or modified phosphate (preferably a thiophosphate);
$X^2$ is an alkylene ether of formula —$C_3H_6$—O—$CH_2$—;
A is a branching unit;
$X^3$ is an alkylene ether of formula selected from the group consisting of —$CH_2$—O—$CH_2$—, —$CH_2$—O—$C_2H_4$—, —$CH_2$—O—$C_3H_6$—, —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—, wherein in each case the —$CH_2$— group is linked to A, and wherein $X^3$ is conjugated to a nucleic acid according to the present invention by a phosphate or modified phosphate (preferably a thiophosphate).

The branching unit may comprise carbon. Preferably, the branching unit is carbon.

$X^3$ may be selected from the group consisting of —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—. Preferably, $X^3$ is selected from the group consisting of —$CH_2$—O—$C_4H_8$—, —$CH_2$—O—$C_6H_{12}$— and —$CH_2$—O—$C_8H_{16}$.

For any of the above aspects, when P represents a modified phosphate group, P can be represented by:

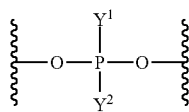

wherein $Y^1$ and $Y^2$ each independently represent =O, =S, —O—, —OH, —SH, —BH$_3$, —OCH$_2$CO$_2$, —OCH$_2$CO$_2$R$^x$, —OCH$_2$C(S)OR$^x$, and —OR$^x$, wherein R$^x$ represents $C_1$-$C_6$ alkyl and wherein ⊣ indicates attachment to the remainder of the compound.

By modified phosphate it is meant a phosphate group wherein one or more of the non-linking oxygens is replaced. Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

For example, $Y^1$ may represent —OH and $Y^2$ may represent =O or =S; or $Y^1$ may represent —O$^-$ and $Y^2$ may represent =O or =S;

$Y^1$ may represent =O and $Y^2$ may represent —CH$_3$, —SH, —OR$^x$, or —BH$_3$ $Y^1$ may represent =S and $Y^2$ may represent —CH$_3$, OR$^x$ or —SH.

It will be understood by the skilled person that in certain instances there will be delocalisation between $Y^1$ and $Y^2$.

Preferably, the modified phosphate group is a thiophosphate group. Thiophosphate groups include bithiophosphate (i.e. where $Y^1$ represents =S and $Y^2$ represents —S$^-$) and monothiophosphate (i.e. where $Y^1$ represents —O$^-$ and $Y^2$ represents =S, or where $Y^1$ represents =O and $Y^2$ represents —S$^-$). Preferably, P is a monothiophosphate. The inventors have found that conjugates having thiophosphate groups in replacement of phosphate groups have improved potency and duration of action in vivo.

P may also be an ethylphosphate (i.e. where $Y^1$ represents =O and $Y^2$ represents OCH$_2$CH$_3$).

The saccharide may be selected to have an affinity for at least one type of receptor on a target cell. In particular, the receptor is on the surface of a mammalian liver cell, for example, the hepatic asialoglycoprotein receptor complex (ASGP-R).

For any of the above aspects, the saccharide may be selected from N-acetyl with one or more of galactosamine, mannose, galactose, glucose, glucosamine and fructose. Typically a ligand to be used in the present invention may include N-acetyl galactosamine (GalNAc). Preferably the compounds of the invention may have 3 ligands, which will each preferably include N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylarnino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylarnino)-2-deoxy-β-D-galactopyranose.

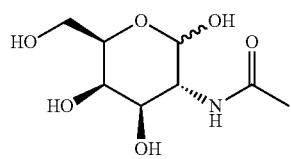

2-(Acetylamino)-2-deoxy-D-galactopyranose

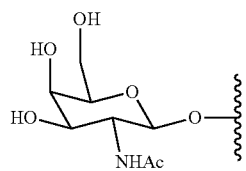

2-(Acetylamino)-β-deoxy-D-galactopyranose

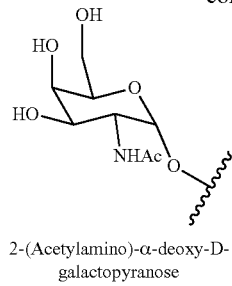

2-(Acetylamino)-α-deoxy-D-galactopyranose

For any of the above compounds of formula (III), $X^1$ may be (—$CH_2$—$CH_2$—O)(—$CH_2$)$_2$—. $X^1$ may be (—$CH_2$—$CH_2$—O)$_2$(—$CH_2$)$_2$—. $X^1$ may be (—$CH_2$—$CH_2$—O)$_3$(—$CH_2$)$_2$—. Preferably, $X^1$ is (—$CH_2$—$CH_2$—O)$_2$(—$CH_2$)$_2$—. Alternatively, $X^1$ represents $C_3$-$C_6$ alkylene. $X^1$ may be propylene. $X^1$ may be butylene. $X^1$ may be pentylene. $X^1$ may be hexylene. Preferably the alkyl is a linear alkylene. In particular, $X^1$ may be butylene.

For compounds of formula (III), $X^2$ represents an alkylene ether of formula —$C_3H_6$—O—$CH_2$— i.e. $C_3$ alkoxy methylene, or —$CH_2CH_2CH_2OCH_2$—.

The invention provides a conjugated nucleic acid having one of the following structures:

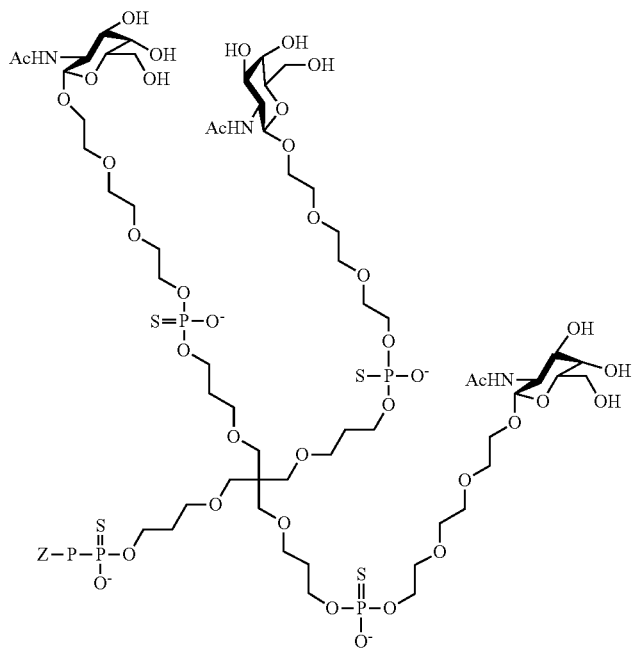

-continued
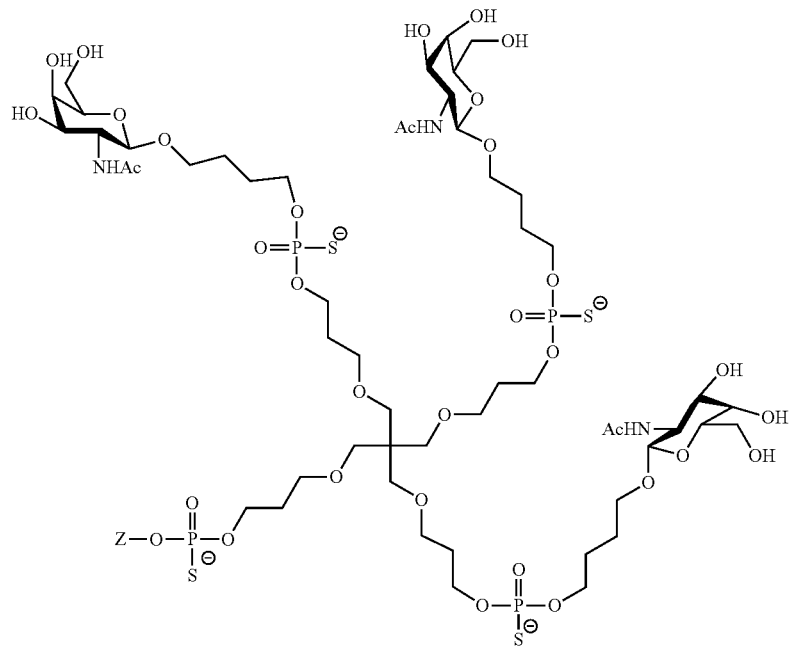
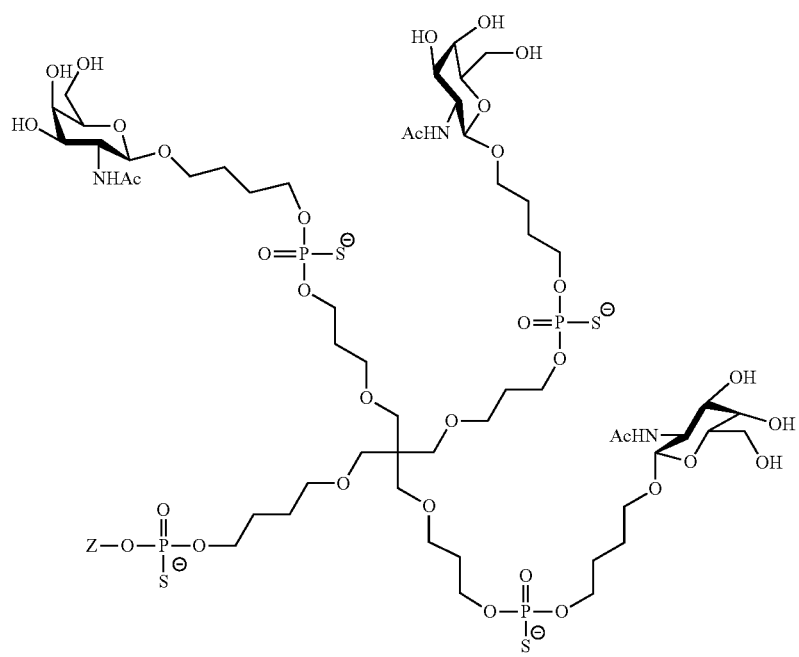

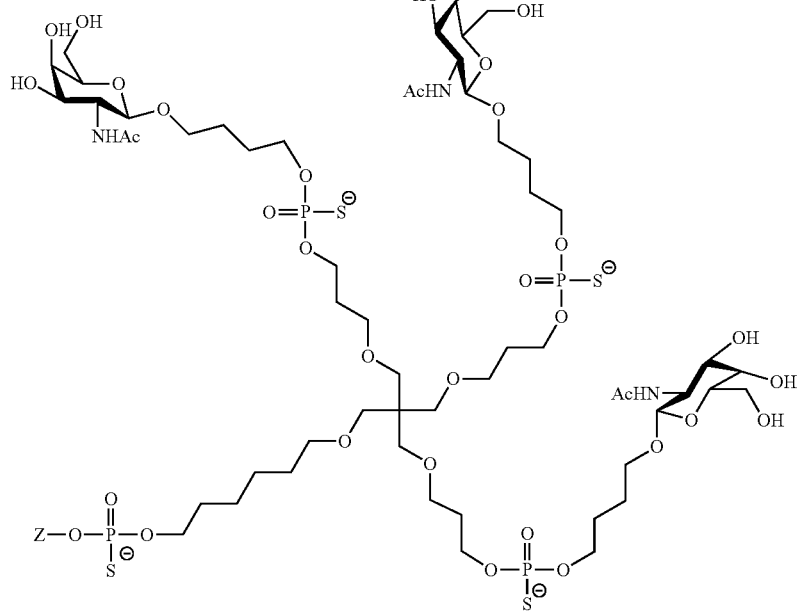
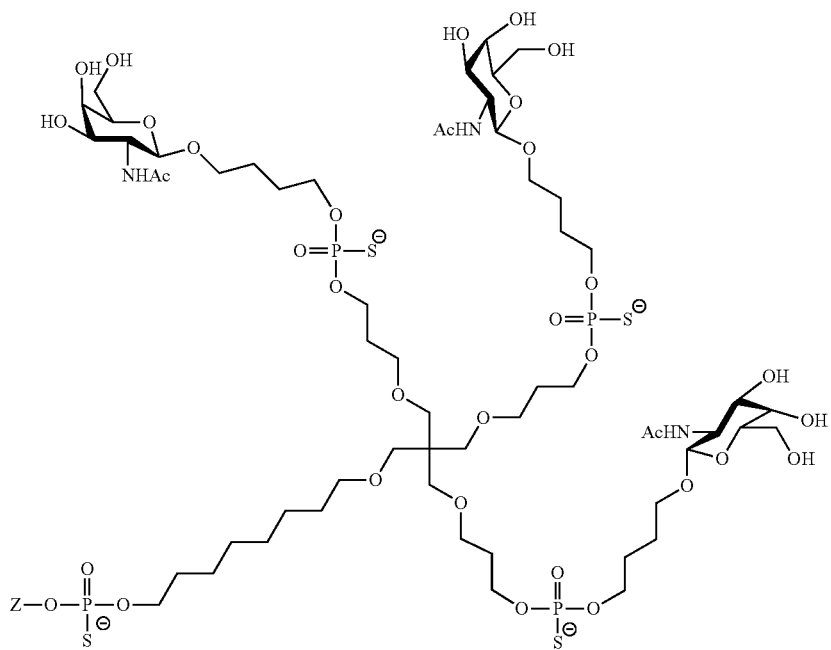

-continued
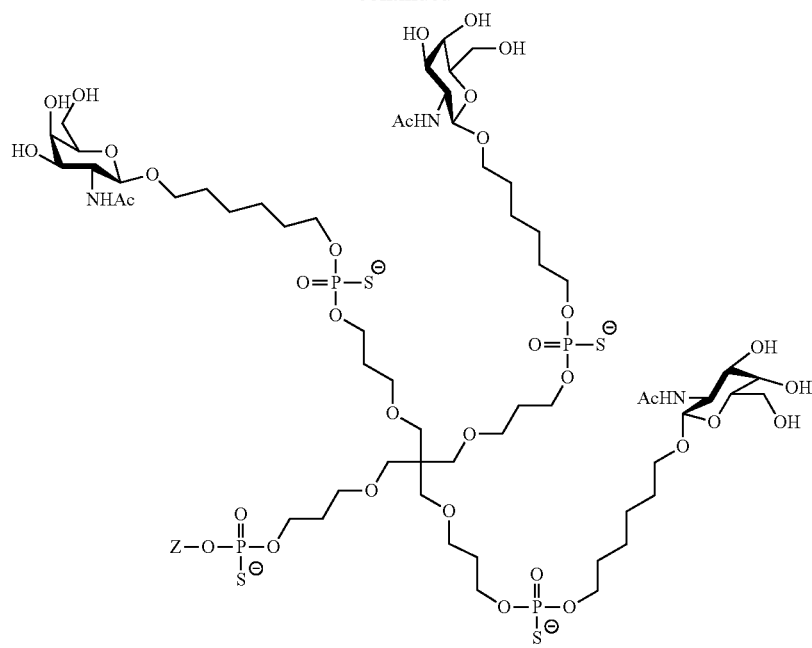
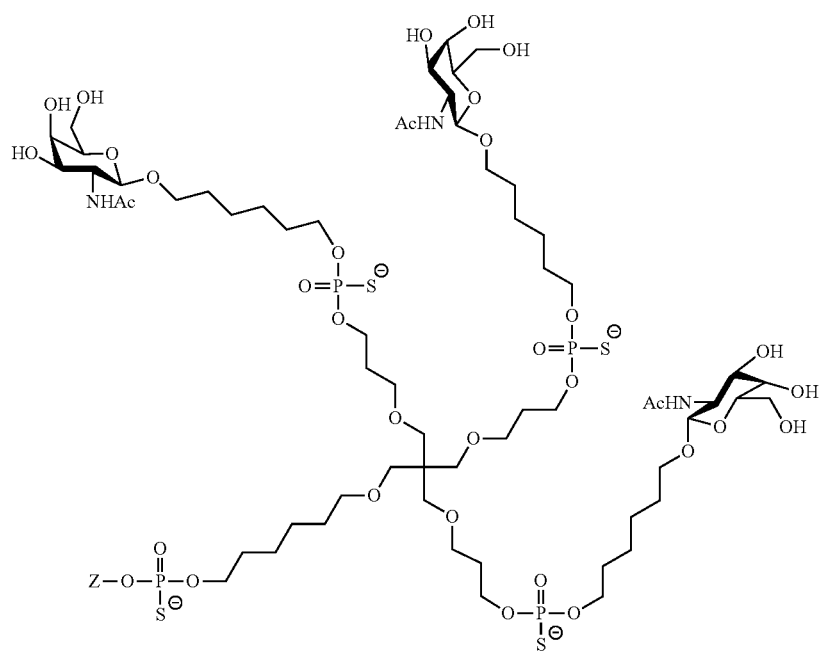

-continued

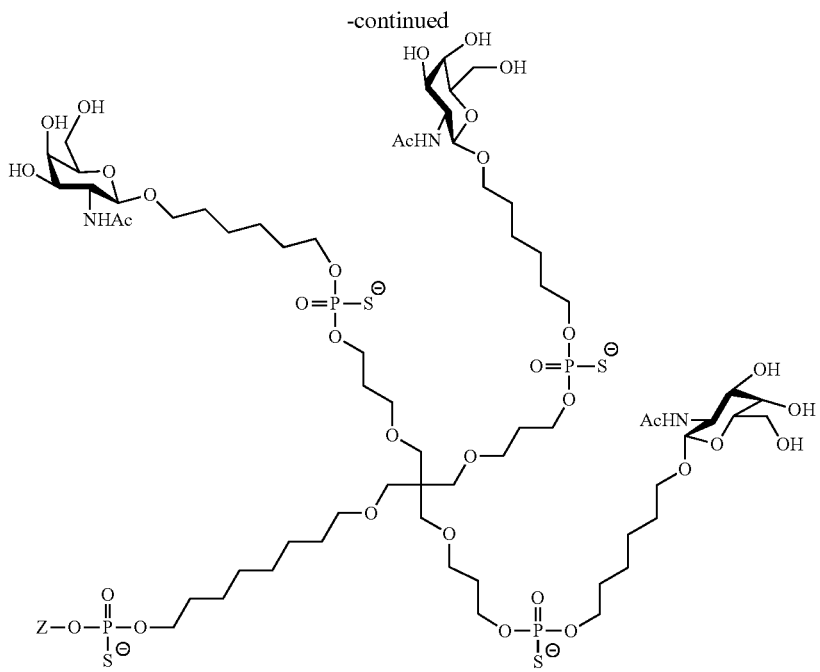

wherein Z is a nucleic acid as defined herein before.

A ligand of formula (I), (II) or (III) can be attached at the 3'-end of the first (antisense) strand and/or at any of the 3'- and/or 5'-end of the second (sense) strand. The nucleic acid can comprise more than one ligand of formula (I), (II), or (III). However, a single ligand of formula (I), (II) or (III) is preferred because a single such ligand is sufficient for efficient targeting of the nucleic acid to the target cells.

Preferably, the 5'-end of the first (antisense) strand is not attached to a ligand of formula (I), (II) or (III), since a ligand in this position can potentially interfere with the biological activity of the nucleic acid.

A nucleic acid with a single ligand of formula (I), (II) or (III) at the 5'-end of a strand is easier and therefore cheaper to synthesis than the same nucleic acid with the same ligand at the 3'-end. Preferably therefore, a single ligand of any of formulae (I), (II) or (III) is covalently attached to (conjugated with) the 5'-end of the second strand of the nucleic acid.

In one embodiment, the nucleic acid is conjugated to a ligand that comprises a lipid, and more preferably a ligand that comprises a cholesterol.

A conjugate of the invention can comprise any nucleic acid as disclosed herein conjugated to any ligand or ligands as disclosed herein.

The present invention also relates to a conjugate for inhibiting expression of a LPA gene in a cell, said conjugate comprising a nucleic acid portion, comprising the nucleic acid of any aspect of the invention, and at least one ligand portion, said nucleic acid portion comprising at least one duplex region that comprises at least a portion of a first RNA strand and at least a portion of a second RNA strand that is at least partially complementary to the first strand, wherein said first strand is at least partially complementary to at least a portion of RNA transcribed from said LPA gene, said at least one ligand portion comprising a linker moiety, preferably a serinol-derived linker moiety, and a targeting ligand for in vivo targeting of cells and being conjugated exclusively to the 3' and/or 5' ends of one or both RNA strands, wherein the 5' end of the first RNA strand is not conjugated, wherein:

(i) the second RNA strand is conjugated at the 5' end to the targeting ligand, and wherein (a) the second RNA strand is also conjugated at the 3' end to the targeting ligand and the 3' end of the first RNA strand is not conjugated; or (b) the first RNA strand is conjugated at the 3' end to the targeting ligand and the 3' end of the second RNA strand is not conjugated; or (c) both the second RNA strand and the first RNA strand are also conjugated at the 3' ends to the targeting ligand; or (ii) both the second RNA strand and the first RNA strand are conjugated at the 3' ends to the targeting ligand and the 5' end of the second RNA strand is not conjugated.

In an embodiment of the present invention, the second RNA strand (i.e. the sense strand) is conjugated at the 5' end to a targeting ligand, the first RNA strand (i.e. the antisense strand) is conjugated at the 3' end to the targeting ligand and the 3' end of the second RNA strand (i.e. the sense strand) is not conjugated, such that a conjugate with the schematic structure as shown in FIG. 40A is formed.

In an embodiment of the present invention, the second RNA strand (i.e. the sense strand) is conjugated at the 5' end to the targeting ligand, the second RNA strand (i.e. the sense strand) is also conjugated at the 3' end to the targeting ligand and the 3' end of the first RNA strand (i.e. the antisense strand) is not conjugated, such that a conjugate with the schematic structure as shown in FIG. 40B is formed.

In an embodiment of the present invention, both the second RNA strand (i.e. the sense strand) and the first RNA strand (i.e. the antisense strand) are conjugated at the 3' ends to the targeting ligand and the 5' end of the second RNA strand (i.e. the sense strand) is not conjugated, such that a conjugate with the schematic structure as shown in FIG. 40C is formed.

In an embodiment of the present invention, the second RNA strand (i.e. the sense strand) is conjugated at the 5' end to the targeting ligand and both the second RNA strand (i.e.

the sense strand) and the first RNA strand (i.e. the antisense strand) are also conjugated at the 3' ends to the targeting ligand, such that a conjugate with the schematic structure as shown in FIG. 40D is formed.

In any one of the above embodiments, ~~~~ indicates the linker which conjugates the ligand to the ends of the nucleic acid portion; the ligand may be a GalNAc moiety such as GalNAc; and the schematic structure as shown in FIG. 40E represents the nucleic acid portion.

These schematic diagrams are not intended to limit the number of nucleotides in the first or second strand, nor do the diagrams represent any kind of limitation on complementarity of the bases or any other limitation.

The ligands may be monomeric or multimeric (e.g. dimeric, trimeric, etc.).

Suitably, the ligands are monomeric, thus containing a single targeting ligand moiety, e.g. a single GalNAc moiety.

Alternatively, the ligands may be dimeric ligands wherein the ligand portions comprise two linker moieties, such as serinol-derived linker moeities or non-serinol linker moieties, each linked to a single targeting ligand moiety.

The ligands may be trimeric ligands wherein the ligand portions comprise three linker moieties, such as serinol-derived linker moeities or non-serinol linker moieties, each linked to a single targeting ligand moiety.

The two or three serinol-derived linker moieties may be linked in series e.g. as shown below:

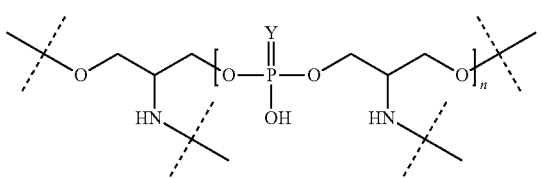

wherein n is 1 or 2 and Y is S or O.

Preferably, the ligands are monomeric.

Suitably, the conjugated RNA strands are conjugated to a targeting ligand via a linker moiety including a further linker wherein the further linker is or comprises a saturated, unbranched or branched $C_{1-15}$ alkyl chain, wherein optionally one or more carbons (for example 1, 2 or 3 carbons, suitably 1 or 2, in particular 1) is/are replaced by a heteroatom selected from O, N, $S(O)_p$, wherein p is 0, 1 or 2 (for example a $CH_2$ group is replaced with O, or with NH, or with S, or with $SO_2$ or a —$CH_3$ group at the terminus of the chain or on a branch is replaced with OH or with $NH_2$) wherein said chain is optionally substituted by one or more oxo groups (for example 1 to 3, such as 1 group).

Suitably, the linker moiety is a serinol-derived linker moiety.

More suitably, the further linker comprises a saturated, unbranched $C_{1-15}$ alkyl chain wherein one or more carbons (for example 1, 2 or 3 carbons, suitably 1 or 2, in particular 1) is/are replaced by an oxygen atom.

More suitably, the further linker comprises a PEG-chain.

More suitably, the further linker comprises a saturated, unbranched $C_{1-15}$ alkyl chain.

More suitably, the further linker comprises a saturated, unbranched $C_{1-6}$ alkyl chain.

More suitably, the further linker comprises a saturated, unbranched $C_4$ or $C_6$ alkyl chain, e.g. a $C_4$ alkyl chain.

In an embodiment, ~~~~ is a linking moiety of formula (V):

(V)

wherein n, Y and $L_1$ are defined below and the O of the phosphoro-group is attached to the terminal oligonucleoside of the RNA strands.

Thus in an embodiment, the targeting ligand portion is a linking moiety of formula (VI):

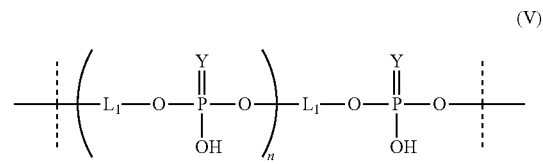

(VI)

wherein n, Y and $L_1$ are defined below and the O of the phosphoro-group is attached to the terminal oligonucleoside of the RNA strands.

Suitably, ~~~~ is a linking moiety of formula (XIV):

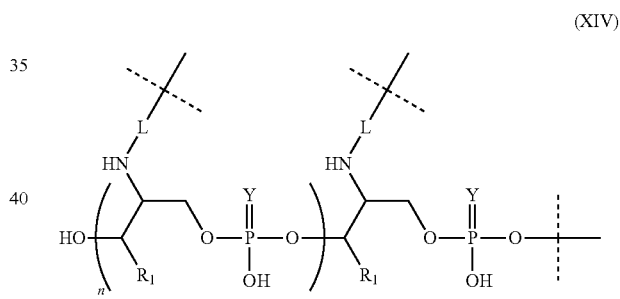

(XIV)

wherein n, Y, $R_1$ and L are defined below, L is connected to the targeting ligand e.g. GalNAc and the O of the phosphoro-group is attached to the terminal oligonucleoside of the RNA strands.

Suitably, the targeting ligand portion is a linking moiety of formula (IV):

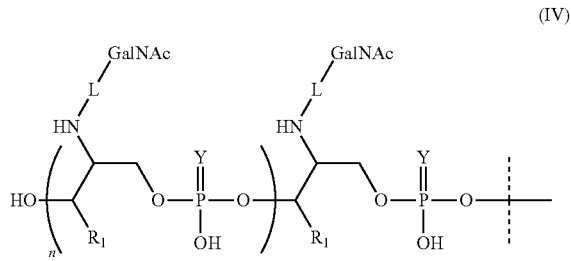

(IV)

wherein n, Y, $R_1$ and L are defined below and the O of the phosphoro-group is attached to the terminal oligonucleoside of the RNA strands.

Suitably, ~~~ is a linking moiety of formula (VII):

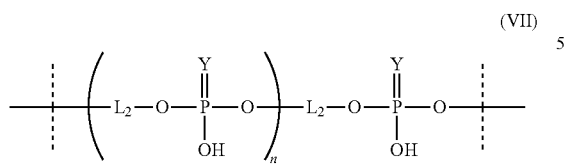
(VII)

wherein n, Y and $L_2$ are defined below and the O of the phosphoro-group is attached to the terminal oligonucleoside of the RNA strands.

Suitably, the targeting ligand portion is a linking moiety of formula (VIII):

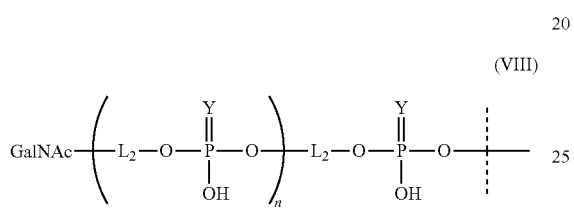
(VIII)

wherein n, Y and $L_2$ are defined below and the O of the phosphoro-group is attached to the terminal oligonucleoside of the RNA strands.

Suitably, ~~~ is a linking moiety of formula (IX):

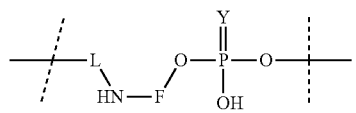
(IX)

wherein F, Y and L are defined below and the O of the phosphoro-group is attached to the terminal oligonucleoside of the RNA strands.

Suitably, the targeting ligand portion is a linking moiety of formula (IXa):

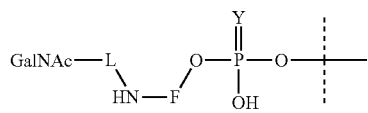
(IXa)

wherein F, Y and L are defined below and the O of the phosphoro-group is attached to the terminal oligonucleoside of the RNA strands.

Suitably, L is:

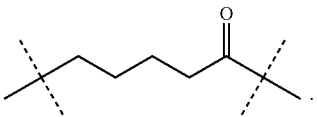

In any of the above structures, suitably the ligands are selected from GalNAc and galactose moieties, especially GalNAc moieties. Alternatively, GalNac may be replaced by another targeting ligand, e.g. a saccharide.

In an embodiment of the invention, the first RNA strand is a compound of formula (X):

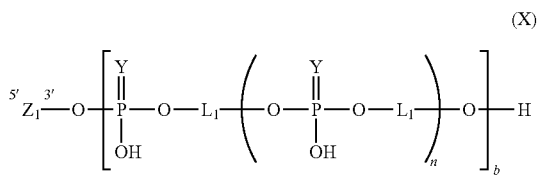
(X)

wherein b is 0 or 1; and
the second RNA strand is a compound of formula (XI):

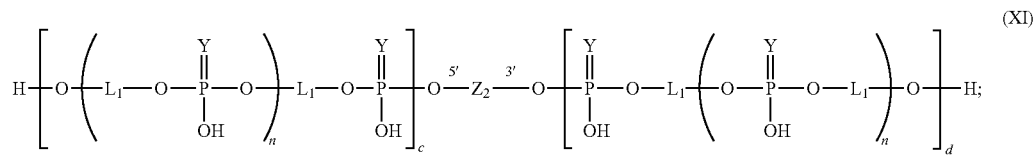
(XI)

wherein:
c and d are independently 0 or 1;
$Z_1$ and $Z_2$ are the RNA portions of the first and second RNA strands respectively;
Y is O or S;
n is 0, 1, 2 or 3; and
$L_1$ is a linker to which a ligand is attached;
and wherein b+c+d is 2 or 3.

Suitably, the first RNA strand is a compound of formula (XV)

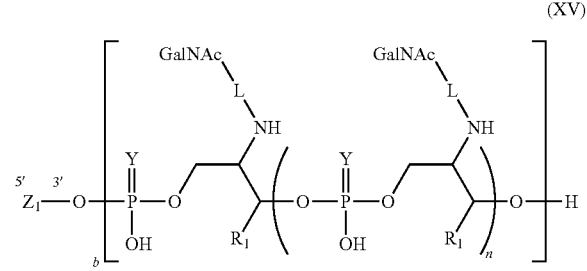
(XV)

wherein b is 0 or 1; and the second RNA strand is a compound of formula (XVI):

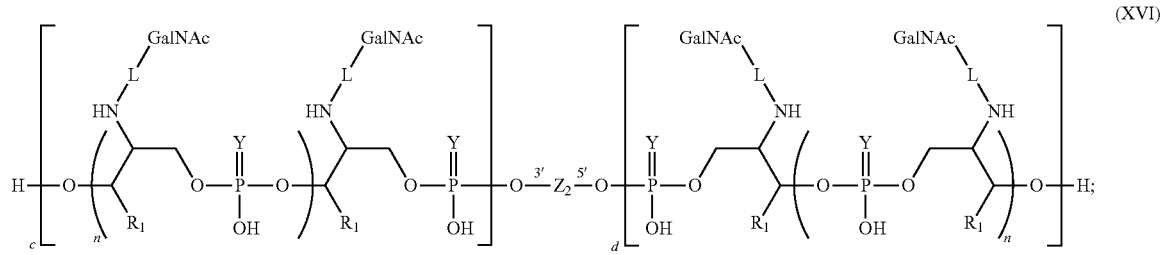

wherein c and d are independently 0 or 1;
wherein:
  $Z_1$ and $Z_2$ are the RNA portions of the first and second RNA strands respectively;
  Y is O or S;
  $R_1$ is H or methyl;
  n is 0, 1, 2 or 3; and
  L is the same or different in formulae (XV) and (XVId is selected from the group consisting of:
    —$(CH_2)_r$—C(O)—, wherein r=2-12;
    —$(CH_2$—$CH_2$—$O)_s$—$CH_2$—C(O)—, wherein s=1-5;
    —$(CH_2)_t$—CO—NH—$(CH_2)_t$—NH—C(O)—, wherein t is independently 1-5;
    —$(CH_2)_u$—CO—NH—$(CH_2)_u$—C(O)—, wherein u is independently 1-5; and
    —$(CH_2)_v$—NH—C(O)—, wherein v is 2-12; and
  wherein the terminal C(O) (if present) is attached to the NH group;
and wherein b+c+d is 2 or 3.

Suitably, the first RNA strand is a compound of formula (XII):

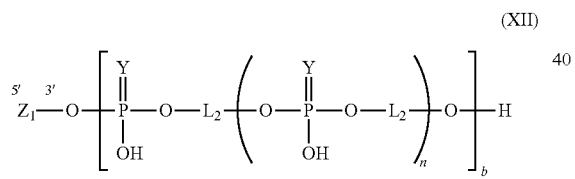

wherein b is 0 or 1; and
the second RNA strand is a compound of formula (XIII):

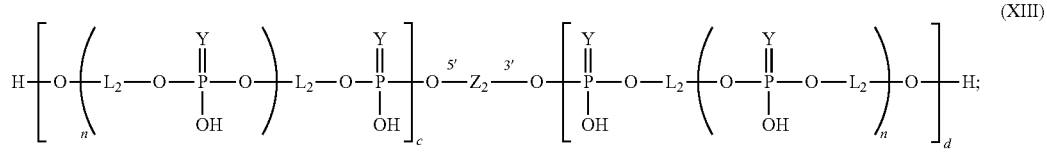

wherein:
  c and d are independently 0 or 1;
  $Z_1$ and $Z_2$ are the RNA portions of the first and second RNA strands respectively;
  Y is O or S;
  n is 0, 1, 2 or 3; and
  $L_2$ is the same or different in formulae (XII) and (XIII) and is the same or different in moieties bracketed by b, c and d, and is selected from the group consisting of:

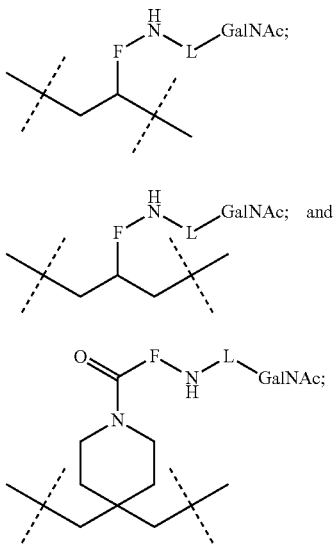

n is 0 and $L_2$ is:

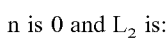

and the terminal OH group is absent such that the following moiety is formed:

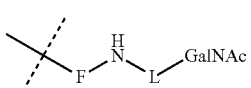

wherein
F is a saturated branched or unbranched (such as unbranched) $C_{1-8}$alkyl (e.g. $C_{1-6}$alkyl) chain wherein one of the carbon atoms is optionally replaced with an oxygen atom provided that said oxygen atom is separated from another heteroatom (e.g. an O or N atom) by at least 2 carbon atoms;

L is the same or different in formulae (I) and (II) and is selected from the group consisting of:
- —(CH$_2$)$_r$—C(O)—, wherein r=2-12;
- —(CH$_2$—CH$_2$—O)$_s$—CH$_2$—C(O)—, wherein s=1-5;
- —(CH$_2$)$_t$—CO—NH—(CH$_2$)$_t$—NH—C(O)—, wherein t is independently 1-5;
- —(CH$_2$)$_u$—CO—NH—(CH$_2$)$_u$—C(O)—, wherein u is independently 1-5; and
- —(CH$_2$)$_v$—NH—C(O)—, wherein v is 2-12; and wherein the terminal C(O) (if present) is attached to the NH group;

and wherein b+c+d is 2 or 3.

In any one of the above formulae where GalNAc is present, the GalNAc may be substituted for any other targeting ligand, such as those mentioned herein.

Suitably, b is 0, c is 1 and d is 1; b is 1, c is 0 and d is 1; b is 1, c is 1 and d is 0; or b is 1, c is 1 and d is 1.

More suitably, b is 0, c is 1 and d is 1; b is 1, c is 0 and d is 1; or b is 1, c is 1 and d is 1.

Most suitably, b is 0, c is 1 and d is 1.

In one embodiment, Y is O. In another embodiment, Y is S.

In one embodiment, R$_1$ is H or methyl. In one embodiment, R$_1$ is H. In another embodiment, R$_1$ is methyl.

In one embodiment, n is 0, 1, 2 or 3. Suitably, n is 0.

In one embodiment, L is selected from the group consisting of:
- —(CH$_2$)$_r$—C(O)—, wherein r=2-12;
- —(CH$_2$—CH$_2$—O)$_s$—CH$_2$—C(O)—, wherein s=1-5;
- —(CH$_2$)$_t$—CO—NH—(CH$_2$)$_t$—NH—C(O)—, wherein t is independently 1-5;
- —(CH$_2$)$_u$—CO—NH—(CH$_2$)$_u$—C(O)—, wherein u is independently 1-5; and
- —(CH$_2$)$_v$—NH—C(O)—, wherein v is 2-12;

wherein the terminal C(O) is attached to the NH group.

Suitably, L is —(CH$_2$)$_r$—C(O)—, wherein r=2-12. Suitably, r=2-6. More suitably, r=4 or 6 e.g. 4.

Suitably, L is:

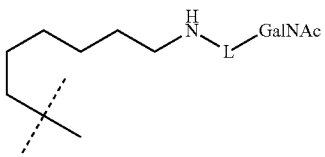

Example F moieties include (CH$_2$)$_{1-6}$ e.g. (CH$_2$)$_{1-4}$ e.g. CH$_2$, (CH$_2$)$_4$, (CH$_2$)$_5$ or (CH$_2$)$_6$, or CH$_2$O(CH$_2$)$_{2-3}$, e.g. CH$_2$O(CH$_2$)CH$_3$.

Suitably, L$_2$ is:

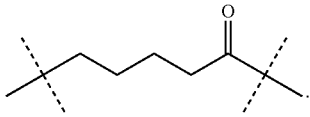

Suitably, L$_2$ is:

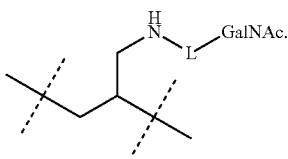

Suitably, L$_2$ is:

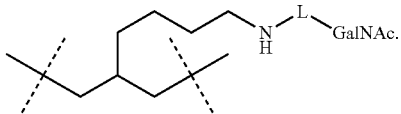

Suitably, L$_2$ is:

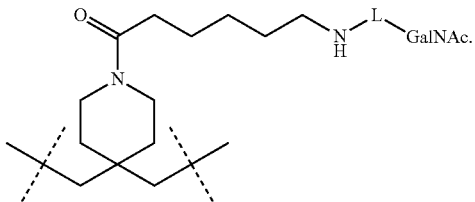

Suitably, n is 0 and L$_2$ is:

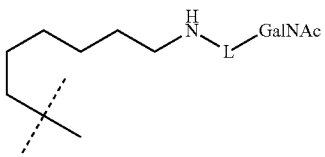

and the terminal OH group is absent such that the following moiety is formed:

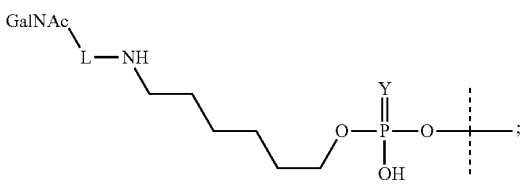

wherein Y is as defined elsewhere herein.

Within the moiety bracketed by b, c and d, L$_2$ is typically the same. Between moieties bracketed by b, c and d, L$_2$ may be the same or different. In an embodiment, L$_2$ in the moiety bracketed by c is the same as the L$_2$ in the moiety bracketed by d. In an embodiment, L$_2$ in the moiety bracketed by c is not the same as L$_2$ in the moiety bracketed by d. In an embodiment, the L$_2$ in the moieties bracketed by b, c and d is the same, for example when the linker moiety is a serinol-derived linker moiety.

Serinol derived linker moieties may be based on serinol in any stereochemistry i.e. derived from L-serine isomer, D-serine isomer, a racemic serine or other combination of isomers. In a preferred aspect of the invention, the serinol-GalNAc moiety (SerGN) has the following stereochemistry:

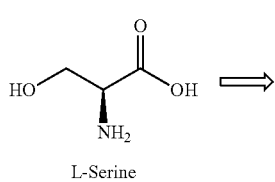

L-Serine

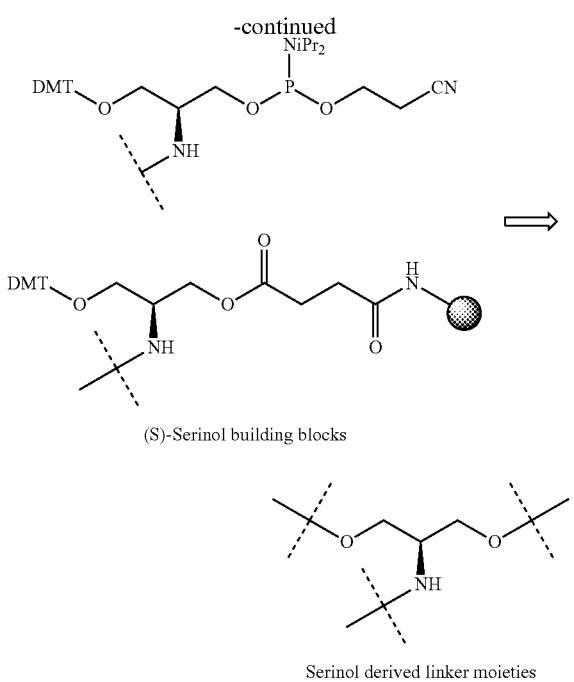

(S)-Serinol building blocks

Serinol derived linker moieties i.e. is based on an (S)-serinol-amidite or (S)-serinol succinate solid supported building block derived from L-serine isomer.

In one embodiment, the targeted cells are hepatocytes.

General Synthesis Schemes: 1

Example compounds can be synthesised according to methods described below and known to the person skilled in the art. Whilst the schemes illustrate the synthesis of particular conjugates, it will be understood that other claimed conjugates may be prepared by analogous methods. Assembly of the oligonucleotide chain and linker building blocks may, for example, be performed by solid phase synthesis applying phosphoramidite methodology. Solid phase synthesis may start from a base or modified building block loaded Icaa CPG. Phosphoramidite synthesis coupling cycle consists of 1) DMT-removal, 2) chain elongation using the required DMT-masked phosphoramidite and an activator, which may be benzylthiotetrazole (BTT), 3) capping of non-elongated oligonucleotide chains, followed by oxidation of the P(III) to P(V) either by Iodine (if phosphodiester linkage is desired) or EDITH (if phosphorothioate linkage is desired) and again capping (Cap/Ox/Cap or Cap/Thio/Cap). GalNAc conjugation may be achieved by peptide bond formation of a GalNAc-carboxylic acid building block to the prior assembled and purified oligonucleotide having the necessary number of amino modified linker building blocks attached. The necessary building blocks are either commercially available or synthesis is described below.

All final single stranded products were analysed by AEX-HPLC to prove their purity. Purity is given in % FLP (% full length product) which is the percentage of the UV-area under the assigned product signal in the UV-trace of the AEX-HPLC analysis of the final product. Identity of the respective single stranded products was proved by LC-MS analysis.

Synthesis of Synthons

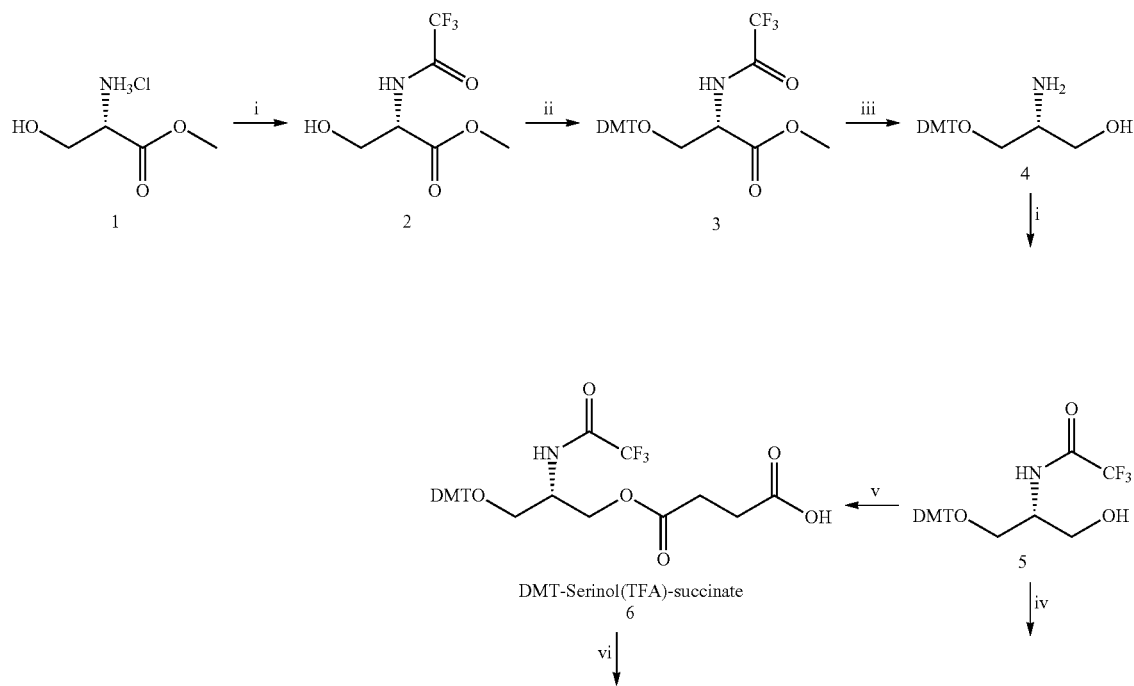

-continued

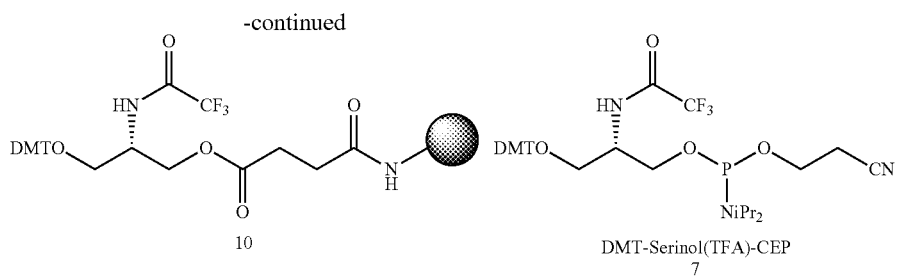

10           DMT-Serinol(TFA)-CEP
                                7 i) ethyl trifluoroacetate, NEt₃, MeOH, 0° C., 16 h, 2: 86% 5: 90%, ii) DMTCl, pyridine, 0° C., 16 h, 74%, iii) LiBH4, EtOH/THF (1/1, v/v), 0° C., 1 h, 76%, iv) 2-cyanoethyl-N,N-diisopropylchloro phosphoramidite, EtNiPr₂, CH₂Cl₂, 56%, v) succinic anhydride, DMAP, pyridine, RT, 16 h, 38%, vi) HBTU, DIEA, amino-Icaa CPG (500A), RT, 18 h, 29% (26 umol/g loading).

(S)-DMT-Serinol(TFA)-phosphoramidite 7 can be synthesised from (L)-serine methyl ester derivative 1 according to literature published methods (Hoevelmann et al. Chem. Sci., 2016, 7, 128-135).

(S)-DMT-Serinol(TFA)-succinate 6 can be made by conversion of intermediate 5 with succinic anhydride in presence of a catalyst such as DMAP.

Loading of 6 to a solid support such as a controlled pore glass (CPG) support may be achieved by peptide bond formation to a solid support such as an amino modified native CPG support (500 A) using a coupling reagent such as HBTU. The (S)-DMT-Serinol(TFA)-succinate 6 and a coupling reagent such as HBTU is dissolved in a solvent such as CH₃CN. A base, such as diisopropylethylamine, is added to the solution, and the reaction mixture is stirred for 2 min. A solid support such as a native amino-Icaa-CPG support (500 A, 3 g, amine content: 136 umol/g) is added to the reaction mixture and a suspension forms. The suspension is gently shaken at room temperature on a wrist-action shaker for 16 h then filtered, and washed with solvent such as DCM and EtOH. The support is dried under vacuum for 2 h. The unreacted amines on the support can be capped by stirring with acetic anhydride/lutidine/N-methylimidazole at room temperature. Washing of the support may be repeated as above. The solid support is dried under vacuum to yield solid support 10.

Scheme 2: Synthesis of GalNAc synthon 9

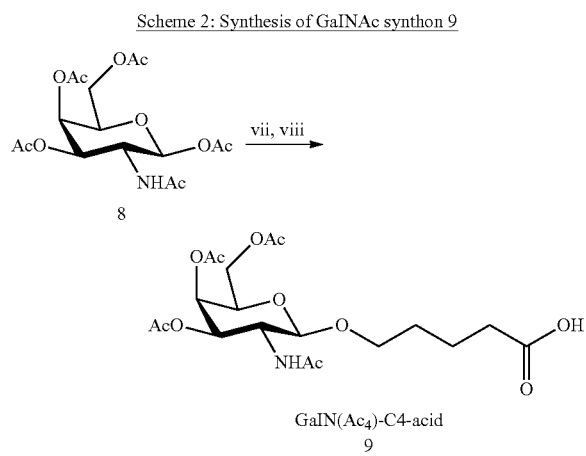

GalN(Ac₄)-C4-acid
9

(vii) TMSOTf, DCM, hexenol, viii) RuCl₃, NaIO₄, DCM, CH₃CN, H₂O, 46% over two steps.

Synthesis of the GalNAc synthon 9 can be prepared according to methods as described in Nair et al. (2014), starting from commercially available per-acetylated galactose amine 8.

Synthesis of Single Stranded Serinol-Derived GalNAc Conjugates

Scheme 3: General procedure of oligonucleotide synthesis for serinol-derived linkers

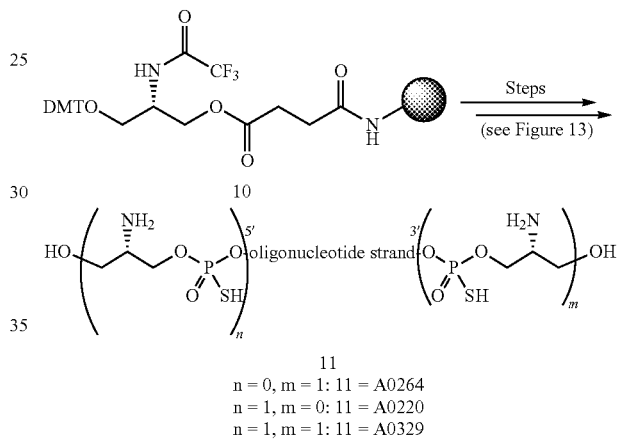

11
n = 0, m = 1: 11 = A0264
n = 1, m = 0: 11 = A0220
n = 1, m = 1: 11 = A0329

Oligonucleotide synthesis of 3' mono-GalNAc conjugated oligonucleotides (such as compound A0264) is outlined in FIG. 13 and summarised in Scheme 3. Synthesis is commenced using (S)-DMT-Serinol(TFA)-succinate-Icaa-CPG 10 as in example compound A0264. In case additional serinol building blocks are needed the (S)-DMT-serinol (TFA) amidite (7) is used in the appropriate solid phase synthesis cycle. For example, to make compound A0329, the chain assembly is finished with an additional serinol amidite coupling after the base sequence is fully assembled. Further, oligonucleotide synthesis of 5' mono-GalNAc conjugated oligonucleotides may be commenced from a solid support loaded with the appropriate nucleoside of its respected sequence. In example compound A0220 this may be 2'fA. The oligonucleotide chain is assembled according to its sequence and as appropriate, the building block (S)-DMT-serinol(TFA)-amidite (7) is used. Upon completion of chain elongation, the protective DMT group of the last coupled amidite building block is removed, as in step 1) of the phosphoramidite synthesis cycle.

Upon completion of the last synthesizer step, the single strands can be cleaved off the solid support by treatment with an amine such as 40% aq. methylamine treatment. Any remaining protecting groups are also removed in this step and methylamine treatment also liberates the serinol amino function. The crude products were then purified each by AEX-HPLC and SEC to yield the precursor oligonucleotide for further GalNAc conjugation.

Scheme 4: GalNAc conjugation synthesis of serinol-derived precursor oligonucleotides

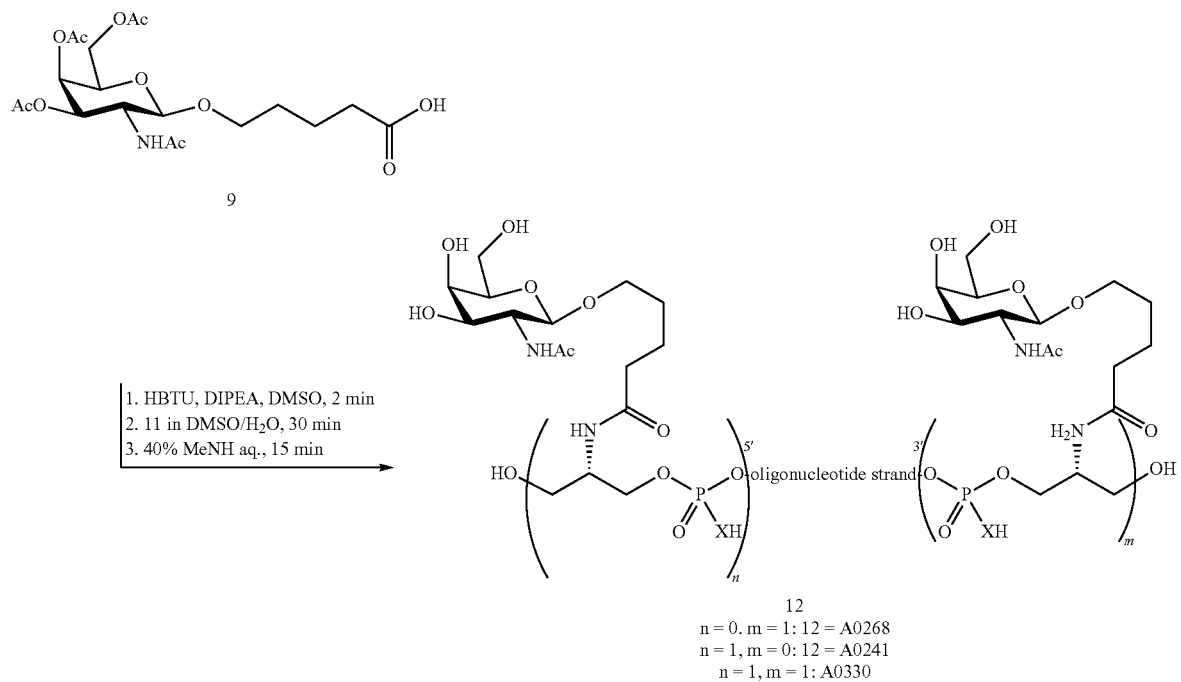

12
n = 0, m = 1: 12 = A0268
n = 1, m = 0: 12 = A0241
n = 1, m = 1: A0330

Post solid phase synthesis GalNAc-conjugation was achieved by pre-activation of the GalN(Ac4)-C4-acid (9) by a peptide coupling reagent such as HBTU. The pre-activated acid 9 was then reacted with the amino-groups in 11 (e.g. A0264) to form the intermediate GalN(Ac4)-conjugates. The acetyl groups protecting the hydroxyl groups in the GalNAc-moieties were cleaved off by methylamine treatment to yield the desired example compounds 12 (e.g. A0268), which were further purified by AEX-HPLC and SEC.

Synthesis of Single Stranded Non-Serinol-Derived GalNAc Conjugates

Amino modified building blocks other than serinol are commercially available from various suppliers and can be used instead of serinol to provide reactive amino-groups that allow for GalNAc conjugation. For example the commercially available building blocks shown in Table 6 below can be used to provide non-serinol-derived amino modified precursor oligonucleotides 14 (Scheme 5A) by using amino-modifier loaded CPG such as 10-1 to 10-3 followed by sequence assembly as described above and finally coupling of amino-modifier phosphoramidites such as 13-1, 13-2 or 13-4.

For example, to make 14 (A0653) GlyC3Am-CPG (10-2) was used in combination with GlyC3Am-Amidite 13-2. Structurally differing modifiers can be used to make 14, for example for A0651 C7Am-CPG was used in combination with C6Am-Amidite as second amino modification. In a similar fashion commercially available amino-modifier loaded CPG 10-5 and amino-modified phosphoramidite 13-5 can be used to synthesise amino-modified precursor molecules 14 (A0655).

TABLE 6

Commercially available building blocks

C3Am-CPG (10-1) is:

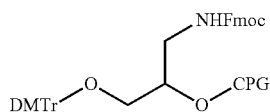

GlyC3Am-CPG (10-2) is:

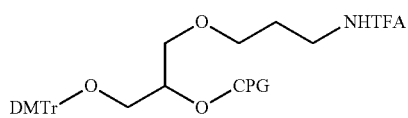

C7Am-CPG (10-3) is:

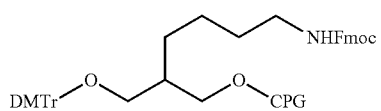

PipAm-CPG (10-5) is:

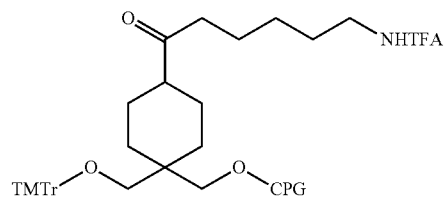

TABLE 6-continued

Commercially available building blocks

C3Am-Phos (13-1) is:

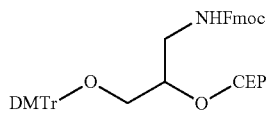

GlyC3Am-Phos (13-2) is:

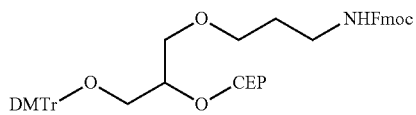

C6Am-Phos- (13-4) is:

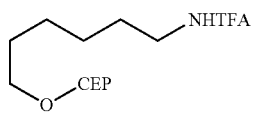

PipAm-Phos (13-5) is:

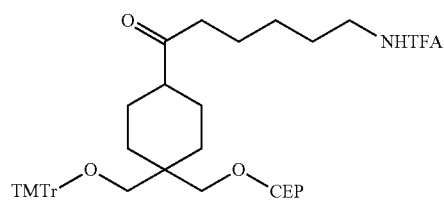

Scheme 5: General procedure for oligonucleotide synthesis

A)

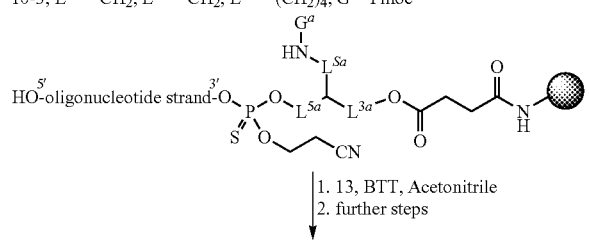

10-1, 10-2, 10-3
10-1, $L^{5a} = CH_2$, $L^{3a}$ absent, $L^{Sa} = CH2$, G = Fmoc
10-2, $L^{5a} = CH_2$, $L^{3a}$ absent, $L^{Sa} = CH_2O(CH_2)_3$, G = TFA
10-3, $L^{5a} = CH_2$, $L^{3a} = CH_2$, $L^{Sa} = (CH_2)_4$, G = Fmoc

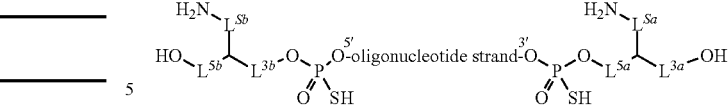

1. 13, BTT, Acetonitrile
2. further steps

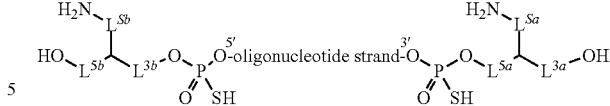

14
A0653: $L^{5a}$, $L^{5b} = CH_2$, $L^{3a}$, $L^{3b}$ absent, $L^{Sa}$, $L^{Sb} = CH_2O(CH_2)_3$
A0563: $L^{5a}$, $L^{5b} = CH_2$, $L^{3a}$, $L^{3b}$ absent, $L^{Sa}$, $L^{Sb} = CH_2$ or

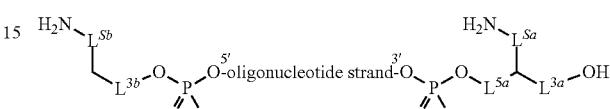

14
A0561: $L^{5a} = CH_2$, $L^{3a}$, $L^{3b}$ absent, $L^{Sa} = CH_2O(CH_2)_3$, $L^{Sb} = (CH_2)_5$
A0651: $L^{5a}$, $L^{3a} = CH_2$, $L^{3b}$ absent, $L^{Sa} = (CH_2)_4$, $L^{Sb} = (CH_2)_5$

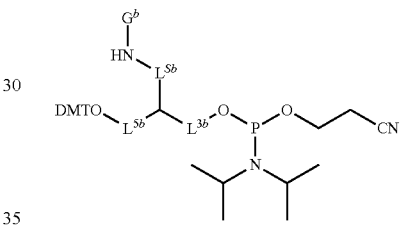

13-1, 13-2
13-1, $L^{5b} = CH_2$, $L^{3b}$ absent, $L^{SCb} = CH2$, G = Fmoc
13-2, $L^{5b} = CH_2$, $L^{3b}$ absent, $L^{SCb} = CH_2O(CH_2)_3$, G = TFA

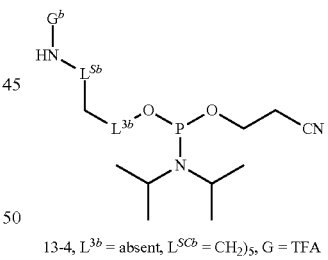

13-4, $L^{3b}$ absent, $L^{SCb} = (CH_2)_5$, G = TFA

B)

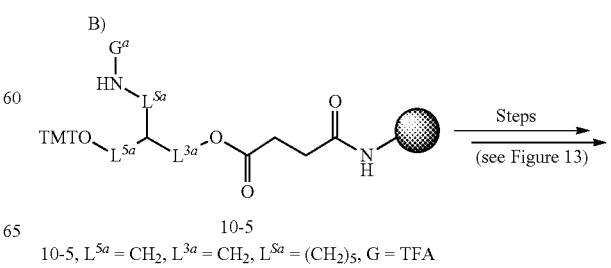

10-5
10-5, $L^{5a} = CH_2$, $L^{3a} = CH_2$, $L^{Sa} = (CH_2)_5$, G = TFA

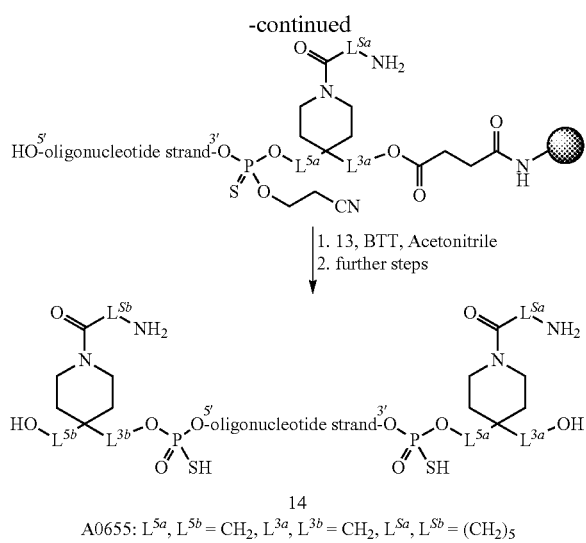
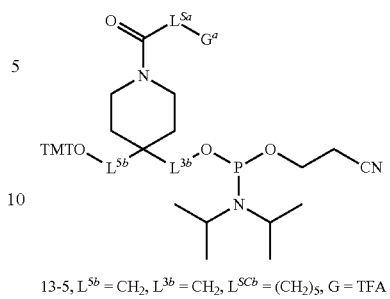
13-5, $L^{5b} = CH_2$, $L^{3b} = CH_2$, $L^{SCb} = (CH_2)_5$, G = TFA
The resulting precursor oligonucleotides 14 can then be conjugated with GalN(Ac4)-C4-acid (9) to yield the desired example compounds 15 (Scheme 6).
Scheme 6: GalNAc conjugation synthesis of precursor oligonucleotides
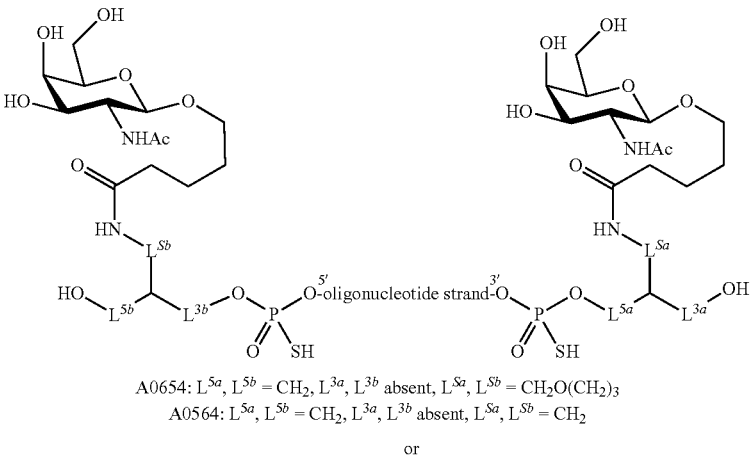
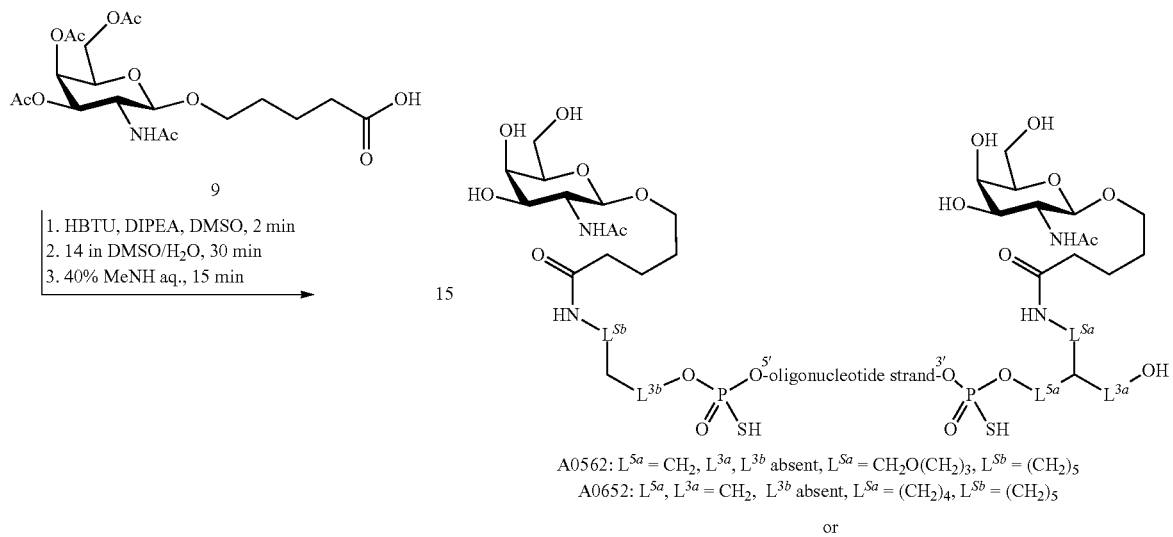

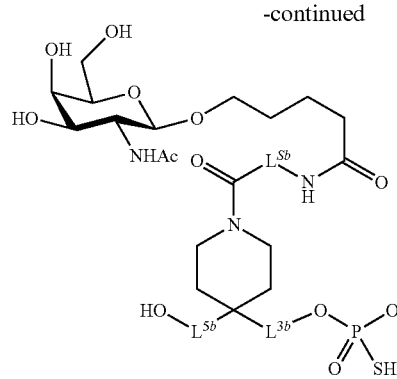
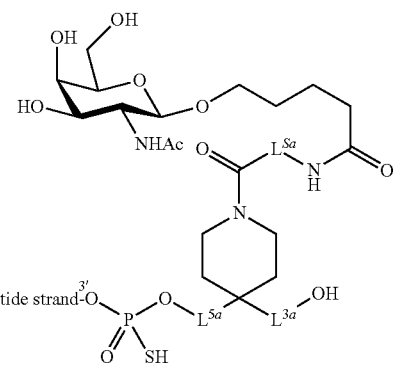

A0656: $L^{5a}, L^{5b} = CH_2, L^{3a}, L^{3b} = CH_2, L^{Sa}, L^{Sb} = (CH_2)_5$

Synthesis of the Single Stranded Tri-Antennary GalNAc Conjugates in Reference Conjugates 3-4

Oligonucleotides synthesis of tri-antennary GalNAc-cluster conjugated siRNA is outlined in FIG. 14. Oligonucleotide chain assembly is commenced using base loaded support e.g. 5'DMT-2'FdA(bz)-succinate-Icaa-CPG as in example compound A0006. Phosphoramidite synthesis coupling cycle consisting of 1) DMT-removal, 2) chain elongation using the required DMT-masked phosphoramidite, 3) capping of non-elongated oligonucleotide chains, followed by oxidation of the P(III) to P(V) either by Iodine or EDITH (if phosphorothioate linkage is desired) and again capping (Cap/Ox/Cap or Cap/Thio/Cap) is repeated until full length of the product is reached. For the on column conjugation of a trivalent tri-antennary GalNAc cluster the same synthesis cycle was applied with using the necessary trivalent branching amidite C4XLT-phos followed by another round of the synthesis cycle using the GalNAc amidite ST23-phos. Upon completion of this last synthesizer step, the oligonucleotide was cleaved from the solid support and additional protecting groups may be removed by methylamine treatment. The crude products were then purified each by AEX-HPLC and SEC.

General Procedure of Double Strand Formation

In order to obtain the double stranded conjugates, individual single strands are dissolved in a concentration of 60 OD/mL in H₂O. Both individual oligonucleotide solutions can be added together to a reaction vessel. For reaction monitoring a titration can be performed. The first strand is added in 25% excess over the second strand as determined by UV-absorption at 260 nm. The reaction mixture is heated e.g. to 80° C. for 5 min and then slowly cooled to RT. Double strand formation may be monitored by ion pairing reverse phase HPLC. From the UV-area of the residual single strand the needed amount of the second strand can be calculated and added to the reaction mixture. The reaction is heated e.g. to 80° C. again and slowly cooled to RT. This procedure can be repeated until less than 10% of residual single strand is detected.

The above process (including Schemes 1-6 and FIGS. 13 and 14) may be easily adapted to replace GalNac with another targeting ligand e.g. a saccharide.

In any of the above aspects, instead of post solid phase synthesis conjugation it is possible to make a preformed Serinol(GN)-phosphoramidite and use this for on-column conjugation.

General Synthesis Schemes: 2

Example compounds can be synthesised according to methods described below and known to the person skilled in the art. Assembly of the oligonucleotide chain and linker building blocks may, for example, be performed by solid phase synthesis applying phosphoramidite methodology. GalNAc conjugation may be achieved by peptide bond formation of a GalNAc-carboxylic acid building block to the prior assembled and purified oligonucleotide having the necessary number of amino modified linker building blocks attached.

Scheme 1: Synthesis of DMT-serinol(TFA) linker synthons

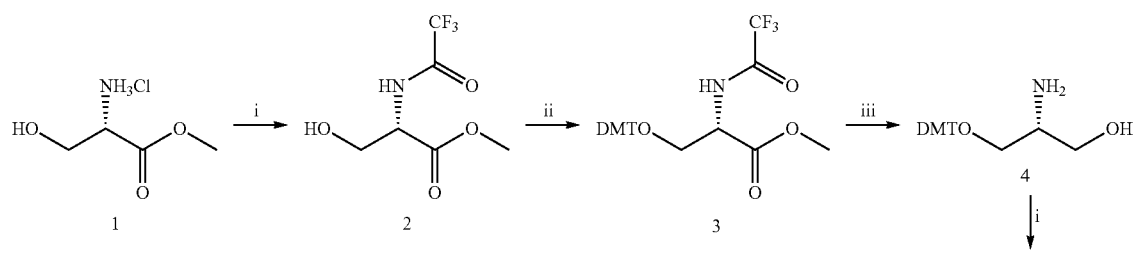

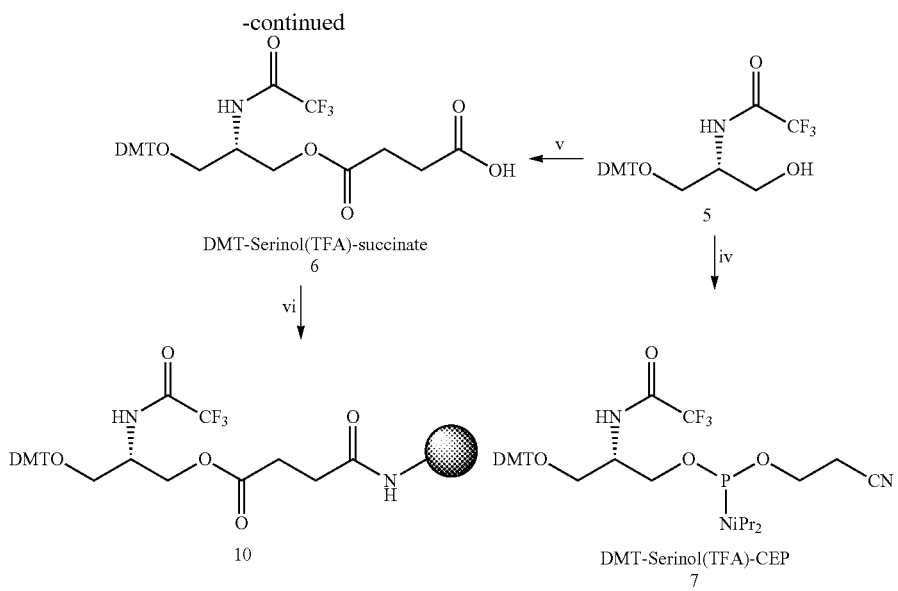

i) ethyl trifluoroacetate, NEt₃, MeOH, 0° C., 16 h, 2: 86% 5: 90%, ii) DMTCl, pyridine, 0° C., 16 h, 74%, iii) LiBH₄, EtOH/THF (1/1, v/v), 0° C., 1 h, 76%, iv) 2-cyanoethyl-N,N-diisopropylchloro phosphoramidite, EtNiPr₂, CH₂Cl₂, 56%, v) succinic anhydride, DMAP, pyridine, RT, 16 h, 38%, vi) HBTU, DIEA, amino-Icaa CPG (500A), RT, 18 h, 29%.

DMT-Serinol(TFA)-phosphoramidite 7 can be synthesised from serinol derivative 1 according to literature published methods (Hoevelmann et al. Chem. Sci., 2016, 7, 128-135).

DMT-Serinol(TFA)-succinate 6 can be made by conversion of intermediate 5 with succinic anhydride in presence of a catalyst such as DMAP.

Loading of 6 to a solid support such as a CPG support may be achieved by peptide bond formation to a solid support such as an amino modified native CPG support (500 A) using a coupling reagent such as HBTU. The DMT-Serinol (TFA)-succinate 6 and a coupling reagent such as HBTU is dissolved in a solvent such as CH₃CN. A base, such as diisopropylethylamine, is added to the solution, and the reaction mixture is stirred for 2 min. A solid support such as a native amino-Icaa-CPG support (500 A, 3 g, amine content: 136 micromol/g) is added to the reaction mixture and a suspension forms. The suspension is gently shaken at room temperature on a wrist-action shaker for 16 h then filtered and washed with solvent such as DCM and EtOH. The support is dried under vacuum for 2 h. The unreacted amines on the support can be capped by stirring with acetic anhydride/lutidine/N-methylimidazole at room temperature. Washing of the support may be repeated as above. The solid support is dried under vacuum to yield solid support 10.

Scheme 2: Synthesis of GalNAc synthon 9

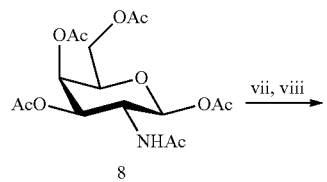

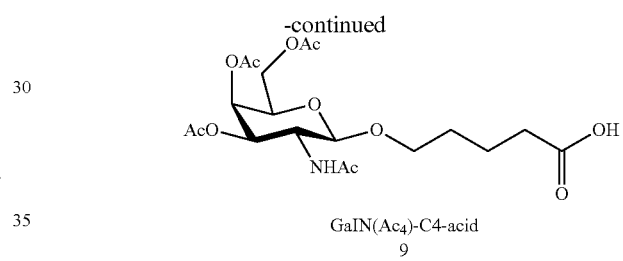

GalN(Ac₄)-C4-acid
9

(vii) TMSOTf, DCM, hexenol, viii) RuCl₃, NaIO₄, DCM, CH₃CN, H₂O, 46% over two steps.

Synthesis of the GalNAc synthon 9 can be prepared according to methods as described in Nair et al. J. Am. Chem. Soc., 2014, 136 (49), pp 16958-16961, starting from commercially available per-acetylated galactose amine 8.

Scheme 3: General procedure of oligonucleotide synthesis

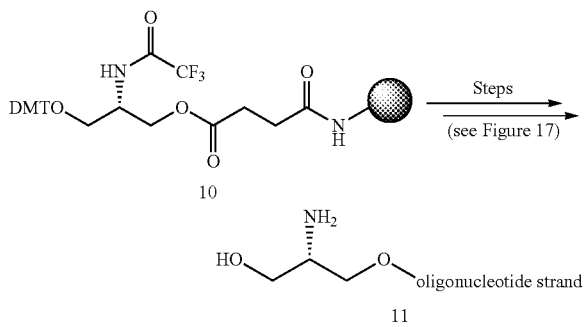

All Oligonucleotides can be synthesized on an AKTA oligopilot 10 synthesizer using standard phosphoramidite chemistry which is described in detail below.

Oligonucleotide synthesis of 3' and 5' GalNAc conjugated oligonucleotides precursors (such as compound X0385B-prec) is outlined in FIG. 17 and summarised in Scheme 3.

Synthesis is commenced using DMT-Serinol(TFA)-succinate-Icaa-CPG 10. A phosphoramidite synthesis cycle is applied until full length of the product was reached. Upon completion of chain elongation, the protective DMT group of the last coupled amidite building block can be removed in the same manner as in every individual synthesis cycle. To complete synthesis of example compound X0385B-prec (which has a serinol-derived linker moiety at the 3' and 5' ends of the second strand), the chain assembly was finished with an additional serinol amidite coupling after the base sequence was fully assembled.

Upon completion of the last synthesizer step, the single strands can be cleaved off the solid support by treatment with an amine such as 40% aq. methylamine. Any remaining protecting groups are also removed in this step and methylamine treatment also liberates the serinol amino function. The resulting crude oligonucleotide can be purified by ion exchange chromatography (Resource Q, 6 mL, GE Healthcare) on a AKTA Pure HPLC System using a gradient such as a sodium chloride gradient. Excess salt from IEX purification can be removed by SEC to yield the amino modified precursor oligonucleotide 11. Product containing fractions are pooled, desalted on a size exclusion column (Zetadex, EMP Biotech) and lyophilised.

Scheme 4: General procedure for GalNAc conjugation

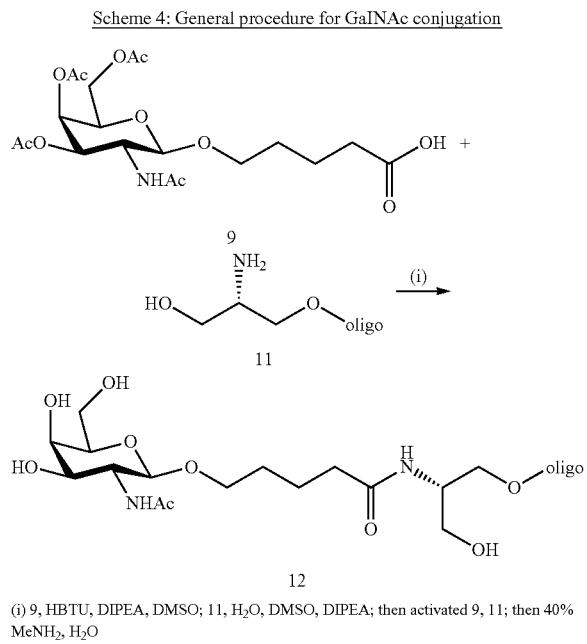

(i) 9, HBTU, DIPEA, DMSO; 11, $H_2O$, DMSO, DIPEA; then activated 9, 11; then 40% MeNH$_2$, $H_2O$ Conjugation of the GalNAc synthon 9, as described above, can be achieved by coupling 9 to the serinol-amino function of the respective oligonucleotide strand 11 using standard peptide coupling conditions known to the skilled person. For example, the respective amino-modified precursor molecule 11 is dissolved in $H_2O$ and a polar solvent such as DMSO (e.g. DMSO/$H_2O$, 2/1, v/v) is added, followed by a base such as DIPEA (e.g. 2.5% of total volume). In a separate reaction vessel pre-activation of the GalNAc synthon 9 can be performed by reacting 2 eq. (per amino function in the amino-modified precursor oligonucleotide) of the carboxylic acid component with 2 eq. of a coupling reagent such as HBTU in presence of 8 eq. of a base, such as DIPEA, in a polar solvent such as DMSO. After 2 min the activated compound 9 is added to the solution of the respective amino-modified precursor molecule 11. The reaction progress can be monitored by LCMS or AEX-HPLC. Upon completion of the conjugation reaction (e.g. 30 minutes) the crude product can be precipitated by addition of 10× iPrOH 0.1×2M NaCl and harvested by centrifugation decantation. The acetyl hydroxy-protecting groups are removed under basic conditions, such as 40% MeNH$_2$ (1 mL per 500 OD). After 15 min at RT $H_2O$ (1:10 v/v) is added and compound 12 (such as X0385B shown in FIG. 17) are isolated, purified again by anion exchange and size exclusion chromatography and then lyophilised.

General Procedure of Double Strand Formation

Individual single strands are dissolved in a concentration of 60 OD/mL in $H_2O$. Both individual oligonucleotide solutions can be added together to a reaction vessel. For reaction monitoring a titration can be performed. The first strand is added in 25% excess over the second strand as determined by UV-absorption at 260 nm. The reaction mixture is heated e.g. to 80° C. for 5 min and then slowly cooled to RT. Double strand formation may be monitored by ion pairing reverse phase HPLC. From the UV-area of the residual single strand the needed amount of the second strand can be calculated and added to the reaction mixture. The reaction is heated e.g. to 80° C. again and slowly cooled to RT. This procedure can be repeated until less than 10% of residual single strand is detected.

The above process (including Schemes 1-4 and FIG. 17) may be easily adapted to replace GalNac with another targeting ligand e.g. a saccharide.

The present invention relates to a conjugate for inhibiting expression of a LPA gene in a cell, said conjugate comprising a nucleic acid portion and ligand portions, said nucleic acid portion comprising at least one duplex region that comprises at least a portion of a first RNA strand and at least a portion of a second RNA strand that is at least partially complementary to the first strand, wherein said first strand is at least partially complementary to at least a portion of RNA transcribed from said LPA gene, said ligand portions comprising a linker moiety and a targeting ligand for in vivo targeting of cells and being conjugated exclusively to the 3' and/or 5' ends of one or both RNA strands, wherein the 5' end of the first RNA strand is not conjugated, wherein:
  (i) the second RNA strand is conjugated at the 5' end to the targeting ligand, and wherein (a) the second RNA strand is also conjugated at the 3' end to the targeting ligand and the 3' end of the first RNA strand is not conjugated; or (b) the first RNA strand is conjugated at the 3' end to the targeting ligand and the 3' end of the second RNA strand is not conjugated; or (c) both the second RNA strand and the first RNA strand are also conjugated at the 3' ends to the targeting ligand; or
  (ii) both the second RNA strand and the first RNA strand are conjugated at the 3' ends to the targeting ligand and the 5' end of the second RNA strand is not conjugated.

The linker moiety may for example be a serinol-derived linker moiety or one of the other linker types described herein.

The invention provides, as another aspect, a nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of a RNA transcribed from the LPA gene, wherein said first strand comprises a nucleotide sequence selected from the following sequences: SEQ ID NOs: 1, 3, 5, 7, 9, 11, 13, 15, 17, 19, 21, 23, 25, 27, 29, 31, 33, 35, 37, 39, 41, 43, 63, 65, 67, 69, 71 or 73, wherein the nucleic acid is conjugated to a ligand. The second strand may comprise a nucleotide sequence of SEQ ID NO: 2, 4, 6, 8, 10, 12, 14, 16, 18, 20, 22, 24, 26, 28, 30, 32, 34, 36, 38, 40, 42, 44, 64, 66, 68, 70, 72 or 74. The nucleotides of the first and/or second strand may be modified, as herein described.

Preferably, the nucleic acid comprises SEQ ID NO:5 or SEQ ID NO:9 and SEQ ID NO:6 or SEQ ID NO:10 conjugated to a ligand of formula I (as set out above), wherein the ligand is conjugated to the nucleic acid as described and wherein the first strand is modified with a 2'OMe modification on the odd numbered nucleotides, and modified with a 2'F on the even numbered nucleotides, and the second strand is modified with a 2'OMe on the even numbered nucleotides and modified with a 2'F on the odd numbered nucleotides.

More preferably, the nucleic acid comprises SEQ ID NO:5 or SEQ ID NO:9 and SEQ ID NO:6 or SEQ ID NO:10, wherein the nucleic acid is conjugated to a ligand of formula I (as set out above), and furthermore wherein the nucleic acid has a modification pattern as shown below which is an extract of Table 1 as herein provided.

```
SEQ ID   5'  auaacucuguccauuacca  3'6162717181736152736
NO: 5

SEQ ID   5'  ugguaauggacagaguuau  3'1845261846364645161
NO: 6

SEQ ID   5'  auaacucuguccauuaccg  3'6162717181736152738
NO: 9

SEQ ID   5'  cgguaauggacagaguuau  3'38452618463646451611
NO: 10
``` wherein the specific modifications are depicted by numbers
1=2'F-dU,
2=2'-F-dA,
3=2'F-dC,
4=2'F-dG,
5=2'-OMe-rU;
6=2'-OMe-rA;
7=2'-OMe-rC;
8=2'-OMe-rG.

The ligand may comprise GalNAc and FIG. 4A or FIG. 4B further illustrate examples of the present invention.

The present invention also provides pharmaceutical compositions comprising the nucleic acid or conjugated nucleic acid of the invention. The pharmaceutical compositions may be used as medicaments or as diagnostic agents, alone or in combination with other agents. For example, one or more nucleic acid conjugates of the invention can be combined with a delivery vehicle (e.g., liposomes) and/or excipients, such as carriers, diluents. Other agents such as preservatives and stabilizers can also be added. Methods for the delivery of nucleic acids are known in the art and within the knowledge of the person skilled in the art.

The nucleic acid or conjugated nucleic acid of the present invention can also be administered in combination with other therapeutic compounds, either administrated separately or simultaneously, e.g., as a combined unit dose. The invention also includes a pharmaceutical composition comprising one or more nucleic acids or conjugated nucleic acids according to the present invention in a physiologically/pharmaceutically acceptable excipient, such as a stabilizer, preservative, diluent, buffer, and the like.

Dosage levels for the medicament and pharmaceutical compositions of the invention can be determined by those skilled in the art by routine experimentation. In one embodiment, a unit dose may contain between about 0.01 mg/kg and about 100 mg/kg body weight of nucleic acid or conjugated nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Dosage levels may also be calculated via other parameters such as, e.g., body surface area.

The pharmaceutical composition may be a sterile injectable aqueous suspension or solution, or in a lyophilized form.

The pharmaceutical compositions and medicaments of the present invention may be administered to a mammalian subject in a pharmaceutically effective dose. The mammal may be selected from a human, a non-human primate, a simian or prosimian, a dog, a cat, a horse, cattle, a pig, a goat, a sheep, a mouse, a rat, a hamster, a hedgehog and a guinea pig, or other species of relevance. On this basis, the wording "LPA" or "LPA" as used herein denotes nucleic acid or protein in any of the above mentioned species, if expressed therein naturally or artificially, but preferably this wording denotes human nucleic acids or proteins.

A further aspect of the invention relates to a nucleic acid or conjugated nucleic acid of the invention or the pharmaceutical composition comprising the nucleic acid or conjugated nucleic acid of the invention for use in the treatment of a disease, disorder or syndrome. The treatment may be to prevent and reduce risk to suffer from stroke, atherosclerosis, thrombosis or cardiovascular diseases such as coronary heart disease or aortic stenosis and any other disease or pathology associated to elevated levels Lp(a)-containing particles. The invention includes a pharmaceutical composition comprising one or more nucleic acids or conjugated nucleic acids according to the present invention in a physiologically/pharmaceutically acceptable excipient, such as a stabiliser, preservative, diluent, buffer and the like.

The pharmaceutical composition may be a sterile injectable aqueous suspension or solution, or in a lyophilised form or adhered, absorbed or included to or into any other suitable galenic carrier substance such as pellets, tablets, capsules, nanoparticles, gels, tablets, beads or similar structures.

The nucleic acid described herein may be capable of inhibiting the expression of LPA. The nucleic acid described herein may be capable of partially inhibiting the expression of LPA. Inhibition may be complete, i.e. 0% compared of the expression level of LPA in the absence of the nucleic acid of the invention. Inhibition of LPA expression may be partial, i.e. it may be 15%, 20%, 30%, 40%, 50%, 60%, 70%, 75%, 80%, 85%, 90%, 95% or intermediate values of LPA expression in the absence of a nucleic acid of the invention. Inhibition may last 2 weeks, 3 weeks, 4 weeks, 5 weeks, 6 weeks, 7 weeks, 8 weeks, 10 weeks, 11 weeks, 12 weeks, 13 weeks, 14 weeks or up to 3 months, when used in a subject, such as a human patient. A nucleic acid or conjugated nucleic acid of the invention, or compositions including the same, may be for use in a regimen comprising treatments once or twice weekly, every week, every two weeks, every three weeks, every four weeks, every five weeks, every six weeks, every seven weeks, or every eight weeks, or in regimens with varying dosing frequency such as combinations of the before-mentioned intervals. The nucleic acid may be for use subcutaneously, intravenously or using any other application routes such as oral, rectal or intraperitoneal.

In cells and/or subjects treated with or receiving the nucleic acid or conjugated nucleic acid of the present invention, the LPA expression may be inhibited compared to untreated cells and/or subjects by a range from 15% up to 100% but at least about 30%, 35%, 40%, 45%, 50%, 55%, 60%, 65%, 70%, 75%, 80%, 85%, 90%, 95%, 98%, or 100% or intermediate values. The level of inhibition may allow treatment of a disease associated with LPA expression or overexpression, or may serve to further investigate the functions and physiological roles of the LPA gene product.

A further aspect of the invention relates to a nucleic acid or conjugated nucleic acid of the invention in the manufacture of a medicament for treating a disease, disorder or syndromes, such as those as listed above or additional pathologies associated with elevated levels of Lp(a), or additional therapeutic approaches where inhibition of LPA expression is desired.

Also included in the invention is a method of treating or preventing a disease, disorder or syndrome, such as those listed above, comprising administration of a pharmaceutical composition comprising a nucleic acid or conjugated nucleic acid as described herein, to an individual in need of treatment (to improve such pathologies). The nucleic acid composition may be administered in a regimen comprising treatments twice every week, once every week, every two weeks, every three weeks, every four weeks, every five weeks, every six weeks, every seven weeks, or every eight weeks or in regimens with varying dosing frequency such as combinations of the before-mentioned intervals. The nucleic acid or conjugated nucleic acid may be for use subcutaneously or intravenously or other application routes such as oral, rectal or intraperitoneal.

The nucleic acid or conjugated nucleic acid of the present invention can also be administered for use in combination with other therapeutic compounds, either administered separately or simultaneously, e.g., as a combined unit dose. A molecular conjugation to other biologically active molecular entities such as peptides, cellular or artificial ligands or small and large molecules is also possible.

The nucleic acid or conjugated nucleic acid of the present invention can be produced using routine methods in the art including chemical synthesis or expressing the nucleic acid either in vitro (e.g., run off transcription) or in vivo. For example, using solid phase chemical synthesis or using a nucleic acid-based expression vector including viral derivates or partially or completely synthetic expression systems. In one embodiment, the expression vector can be used to produce the nucleic acid of the invention in vitro, within an intermediate host organism or cell type, within an intermediate or the final organism or within the desired target cell. Methods for the production (synthesis or enzymatic transcription) of the nucleic acid described herein are known to persons skilled in the art.

The invention consists of chemical molecular entities that mediate LPA mRNA degradation by binding to the LPA gene transcripts through cellular RNA interference mechanisms. The molecular compounds invented may be used as conjugates with, but are not limited to an N-acetylgalactosamin (GalNAc) sugar moiety that ensures hepatocyte-specific cellular uptake, though specific binding to the asialoglycoprotein receptor complex (ASGPR). The invention may be linked to other different chemical structures conferring different properties as referred to in the following. The use of a chemical modification pattern of the nucleic acids confers nuclease stability in serum and makes for example subcutaneous application route feasible.

The invention is characterized by high specificity at the molecular and tissue-directed delivery level, potentially conferring a better safety profile than the currently available treatments.

The invention also provides a nucleic acid according to any aspect of the invention described herein, wherein the first RNA strand has a terminal 5' (E)-vinylphosphonate nucleotide, and the terminal 5' (E)-vinylphosphonate nucleotide is linked to the second nucleotide in the first strand by a phosphodiester linkage.

In one embodiment, the first strand may include more than 1 phosphodiester linkage.

In one embodiment, the first strand may comprise phosphodiester linkages between at least the terminal three 5' nucleotides.

In one embodiment, the first strand may comprise phosphodiester linkages between at least the terminal four 5' nucleotides.

In one embodiment, the first strand may comprise formula (XVII):

$(vp)\text{-}N_{(po)}[N_{(po)}]_n\text{-}$ (XVII)

where '(vp)-' is the 5' (E)-vinylphosphonate, 'N' is a nucleotide, 'po' is a phosphodiester linkage, and n is from 1 to (the total number of nucleotides in the first strand—2), preferably wherein n is from 1 to (the total number of nucleotides in the first strand—3), more preferably wherein n is from 1 to (the total number of nucleotides in the first strand—4).

In one embodiment, the first strand may include at least one phosphorothioate (ps) linkage.

In one embodiment, the first strand may further comprise a phosphorothioate linkage between the terminal two 3' nucleotides or phosphorothioate linkages between the terminal three 3' nucleotides.

In one embodiment, the linkages between the other nucleotides in the first strand are phosphodiester linkages.

In one embodiment, the first strand may include more than 1 phosphorothioate linkage.

In a further embodiment, the second strand may comprise a phosphorothioate linkage between the terminal two 3' nucleotides or phosphorothioate linkages between the terminal three 3' nucleotides.

In another further embodiment, the second strand may comprise a phosphorothioate linkage between the terminal two 5' nucleotides or phosphorothioate linkages between the terminal three 5' nucleotides.

In an embodiment, the terminal 5' (E)-vinylphosphonate nucleotide is an RNA nucleotide.

A terminal 5' (E)-vinylphosphonate nucleotide is a nucleotide wherein the natural phosphate group at the 5'-end has been replaced with a E-vinylphosphonate, in which the bridging 5'-oxygen atom of the terminal nucleotide of the 5' phosphorylated strand is replaced with a methenyl (—CH=) group:

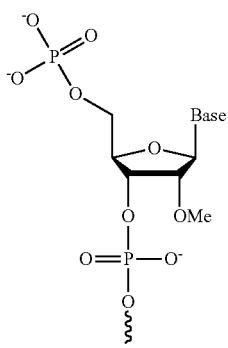

Nucleotides with a natural phosphate at the 5'-end

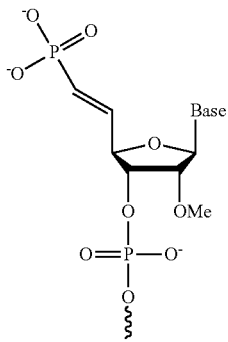

Nucleotide with a E-vinylphosphonate at the 5'-end

5' (E) vinylphosphonate is a 5' phosphate mimic. A biological mimic is a molecule that is capable of carrying out the same function as and is structurally very similar to the original molecule that is being mimicked. In the context of the present invention, 5' (E) vinylphosphonate mimics the function of a normal 5' phosphate, e.g. enabling efficient RISC loading. In addition, because of its slightly altered structure, 5' (E) vinylphosphonate is capable of stabilizing the 5'-end nucleotide by protecting it from dephosphorylation by enzymes such as phosphatases.

One aspect of the invention is a nucleic acid as disclosed herein for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene, wherein said first strand includes modified nucleotides or unmodified nucleotides at a plurality of positions in order to facilitate processing of the nucleic acid by RISC.

In one aspect "facilitate processing by RISC" means that the nucleic acid can be processed by RISC, for example any modification present will permit the nucleic acid to be processed by RISC, suitably such that siRNA activity can take place.

A nucleic acid as disclosed herein, wherein the nucleotides at positions 2 and 14 from the 5' end of the first strand are not modified with a 2' O-methyl modification, and the nucleotide on the second strand which corresponds to position 13 of the first strand is not modified with a 2'O-methyl modification.

A nucleotide on the second strand that "corresponds to" a position on the first strand is suitably the nucleotide that base pairs with that nucleotide on the first strand.

In one aspect the nucleotide on the second strand which corresponds to position 13 of the first strand is the nucleotide that forms a base pair with position 13 of the first strand.

In one aspect the nucleotide on the second strand which corresponds to position 11 of the first strand is the nucleotide that forms a base pair with position 11 of the first strand.

In one aspect the nucleotide on the second strand which corresponds to position 12 of the first strand is the nucleotide that forms a base pair with position 12 of the first strand.

This nomenclature may be applied to other positions of the second strand. For example, in a 19-mer nucleic acid which is double stranded and blunt ended, position 13 of the first strand would pair with position 7 of the second strand. Position 11 of the first strand would pair with position 9 of the second strand. This nomenclature may be applied to other positions of the second strand.

The nucleotide that corresponds to position 13 of the first strand is suitably position 13 of the second strand, counting from the 3' of the second strand, starting from the first nucleotide of the double stranded region. Likewise position 11 of the second strand is suitably the $11^{th}$ nucleotide from the 3' of the second strand, starting from the first nucleotide of the double stranded region. This nomenclature may be applied to other positions of the second strand.

In one aspect, in the case of a partially complementary first and second strand, the nucleotide on the second strand that "corresponds to" a position on the first strand may not necessarily form a base pair if that position is the position in which there is a mismatch, but the principle of the nomenclature still applies.

Preferred is a first and second strand that are fully complementary over the duplex region (ignoring any overhang regions) and there are no mismatches within the double stranded region of the nucleic acid.

Also preferred are:

A nucleic acid as disclosed herein, wherein the nucleotides at positions 2 and 14 from the 5' end of the first strand are not modified with a 2' O-methyl modification, and the nucleotide on the second strand which corresponds to position 11 of the first strand is not modified with a 2'O-methyl modification.

A nucleic acid as disclosed herein, wherein the nucleotides at positions 2 and 14 from the 5' end of the first strand are not modified with a 2' O-methyl modification, and the nucleotides on the second strand which corresponds to position 11 and 13 of the first strand are not modified with a 2' O-methyl modification.

In one aspect the nucleotide on the second strand which corresponds to position 12 of the first strand is not modified with a 2' O-methyl modification. This limitation on the nucleic acid may be seen with any other limitation described herein.

Therefore another aspect of the invention is a nucleic acid as disclosed herein, wherein the nucleotides at positions 2 and 14 from the 5' end of the first strand are not modified with a 2' O-methyl modification, and the nucleotides on the second strand which corresponds to position 11-13 of the first strand are not modified with a 2' O-methyl modification.

A nucleic acid as disclosed herein, wherein the nucleotides at positions 2 and 14 from the 5' end of the first strand are not modified with a 2' O-methyl modification, and the nucleotides on the second strand which correspond to position 11, or 13, or 11 and 13, or 11-13 of the first strand are modified with a 2' fluoro modification.

A nucleic acid as disclosed herein, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are not modified with a 2' O-methyl modification.

A nucleic acid as disclosed herein, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are modified with a 2' fluoro modification.

A nucleic acid as disclosed herein wherein greater than 50% of the nucleotides of the first and/or second strand comprise a 2' O-methyl modification, such as greater than 55%, 60%, 65%, 70%, 75%, 80%, or 85%, or more, of the first and/or second strand comprise a 2' O-methyl modification, preferably measured as a percentage of the total nucleotides of both the first and second strands.

A nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification, preferably measured as a percentage of the total nucleotides of both the first and second strands. Suitable naturally occurring modifications include, as well as 2 O' methyl, other 2' sugar modifications, in particular a 2' H modification resulting in a DNA nucleotide.

A nucleic acid as disclosed herein comprising no more than 20%, such as no more than 15% such as more than 10%, of nucleotides which have 2' modifications that are not 2' O methyl modifications on the first and/or second strand, preferably as a percentage of the total nucleotides of both the first and second strands.

A nucleic acid as disclosed herein comprising no more than 20%, (such as no more than 15% or no more than 10%) of 2' fluoro modifications on the first and/or second strand, preferably as a percentage of the total nucleotides of both strands.

A nucleic acid as disclosed herein, wherein all nucleotides are modified with a 2' O-methyl modification except positions 2 and 14 from the 5' end of the first strand and the nucleotides on the second strand which correspond to position 11, or 13, or 11 and 13, or 11-13 of the first strand. Preferably the nucleotides that are not modified with 2' O-methyl are modified with fluoro at the 2' position.

Preferred is a nucleic acid as disclosed herein wherein all nucleotides of the nucleic acid are modified at the 2' position of the sugar. Preferably these nucleotides are modified with a 2'-fluoro modification where the modification is not a 2' O-Methyl modification.

Nucleic acids of the invention may comprise one or more nucleotides modified at the 2' position with a 2' H, and therefore having a DNA nucleotide within the nucleic acid. Nucleic acids of the invention may comprise DNA nucleotides at positions 2 and/or 14 of the first strand counting from the 5' end of the first strand. Nucleic acids may comprise DNA nucleotides on the second strand which correspond to position 11, or 13, or 11 and 13, or 11-13 of the first strand.

In one aspect there is no more than one DNA per nucleic acid of the invention.

Nucleic acids of the invention may comprise one or more LNA nucleotides. Nucleic acids of the invention may comprise LNA nucleotides at positions 2 and/or 14 of the first strand counting from the 5' end of the first strand. Nucleic acids may comprise LNA on the second strand which correspond to position 11, or 13, or 11 and 13, or 11-13 of the first strand.

In one aspect the nucleic acid is modified on the first strand with alternating 2-O methyl modifications and 2 fluoro modifications, and positions 2 and 14 (starting from the 5' end) are modified with 2' fluoro. Preferably the second strand is modified with 2' fluoro modifications at nucleotides on the second strand which correspond to position 11, or 13, or 11 and 13, or 11-13 of the first strand. Preferably the second strand is modified with 2' fluoro modifications at positions 11-13 counting from the 3' end starting at the first position of the complementary (double stranded) region, and the remaining modifications are naturally occurring modifications, preferably 2' O-methyl.

In one aspect the nucleic acid of the invention comprise one or more inverted ribonucleotides, preferably an inverted adenine, using a 5'-5' linkage or a 3'-3' linkage, preferably a 3'-3' linkage at the 3' end of the second strand.

In one aspect the nucleic acid comprises one or more phosphorodithioate linkages, such as 1, 2, 3 or 4 phosphorodithioate linkages. Preferably there are up to 4 phosphorodithioate linkages, one each at the 5' and 3' ends of the first and second strands.

All the features of the nucleic acids can be combined with all other aspects of the invention disclosed herein.

In particular, preferred are nucleic acids which are SiRNA molecules wherein the nucleotides at positions 2 and 14 from the 5' end of the first strand are not modified with a 2' O-methyl modification, and the nucleic acid comprises one or more or all of:

(i) an inverted nucleotide, preferably a 3'-3' linkage at the 3' end of the second strand;
(ii) one or more phosphorodithioate linkages;
(iii) the second strand nucleotide corresponding to position 11 or 13 of the first strand is not modified with a 2' O-methyl modification, preferably wherein one or both of these positions comprise a 2' fluoro modification;
(iv) the nucleic acid comprises at least 80% of all nucleotides having a 2'-O-methyl modification;
(v) the nucleic acid comprises no more than 20% of nucleotides which have 2' fluoro modifications.

Also provided by the present invention is a nucleic acid as disclosed herein, wherein the nucleotides at positions 2 and 14 from the 5' end of the first strand and the nucleotides at positions 7 and/or 9, or 7-9 from the 5' end of the second strand are modified with a 2' fluoro modification, and at least 90% of the remaining nucleotides are 2'-O methyl modified or comprise another naturally occurring 2' modification.

Specific preferred examples, for a blunt double stranded 19 base nucleic acid, with no overhang, are:

A nucleic acid as disclosed herein, wherein the nucleotides at positions 2 and 14 from the 5' end of the first strand are not modified with a 2' O-methyl modification, and the nucleotide at position 7 from the 5' end of the second strand is not modified with a 2' O-methyl modification.

A nucleic acid as disclosed herein, wherein the nucleotides at positions 2 and 14 from the 5' end of the first strand are not modified with a 2' O-methyl modification, and the nucleotide at position 9 from the 5' end of the second strand is not modified with a 2' O-methyl modification A nucleic acid as disclosed herein, wherein the nucleotides at positions 2 and 14 from the 5' end of the first strand are not modified with a 2' O-methyl modification, and the nucleotides at position 7 and 9 from the 5' end of the second strand are not modified with a 2'O-methyl modification.

A nucleic acid as disclosed herein, wherein the nucleotides at positions 2 and 14 from the 5' end of the first strand are not modified with a 2' O-methyl modification, and the nucleotides at positions 7-9 from the 5' end of the second strand are not modified with a 2'O-methyl modification.

A nucleic acid as disclosed herein, wherein the nucleotides at positions 2 and 14 from the 5' end of the first strand are not modified with a 2' O-methyl modification, and the nucleotides at positions 7 and/or 9, or 7-9 from the 5' end of the second strand are modified with a 2' fluoro modification.

A nucleic acid as disclosed herein, wherein the nucleotides at positions 2 and 14 from the 5' end of the first strand are modified with a 2' fluoro modification, and the nucleotides at positions 7 and/or 9, or 7-9 from the 5' end of the second strand are not modified with a 2'O-methyl modification.

A nucleic acid as disclosed herein, wherein the nucleotides at positions 2 and 14 from the 5' end of the first strand are modified with a 2' fluoro modification, and the nucleotides at positions 7 and/or 9, or 7-9 from the 5' end of the second strand are modified with a 2' fluoro modification.

A nucleic acid as disclosed herein wherein greater than 50% of the nucleotides of the first and/or second strand comprise a 2' O-methyl modification, such as greater than 55%, 60%, 65%, 70%, 75%, 80%, or 85%, or more, of the first and/or second strand comprise a 2' O-methyl modification, preferably measured as a percentage of the total nucleotides of both the first and second strands.

A nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification, preferably measured as a percentage of the total nucleotides of both the first and second strands. Suitable naturally occurring modifications include, as well as 2 O' methyl, other 2' sugar modifications, in particular a 2' H modification resulting in a DNA nucleotide.

A nucleic acid as disclosed herein comprising no more than 20%, such as no more than 15% such as more than 10%, of nucleotides which have 2' modifications that are not 2' O methyl modifications on the first and/or second strand, preferably as a percentage of the total nucleotides of both the first and second strands.

A nucleic acid as disclosed herein comprising no more than 20%, (such as no more than 15% or no more than 10%) of 2' fluoro modifications on the first and/or second strand, preferably as a percentage of the total nucleotides of both strands.

A nucleic acid as disclosed herein, wherein all nucleotides are modified with a 2' O-methyl modification except positions 2 and 14 from the 5' end of the first strand and the nucleotides at positions 7 and/or 9 from the 5' end of the second strand. Preferably the nucleotides that are not modified with 2' O-methyl are modified with fluoro at the 2' position.

A nucleic acid as disclosed herein, wherein all nucleotides are modified with a 2' O-methyl modification except positions 2 and 14 from the 5' end of the first strand and the nucleotides at positions 7-9 from the 5' end of the second strand. Preferably the nucleotides that are not modified with 2' O-methyl are modified with fluoro at the 2' position.

For a nucleic acid comprising a 20 base pair duplex region, the second strand preferably does not have a 2' O-methyl group at nucleotides 8 or 9 or 10 counting from the 5' end of the duplex corresponding to positions 13, 12, and 11 of the first strand respectively.

For a nucleic acid comprising a 21 base pair duplex region, the second strand preferably does not have a 2' O-methyl group at nucleotides 9 or 10 or 11 counting from the 5' end of the duplex corresponding to positions 13, 12, and 11 of the first strand respectively.

The present invention also relates to the unmodified sequences of all modified sequences disclosed herein.

The invention will now be described with reference to the following non-limiting Figures and Examples.

FIGURES

Figure 6:
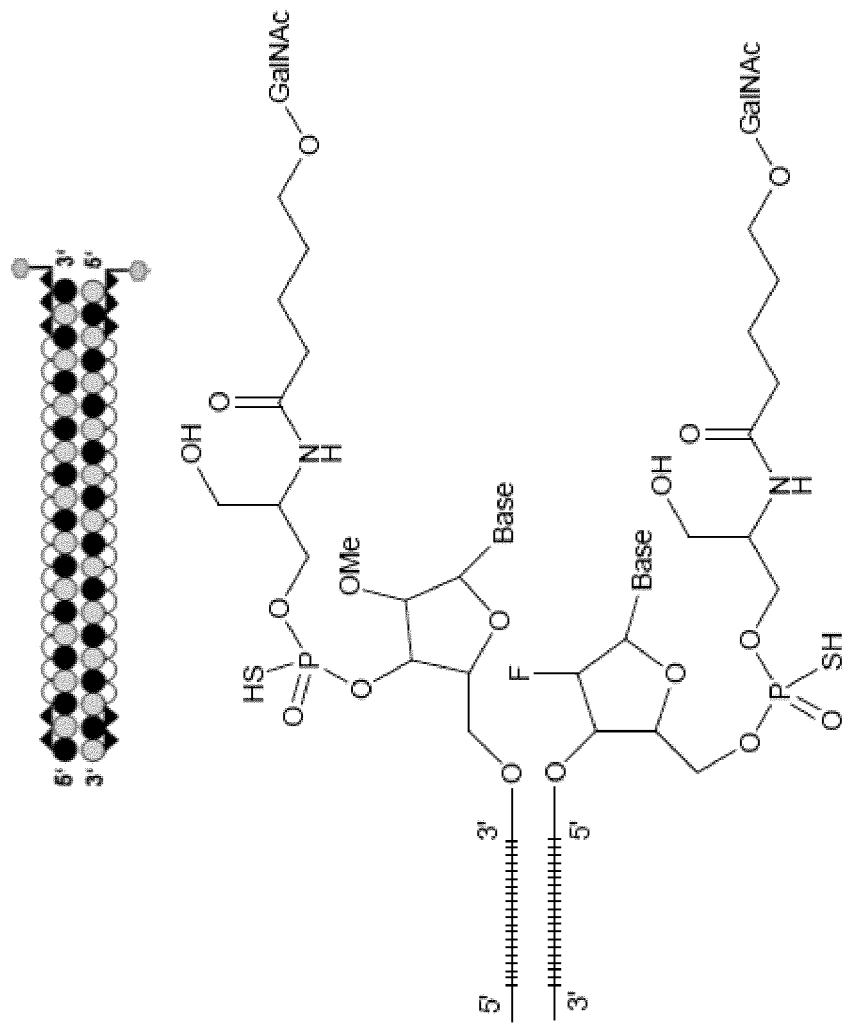
Figure 7:
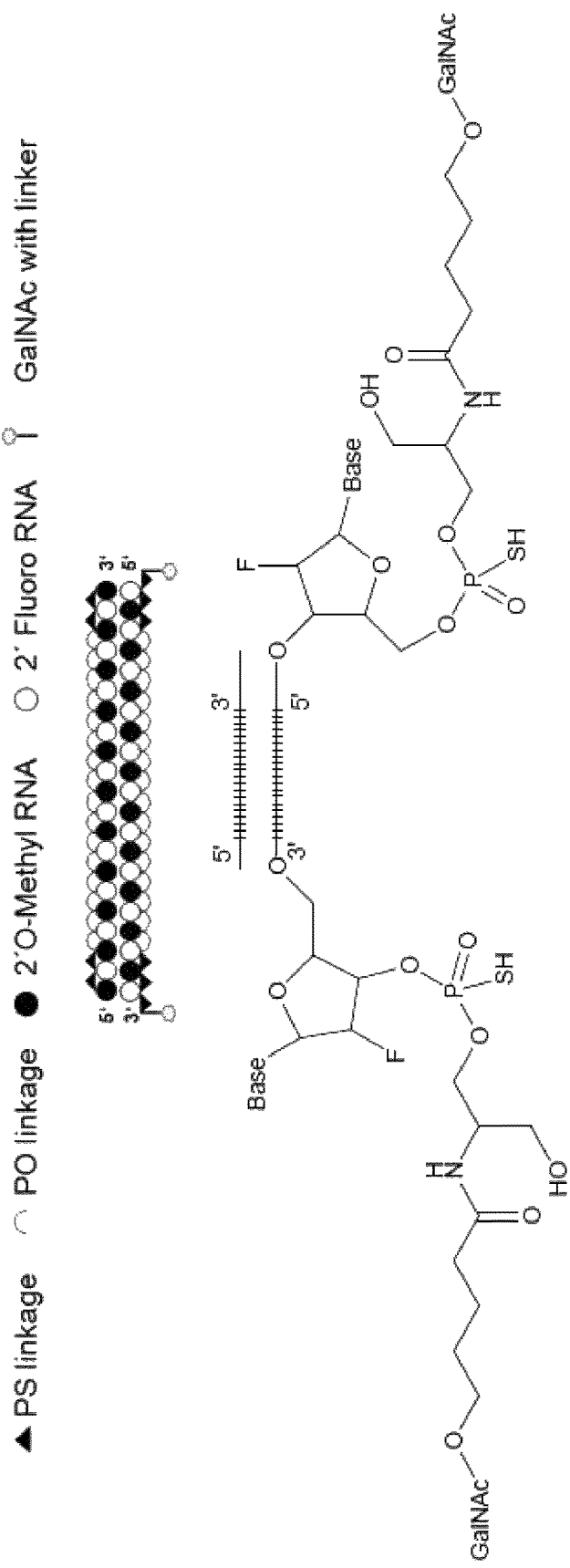
Figure 8:
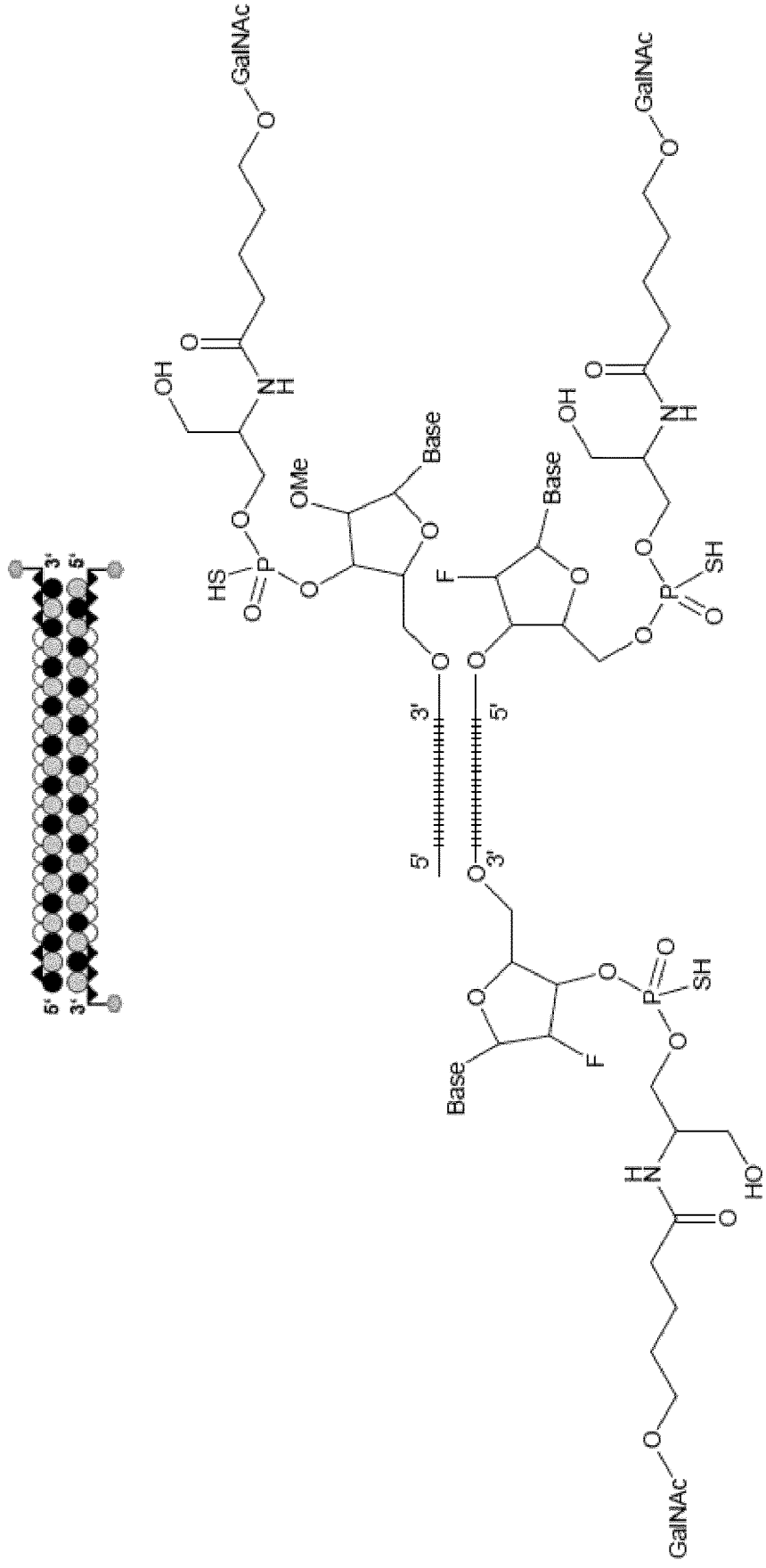
Figure 9:
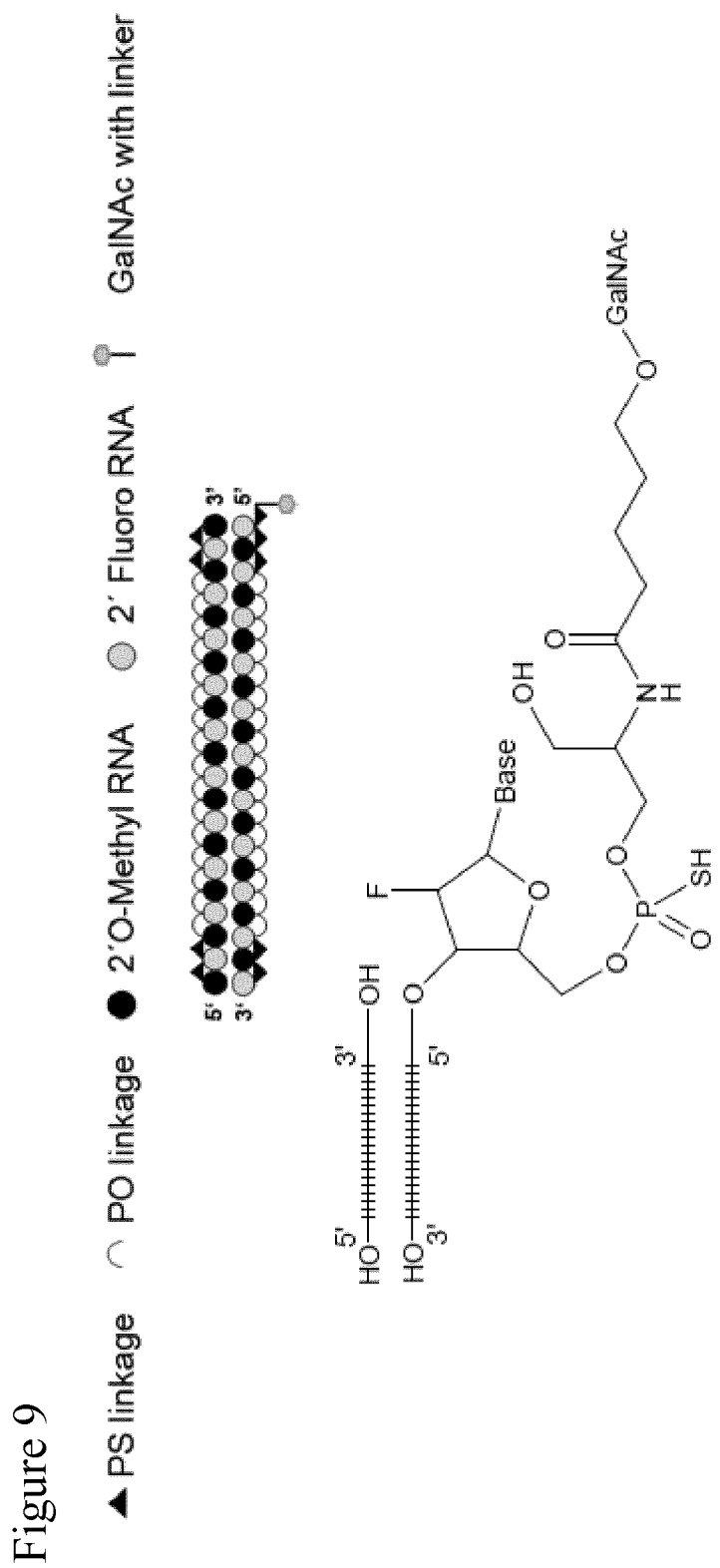
Figure 10:
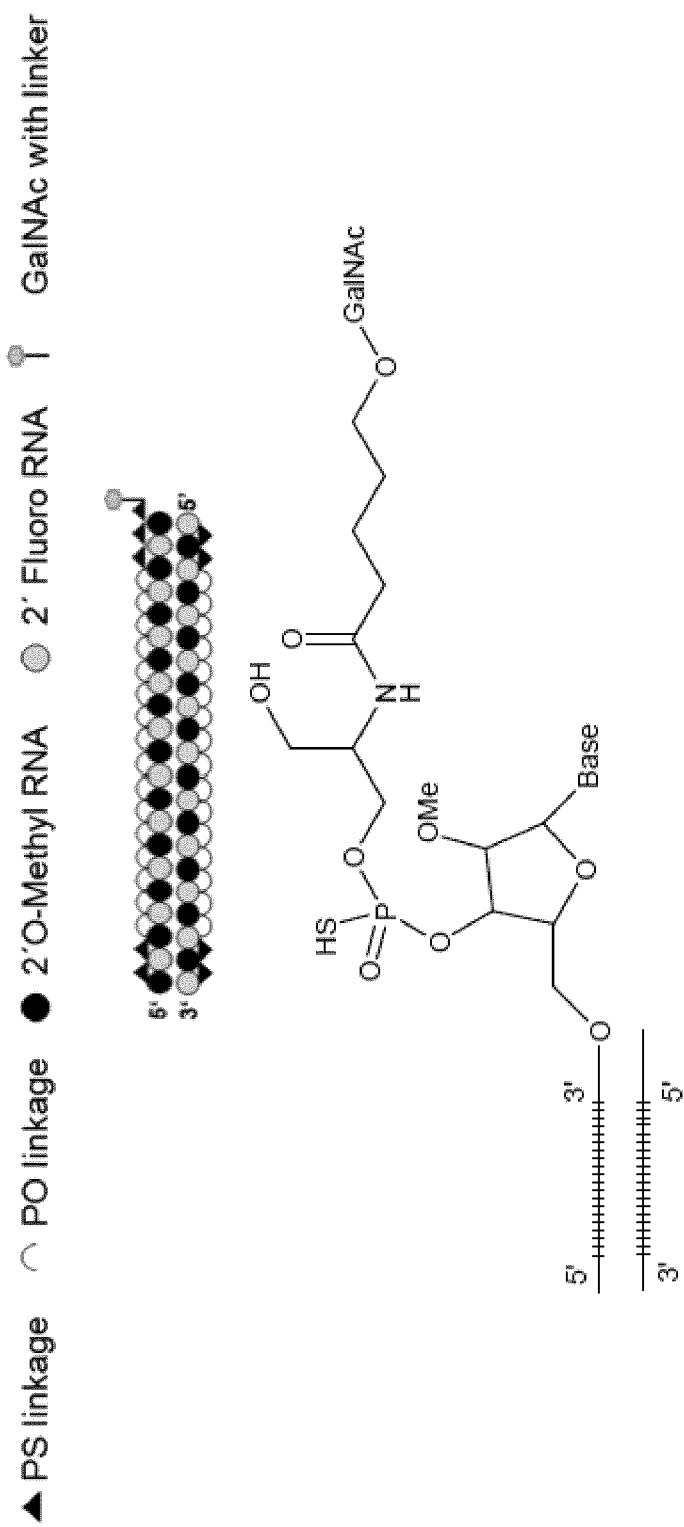
Figure 11:
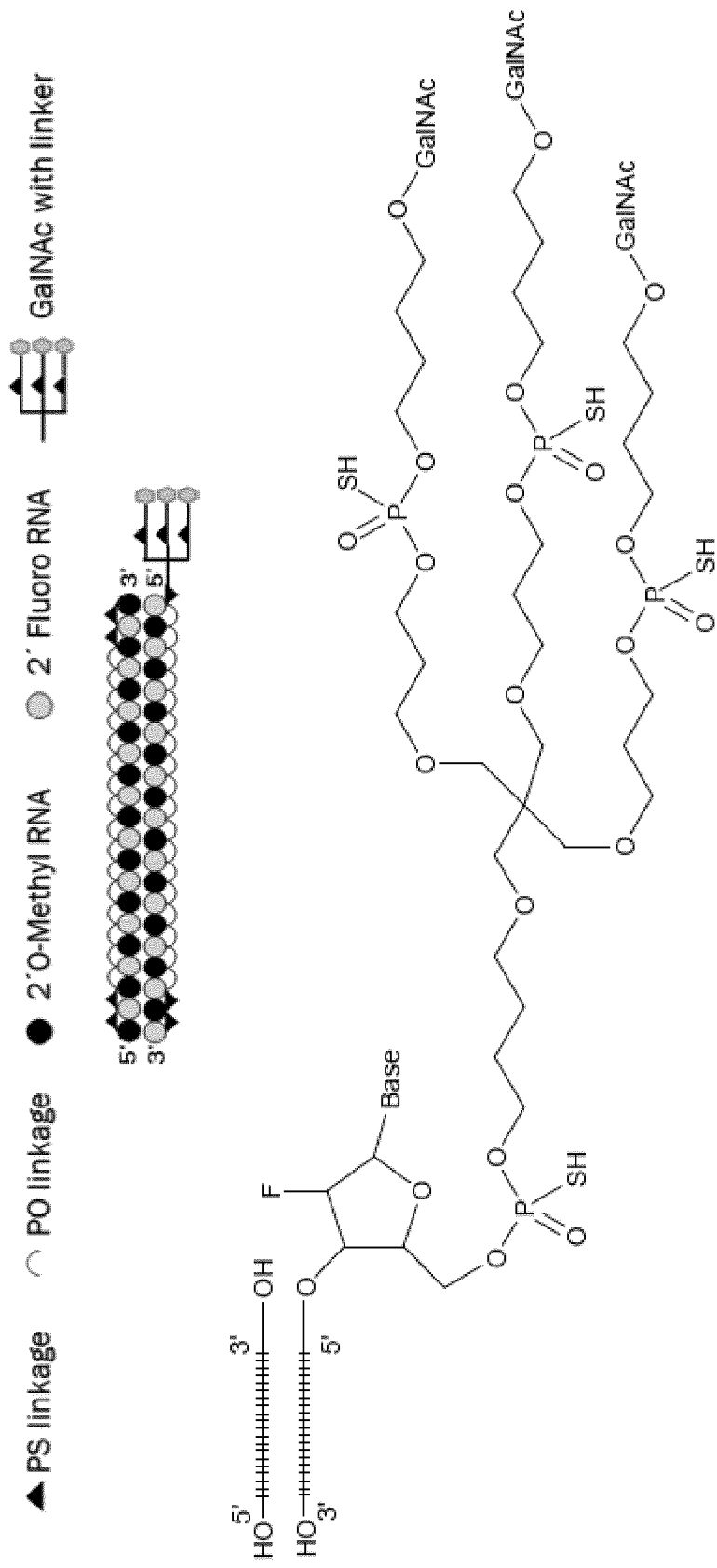
Figure 12:
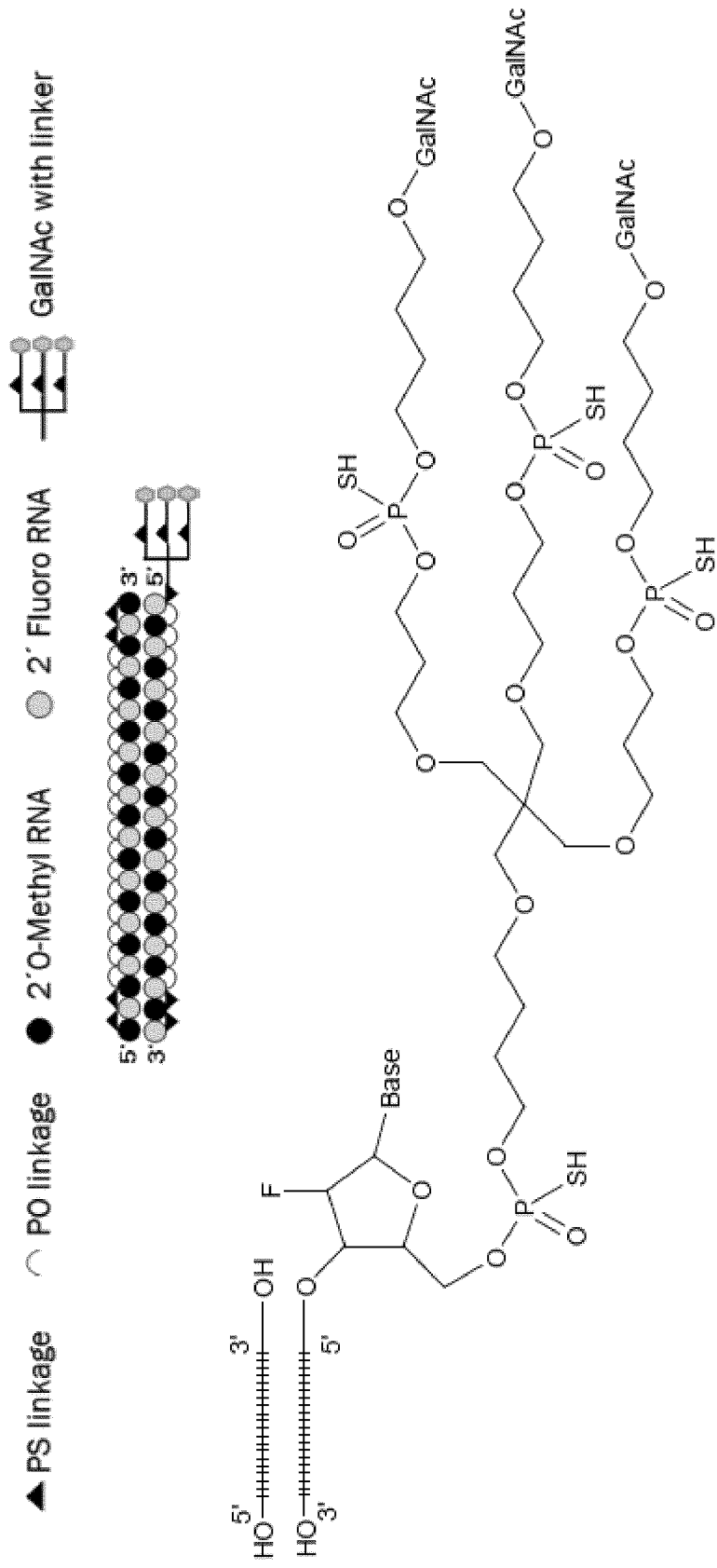

FIG. 6 depicts Conjugate 1.
FIG. 7 depicts Conjugate 2.
FIG. 8 depicts Conjugate 3.
FIG. 9 depicts Reference Conjugate 1.
FIG. 10 depicts Reference Conjugate 2.
FIG. 11 depicts Reference Conjugate 3.
FIG. 12 depicts Reference Conjugate 4.

In each of FIGS. 6-12 and 19-30, the top strand is the antisense strand and the bottom strand is the sense strand. In addition, to show more clearly the connection between the nucleic acid and ligand portions, the nucleotide at the end of the respective conjugated strands is drawn in full.

Figure 13:
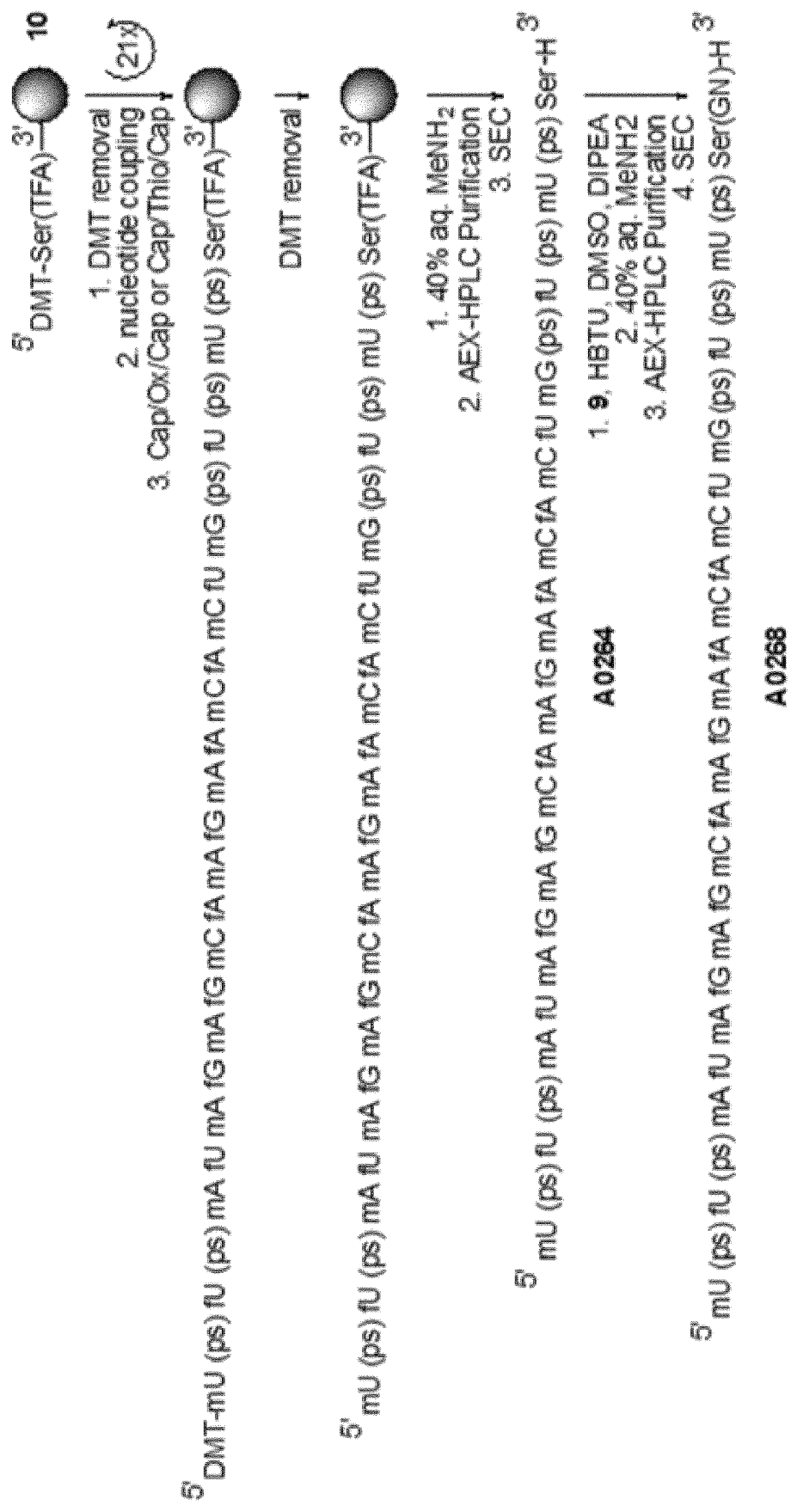

FIG. 13 shows the synthesis of A0268, which is a 3' mono-GalNAc conjugated single stranded oligonucleotide and is the starting material in the synthesis of Conjugate 1 and Conjugate 3. (ps) denotes phosphorothioate linkage.

Figure 14:
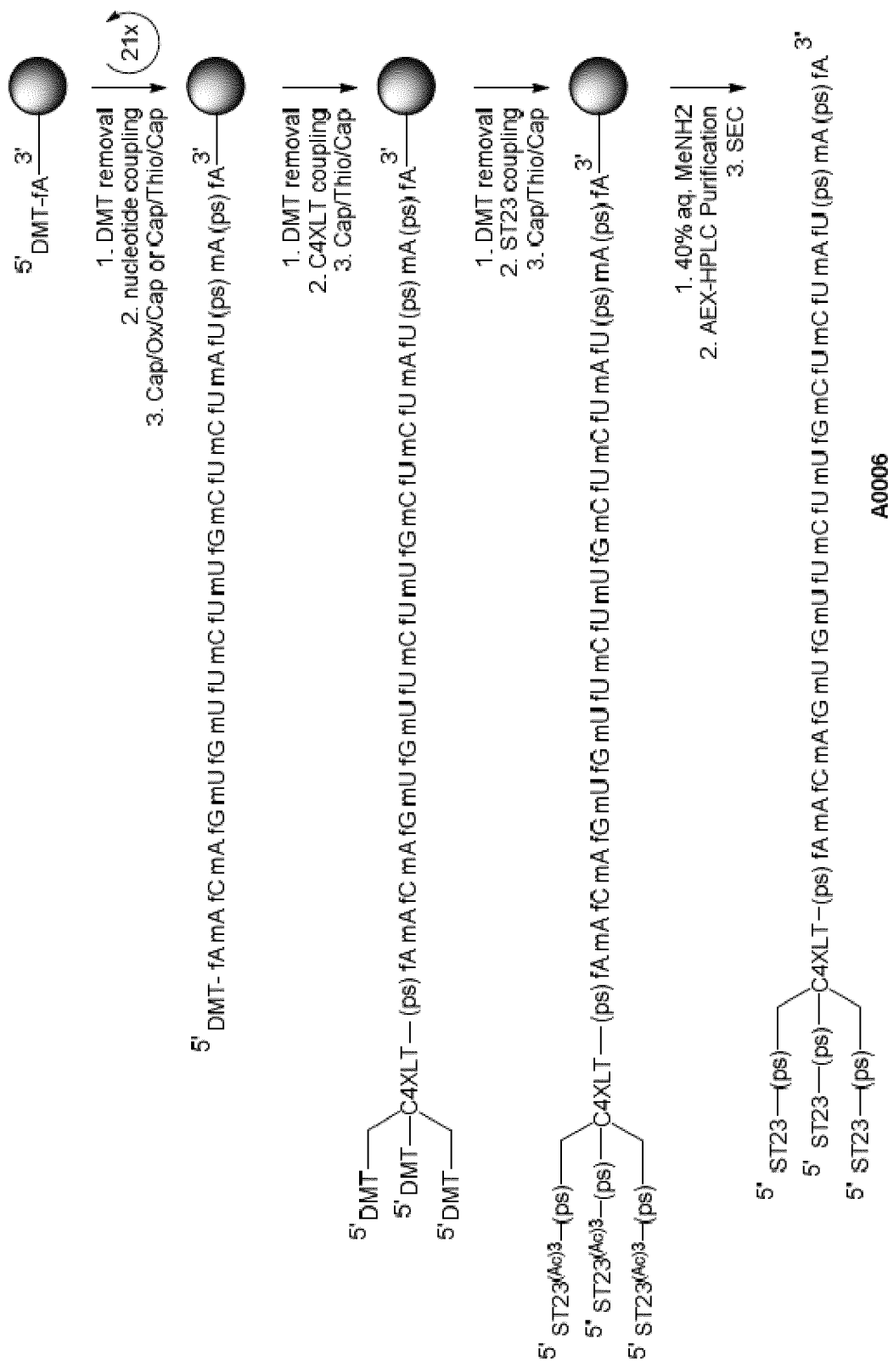

FIG. 14 shows the synthesis of A0006 which is a 5' tri-antennary GalNAc conjugated single stranded oligonucleotide used for the synthesis of Reference Conjugate 4. (ps) denotes phosphorothioate linkage.

Figure 15B:
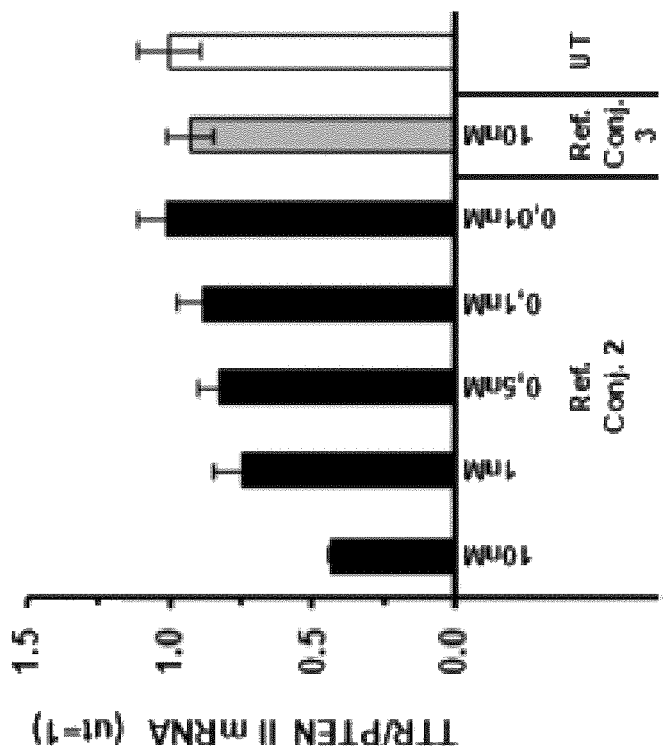
Figure 15A:
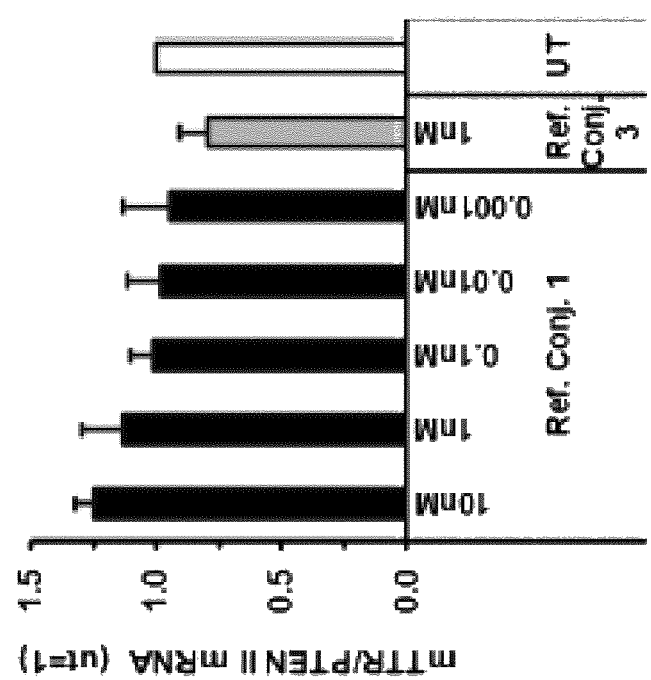
Figure 15C:
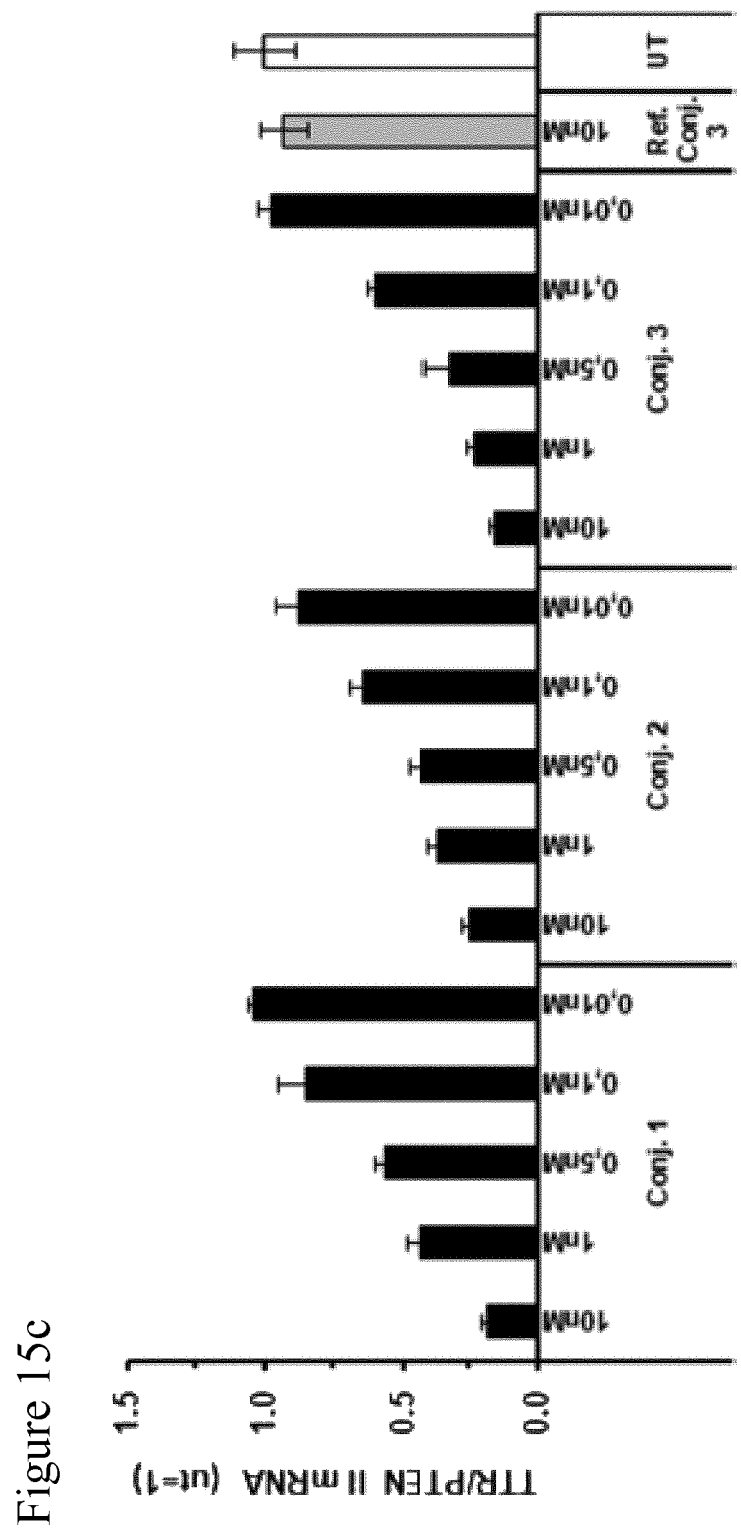

FIG. 15 illustrates the in vitro determination of TTR knockdown. In particular, FIG. 15A shows the in vitro determination of TTR knockdown by Reference Conjugates (RC) 1 and 3 as well as the untreated control "UT"; FIG. 15B shows the in vitro determination of TTR knockdown by Reference Conjugates (RC) 2 and 3, as well as the untreated control "UT"; and FIG. 15C shows the in vitro determination of TTR knockdown by Conjugates 1, 2 and 3, as well as by RC3 and untreated control "UT". Reference Conjugates 1 and 2 represent comparator conjugates. Reference Conjugate 3 represents a non-targeting GalNAc siRNA and "untreated" ("UT") represents untreated cells. Both RC3 and UT are negative controls. mRNA levels were normalised against PtenII.

Figure 16:
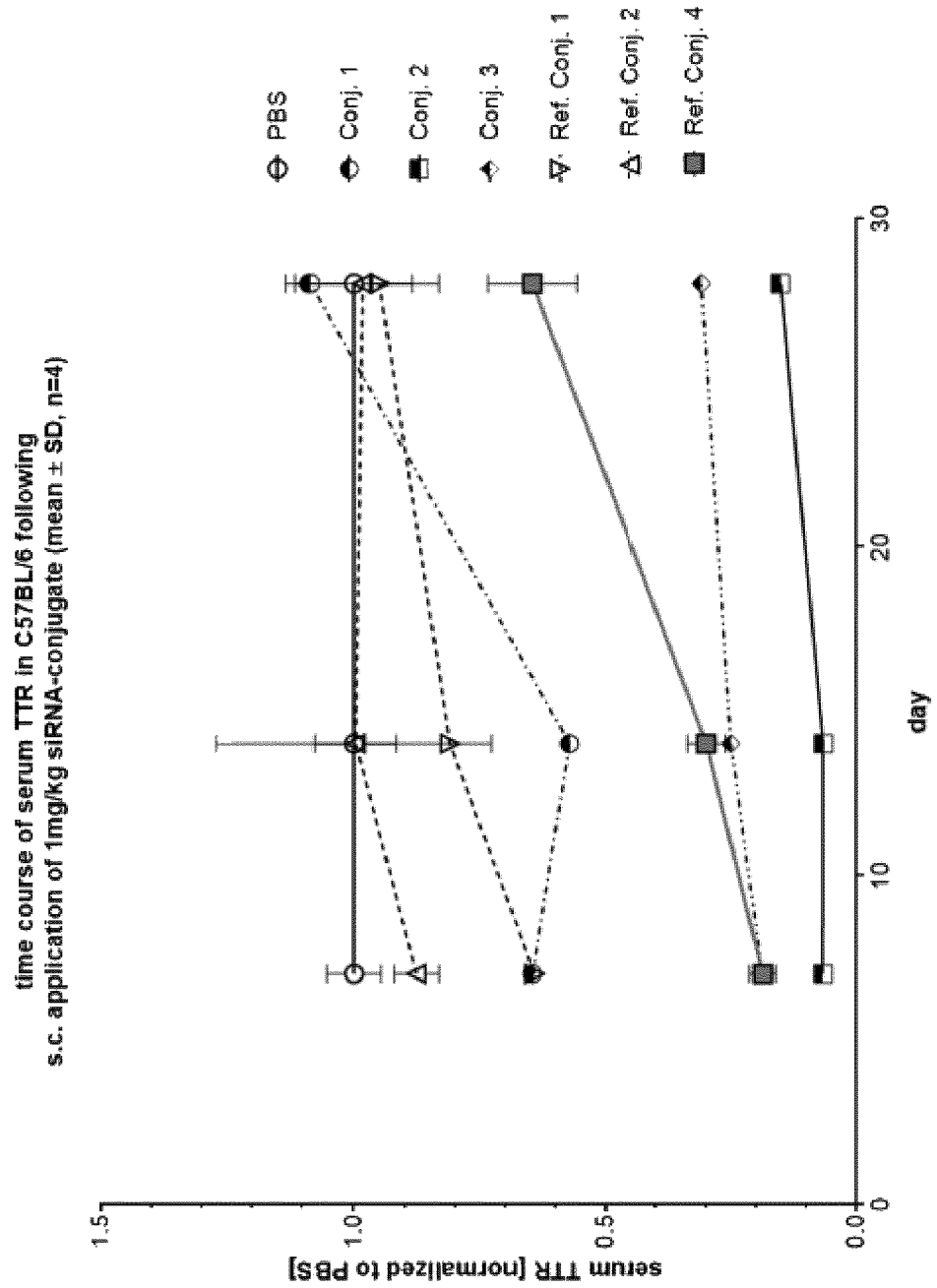

FIG. 16 shows a time course of serum TTR in c57BL/6 mice cohorts of n=4 at 7, 14, and 27 days post s.c. treatment with 1 mg/kg-Conjugates 1-3, Reference Conjugates (RC) 1, 2 and 4 and mock treated (PBS) individuals.

Figure 17:
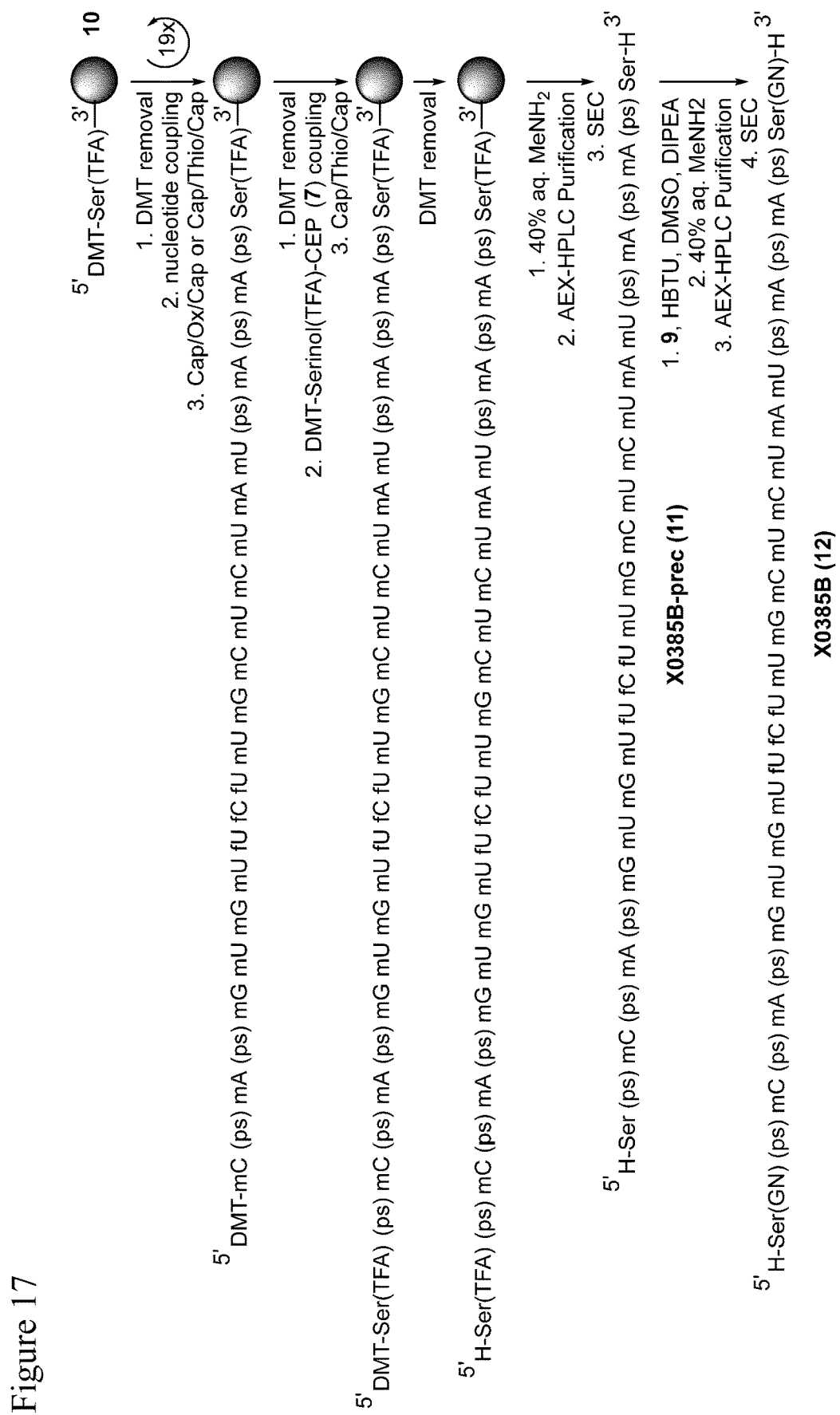

FIG. 17 shows oligonucleotide synthesis of 3' and 5' GalNAc conjugated oligonucleotides precursors (such as compound X0385B-prec).

Figure 18:
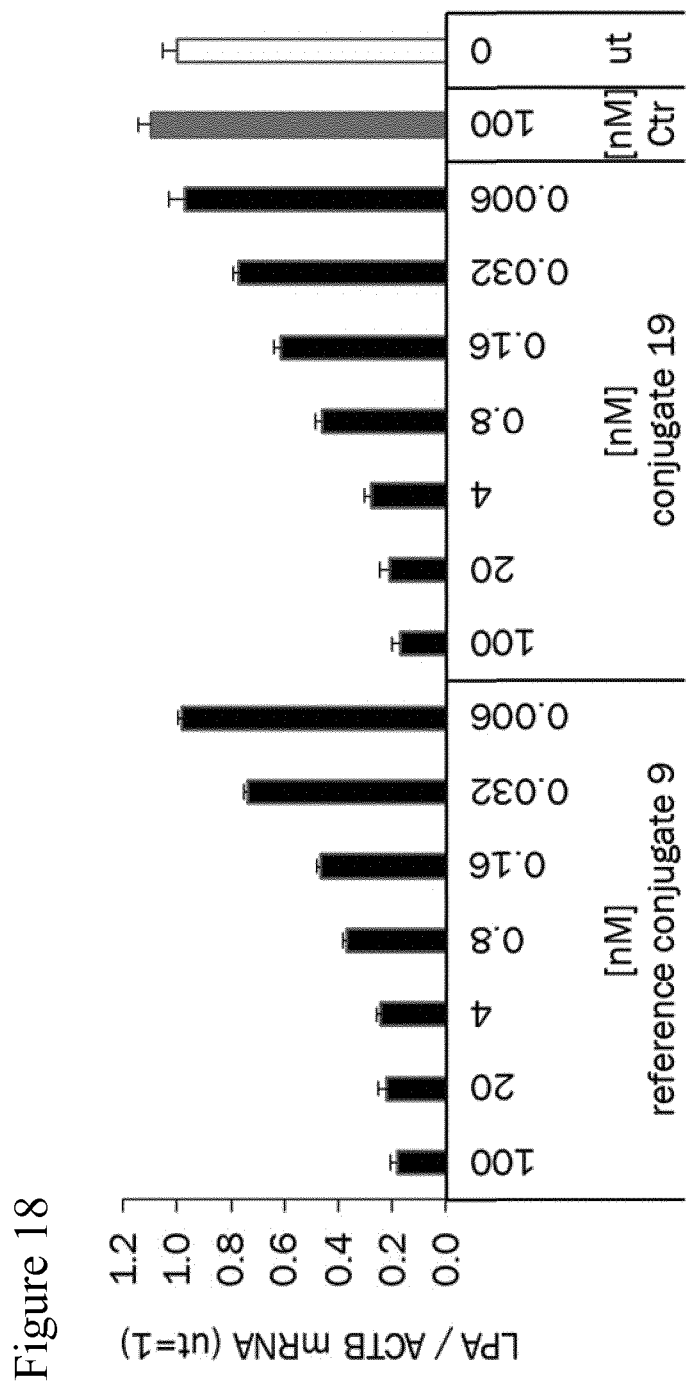

FIG. 18 shows equal dose response of knock down for LPA targeting siRNA with two single GalNAc units conjugated to the second strand as compared to a triantennary GalNAc unit at the 5' second strand in primary cynomolgus hepatocytes.

Figure 19A:
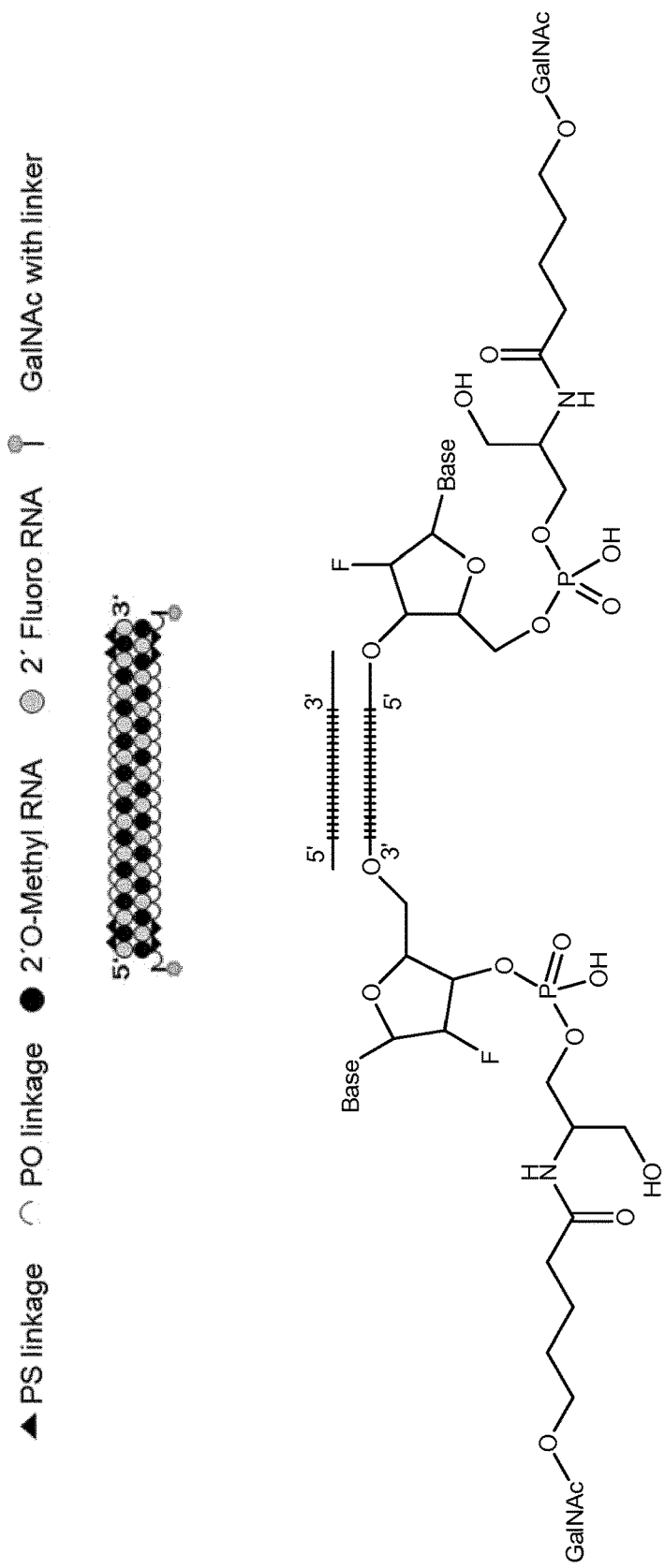

FIG. 19A depicts Conjugate 4. The last three nucleotides at the 5' and 3' ends of the antisense and sense strands are connected by a phosphorothioate linker between each nucleotide. The serinol-GalNAc-linkers are conjugated via a phosphodiester bond to the 3' end and the 5' end of the sense strand.

Figure 19B:
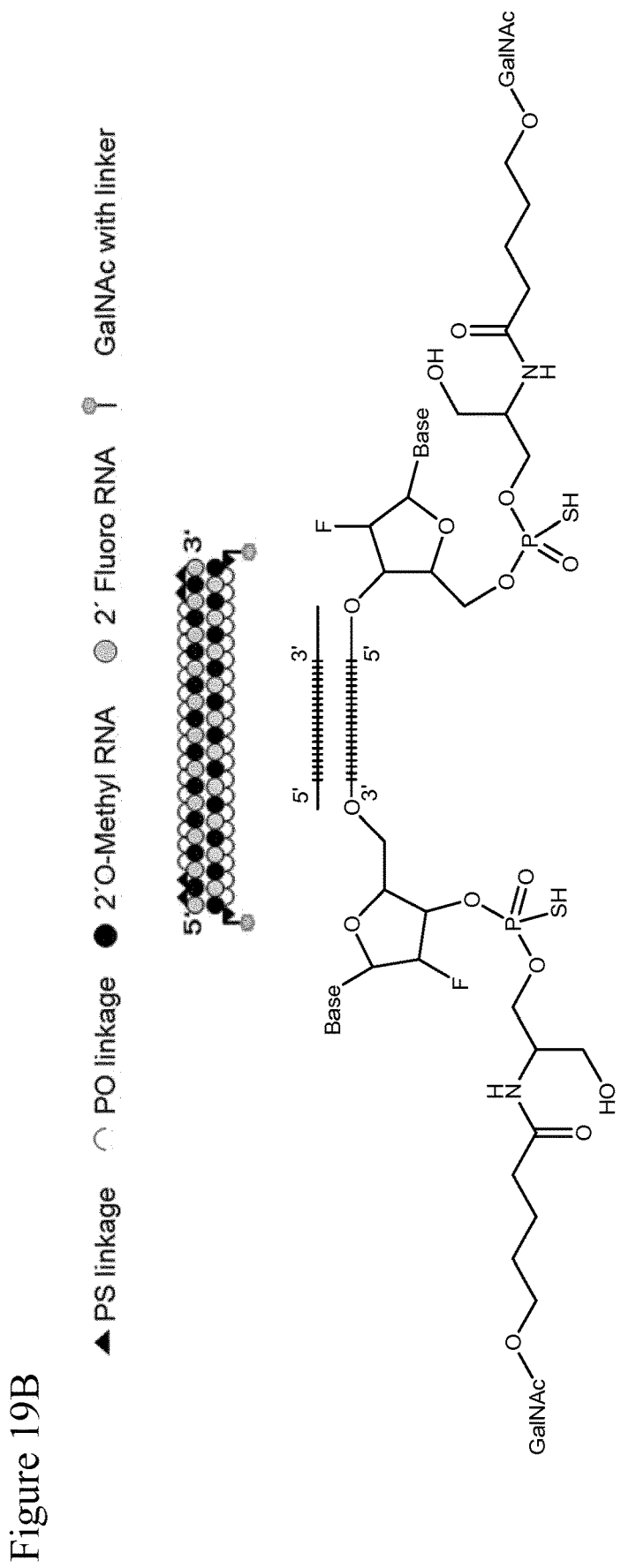

FIG. 19B depicts Conjugate 5. The last three nucleotides at the 5' and 3' ends of the antisense strand are connected by a phosphorothioate linker between each nucleotide. The serinol-GalNAc-linkers are conjugated via a phosphorothioate bond to the 3' end and the 5' end of the sense strand.

Figure 20:
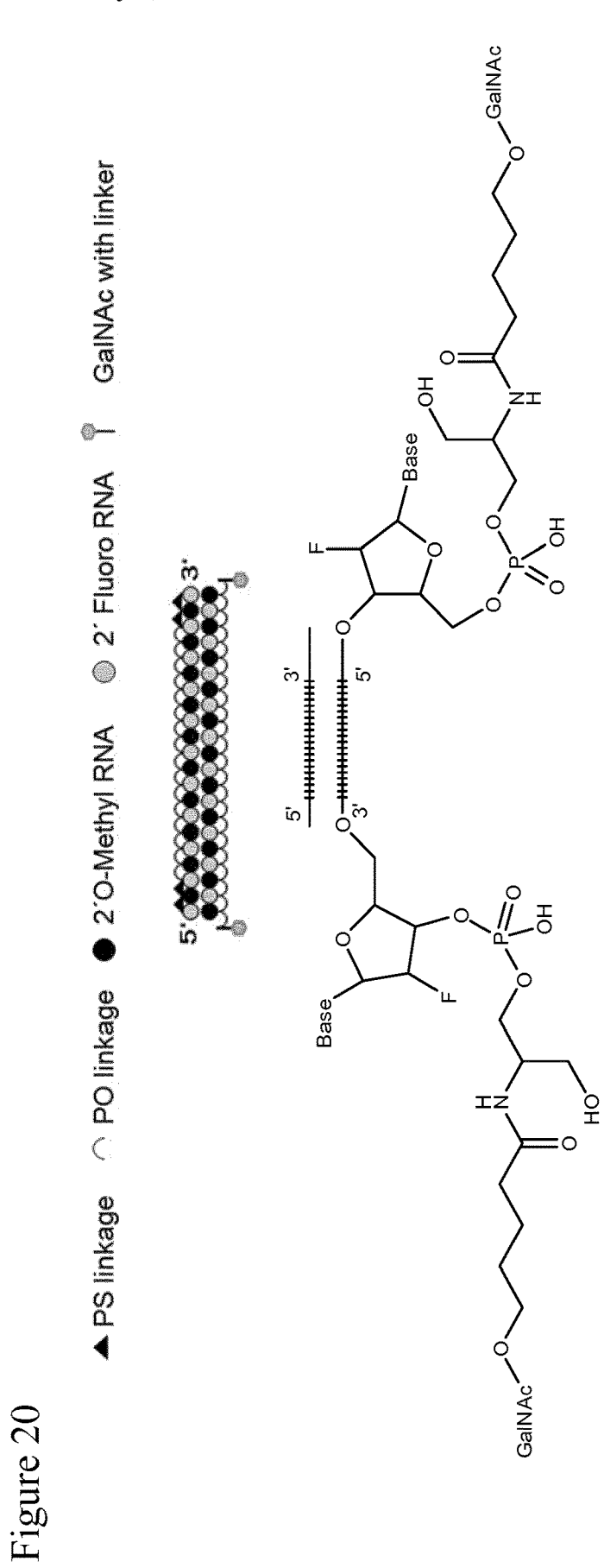

FIG. 20 depicts Conjugate 6. The last three nucleotides at the 5' and 3' ends of the antisense strand are connected by a phosphorothioate linker between each nucleotide. The serinol-GalNAc-linkers are conjugated via a phosphodiester bond to the 3' end and the 5' end of the sense strand.

Figure 21:
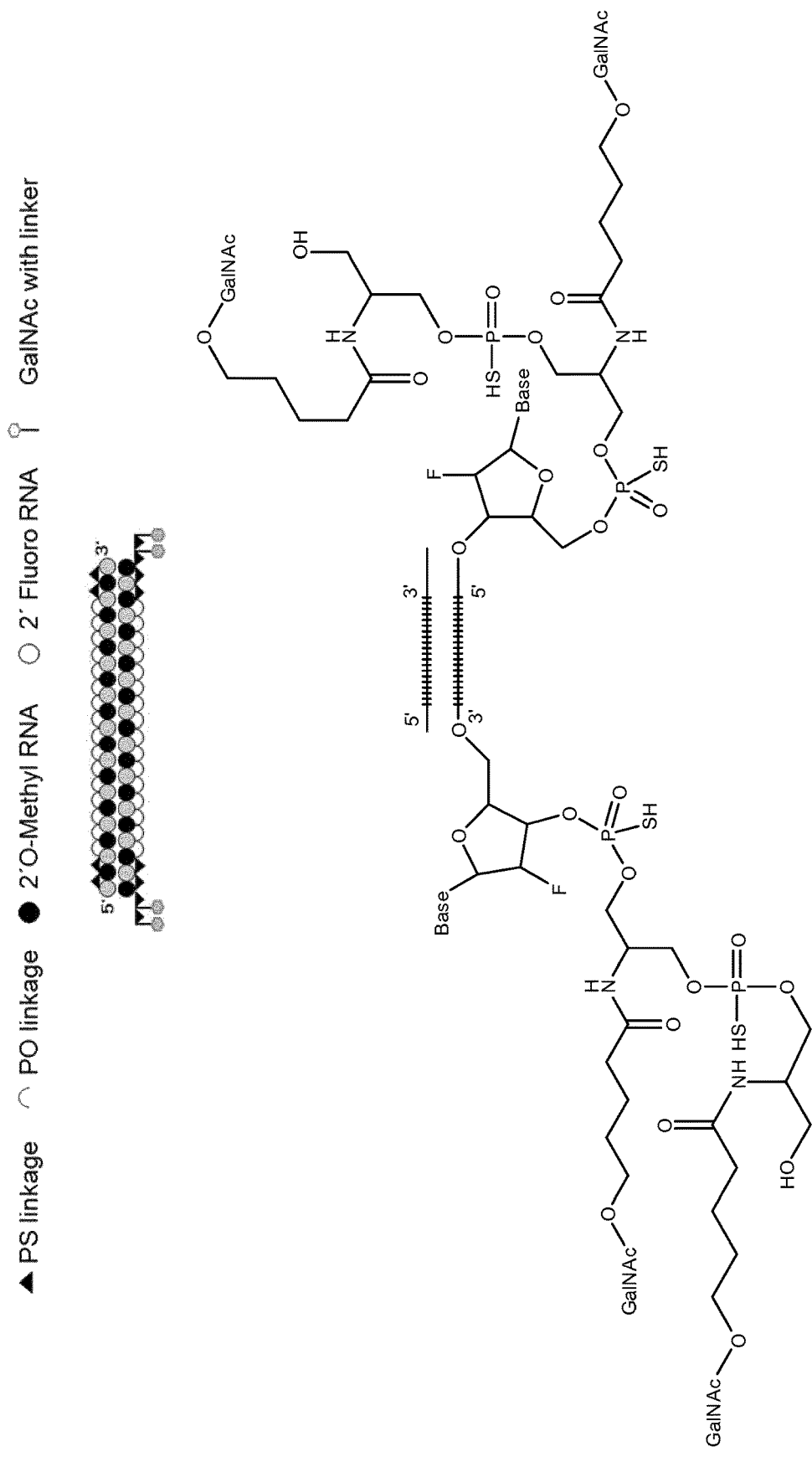

FIG. 21 depicts Conjugate 7. The last three nucleotides at the 5' and 3' ends of the antisense and sense strands are connected by a phosphorothioate linker between each nucleotide. The serinol-GalNAc-linkers are conjugated via a phosphorothioate bond to the 3' end and the 5' end of the sense strand. The serinol-GalNAc-linkers are connected to each other via a phosphorothioate bond.

Figure 22:
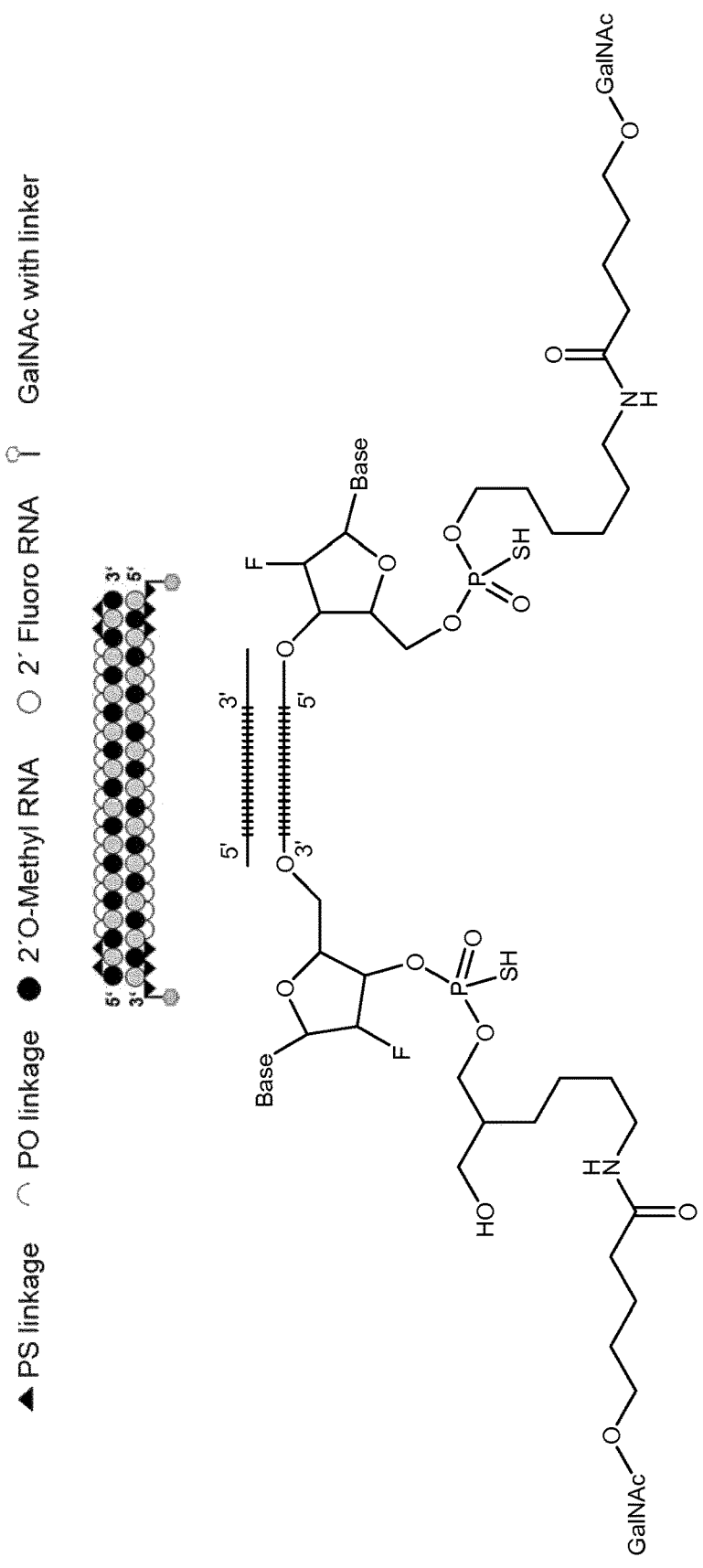

FIG. 22 depicts Conjugate 8. The last three nucleotides at the 5' and 3' ends of the antisense and sense strands are connected by a phosphorothioate linker between each nucleotide. A GalNAc-C6-amino-modifier linker is conjugated at the 5' end of the sense strand and a GalNAc-C7-amino-modifier linker is conjugated at the 3' end of the sense strand.

Figure 23:
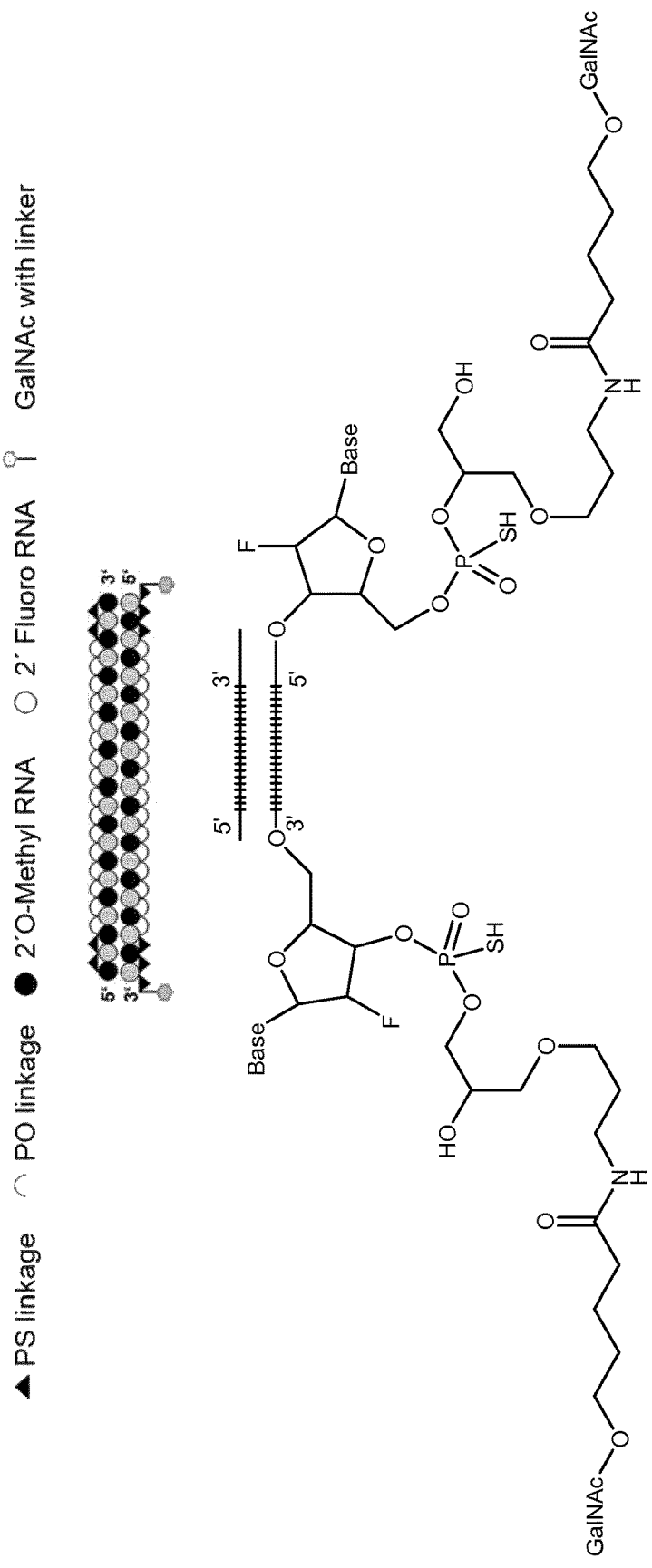

FIG. 23 depicts Conjugate 9. The last three nucleotides at the 5' and 3' ends of the antisense and sense strands are connected by a phosphorothioate linker between each nucleotide. A GalNAc-GlyC3-amino-modifier linker is conjugated at the 5' and 3' ends of the sense strand.

Figure 24:
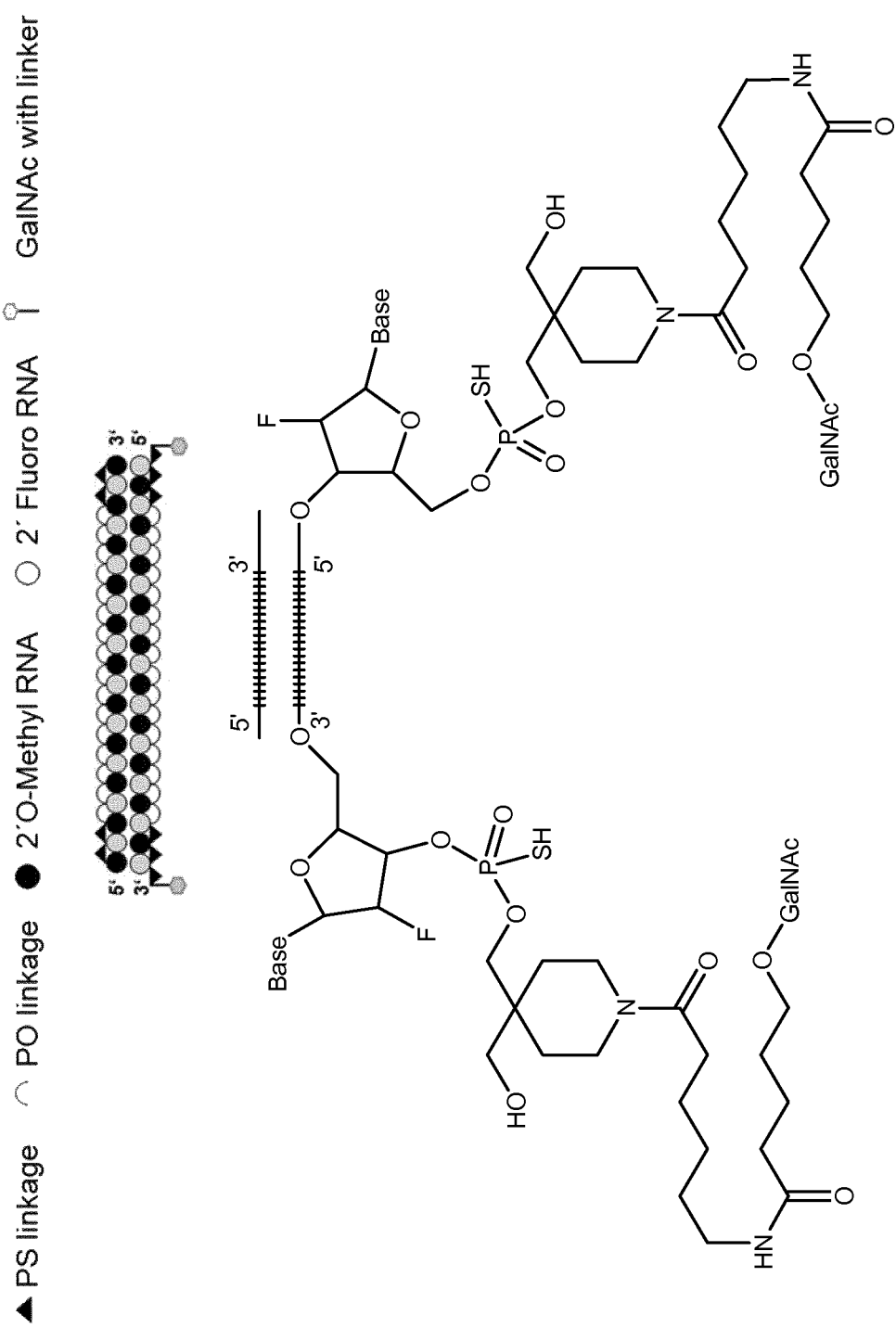

FIG. 24 depicts Conjugate 10. The last three nucleotides at the 5' and 3' ends of the antisense and sense strands are connected by a phosphorothioate linker between each nucleotide. and sense strands are connected by a phosphorothioate linker between each nucleotide. A GalNAc-piperidyl-amino-modifier linker is conjugated at the 5' and 3' ends of the sense strand.

Figure 25:
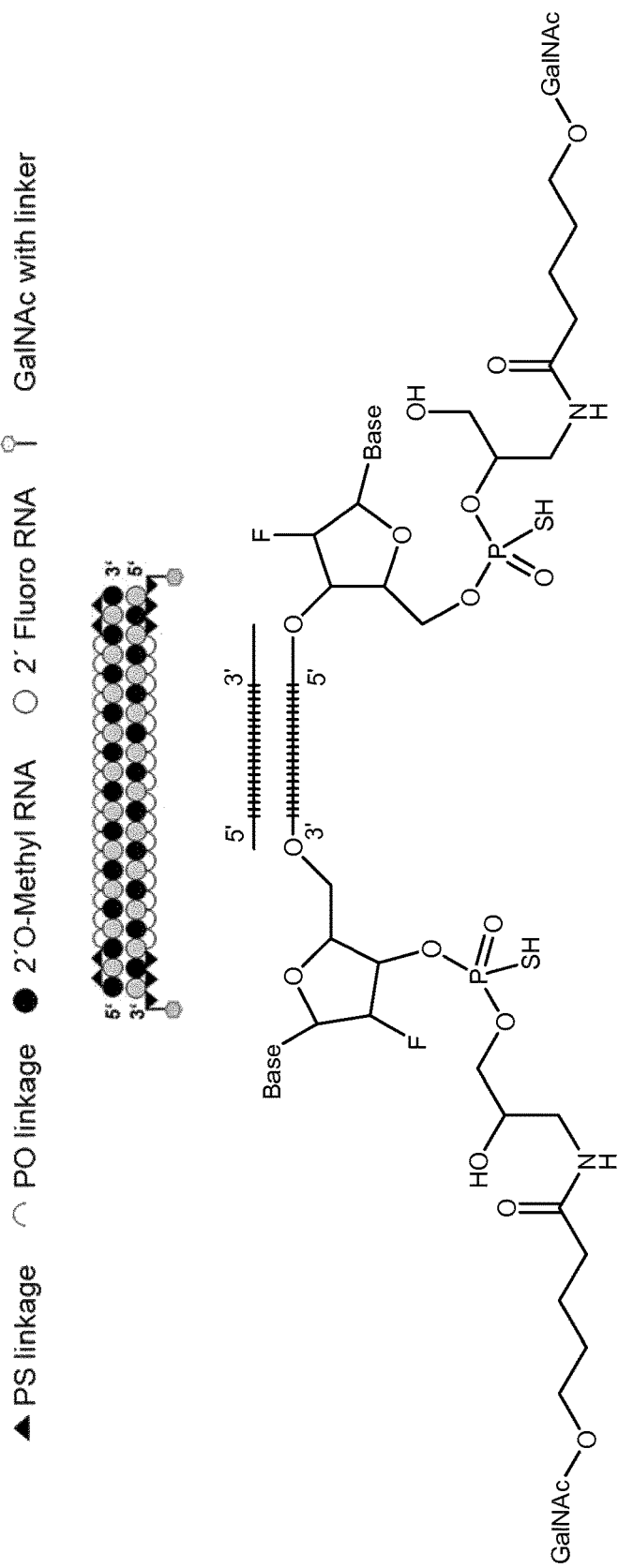

FIG. 25 depicts Conjugate 11. The last three nucleotides at the 5' and 3' ends of the antisense and sense strands are connected by a phosphorothioate linker between each nucleotide. A GalNAc-C3-amino-modifier linker is conjugated at the 5' and 3' ends of the sense strand.

Figure 26:
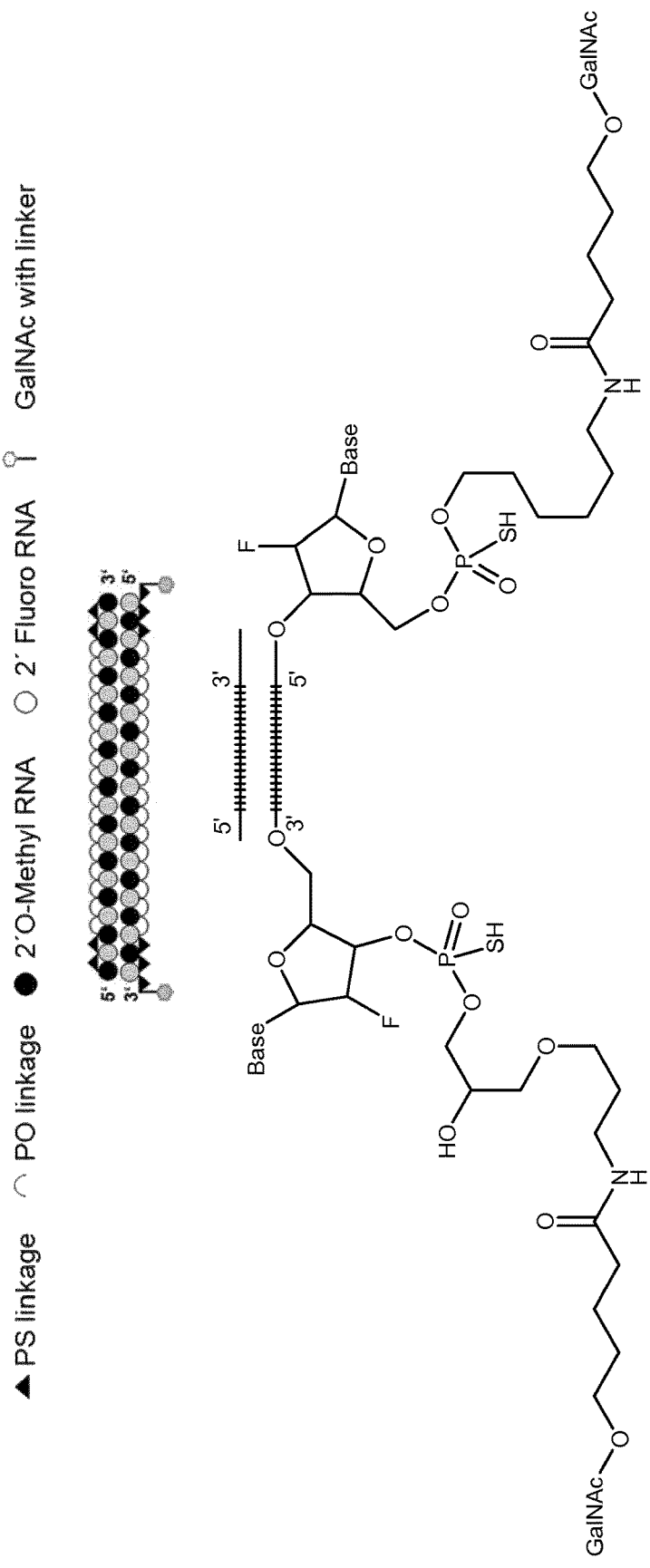

FIG. 26 depicts Conjugate 12. The last three nucleotides at the 5' and 3' ends of the antisense and sense strands are connected by a phosphorothioate linker between each nucleotide. A GalNAc-C6-amino-modifier linker is conjugated at the 5' end of the sense strand and a GalNAc-GlyC3-amino-modifier linker is conjugated at the 3' end of the sense strand.

Figure 27:
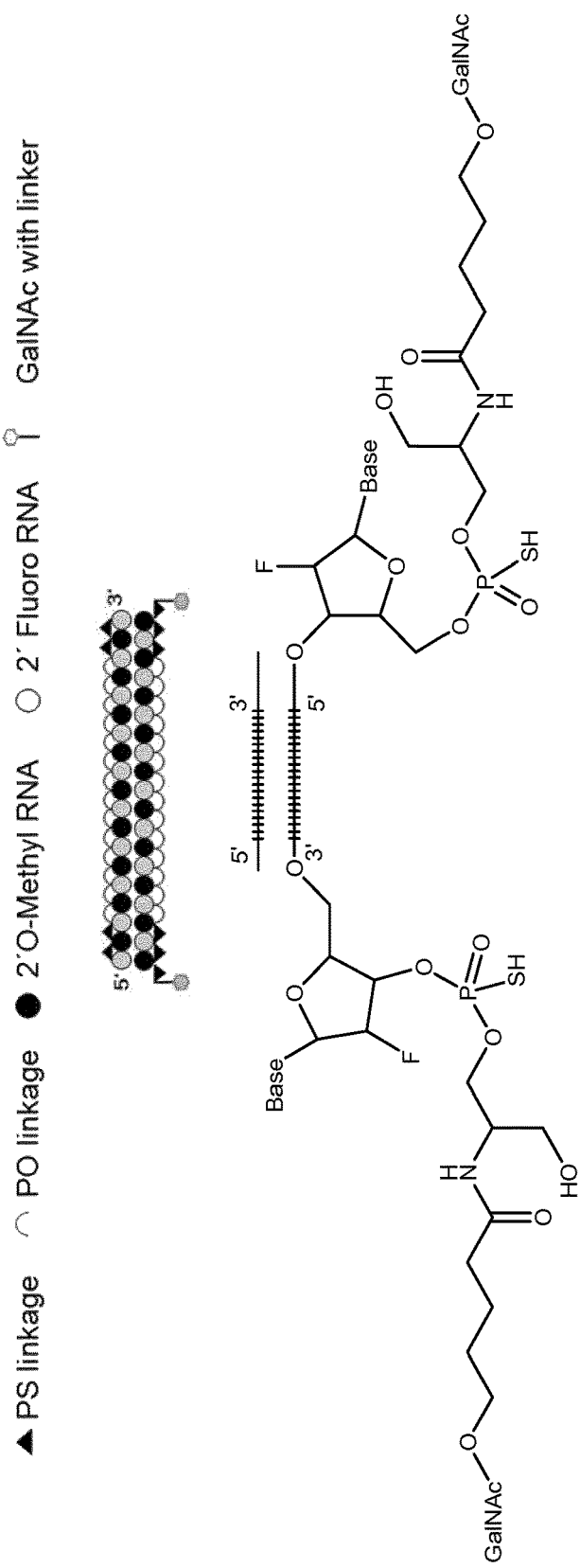

FIG. 27 depicts Conjugates 15, 16, 18 and 19 which differ only by their RNA sequences. The last three nucleotides at the 5' and 3' ends of the antisense and sense strands are connected by a phosphorothioate linker between each nucleotide in each conjugate. The serinol-GalNAc-linkers are conjugated via a phosphorothioate bond to the 3' end and the 5' end of the sense strand.

Figure 28:
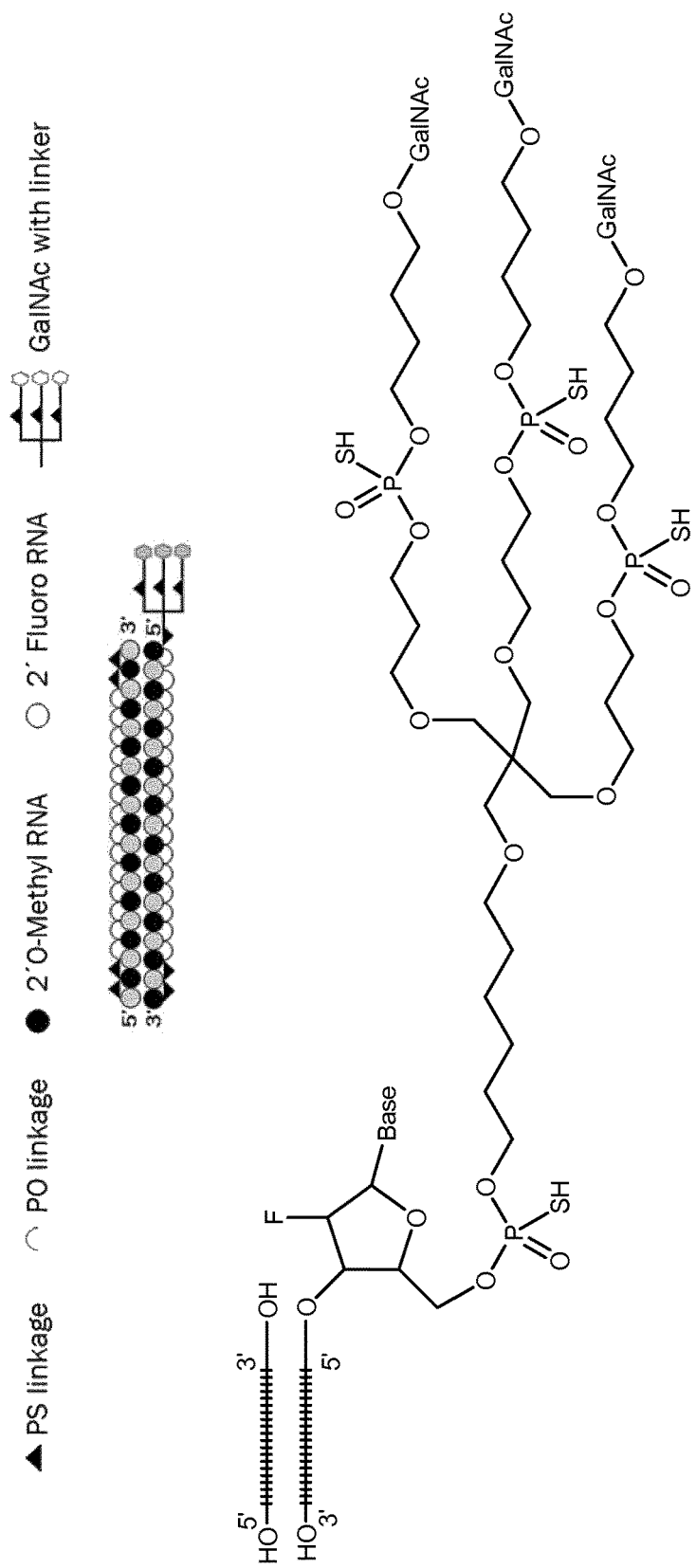

FIG. 28 depicts Reference Conjugate 5 and Reference Conjugate 9 which differ only by their RNA sequences. The last three nucleotides at the 5' and 3' ends of the antisense strand and 3' end of the sense strand are connected by a phosphorothioate linker between each nucleotide in both conjugates. The trimeric GalNAc-linker is conjugated via a phosphorothioate bond to the 5' end of the sense strand in both conjugates.

Figure 29:
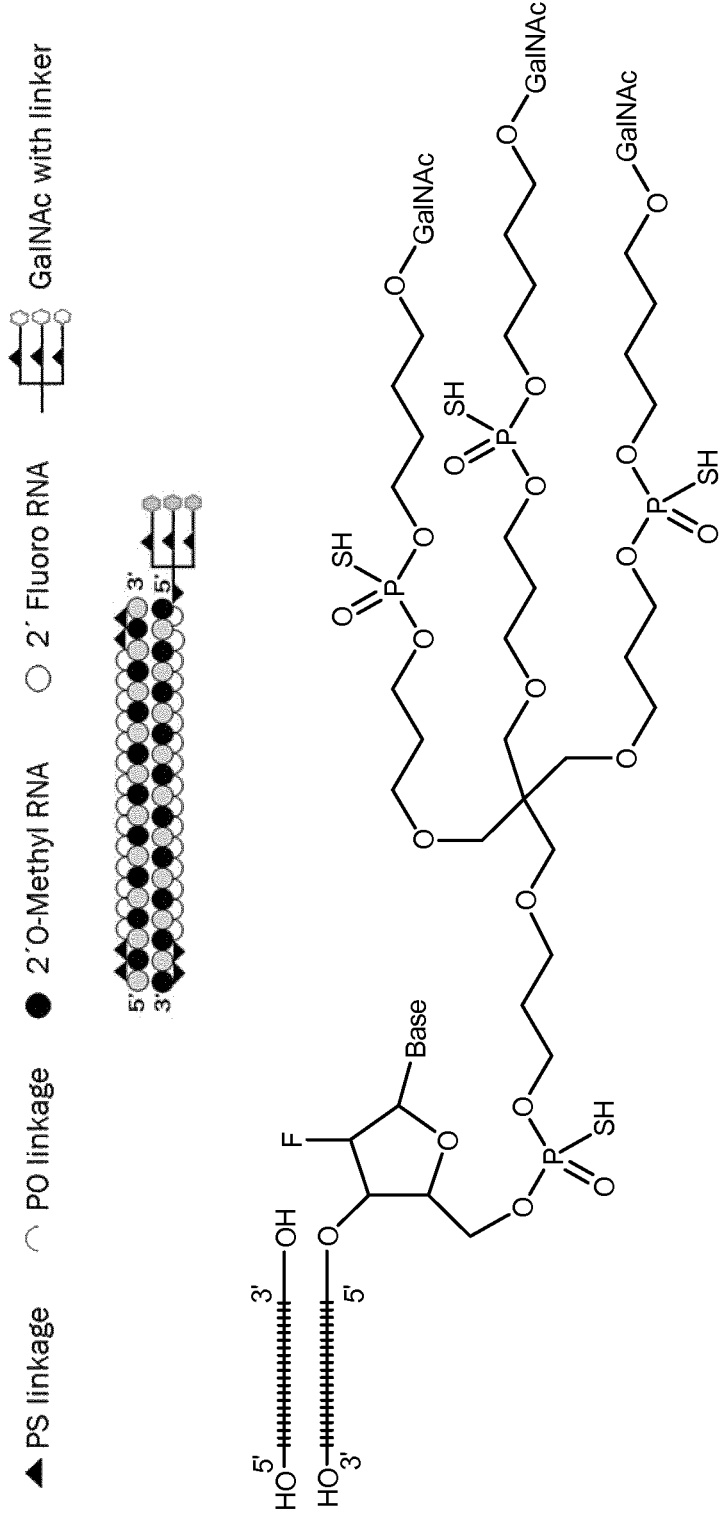

FIG. 29 depicts Reference Conjugate 6 and Reference Conjugate 7 which differ only by their RNA sequences. The last three nucleotides at the 5' and 3' ends of the antisense strand and 3' end of the sense strand are connected by a phosphorothioate linker between each nucleotide in both conjugates. The trimeric GalNAc-linker is conjugated via a phosphorothioate bond to the 5' end of the sense strand in both conjugates.

Figure 30:
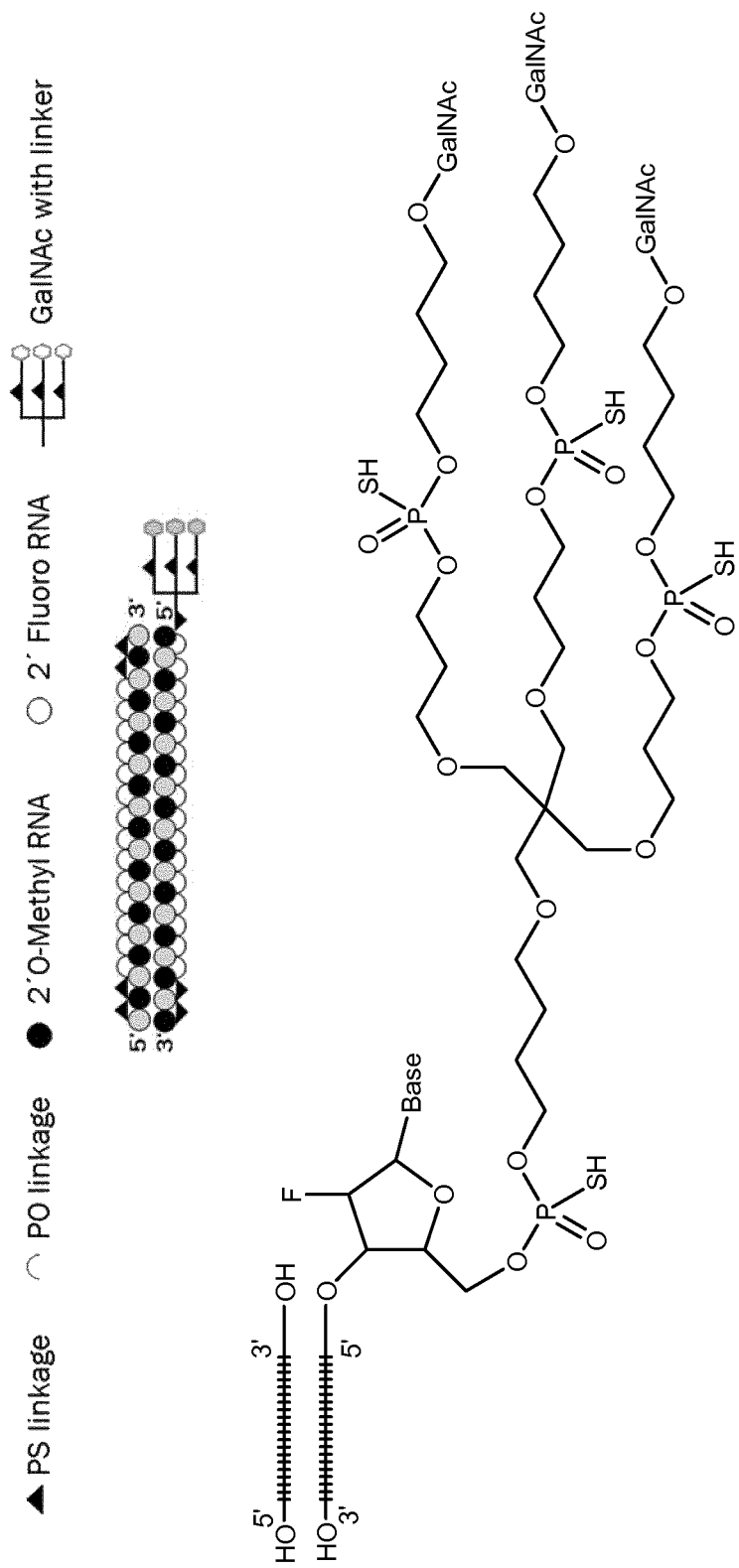

FIG. 30 depicts Reference Conjugate 8. The last three nucleotides at the 5' and 3' ends of the antisense strand and 3' end of the sense strand are connected by a phosphorothioate linker between each nucleotide. The trimeric GalNAc-linker is conjugated via a phosphorothioate bond to the 5' end of the sense strand.

Figure 31A:
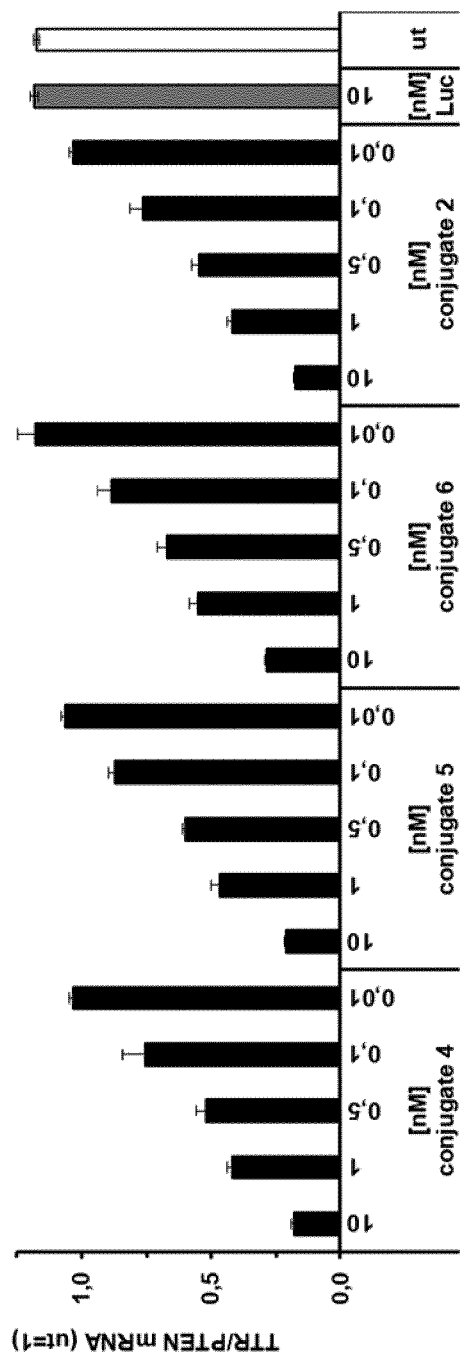
Figure 31B:
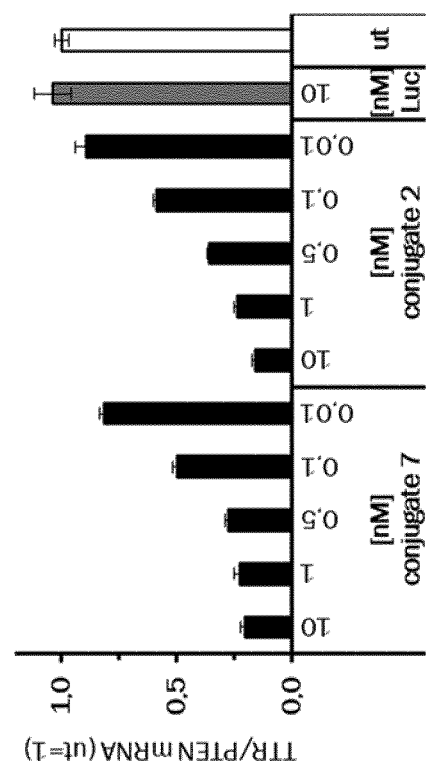

FIG. 31 illustrates the in vitro determination of TTR knockdown. In particular, FIG. 31A shows the in vitro determination of TTR knockdown by Conjugates 4, 5, 6 and 2 compared to "Luc" (Reference Conjugate 3) as well as the untreated control "UT"; FIG. 31B shows the in vitro determination of TTR knockdown by Conjugates 7 and 2, compared to "Luc" (Reference Conjugate 3) as well as the untreated control "UT". Luc or Reference Conjugate 3 (RC3) represents a non-targeting GalNAc siRNA and "untreated" ("UT") represents untreated cells. Both RC3 and UT are negative controls. mRNA level were normalised against PtenII.

Figure 32A:
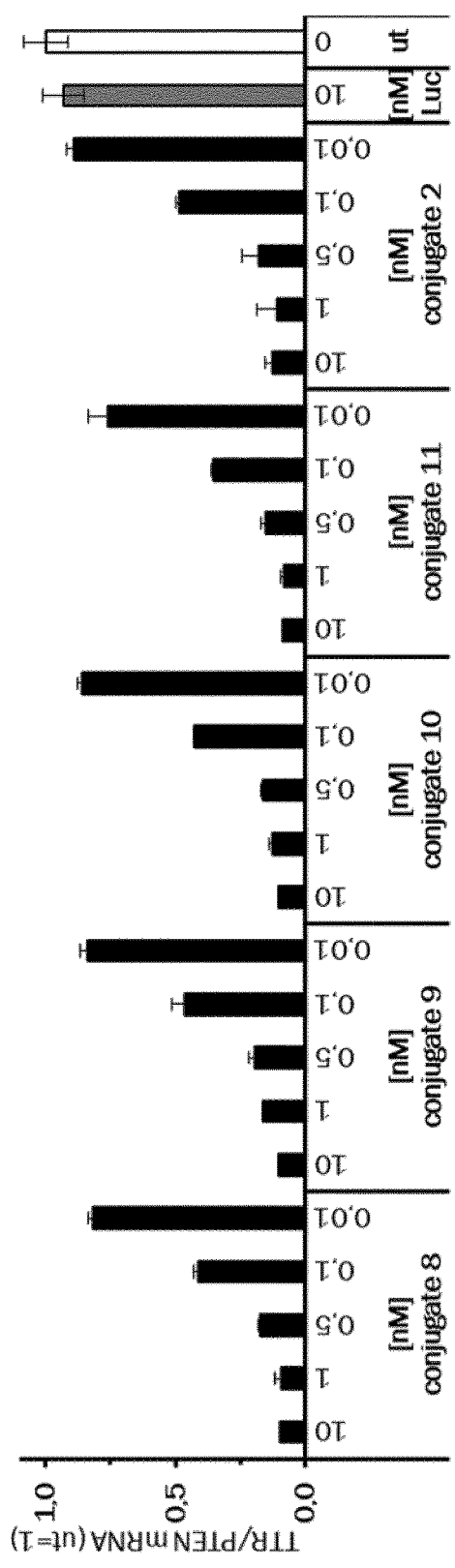
Figure 32B:
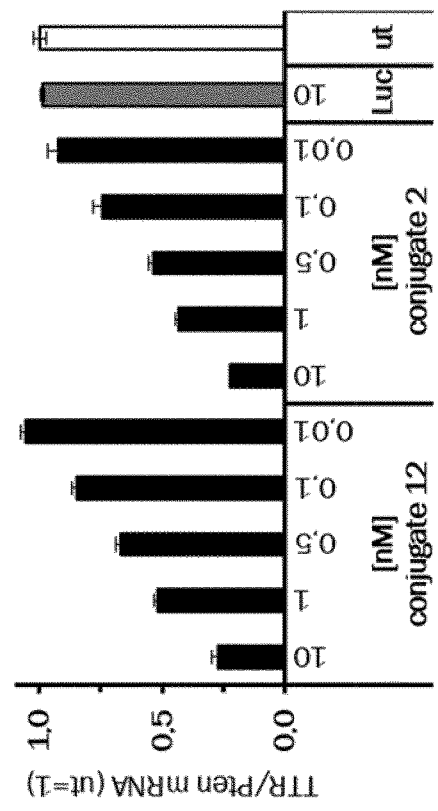

FIG. 32 illustrates the in vitro determination of TTR knockdown. In particular, FIG. 32A shows the in vitro determination of TTR knockdown by Conjugates 8, 9, 10, 11 and 2 compared to "Luc" (Reference Conjugate 3) as well as the untreated control "UT"; FIG. 32B shows the in vitro determination of TTR knockdown by Conjugates 12 and 2, compared to "Luc" (Reference Conjugate 3) as well as the untreated control "UT". Luc or Reference Conjugate 3 represents a non-targeting GalNAc siRNA and "untreated" ("UT") represents untreated cells. Both RC3 and UT are negative controls. mRNA level were normalised against PtenII.

Figure 33:
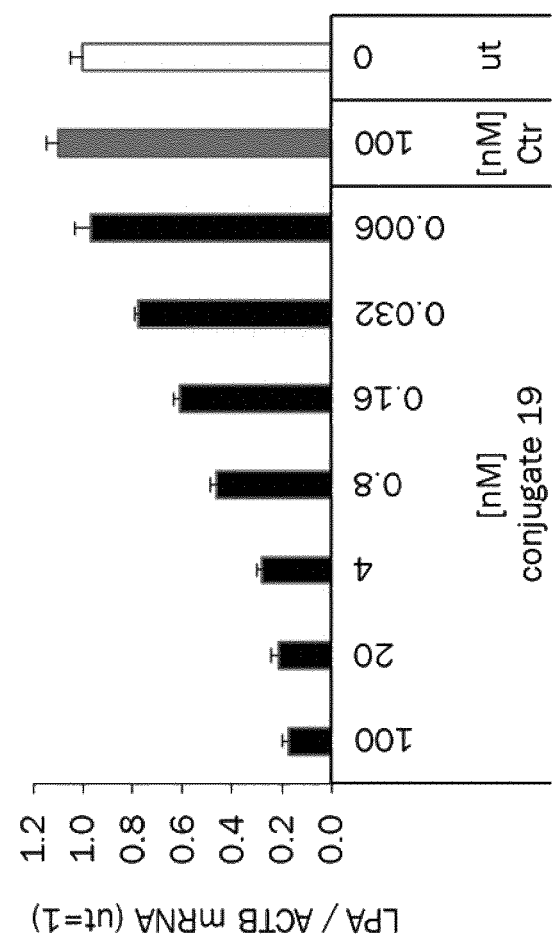

FIG. 33 illustrates the in vitro determination of LPA mRNA knockdown by Conjugate 19 compared to controls. Ctr represents a non-targeting GalNAc siRNA and "untreated" ("UT") represents untreated cells. Both Ctr and UT are negative controls. mRNA level were normalised against ACTB.

Figure 34:
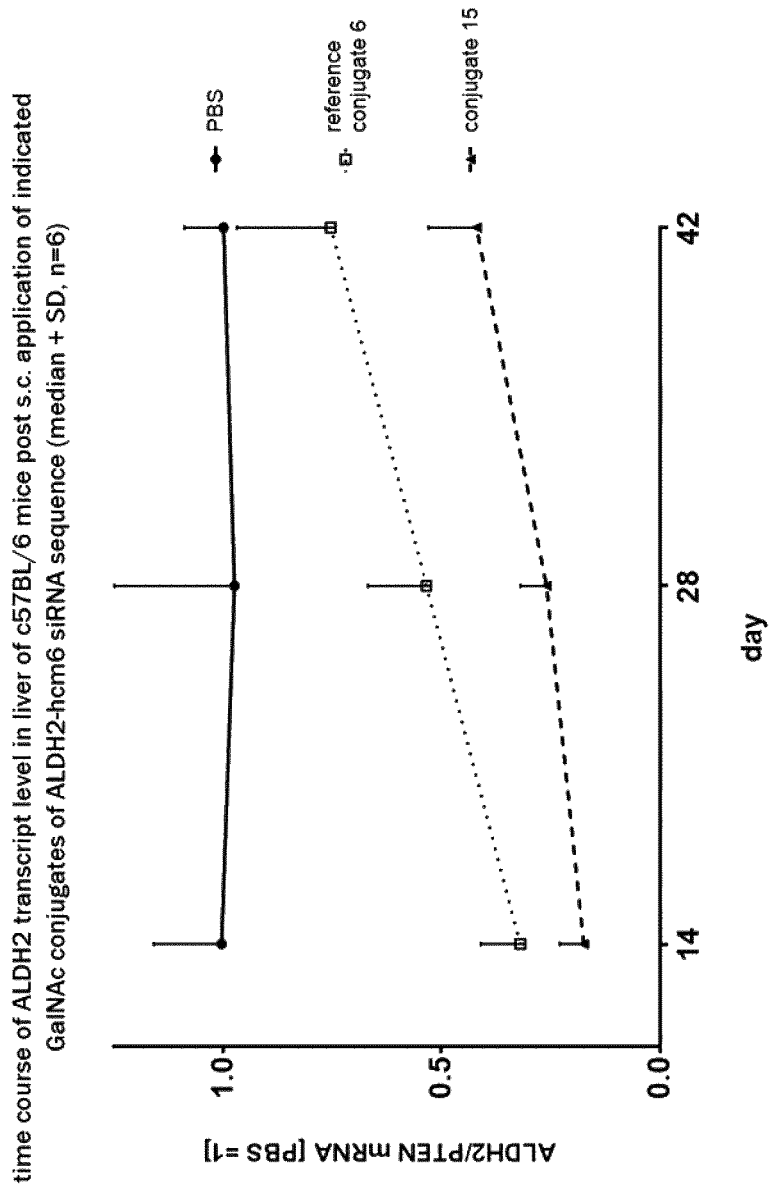

FIG. 34 shows a time course of Aldh2 liver mRNA levels in c57BL/6 mice cohorts of n=6 at 14, 28 and 42 days post s.c. treatment with 1 mg/kg-Conjugate 15, Reference Conjugate (RC) 6 and mock treated (PBS) individuals. mRNA level were normalised against Pten.

Figure 35:
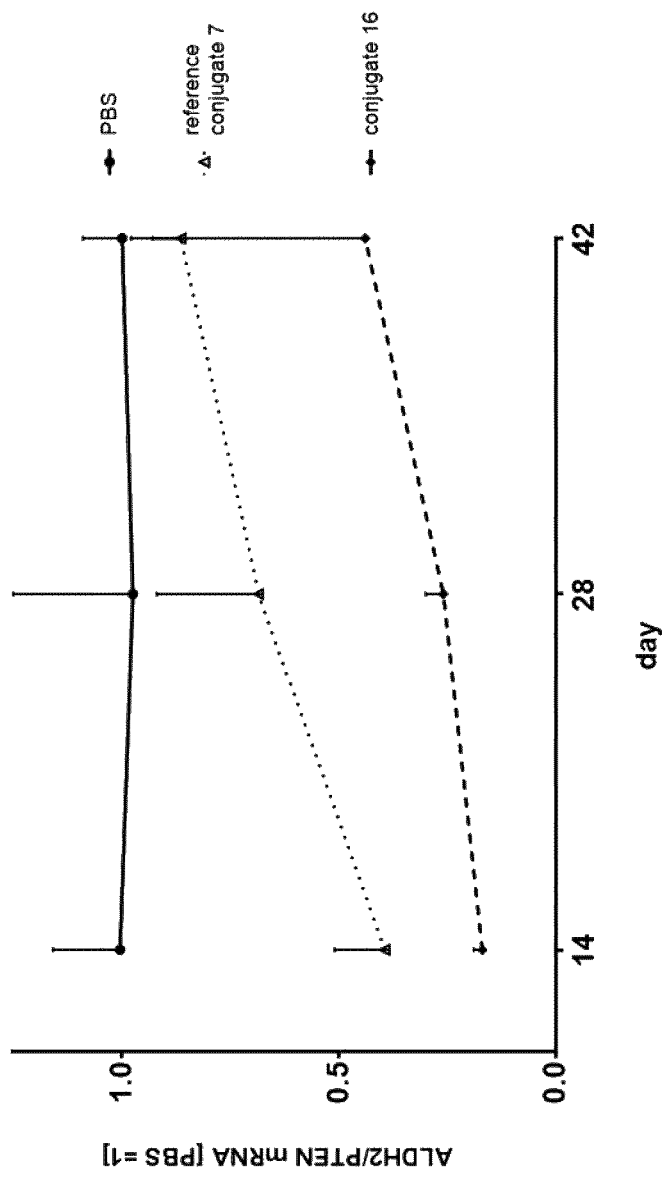

FIG. 35 shows a time course of Aldh2 liver mRNA levels in c57BL/6 mice cohorts of n=6 at 14, 28 and 42 days post s.c. treatment with 1 mg/kg-Conjugate 16, Reference Conjugate (RC) 7 and mock treated (PBS) individuals. mRNA level were normalised against Pten.

Figure 36:
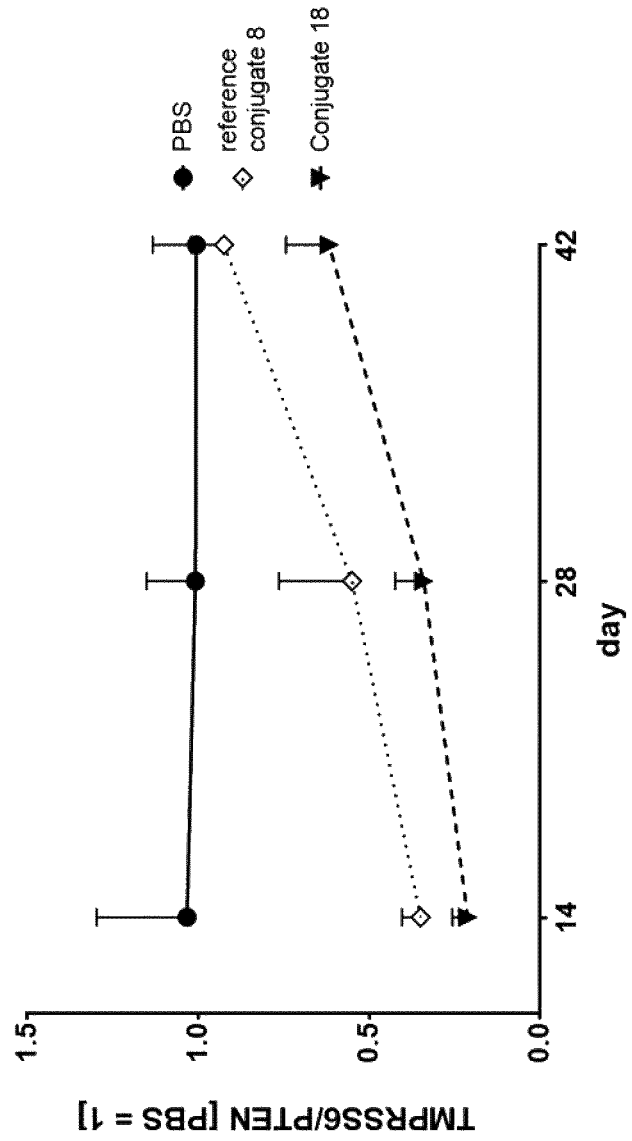

FIG. 36 shows a time course of Tmprss6 liver mRNA levels in c57BL/6 mice cohorts of n=6 at 14, 28 and 42 days post s.c. treatment with 1 mg/kg-Conjugate 18, Reference Conjugate (RC) 8 and mock treated (PBS) individuals. mRNA level were normalised against Pten.

Figure 37:
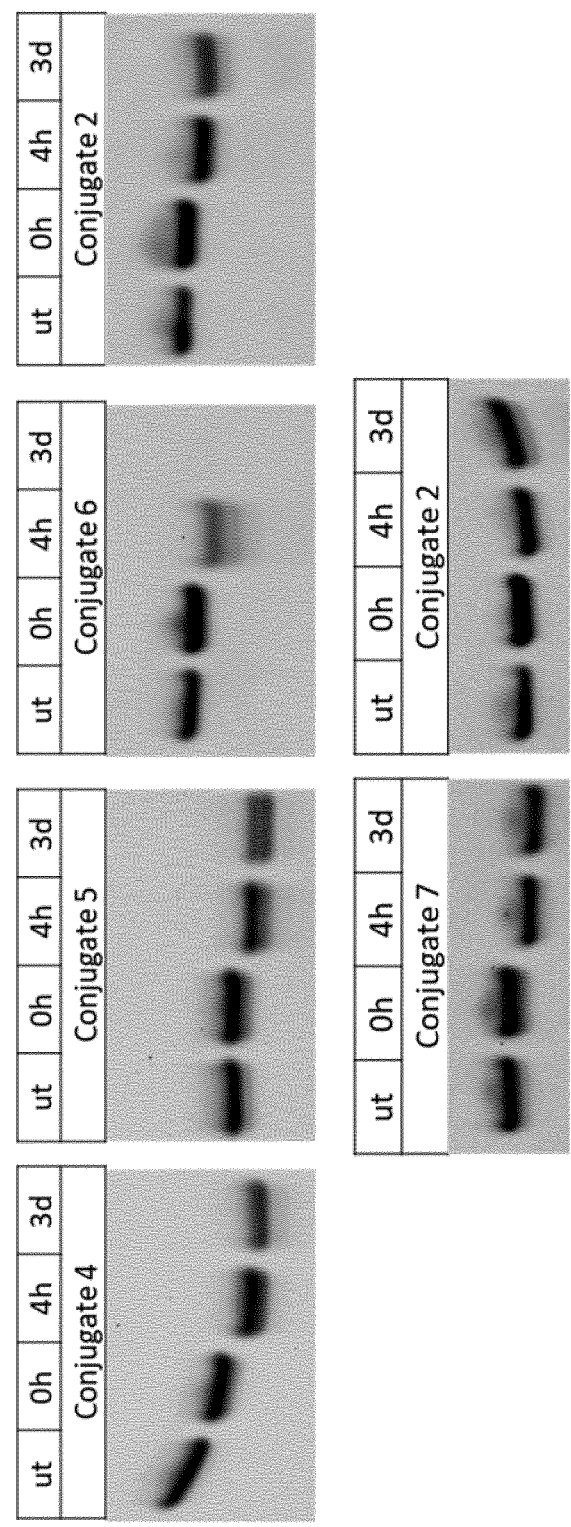

FIG. 37 shows serum stability of Conjugates 4, 5, 6, 7 and 2, and untreated control (UT) at 37° C. over 3 days.

Figure 38:
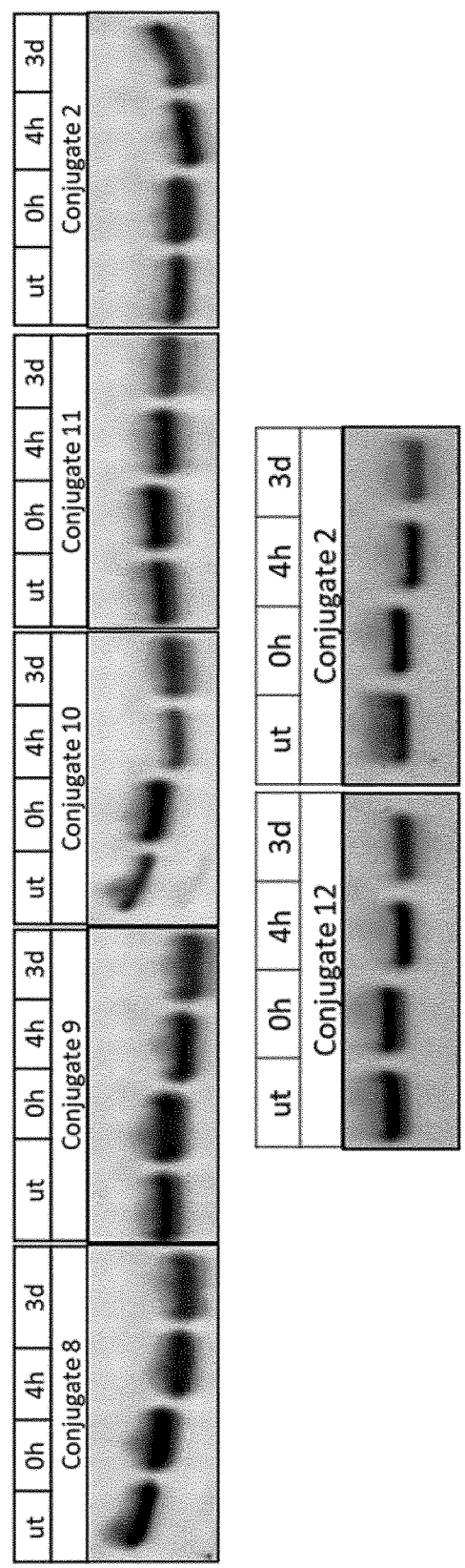

FIG. 38 shows serum stability of Conjugates 8, 9, 10, 11, 12 and 2, and untreated control (UT) at 37° C. over 3 days.

Figure 39:
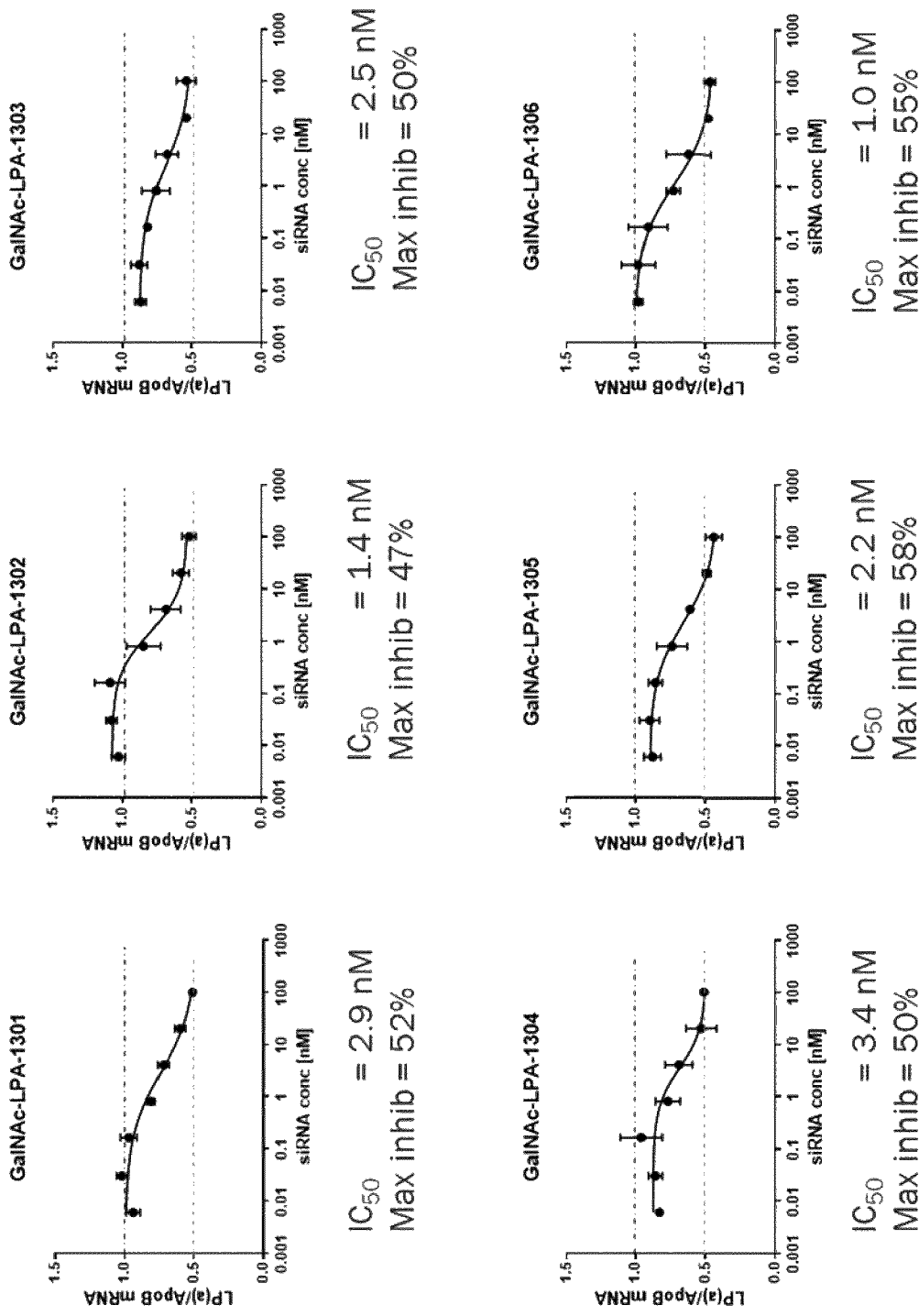
Figure 40A:
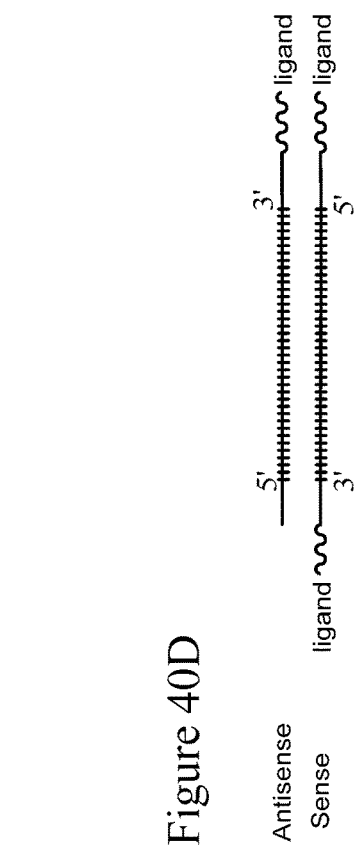
Figure 40B:
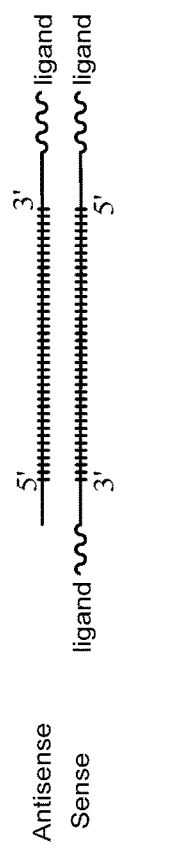
Figure 40C:
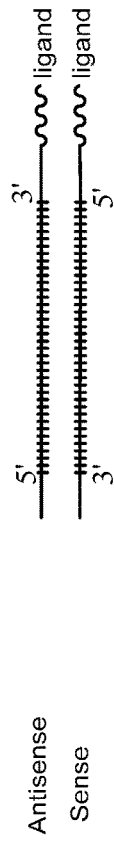
Figure 40D:
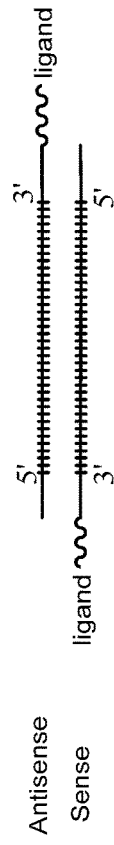
Figure 40E:
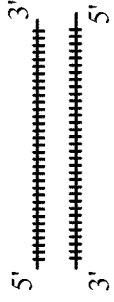

FIG. 39 shows inhibition of LPA mRNA expression in human primary hepatocytes by different doses of GalNAc-L6 coupled siRNAs delivered by receptor-mediated uptake FIG. 40 shows schematic representations of various embodiments of nucleic acids conjugated with ligands via linkers.

EXAMPLES

The numbering referred to in each example is specific for said example.

Example 1

Modified and conjugated siRNA molecules used for functional examples herein.

LPA-1038 Derivatives

GalNAc-LPA-1038-L1

First strand
            (SEQ ID NO: 119, based on SEQ ID NO 5)
OMeA-(ps)-FU-(ps)-OMeA-FA-OMeC-FU-OMeC-FU-OMeG-FU- OMeC-FC-OMeA-FU-OMeU-FA-OMeC-(ps)-FC-(ps)-OMeA 3'

Second strand
  (SEQ ID NO: 120, based on SEQ ID NO SEQ ID NO 6)
5'[ST23 (ps)]3 long trebler (ps)FU-OMeG-FG-OMeU- FA-OMeA-FU-OMeG-FG-OMeA-FC-OMeA-FG-OMeA-FG-OMeU- FU-(ps)-OMeA-(ps)-FU 3'

GalNAc-LPA-1038-L6

First strand
            (SEQ ID NO: 121, based on SEQ ID NO 5)
OMeA-(ps)-FU-(ps)-OMeA-FA-OMeC-FU-OMeC-FU-OMeG-FU- OMeC-FC-OMeA-FU-OMeU-FA-OMeC-(ps)-FC-(ps)-OMeA 3'

Second strand
            (SEQ ID NO: 122, based on SEQ ID NO 6)
5'[ST23 (ps)]3 ST43 (ps)FU-OMeG-FG-OMeU-FA-OMeA-FU- OMeG-FG-OMeA-FC-OMeA-FG-OMeA-FG-OMeU-FU-(ps)-OMeA- (ps)-FU 3'

FN (N=A, C, G, U) denotes 2' Fluoro, 2' DeoxyNucleosides
OMeN (N=A, C, G, U) denotes 2'O Methyl Nucleosides
(ps) indicates a phosphorothioate linkage
   ST23 and ST43 are as below.

A Further Example are LPA 1041 Derivatives

GalNAc-LPA-1041-L1

First strand
            (SEQ ID NO: 123, based on SEQ ID NO 9)
5' OMeA-(ps)-FU-(ps)-OMeA-FA-OMeC-FU-OMeC-FU-OMeG- FU-OMeC-FC-OMeA-FU-OMeU-FA-OMeC-(ps)-FC-(ps)-OMeG

3'

Second strand
            (SEQ ID NO: 124, based on SEQ ID NO 10)
5'[ST23 (ps)]3 long trebler (ps) FC-OMeG-FG-OMeU- FA-OMeA-FU-OMeG-FG-OMeA-FC-OMeA-FG-OMeA-FG-OMeU-FU- (ps)-OMeA-(ps)-FU 3'

GalNAc-LPA-1041-L6

First strand
            (SEQ ID NO: 125, based on SEQ ID NO 9)
5' OMeA-(ps)-FU-(ps)-OMeA-FA-OMeC-FU-OMeC-FU-OMeG- FU-OMeC-FC-OMeA-FU-OMeU-FA-OMeC-(ps)-FC-(ps)-OMeG

3'

Second strand
            (SEQ ID NO: 126, based on SEQ ID NO 10)
5'[ST23 (ps)]3 ST43 (ps) FC-OMeG-FG-OMeU-FA-OMeA- FU-OMeG-FG-OMeA-FC-OMeA-FG-OMeA-FG-OMeU-FU-(ps)-

OMeA-(ps)-FU 3'

FN (N=A, C, G, U) denotes 2' Fluoro, 2' DeoxyNucleosides
OMeN (N=A, C, G, U) denotes 2'O Methyl Nucleosides
(ps) indicates a phosphorothioate linkage
   ST23 and ST43 are as below.
   ST23 is a GalNac C4 phosphoramidite (structure components as below)

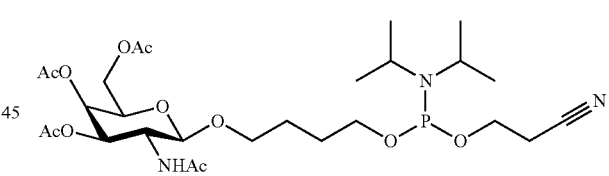

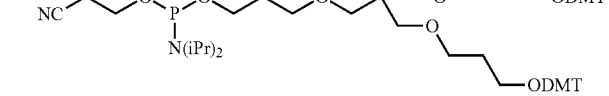

Long trebler (STKS)

ST41 is as follows:

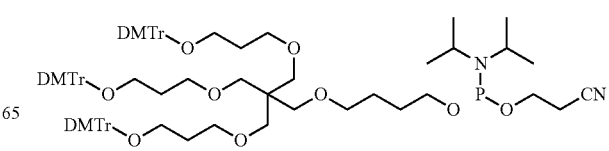

ST43 is as follows and as described in WO2017/174657:

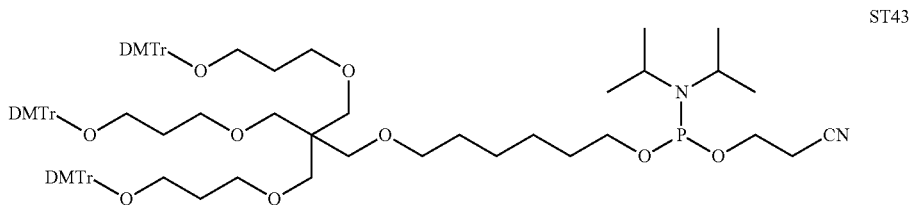

ST43

All oligonucleotides were either obtained from commercial oligonucleotide manufacturers (Biospring, Frankfurt, Germany, or RiboBio, Guangzhou, Guangdong, PRC) or synthesized on an AKTA oligopilot synthesizer (in house) using standard phosphoramidite chemistry. Commercially available solid support and 2'O-Methyl RNA phosphoramidites, 2' Fluoro DNA phosphoramidites (all standard protection) and commercially available long trebler phosphoramidite (Glen research) were used. Synthesis was performed using 0.1 M solutions of the phosphoramidite in dry acetonitrile and benzylthiotetrazole (BTT) was used as activator (0.3M in acetonitrile). All other reagents were commercially available standard reagents.

Conjugation of the respective GalNac synthon (e.g., ST23, ST41 or ST43) was achieved by coupling of the respective phosphoramidite to the 5' end of the oligochain under standard phosphoramidite coupling conditions. Phosphorothioates were introduced using standard commercially available thiolation reagents (EDITH, Link technologies).

The single strands were cleaved off the CPG by using methylamine (40% aqueous) and the resulting crude oligonucleotide was purified by Ion exchange chromatography (Resource Q, 6 mL, GE Healthcare) on a AKTA Pure HPLC System using a Sodium chloride gradient. Product containing fractions were pooled, desalted on a size exclusion column (Zetadex, EMP Biotech) and lyophilised.

For annealing, equimolar amounts of the respective single strands were dissolved in water and heated to 80° C. for 5 min. After gradual cooling to RT the resulting duplex was lyophilised.

The sequences of the resulting nucleic acids (siRNAs) are set out in Table 1 below.

TABLE 1

Table 1: Non-conjugated nucleic acid sequences tested for inhibition of LPA mRNA expression. Sequences and applied modification pattern are indicated

| SEQ. ID NO: | siRNA ID | strand | Sequence | Modifications |
|---|---|---|---|---|
| 1 | LPA-1014 | first strand | 5'ucguauaacaauaaggggc 3' | 5381616272616284847 |
| 2 | | second strand | 5'gccccuuauuguuauacga 3' | 4737351615451616382 |
| 3 | LPA-1024 | first strand | 5'gauaacucuguccauuacc 3' | 8252635354537251637 |
| 4 | | second strand | 5'gguaauggacagaguuauc 3' | 4816254827282815253 |
| 5 | LPA-1038 | first strand | 5'auaacucuguccauuacca 3' | 6162717181736152736 |
| 6 | | second strand | 5'ugguaauggacagaguuau 3' | 1845261846364645161 |
| 7 | LPA-1040 | first strand | 5'uaacucuguccauuaccgu 3' | 5263535453725163745 |
| 8 | | second strand | 5'acgguaauggacagaguua 3' | 2748162548272828152 |
| 9 | LPA-1041 | first strand | 5'auaacucuguccauuaccg 3' | 6162717181736152738 |
| 10 | | second strand | 5'cgguaauggacagaguuau 3' | 3845261846364645161 |
| 11 | LPA-1055 | first strand | 5'agaaugugccucgauaacu 3' | 6462545473538252635 |
| 12 | | second strand | 5'aguuaucgaggcacauucu 3' | 2815253828472725171 |
| 13 | LPA-1057 | first strand | 5'auaacucuguccaucacca 3' | 6162717181736172736 |
| 14 | | second strand | 5'uggugauggacagaguuau 3' | 1845461846364645161 |
| 15 | LPA-1058 | first strand | 5'auaacucuguccaucaccu 3' | 6162717181736172735 |
| 16 | | second strand | 5'aggugauggacagaguuau 3' | 2845461846364645161 |
| 17 | LPA-1061 | first strand | 5'uaacucuguccauuaccau 3' | 5263535453725163725 |
| 18 | | second strand | 5'augguaauggacagaguua 3' | 2548162548272828152 |

TABLE 1-continued

Table 1: Non-conjugated nucleic acid sequences tested for inhibition of LPA mRNA expression. Sequences and applied modification pattern are indicated

| SEQ. ID NO: | siRNA ID | strand | Sequence | Modifications |
|---|---|---|---|---|
| 19 | LPA-1086 | first strand | 5'augugccuugauaacucug 3' | 6181837154616271718 |
| 20 | | second strand | 5'cagaguuaucaaggcacau 3' | 3646451617264836361 |
| 21 | LPA-1099 | first strand | 5'aguuggugcugcuucagaa 3' | 6451845471835172826 |
| 22 | | second strand | 5'uucugaagcagcaccaacu 3' | 1535462836472736271 |
| 23 | LPA-1102 | first strand | 5'aauaaggggcugccacagg 3' | 6252648483547363648 |
| 24 | | second strand | 5'ccuguggcagccccuuauu 3' | 3718184728373715251 |
| 25 | LPA-1116 | first strand | 5'uaacucuguccaucaccau 3' | 5263535453725363725 |
| 26 | | second strand | 5'auggugauggacagaguua 3' | 2548182548272828152 |
| 27 | LPA-1127 | first strand | 5'augagccucgauaacucug 3' | 6182837174616271718 |
| 28 | | second strand | 5'cagaguuaucgaggcucau 3' | 3646451617464835361 |
| 29 | LPA-1128 | first strand | 5'aaugagccucgauaacucu 3' | 6254647353825263535 |
| 30 | | second strand | 5'agaguuaucgaggcucauu 3' | 2828152538284717251 |
| 31 | LPA-1141 | first strand | 5'aaugcuuccaggacauuuc 3' | 6254715372846361517 |
| 32 | | second strand | 5'gaaauguccuggaagcauu 3' | 4626181735482647251 |
| 33 | LPA-1151 | first strand | 5'acagugguggagaaugugc 3' | 6364548184646254547 |
| 34 | | second strand | 5'gcacauucuccaccacugu 3' | 4727251717363727181 |
| 35 | LPA-1171 | first strand | 5'guaugugccucgauaacuc 3' | 8161818371746162717 |
| 36 | | second strand | 5'gaguuaucgaggcacauac 3' | 4645161746483636163 |
| 37 | LPA-1177 | first strand | 5'ucgauaacucuguccauca 3' | 5382526353545372536 |
| 38 | | second strand | 5'ugauggacagaguuaucga 3' | 1825482728281525382 |
| 39 | LPA-1189 | first strand | 5'ugucacuggacauuguguc 3' | 5453635482725181817 |
| 40 | | second strand | 5'gacacaauguccagugaca 3' | 4636362545372818272 |
| 41 | LPA-1244 | first strand | 5'cugggauccaugguguaac 3' | 7184825372548181627 |
| 42 | | second strand | 5'guuacaccauggaucccag 3' | 4516363725482537364 |
| 43 | LPA-1248 | first strand | 5'agaugaccaagcuuggcag 3' | 6461827362835184728 |
| 44 | | second strand | 5'cugccaagcuuggucaucu 3' | 3547362835184536171 |

Table 1: Nucleotides modifications are depicted by the following numbers (column 4),
1 = 2'F-dU, 2 = 2'F-dA, 3 = 2'F-dC, 4 = 2'F-dG, 5 = 2'-OMe-rU; 6 = 2'-OMe-rA; 7 = 2'-OMe-rC; 8 = 2'-OMe-rG.

TABLE 2

Table 2: Sequences of LPA, APOB, beta-Actin and PTEN qPCR amplicon sets that were used to measure mRNA levels are shown below.

| Gene | Species | Sequences | SEQ ID NO: |
|---|---|---|---|
| LPA: (upper) | human | 5' AAGTGTCCTTGCGACGTCC 3' | 45 |
| LPA: (lower) | | 5' CCTGGACTGTGGGGCTTT 3' | 46 |
| LPA: (probe) | | 5' CTGTTTCTGAACAAGCACCAACGGAGC 3' | 47 |
| LPA (upper) | cynomolgus | 5' GTGTCCTCGCAACGTCCA 3' | 48 |
| LPA (lower) | | 5' GACCCCGGGGCTTTG 3' | 49 |
| LPA (probe) | | 5' TGGCTGTTTCTGAACAAGCACCAATGG 3' | 50 |

TABLE 2-continued

Table 2: Sequences of LPA, APOB, beta-Actin and PTEN qPCR amplicon sets that were used to measure mRNA levels are shown below.

| Gene | Species | Sequences | SEQ ID NO: |
|---|---|---|---|
| APOB (upper) | human | 5' TCATTCCTTCCCCAAAGAGACC 3' | 51 |
| APOB (lower) | | 5' CACCTCCGTTTTGGTGGTAGAG 3' | 52 |
| APOB (probe) | | 5' CAAGCTGCTCAGTGGAGGCAACACATTA 3' | 53 |
| beta-Actin (upper) | human | 5' GCATGGGTCAGAAGGATTCCTAT 3' | 54 |
| beta-Actin (lower) | | 5' TGTAGAAGGTGTGGTGCCAGATT 3' | 55 |
| beta-Actin (probe) | | 5' TCGAGCACGGCATCGTCACCAA 3' | 56 |
| beta-Actin (upper) | cynomolgus | 5' AAGGCCAACCGCGAGAAG 3' | 57 |
| beta-Actin (lower) | | 5' AGAGGCGTACAGGGACAGCA 3' | 58 |
| beta-Actin (probe) | | 5' TGAGACCTTCAACACCCCAGCCATGTAC 3' | 59 |
| PPIB (upper) | human | 5' AGATGTAGGCCGGGTGATCTTT 3' | 60 |
| PPIB (lower) | | 5' GTAGCCAAATCCTTTCTCTCCTGT 3' | 61 |
| PPIB (probe) | | 5' TGTTCCAAAAACAGTGGATAATTTTGTGGCC 3' | 62 |

Example 2

Screening of non-conjugated siRNA molecules (Table 1) for inhibition of LPA mRNA expression in human RT-4 cells.

Figure 1:
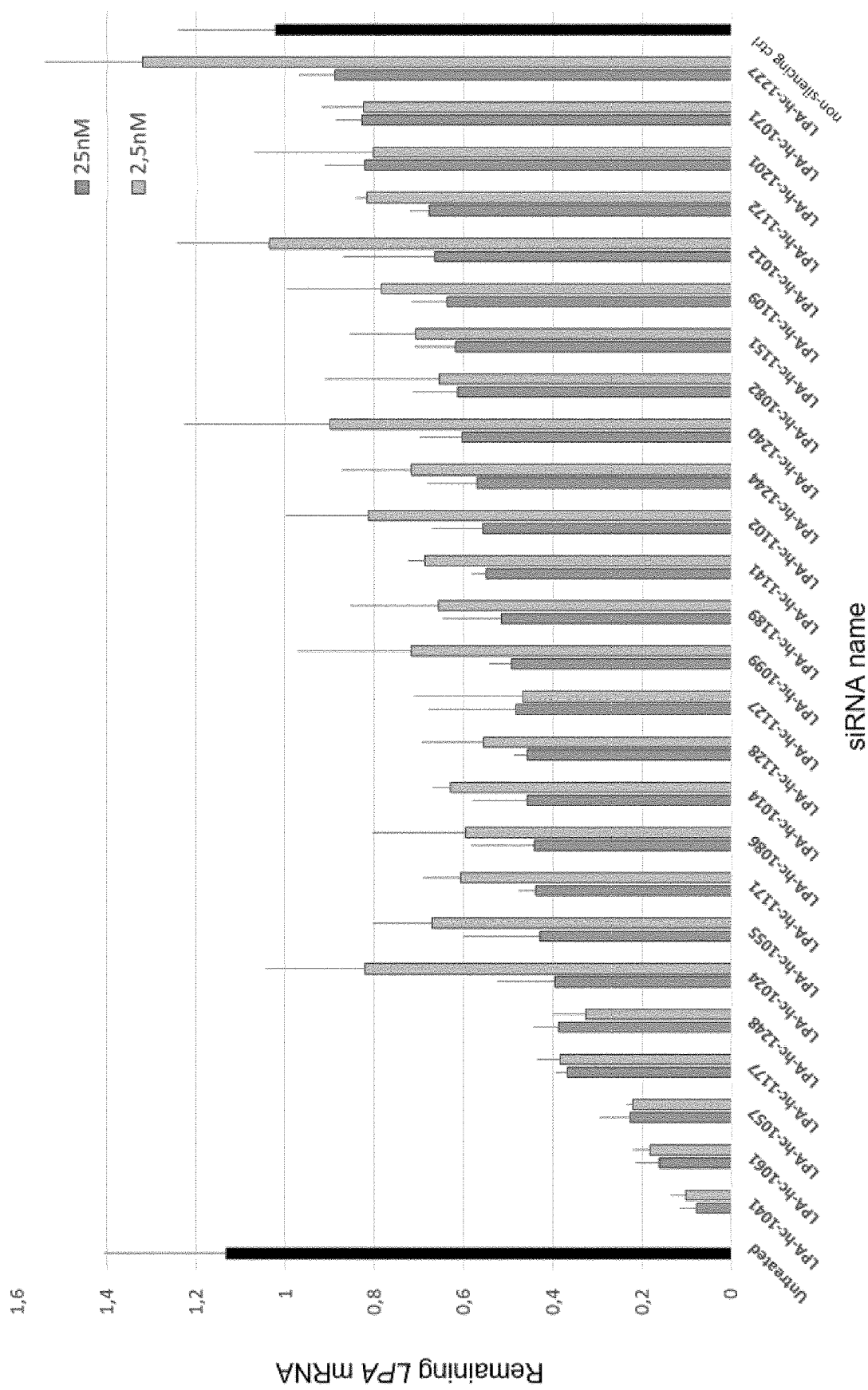
FIG. 1 shows the results of a non-conjugated siRNA molecule screen for inhibition of LPA mRNA expression in human RT-4 cells.

Liposomal transfection complexes were prepared in triplicate at a ratio of 1.5 µl RNAiMax (ThermoFisher)/80 pmol of the indicated siRNA molecules. The complex was diluted to the indicated concentrations of 2.5 nM and 25 nM, respectively (values represented pairwise as light and darker grey bars). RT4 human urinary bladder transitional cell papilloma cells expressing endogenously LPA were seeded at a density of 125.000 cells per well in 24-well format on top of previously plated transfection complexes (reverse transfection) at the indicated concentration. 24 hours after transfection total RNA was isolated using the Spin Cell Mini Kit 250 (Stratec). LPA mRNA levels were determined by qRT-PCR relative to PP/B mRNA expression in the respective samples as housekeeping transcript. Values were normalized to the amount of LPA mRNA detected in untreated cells (intraplate). A non-silencing siRNA compound was transfected as an additional control. Means and SD of normalized triplicate values are shown. Results are shown in FIG. 1.

Example 3

Dose response of non-conjugated LPA-targeting siRNA compounds on LPA mRNA expression in human RT-4 cells.

Figure 2A:
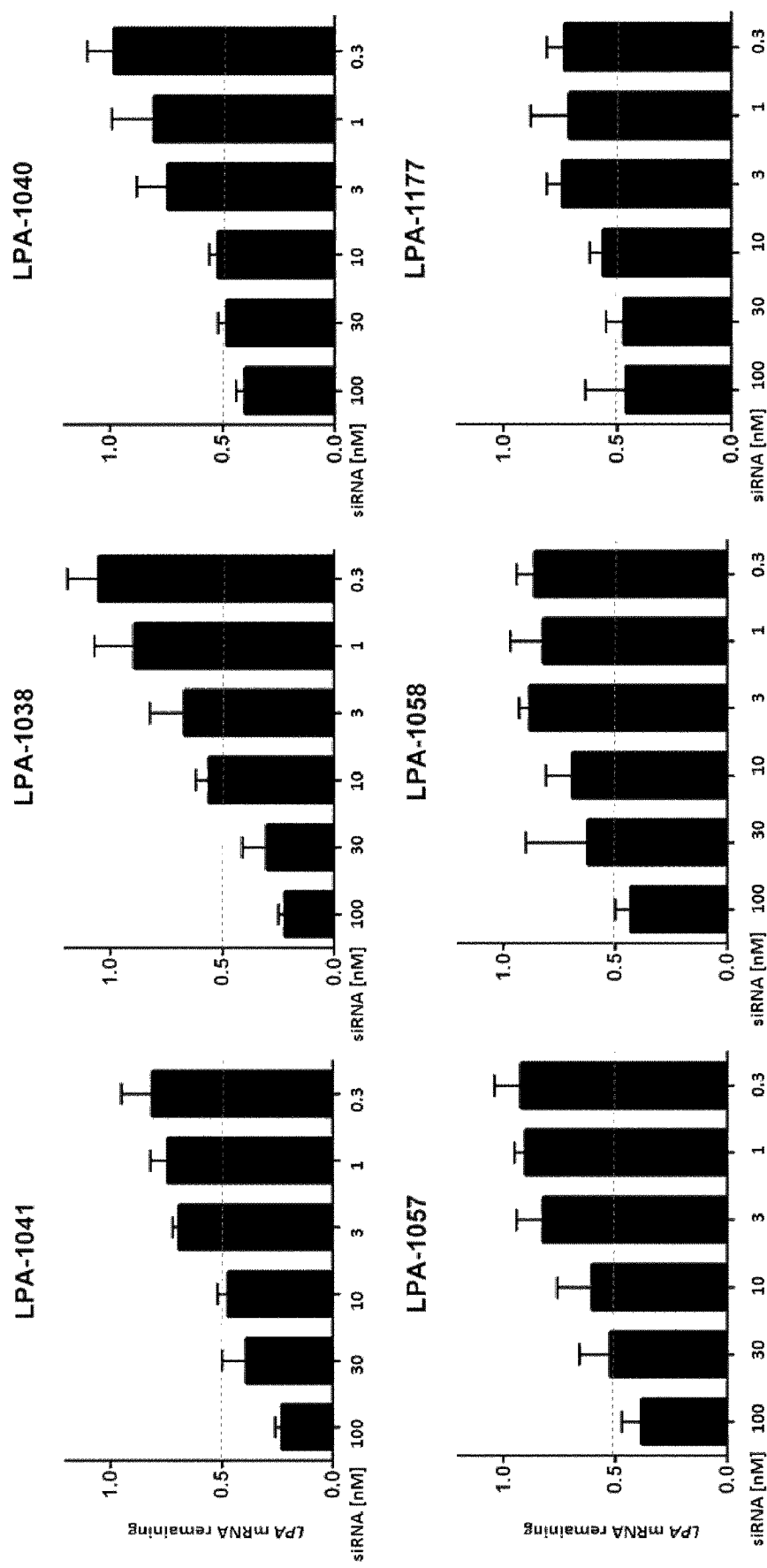
FIGS. 2A and 2B show the dose response of non-conjugated LPA-targeting siRNA molecules on LPA mRNA expression in human RT-4 cells.
Figure 2B:
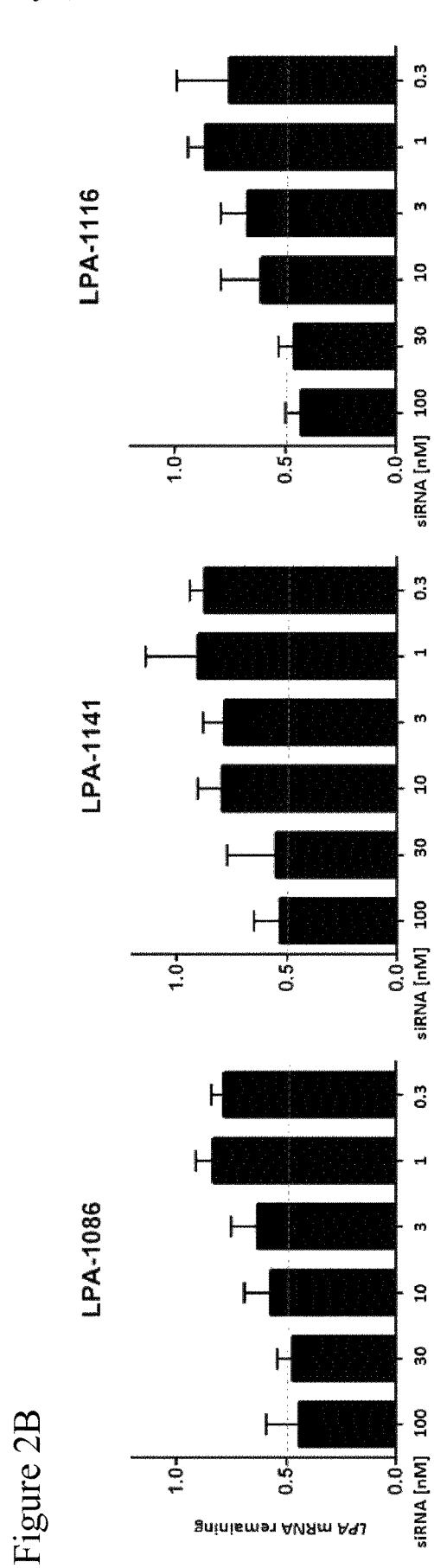

RT4 human urinary bladder transitional cell papilloma cells were reversely transfected as described above (Example 2) and treated at the indicated concentration (range 100 nM to 0.2 nM) with the different non-conjugated siRNA compounds (Table 1) as labeled. 24 h post transfection, total RNA was isolated using the Spin Cell Mini Kit 250 (Stratec). LPA mRNA levels were determined by qRT-PCR relative to PP/B mRNA expression in the respective samples as housekeeping transcript. Values were normalized to the amount of LPA mRNA detected in untreated cells. The bars represent the remaining LPA mRNA expression for each data point. Results are shown in FIG. 2.

Example 4

Inhibition of LPA mRNA expression in human and cynomolgus primary hepatocytes by different doses of GalNAc-L1 LPA-1038 conjugated siRNA molecule delivered by receptor-mediated uptake.

Figure 3:
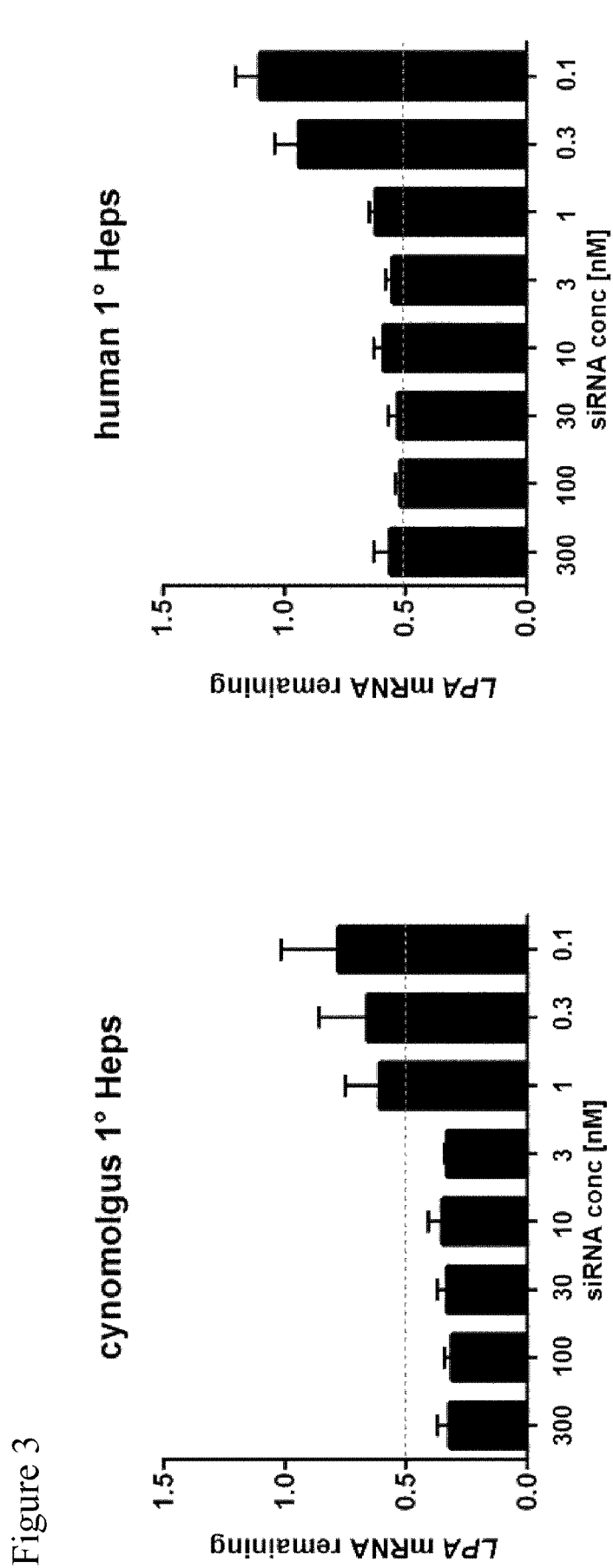
FIG. 3 shows the inhibition of LPA mRNA expression in human and cynomolgus primary hepatocytes by different doses of GalNAc-L1 LPA-1038 conjugated siRNA molecules delivered by receptor-mediated uptake.
Figure 4A:
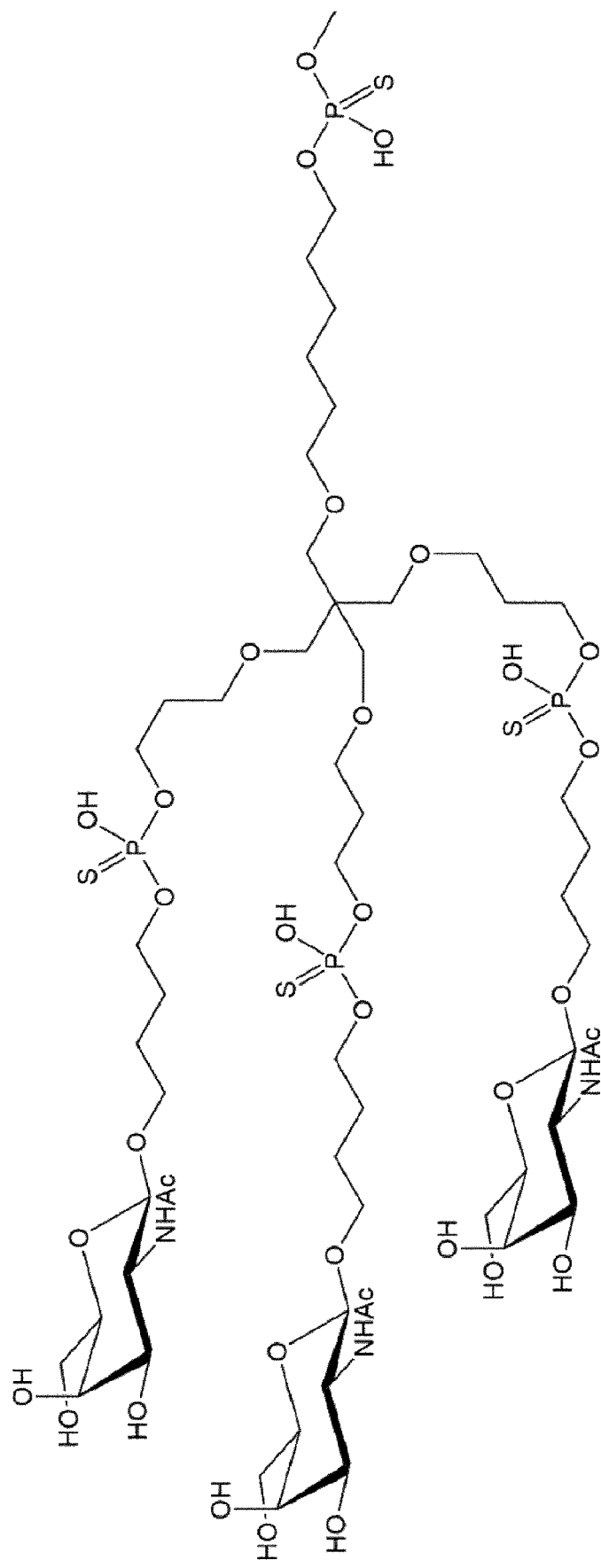
FIGS. 4A and 4B show examples of the structure of the GalNAc ligands with different L1 and L6 linkers, respectively, to which the exemplified oligonucleotides were conjugated.
Figure 4B:
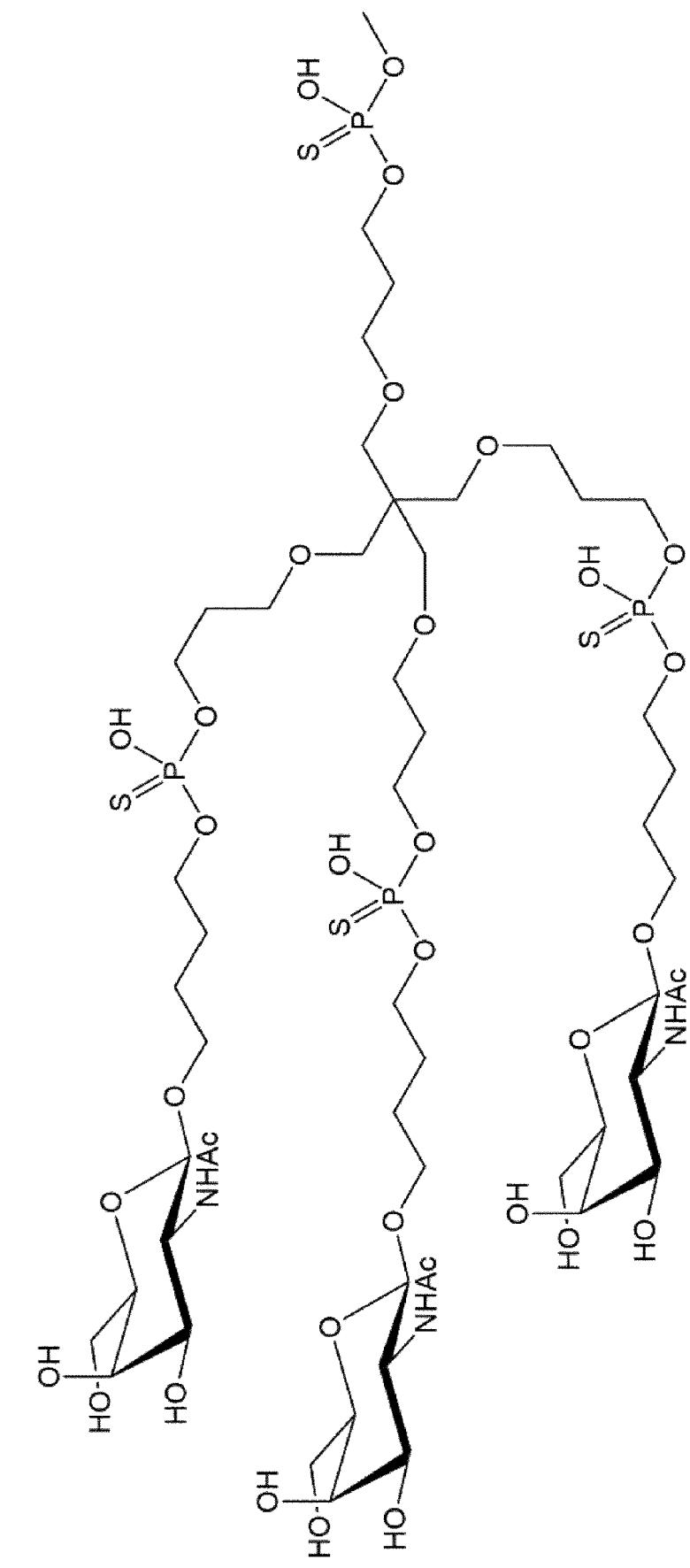

Primary hepatocytes (ThermoFisher) were plated on collagen-coated 96-well plates at densities of 45,000 cells per well (cynomolgus) and 30,000 cells per well (human). GalNAc-L1-conjugated LPA-1038 was added immediately after plating at the indicated concentrations (nM). 24 hours after siRNA treatment total RNA was isolated using the InviTrap RNA cell HTS 96 well kit (Stratec). LPA mRNA levels were determined by qRT-PCR relative to Actin (cynomolgus) or APOB (human) mRNA levels in the respective samples as housekeeping transcript. Values were normalized to LPA expression in untreated cells. Means and SD of normalized triplicate values of remaining LPA mRNA levels are shown as black bars. Results shown in FIG. 3.

Example 5

Knockdown of LPA-mRNA in human primary hepatocytes by the different indicated L6-GalNAc conjugated siRNAs in primary human hepatocytes upon receptor-mediated delivery.

Figure 5:
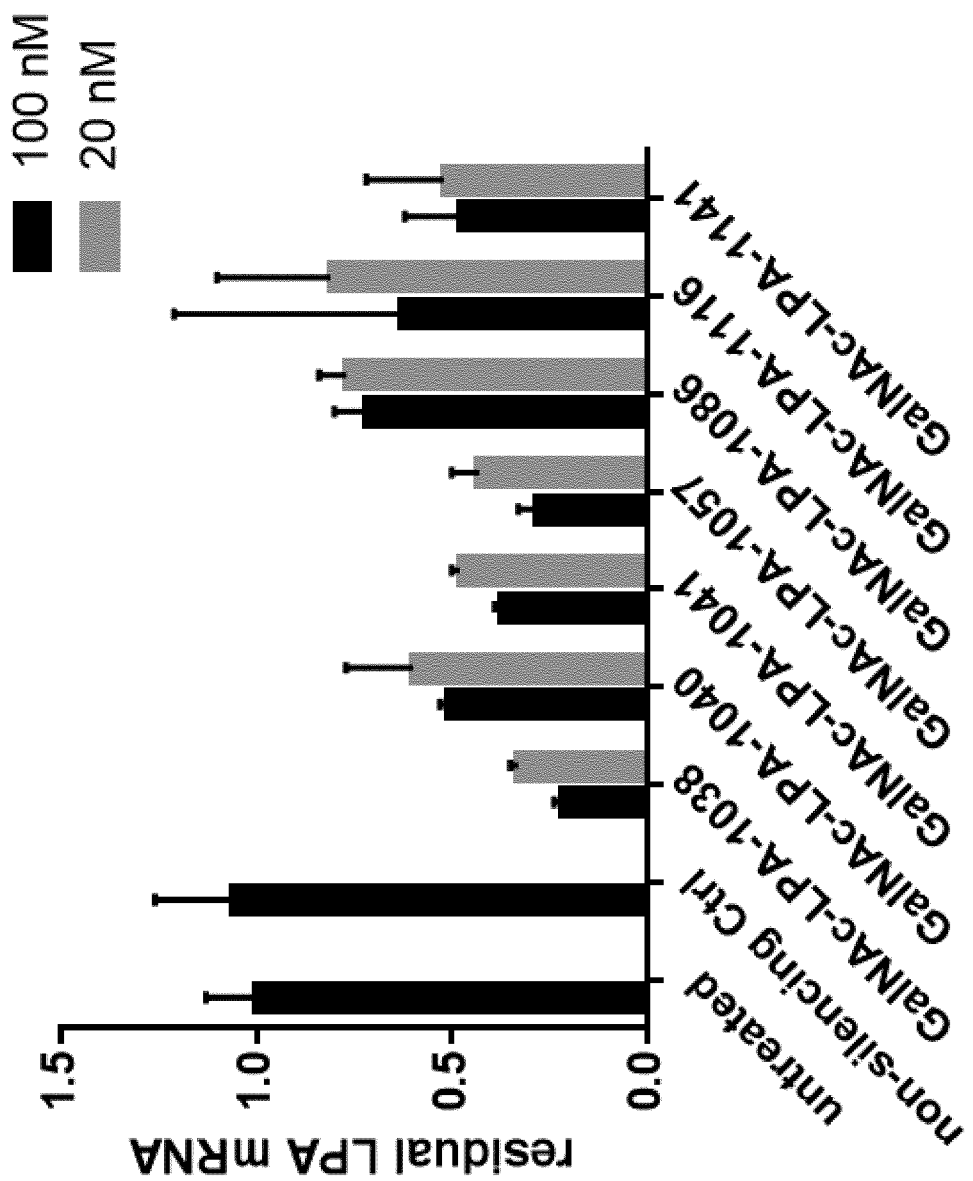
FIG. 5 shows representative examples of the knockdown of LPA-mRNA by L6-conjugated GalNAc siRNAs indicated in primary human hepatocytes delivered by receptor-mediated uptake.

Primary human hepatocytes (ThermoFisher) were plated on collagen-coated 96-well plates at 30,000 cells per well (96 well format). GalNAc-L6-conjugated siRNAs including a non-silencing control were added immediately after cell plating at the two indicated concentrations. 24 hours after siRNA treatment total RNA was isolated using the InviTrap RNA cell HTS 96 well kit (Stratec). LPA mRNA expression levels were determined by qRT-PCR relative to APOB mRNA as housekeeping transcript. Values were normalized to LPA mRNA expression in untreated cells and remaining LPA mRNA levels represented pairwise as bars (100 nM black bars, 20 nM grey bars). Means and SD of normalized triplicate values are shown in FIG. 5.

Example 6—Synthesis of Conjugates

Example compounds were synthesised according to methods described below and methods known to the person skilled in the art. Assembly of the oligonucleotide chain and linker building blocks was performed by solid phase synthesis applying phosphoramidite methodology. GalNAc conjugation was achieved by peptide bond formation of a GalNAc-carboxylic acid building block to the prior assembled and purified oligonucleotide having the necessary number of amino modified linker building blocks attached.

Oligonucleotide synthesis, deprotection and purification followed standard procedures that are known in the art.

All Oligonucleotides were synthesized on an AKTA oligopilot synthesizer using standard phosphoramidite chemistry. Commercially available solid support and 2'O-Methyl RNA phosphoramidites, 2' Fluoro, 2' Deoxy RNA phosphoramidites (all standard protection, ChemGenes, Link-Tech) and commercially available 3'-Amino Modifier TFA Amino C-6 Icaa CPG 500 Å (Chemgenes) were used. Per-acetylated galactose amine 8 is commercially available.

Ancillary reagents were purchased from EMP Biotech. Synthesis was performed using a 0.1 M solution of the phosphoramidite in dry acetonitrile and benzylthiotetrazole (BTT) was used as activator (0.3M in acetonitrile). Coupling time was 15 min. A Cap/OX/Cap or Cap/Thio/Cap cycle was applied (Cap: $Ac_2O$/NMI/Lutidine/Acetonitrile, Oxidizer: 0.1M $I_2$ in pyridine/$H_2O$). Phosphorothioates were introduced using standard commercially available thiolation reagent (EDITH, Link technologies). DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

Attachment of the serinol-derived linker moiety was achieved by use of either base-loaded (S)-DMT-Serinol(TFA)-succinate-Icaa-CPG 10 or a (S)-DMT-Serinol(TFA) phosphoramidite 7 (synthesis was performed as described in Hoevelmann et al. (Chem. Sci., 2016, 7, 128-135)). Triantennary GalNAc clusters (ST23/C4XLT) were introduced by successive coupling of the respective trebler amidite derivatives (C4XLT-phos) followed by the GalNAc amidite (ST23-phos).

The single strands were cleaved off the CPG by 40% aq. methylamine treatment. The resulting crude oligonucleotide was purified by ion exchange chromatography (Resource Q, 6 mL, GE Healthcare) on a AKTA Pure HPLC System using a sodium chloride gradient. Product containing fractions were pooled, desalted on a size exclusion column (Zetadex, EMP Biotech) and lyophilised.

Individual single strands were dissolved in a concentration of 60 OD/mL in $H_2O$. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80° C. for 5 min and then slowly cooled to RT. Double strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

Synthesis of Compounds 2-10

Compounds 2 to 5 and (S)-DMT-Serinol(TFA)-phosphoramidite 7 were synthesised according to literature published methods (Hoevelmann et al. Chem. Sci., 2016, 7, 128-135).

(S)-4-(3-(bis(4-methoxyphenyl)(phenyl)methoxy)-2-(2,2,2-trifluoroacetamido)propoxy)-4-oxobutanoic acid (6)

To a solution of 5 in pyridine was added succinic anhydride, followed by DMAP. The resulting mixture was stirred at room temperature overnight. All starting material was consumed, as judged by TLC. The reaction was concentrated. The crude material was chromatographed in silica gel using a gradient 0% to 5% methanol in DCM (+1% triethylamine) to afford 1.33 g of 6 (yield=38%). m/z (ESI-): 588.2 (100%), (calcd. for $C_{30}H_{29}F_3NO_8^-$ [M-H]$^-$ 588.6). 1H-NMR: (400 MHz, CDCl3) δ [ppm]=7.94 (d, 1H, NH), 7.39-7.36 (m, 2H, CHaryl), 7.29-7.25 (m, 7H, CHaryl), 6.82-6.79 (m, 4H, CHaryl), 4.51-4.47 (m, 1H), 4.31-4.24 (m 2H), 3.77 (s, 6H, 2×DMTr-OMe), 3.66-3.60 (m 16H, HNEt$_3^+$), 3.26-3.25 (m, 2H), 2.97-2.81 (m, 20H, NEt$_3$), 2.50-2.41 (4H, m), 1.48-1.45 (m, 26H, HNEt$_3^+$), 1.24-1.18 (m, 29H, NEt$_3$).

(S)-DMT-Serinol(TFA)-Succinate-Icaa-CPG (10)

The (S)-DMT-Serinol(TFA)-succinate (159 mg, 270 umol) and HBTU (113 mg, 299 umol) were dissolved in $CH_3CN$ (10 mL). Diisopropylethylamine (DIPEA, 94 µL, 540 umol) was added to the solution, and the mixture was swirled for 2 min followed by addition native amino-Icaa-CPG (500 A, 3 g, amine content: 136 umol/g). The suspension was gently shaken at room temperature on a wrist-action shaker for 16 h then filtered, and washed with DCM and EtOH. The solid support was dried under vacuum for 2 h. The unreacted amines on the support were capped by stirring with acetic anhydride/lutidine/N-methylimidazole at room temperature. The washing of the support was repeated as above. The solid was dried under vacuum to yield solid support 10 (3 g, 26 umol/g loading).

GalNAc Synthon (9)

Synthesis of the GalNAc synthon 9 was performed as described in Nair et al. J. Am. Chem. Soc., 2014, 136 (49), pp 16958-16961, in 46% yield over two steps.

The characterising data matched the published data.

Synthesis of Oligonucleotides

All single stranded oligonucleotides were synthesised according to the reaction conditions described above and in FIGS. 13 and 14.

All final single stranded products were analysed by AEX-HPLC to prove their purity. Purity is given in % FLP (% full length product) which is the percentage of the UV-area under the assigned product signal in the UV-trace of the AEX-HPLC analysis of the final product.

Identity of the respective single stranded products (non-modified, amino-modified precursors or GalNAc conjugated oligonucleotides) was proved by LC-MS analysis.

TABLE 3

| Single stranded un-conjugated oligonucleotides | | | |
|---|---|---|---|
| Product (11) | Name | MW calc. | MW (ESI-) found | % FLP (AEX-HPLC) |
| A0002 | STS16001A | 6943.3 Da | 6943.0 Da | 86.6% |
| A0006 | STS16001BL4 | 8387.5 Da | 8387.5 Da | 94.1% |
| A0130 | STS18001A | 6259.9 Da | 6259.8 Da | 76.5% |
| A0131 | STS18001BL4 | 7813.2 Da | 7813.1 Da | 74.3% |
| A0220 | STS16001B-5'1xNH2 | 6982.2 Da | 6982.1 Da | 95.7% |
| A0237 | STS16001A | 6943.3 Da | 6943.3 Da | 95.6% |
| A0244 | STS16001BV1 | 6845.2 Da | 6844.9 Da | 98.2% |
| A0264 | STS16001AV4-3'1xNH2 | 7112.4 Da | 7112.2 Da | 95.4% |
| A0329 | STS16001BV6-3'5'1xNH2 | 7183.3 Da | 7183.2 Da | 88.8% |

5'1xNH2 means refers to the position (5' end) and number (1xNH2) of free serinol derived amino groups which are available for conjugation. For example, 1x3'NH2 on A0264 means there is free amino group which can be reacted with GalNAc synthon 9 at the 3' end of the strand A0264. 3'5'1xNH2 means there is one serinol-derived free amino group which can be reacted with GalNAc linker 9 at the 3' end and the 5' end of the strand.

Synthesis of Conjugates 1-3 and Reference Conjugates 1-2

Conjugated Singles Strands for Conjugates 1-2 and Reference Conjugates 1-2

Conjugation of the GalNac synthon (9) was achieved by coupling to the serinol-amino function of the respective oligonucleotide strand 11 using a peptide coupling reagent. Therefore, the respective amino-modified precursor molecule 11 was dissolved in H₂O (500 OD/mL) and DMSO (DMSO/H₂O, 2/1, v/v) was added, followed by DIPEA (2.5% of total volume). In a separate reaction vessel pre-activation of the GalN(Ac4)-C4-acid (9) was performed by reacting 2 eq. (per amino function in the amino-modified precursor oligonucleotide 11) of the carboxylic acid component with 2 eq. of HBTU in presence of 8 eq. DIPEA in DMSO. After 2 min the pre-activated compound 9 was added to the solution of the respective amino-modified precursor molecule. After 30 min the reaction progress was monitored by LCMS or AEX-HPLC. Upon completion of the conjugation reaction the crude product was precipitated by addition of 10× iPrOH and 0.1×2M NaCl and harvested by centrifugation and decantation. To set free the acetylated hydroxyl groups in the GalNAc moieties the resulting pellet was dissolved in 40% MeNH2 (1 mL per 500 OD) and after 15 min at RT diluted in H₂O (1:10) and finally purified again by anion exchange and size exclusion chromatography and lyophilised to yield the final product 12.

TABLE 4

Single stranded GalNAc-conjugated oligonucleotides

| Product (12) | Starting Material | Name | MW calc. | MW (ESI−) found | % FLP (AEX-HPLC) |
|---|---|---|---|---|---|
| A0241 | A0220 | STS16001BL20 | 7285.5 Da | 7285.3 Da | 91.8% |
| A0268 | A0264 | STS16001AV4L33 | 7415.7 Da | 7415.4 Da | 96.9% |
| A0330 | A0329 | STS16001BV6L42 | 7789.8 Da | 7789.8 Da | 95.5% |

Double Strand Formation

Double strand formation was performed according to the methods described above.

The double strand purity is given in % double strand which is the percentage of the UV-area under the assigned product signal in the UV-trace of the IP-RP-HPLC analysis.

TABLE 5

Nucleic acid conjugates

| Product | Starting Materials | | Name | % double strand |
|---|---|---|---|---|
| | First Strand | Second Strand | | |
| Ref. Conj. 1 | A0237 | A0241 | STS16001L20 | 97.7% |
| Ref. Conj. 2 | A0268 | A0244 | STS16001L33 | 97.8% |
| Ref. Conj. 3 | A0130 | A0131 | STS18001L4 | 96.8% |
| Ref. Conj. 4 | A0002 | A0006 | STS16001L4 | 90.1% |
| Conjugate 1 | A0268 | A0241 | STS16001L24 | 96.0% |
| Conjugate 2 | A0237 | A0330 | STS16001V1L42 | 98.5% |
| Conjugate 3 | A0268 | A0330 | STS16001V1L43 | 98.2% |

Sequences

Modifications key for the following sequences:

f denotes 2' Fluoro 2' deoxyribonucleotide or 2'-fluoro ribonucleotide (the terms are interchangeable)

m denotes 2'O Methyl ribonucleotide (ps) denotes phosphorothioate linkage

Ser(GN) is a GalNAc-C4 building block attached to serinol derived linker moiety:

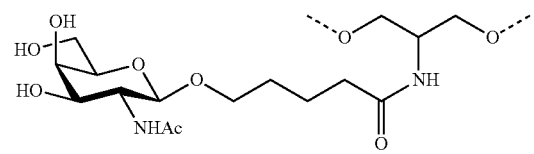

wherein the O— is the linkage between the oxygen atom and e.g. H, phosphodiester linkage or phosphorothioate linkage.

C4XLT is:

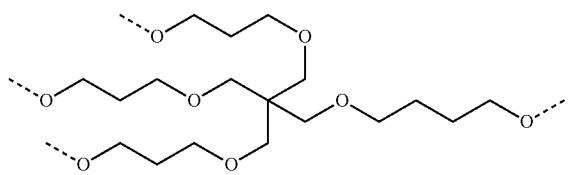

ST23 is:

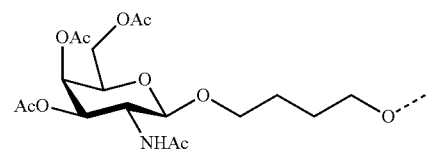

Synthesis of the phosphoramidite derivatives of C4XLT (C4XLT-phos) as well as ST23 (ST23-phos) can be performed as described in WO2017/174657.

C4XLT-phos:

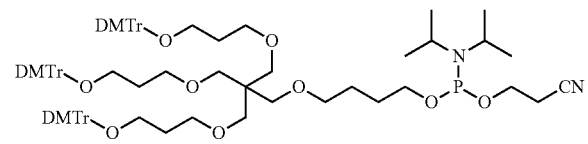

ST23-phos:

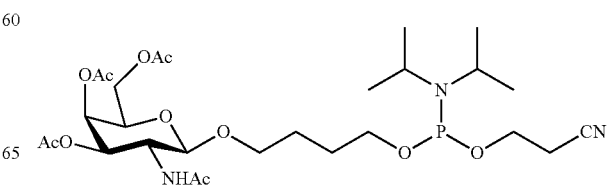

Conjugate 1

Antisense strand - STS16001AL33
(SEQ ID NO: 127)
5' mU (ps) fU (ps) mA fU mA fG mA fG mC fA mA fG mA fA mC fA mC fU mG (ps) fU (ps) mU (ps) Ser(GN) 3'

Sense strand - STS16001BL20
(SEQ ID NO: 128)
5' Ser(GN) (ps) fA mA fC mA fG mU fG mU fU mC fU mU fG mC fU mC fU mA fU (ps) mA (ps) fA 3'

Conjugate 2

Antisense strand - STS16001A
(SEQ ID NO: 129)
mU (ps) fU (ps) mA fU mA fG mA fG mC fA mA fG mA fA mC fA mC fU mG (ps) fU (ps) mU Sense strand - STS16001BV1L42
(SEQ ID NO: 130)
Ser(GN) (ps) fA (ps) mA (ps) fC mA fG mU fG mU fU mC fU mU fG mC fU mC fU mA fU (ps) mA (ps) fA (ps) Ser(GN)

Conjugate 3

Antisense strand - STS16001AL33
(SEQ ID NO: 127)
5' mU (ps) fU (ps) mA fU mA fG mA fG mC fA mA fG mA fA mC fA mC fU mG (ps) fU (ps) mU (ps) Ser(GN) 3'

Sense strand - STS16001BV1L42
(SEQ ID NO: 130)
5' Ser(GN) (ps) fA (ps) mA (ps) fC mA fG mU fG mU fU mC fU mU fG mC fU mC fU mA fU (ps) mA (ps) fA (ps) Ser(GN) 3'

Reference Conjugate 1

Antisense strand - STS16001A
(SEQ ID NO: 129)
mU (ps) fU (ps) mA fU mA fG mA fG mC fA mA fG mA fA mC fA mC fU mG (ps) fU (ps) mU Sense strand - STS16001BL20
(SEQ ID NO: 128)
Ser(GN) (ps) fA mA fC mA fG mU fG mU fU mC fU mU fG mC fU mC fU mA fU (ps) mA (ps) fA

Reference Conjugate 2

Antisense strand - STS16001AL33
(SEQ ID NO: 127)
mU (ps) fU (ps) mA fU mA fG mA fG mC fA mA fG mA fA mC fA mC fU mG (ps) fU (ps) mU (ps) Ser(GN)

Sense strand - STS16001V1B
(SEQ ID NO: 131)
fA (ps) mA (ps) fC mA fG mU fG mU fU mC fU mU fG mC fU mC fU mA fU (ps) mA (ps) fA

Reference Conjugate 3

Antisense strand - STS18001A
(A0130; SEQ ID NO: 132)
mU (ps) fC (ps) mG fA mA fG mU fA mU fU mC fC mG fC mG fU mA (ps) fC (ps) mG Sense strand - STS18001BL4
(A0131, SEQ ID NO: 133)
[(ST23) (ps)]₃ C4XLT (ps) fC mG fU mA fC mG fC mG fG mA fA mU fA mC fU mU fC (ps) mG (ps) fA

Reference Conjugate 4

Antisense strand - STS16001AL33
(SEQ ID NO: 127)
mU (ps) fU (ps) mA fU mA fG mA fG mC fA mA fG mA fA mC fA mC fU mG (ps) fU (ps) mU Sense strand - STS16001BL4
(SE ID NO: 134)
5'[(ST23) (ps)]₃ C4XLT(ps) fA (ps) mA (ps) fC mA fG mU fG mU fU mC fU mU fG mC fU mC fU mA fU (ps) mA (ps) fA

Example 7—In Vitro Determination of TTR Knockdown of Various TTR siRNA GalNAc Conjugates Murine primary hepatocytes were seeded into collagen pre-coated 96 well plates (Thermo Fisher Scientific, #A1142803) at a cell density of 30,000 cells per well and treated with siRNA-conjugates at concentrations ranging from 10 nM to 0.0001 nM. 24 h post treatment cells were lysed and RNA extracted with InviTrap® RNA Cell HTS 96 Kit/C24×96 preps (Stratec #7061300400) according to the manufactures protocol. Transcripts levels of TTR and housekeeping mRNA (PtenII) were quantified by TaqMan analysis.

Target gene expression in primary murine hepatocytes 24 h following treatment with the conjugates of the invention, Conjugates 1-3, showed that target gene expression decreases as the dose of the conjugate increased compared to the negative controls (see "UT" column and Reference Conjugate 3), as shown in FIG. 15. This indicates that the first strand is binding to the target gene, thus lowering gene expression. FIG. 15 also shows the target gene expression levels of Reference Conjugates 1 and 2 which act as comparator conjugates. As can be seen from a comparison between the data presented in FIGS. 15A and 15C, and 15B and 15C, the conjugates of the invention (Conjugates 1-3) decrease the target gene expression compared to Reference Conjugates 1 and 2. The most effective conjugate at 0.01 nM appears to be Conjugate 2. The most effective conjugate at 0.1 nM, 0.5 nM, 1 nM and 10 nM appears to be Conjugate 3.

Example 8—In Vivo Time Course of Serum TTR in Mice

C57BL/6 mice were treated s.c. with 1 mg/kg siRNA-conjugates at day 0. Serum samples were taken at day 7, 14, and 27 by orbital sinus bleeding and stored at −20° C. until analysis. Serum TTR quantification was performed with a Mouse Prealbumin ELISA (ALPCO, 41-PALMS/lot 22, 2008003B) according to the manufacturers protocol (sample dilution 1:8000 or 1:800).

The results of the time course of serum TTR in c57BL/6 mice cohorts of n=4 at 7, 14, and 27 days post s.c. treatment with 1 mg/kg Conjugates 1-3, Reference Conjugates 1, 2 and 4, and mock treated (PBS) individuals is shown in FIG. 16. As indicated by the data in FIG. 16, the conjugates of the invention are particularly effective at reducing target gene expression compared to the negative control (PBS) and Reference Conjugates 1, 2, and in particular to Reference Conjugate 4. Conjugates 2 and 3 are also more effective than Reference Conjugates 1, 2 and 4. The most effective conjugate is Conjugate 2. Thus, it may be expected that the dosing level of Conjugate 3 would be about three times lower to achieve the same initial knock down and would also result in longer duration of knock down as compared to Reference Conjugate 4.

Example 9—Synthesis of Conjugates 2

Example compounds were synthesised according to methods described below and methods known to the person skilled in the art. Assembly of the oligonucleotide chain and linker building blocks was performed by solid phase synthesis applying phosphoramidite methodology. GalNAc conjugation was achieved by peptide bond formation of a GalNAc-carboxylic acid building block to the prior assembled and purified oligonucleotide having the necessary number of amino modified linker building blocks attached.

Oligonucleotide synthesis, deprotection and purification followed standard procedures that are known in the art.

All Oligonucleotides were synthesized on an AKTA oligopilot synthesizer using standard phosphoramidite chemistry. Commercially available solid support and 2'O-Methyl RNA phosphoramidites, 2' Fluoro, 2' Deoxy RNA phosphoramidites (all standard protection, ChemGenes, LinkTech) and commercially available 3'-Amino Modifier TFA Amino C-6 Icaa CPG 500 Å (Chemgenes) were used. Per-acetylated galactose amine 8 is commercially available.

Ancillary reagents were purchased from EMP Biotech. Synthesis was performed using a 0.1 M solution of the phosphoramidite in dry acetonitrile and benzylthiotetrazole (BTT) was used as activator (0.3M in acetonitrile). Coupling time was 15 min. A Cap/OX/Cap or Cap/Thio/Cap cycle was applied (Cap: Ac$_2$O/NMI/Lutidine/Acetonitrile, Oxidizer: 0.1M I$_2$ in pyridine/H$_2$O). Phosphorothioates were introduced using standard commercially available thiolation reagent (EDITH, Link technologies). DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

Attachment of the serinol-derived linker moiety was achieved by use of either base-loaded (S)-DMT-Serinol (TFA)-succinate-Icaa-CPG 10 or a (S)-DMT-Serinol(TFA) phosphoramidite 7 (synthesis was performed as described in literature Hoevelmann et al. Chem. Sci., 2016, 7, 128-135). Tri-antennary GalNAc clusters (ST23/C4XLT or ST23/C6XLT) were introduced by successive coupling of the respective trebler amidite derivatives (C4XLT-phos or C6XLT-phos) followed by the GalNAc amidite (ST23-phos).

The single strands were cleaved off the CPG by 40% aq. methylamine treatment. The resulting crude oligonucleotide was purified by ion exchange chromatography (Resource Q, 6 mL, GE Healthcare) on a AKTA Pure HPLC System using a sodium chloride gradient. Product containing fractions were pooled, desalted on a size exclusion column (Zetadex, EMP Biotech) and lyophilised.

Individual single strands were dissolved in a concentration of 60 OD/mL in H$_2$O. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80° C. for 5 min and then slowly cooled to RT. Double strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

Synthesis of Compounds 2-10

Compounds 2 to 5 and (S)-DMT-Serinol(TFA)-phosphoramidite 7 were synthesised according to literature published methods (Hoevelmann et al. Chem. Sci., 2016, 7, 128-135).

(S)-4-(3-(bis(4-methoxyphenyl)(phenyl)methoxy)-2-(2,2,2-trifluoroacetamido)propoxy)-4-oxobutanoic acid (6)

To a solution of 5 in pyridine was added succinic anhydride, followed by DMAP. The resulting mixture was stirred at room temperature overnight. All starting material was consumed, as judged by TLC. The reaction was concentrated. The crude material was chromatographed in silica gel using a gradient 0% to 5% methanol in DCM (+1% triethylamine) to afford 1.33 g of 6 (yield=38%). m/z (ESI-): 588.2 (100%), (calcd. for C30H29F3NO8$^-$[M-H]$^-$ 588.6). 1H-NMR: (400 MHz, CDCl3) δ [ppm]=7.94 (d, 1H, NH), 7.39-7.36 (m, 2H, CHaryl), 7.29-7.25 (m, 7H, CHaryl), 6.82-6.79 (m, 4H, CHaryl), 4.51-4.47 (m, 1H), 4.31-4.24 (m, 2H), 3.77 (s, 6H, 2×DMTr-OMe), 3.66-3.60 (m, 16H, HNEt$_3$$^+$), 3.26-3.25 (m, 2H), 2.97-2.81 (m, 20H, NEt$_3$), 2.50-2.41 (4H, m), 1.48-1.45 (m, 26H, HNEt$_3$$^+$), 1.24-1.18 (m, 29H, NEt$_3$).

(S)-DMT-Serinol(TFA)-succinate-Icaa-CPG (10)

The (S)-DMT-Serinol(TFA)-succinate (159 mg, 270 umol) and HBTU (113 mg, 299 umol) were dissolved in CH$_3$CN (10 mL). Diisopropylethylamine (DIPEA, 94 μL, 540 umol) was added to the solution, and the mixture was swirled for 2 min followed by addition native amino-Icaa-CPG (500 A, 3 g, amine content: 136 umol/g). The suspension was gently shaken at room temperature on a wrist-action shaker for 16 h then filtered and washed with DCM and EtOH. The solid support was dried under vacuum for 2 h. The unreacted amines on the support were capped by stirring with acetic anhydride/lutidine/N-methylimidazole at room temperature. The washing of the support was repeated as above. The solid was dried under vacuum to yield solid support 10 (3 g, 26 umol/g loading).

GalNAc Synthon (9)

Synthesis of the GalNAc synthon 9 was performed as described in Nair et al. J. Am. Chem. Soc., 2014, 136 (49), pp 16958-16961, in 46% yield over two steps.

The characterising data matched the published data.

Synthesis of Oligonucleotides

All single stranded oligonucleotides were synthesised according to the reaction conditions described above and in FIGS. 13 and 14.

All final single stranded products were analysed by AEX-HPLC to prove their purity. Purity is given in % FLP (% full length product) which is the percentage of the UV-area under the assigned product signal in the UV-trace of the AEX-HPLC analysis of the final product. Identity of the respective single stranded products (non-modified, amino-modified precursors, C4XLT/ST23 or C6XLT/ST23 GalNAc conjugated oligonucleotides) was proved by LC-MS analysis.

TABLE 7

Single stranded un-conjugated and on-column conjugated oligonucleotides

| Product (11) | MW calc. | MW (ESI−) Found | % FLP (AEX-HPLC) |
|---|---|---|---|
| X0385A | 6315.0 Da | 6314.6 Da | 91.0% |
| X0385B-prec | 6593.1 Da | 6593.1 Da | 87.5% |
| X038BA | 6315.0 Da | 6314.6 Da | 91.0% |
| X0386B-prec | 6547.1 Da | 6546.9 Da | 87.5% |
| X0383A | 6315.0 Da | 6314.5 Da | 91.9% |
| X0383B-prec | 6508.8 Da | 6508.6 Da | 84.6% |
| X0371A | 6416.1 Da | 6416.1 Da | 88.4% |
| X0371B-prec | 6522.0 Da | 6521.8 Da | 91.9% |
| X0320A | 6143.8 Da | 6143.7 Da | 94.6% |
| X0320B-prec | 6665.0 Da | 6664.8 Da | 87.0% |
| X0477A | 6143.8 Da | 6143.4 Da | 85.6% |
| X0477B-prec | 6749.3 Da | 6749.2 Da | 83.1% |
| X0027A | 6416.1 Da | 6415.8 Da | 92.8% |
| X0027B | 7642.0 Da | 7641.8 Da | 88.2% |

Synthesis of Conjugates 1-3 and Reference Conjugates 1-2

Conjugated Single Strands for Conjugates 1-2 and Reference Conjugates 1-2

Conjugation of the GalNac synthon (9) was achieved by coupling to the serinol-amino function of the respective oligonucleotide strand 11 using a peptide coupling reagent. Therefore, the respective amino-modified precursor molecule 11 was dissolved in H$_2$O (500 OD/mL) and DMSO (DMSO/H$_2$O, 2/1, v/v) was added, followed by DIPEA (2.5% of total volume). In a separate reaction vessel pre-activation of the GalN(Ac4)-C4-acid (9) was performed by reacting 2 eq. (per amino function in the amino-modified precursor oligonucleotide 11) of the carboxylic acid component with 2 eq. of HBTU in presence of 8 eq. DIPEA in DMSO. After 2 min the pre-activated compound 9 was added to the solution of the respective amino-modified precursor molecule. After 30 min the reaction progress was monitored by LCMS or AEX-HPLC. Upon completion of the conjugation reaction the crude product was precipitated by addition of 10× iPrOH and 0.1×2M NaCl and harvested by centrifugation and decantation. To set free the acetylated hydroxyl groups in the GalNAc moieties the resulting pellet was dissolved in 40% MeNH2 (1 mL per 500 OD) and after 15 min at RT diluted in H$_2$O (1:10) and finally purified again by anion exchange and size exclusion chromatography and lyophilised to yield the final product 12.

TABLE 8

Single stranded GalNAc-conjugated oligonucleotides

| Product (12) | Starting Material (11) | MW calc. | MW (ESI−) found | % FLP (AEX-HPLC) |
|---|---|---|---|---|
| X0385B | X0385B-prec | 7199.8 Da | 7199.3 Da | 93.2% |
| X0386B | X0386B-prec | 7153.8 da | 7153.0 Da | 86.2% |
| X0383B | X0383B-prec | 7115.5 Da | 7115.4 Da | 93.7% |
| X0320B | X0320B-prec | 7271.7 Da | 7271.7 Da | 90.0% |
| X0371B | X0371B-prec | 7128.8 Da | 7128.3 Da | 95.0% |
| X0477B | X0477B-prec | 7356.0 Da | 7355.7 Da | 91.4% |

Double Strand Formation

Double strand formation was performed according to the methods described above.

The double strand purity is given in % double strand which is the percentage of the UV-area under the assigned product signal in the UV-trace of the IP-RP-HPLC analysis.

TABLE 9

Nucleic acid conjugates

| | Starting Materials | | % |
|---|---|---|---|
| Product | First Strand | Second Strand | double strand |
| X0385 | X0385A | X0385B | 97.5% |
| X0386 | X0386A | X0386B | 96.9% |
| X0383 | X0383A | X0383B | 91.9% |
| X0371 | X0371A | X0371B | 97.7% |
| X0027 | X0027A | X0027B | 93.4% |
| X0320 | X0320A | X0320B | 98.6% |
| X0477 | X0477A | X0477B | 96.0% |

Sequences

Modifications key for the following sequences:
f denotes 2' Fluoro 2' deoxyribonucleotide or 2'-fluoro ribonucleotide (the terms are interchangeable)
m denotes 2'O Methyl ribonucleotide
(ps) denotes phosphorothioate linkage
Ser(GN) is a GalNAc-C4 building block attached to serinol derived linker moiety:

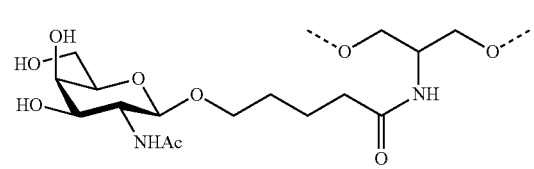

wherein the O— is the linkage between the oxygen atom and e.g. H, phosphodiester linkage or phosphorothioate linkage.

C4XLT is:

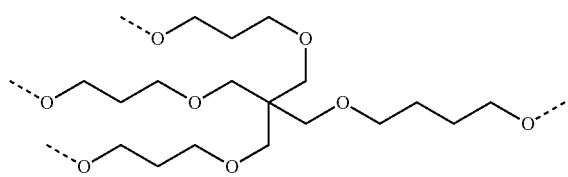

C6XLT is:

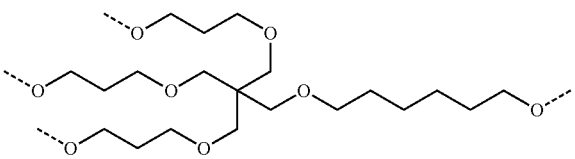

ST23 is:

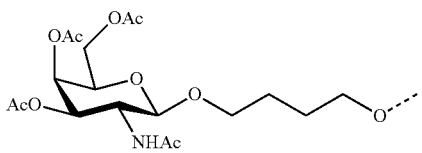

Synthesis of the phosphoramidite derivatives of C4XLT (C4XLT-phos), C6XLT (C6XLT-phos) as well as ST23 (ST23-phos) can be performed as described in WO2017/174657.

C4XLT-phos:

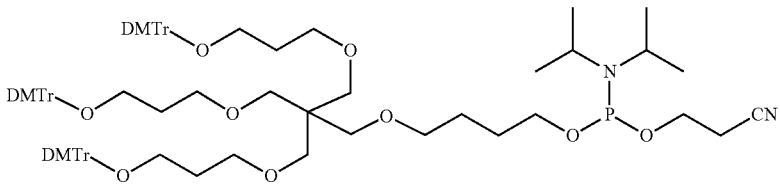

C6XLT-phos:

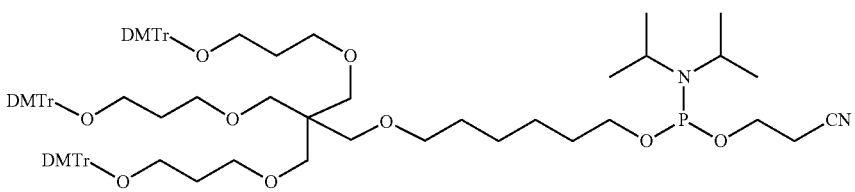

ST23-phos:

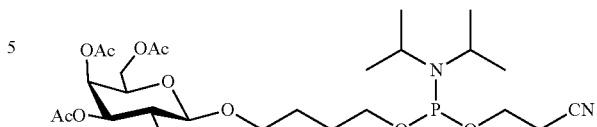

Example 10

Equal dose response of knock down for LPA targeting siRNA with two single GalNAc units conjugated to the second strand as compared to a triantennary GalNAc unit at the 5' second strand in primary cynomolgus hepatocytes.

The siRNAs are modified with alternating 2'-OMe/2'-F and contain each two phosphorothioate (PS) internucleotide linkages at their 5' and 3' terminal two internucleotide linkages. In conjugate 19 one serinol-GalNAc unit each is attached via a PS-bond to the 5' and 3' of the second strand. In conjugate 20 the two terminal 5' internucleotides of the second strand are phosphodiesters and a triantennary GalNAc linker is attached via a PS bond to this end.

Dose response of LPA knockdown in primary cynomolgus hepatocytes was assessed 24 h post treatment with 100, 20, 4, 0.8, 0.16, 0.032, and 0.006 nM siRNA. The reference control is construct 2, the non-targeting control is named Cte. The transcript ct-value for each treatment group was normalized to the transcript ct value for the house keeping gen ACTB ($\Delta$ct) and to untreated hepatocytes, named ut ($\Delta\Delta$ct).

Data are shown in FIG. 18

Material & Methods siRNAs

| SEQ ID NO: | name | batch | strand | sequence |
|---|---|---|---|---|
| 135 | Conjugate 19 | X0373 | X0373A | mA (ps) fU (ps) mA fA mC fU mC fU mG fU mC fC mA fU mU fA mC (ps) fC (ps) mG |
| 136 | | | X0373B | Ser(GN) (ps) fC (ps) mG (ps) fG mU fA mA fU mG fG mA fC mA fG mA fG mU fU (ps) mA (ps) fU (ps) Ser(GN) |
| 135 | Ref. Conjugate 9 | STS20041L6 | STS2041A | mA (ps) fU (ps) mA fA mC fU mC fU mG fU mC fC mA fU mU fA mC (ps) fC (ps) mG |
| 137 | | | STS2041B | ST23 (ps) ST23 (ps) ST23 (ps) C6XLT (ps) fC mG fG mU fA mA fU mG fG mA fC mA fG mA fG mU fU (ps) mA (ps) fU |
| 138 | Reference Conjugate 5 (CTR) | X0125 | X0125A | mC (ps) fU (ps) mU fA mC fU mC fU mC fG mC fC mC fA mA fG mC (ps) fG (ps) mA |
| 139 | | | X0125B | [(ST23) (ps)]₃ (C6XLT) (ps) fU mC fG mC fU mU fG mG fG mC fG mA fG mA fG mU fA (ps) mA (ps) fG |

Legend
mA, mU, mC, mG 2'-O-Methyl RNA
fA, fU, fC, fG 2'-deoxy-2'-fluoro RNA
(ps) phosphorothioate
(po) phosphodiester

Primer

| | | | SEQ ID NO: |
|---|---|---|---|
| LPA | fw | GTGTCCTCGCAACGTCCA | 48 |
| | rev | GACCCCGGGGCTTTG | 49 |
| | probe | BHQ1-TGGCTGTTTCTGAACAAGCACCAATG-FAM | 140 |
| ACTB | fw | GCATGGGTCAGAAGGATTCCTAT | 54 |
| | rev | TGTAGAAGGTGTGGTGCCAGATT | 55 |
| | probe | BHQ1-TCGAGCACGGCATCGTCACCAA-VIC | 141 |

General Methods

In Vitro Experiments

Primary murine hepatocytes (Thermo Scientific: GIBCO Lot: #MC798) were thawed and cryo-preservation medium exchanged for Williams E medium supplemented with 5% FBS, 1 µM dexamethasone, 2 mM GlutaMax, 1% PenStrep, 4 mg/ml human recombinant insulin, 15 mM Hepes. Cell density was adjusted to 250000 cells per 1 ml. 100 µl per well of this cell suspension were seeded into collagen pre-coated 96 well plates. The test article was prediluted in the same medium (5 times concentrated) for each concentration and 25 µl of this prediluted siRNA or medium only were added to the cells. Cells were cultured in at 37° C. and 5% $CO_2$. 24 h post treatment the supernatant was discarded, and cells were washed in cold PBS and 250 µl RNA-Lysis Buffer S (Stratec) was added. Following 15 min incubation at room temperature plates were storage at −80° C. until RNA isolation according to the manufacturers protocol.

TaqMan Analysis

For mTTR & PTEN MultiPlex TaqMan analysis 10 µl isolated RNA for each treatment group were mixed with 10 µl PCR mastermix (TAKYON low Rox) containing 600 nM mTTR-primer, 400 nM ApoB-primer and 200 nM of each probe as well as 0.5 units Euroscript II RT polymerase with 0.2 units RNAse inhibitor. TaqMan analysis was performed in 384-well plate with a 10 min RT step at 48° C., 3 min initial denaturation at 95° C. and 40 cycles of 95° C. for 10 sec and 60° C. for 1 min. The primers contain two of BHQ1, FAM and YY, one at each end of the sequence.

For TMPRSS6 & ApoB MultiPlex TaqMan analysis 10 µl isolated RNA for each treatment group were mixed with 10 µl PCR mastermix (TAKYON low Rox) containing 800 nM TMPRSS6 primer, 100 nM ApoB primer and 200 nM of either probe as well as 0.5 units Euroscript II RT polymerase with 0.2 units RNAse inhibitor. TaqMan analysis was performed in 384-well plate with a 10 min RT step at 48° C., 3 min initial denaturation at 95° C. and 40 cycles of 95° C. for 10 sec and 60° C. for 1 min.

In Vivo Experiments

To compare in vivo potency of different siRNA conjugates 1 mg/kg siRNA dissolved in PBS was administered sub cutaneous in the scapular region of c57BL/6 mice. Cohorts of n=6 for were treated with siRNA targeting Aldh2 or Tmprss6 at day 1 and sacrificed at selected times points post treatment. Liver samples were snap frozen in liquid nitrogen and stored at −80° C. until extraction RNA with InviTrap Spin Tissue RNA Mini Kit (stratec) according to the manufacturers manual. Following, transcript level of Aldh2, Tmprss6 and Pten were quantified as described above.

Tritosome Stability Assay

To probe for RNAase stability in the endosomal/lysosomal compartment of hepatic cells in vitro siRNA was incubated for 0 h, 4 h, 24 h or 72 h in Sprague Dawley Rat Liver Tritosomes (Tebu-Bio, CatN: R0610.LT, lot: 1610405, pH: 7.4, 2.827 Units/ml). To mimic the acidified environment the Tritosomes were mixed 1:10 with low pH buffer (1.5M acetic acid, 1.5M sodium acetate pH 4.75). 30 µl of this acidified Tritosomes. Following 10 µl siRNA (20 µM) were mixed with and incubated for the indicated times at 37° C. Following incubation RNA was isolated with the Clarity OTX Starter Kit-Cartriges (Phenomenex CatNo: KSO-8494) according to the manufactures protocol for biological fluids. Lyophilized RNA was reconstituted in 30 µl $H_2O$, mixed with 4x loading buffer and 5 µl were loaded to a 20% TBE-polyacrylamide gel electrophoresis (PAGE) for separation qualitative semi-quantitative analysis. PAGE was run at 120 V for 2 h and RNA visualized by Ethidum-bromide staining with subsequent digital imaging with a Biorad Imaging system.

Example 11—Synthesis of Conjugates 3

Example compounds were synthesised according to methods described below and methods known to the person skilled in the art. Assembly of the oligonucleotide chain and linker building blocks was performed by solid phase synthesis applying phosphoramidite methodology. GalNAc conjugation was achieved by peptide bond formation of a GalNAc-carboxylic acid building block to the prior assembled and purified oligonucleotide having the necessary number of amino modified linker building blocks attached.

Oligonucleotide synthesis, deprotection and purification followed standard procedures that are known in the art.

All Oligonucleotides were synthesized on an AKTA oligopilot synthesizer using standard phosphoramidite chemistry. Commercially available solid support and 2'O-Methyl RNA phosphoramidites, 2' Fluoro, 2' Deoxy RNA phosphoramidites (all standard protection, ChemGenes, LinkTech) and commercially available 3'-Amino Modifier TFA Amino C-6 Icaa CPG 500 Å (Chemgenes), Fmoc-Amino-DMT C-7 CE phosphoramidite (GlyC3Am), 3'-Amino Modifier C-3 Icaa CPG 500 Å (C3Am), Fmoc-Amino-DMT C-3 CED phosphoramidite (C3Am) and TFA-Amino C-6 CED phosphoramidite (C6Am) (Chemgenes), 3'-Amino-Modifier C7 CPG (C7Am) (Glen Research), Non-nucleosidic TFA amino Phosphoramidite (Pip), Non-nucleosidic TFA amino Solid Support (PipAm) (AM Chemicals) were used. Per-acetylated galactose amine 8 is commercially available.

Ancillary reagents were purchased from EMP Biotech. Synthesis was performed using a 0.1 M solution of the phosphoramidite in dry acetonitrile and benzylthiotetrazole (BTT) was used as activator (0.3M in acetonitrile). Coupling time was 15 min. A Cap/OX/Cap or Cap/Thio/Cap cycle was applied (Cap: $Ac_2O$/NMI/Lutidine/Acetonitrile, Oxidizer: 0.1M $I_2$ in pyridine/$H_2O$). Phosphorothioates were introduced using standard commercially available thiolation reagent (EDITH, Link technologies). DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

Attachment of the serinol-derived linker moiety was achieved by use of either base-loaded (S)-DMT-Serinol (TFA)-succinate-Icaa-CPG 10 or a (S)-DMT-Serinol(TFA) phosphoramidite 7 (synthesis was performed as described in Hoevelmann et al. (2016)). Tri-antennary GalNAc clusters (ST23/C4XLT) were introduced by successive coupling of the respective trebler amidite derivatives (C4XLT-phos) followed by the GalNAc amidite (ST23-phos).

Attachment of amino modified moieties (non-serinol-derived linkers) was achieved by use of either the respective commercially available amino modified building block CPG or amidite.

The single strands were cleaved off the CPG by 40% aq. methylamine treatment. The resulting crude oligonucleotide was purified by ion exchange chromatography (Resource Q, 6 mL, GE Healthcare) on a AKTA Pure HPLC System using a sodium chloride gradient. Product containing fractions were pooled, desalted on a size exclusion column (Zetadex, EMP Biotech) and lyophilised.

Individual single strands were dissolved in a concentration of 60 OD/mL in $H_2O$. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80° C. for 5 min and then slowly cooled to RT. Double strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

Synthesis of Compounds 2-10

Compounds 2 to 5 and (S)-DMT-Serinol(TFA)-phosphoramidite 7 were synthesised according to literature published methods (Hoevelmann et al. Chem. Sci., 2016, 7, 128-135).

(S)-4-(3-(bis(4-methoxyphenyl)(phenyl)methoxy)-2-(2,2,2-trifluoroacetamido)propoxy)-4-oxobutanoic acid (6)

To a solution of 5 in pyridine was added succinic anhydride, followed by DMAP. The resulting mixture was stirred at room temperature overnight. All starting material was consumed, as judged by TLC. The reaction was concentrated. The crude material was chromatographed in silica gel using a gradient 0% to 5% methanol in DCM (+1% triethylamine) to afford 1.33 g of 6 (yield=38%). m/z (ESI−): 588.2 (100%), (calcd. for $C30H29F3NO8^-$ [M-H]$^-$ 588.6). 1H-NMR: (400 MHz, CDCl3) δ [ppm]=7.94 (d, 1H, NH), 7.39-7.36 (m, 2H, CHaryl), 7.29-7.25 (m, 7H, CHaryl), 6.82-6.79 (m, 4H, CHaryl), 4.51-4.47 (m, 1H), 4.31-4.24 (m, 2H), 3.77 (s, 6H, 2xDMTr-OMe), 3.66-3.60 (m, 16H, $HNEt_3^+$), 3.26-3.25 (m, 2H), 2.97-2.81 (m, 20H, $NEt_3$), 2.50-2.41 (4H, m), 1.48-1.45 (m, 26H, $HNEt_3^+$), 1.24-1.18 (m 29H, $NEt_3$).

(S)-DMT-Serinol(TFA)-Succinate-Icaa-CPG (10)

The (S)-DMT-Serinol(TFA)-succinate (159 mg, 270 umol) and HBTU (113 mg, 299 umol) were dissolved in $CH_3CN$ (10 mL). Diisopropylethylamine (DIPEA, 94 µL, 540 umol) was added to the solution, and the mixture was swirled for 2 min followed by addition native amino-Icaa-CPG (500 A, 3 g, amine content: 136 umol/g). The suspension was gently shaken at room temperature on a wrist-action shaker for 16 h then filtered, and washed with DCM and EtOH. The solid support was dried under vacuum for 2 h. The unreacted amines on the support were capped by stirring with acetic anhydride/lutidine/N-methylimidazole at room temperature. The washing of the support was repeated as above. The solid was dried under vacuum to yield solid support 10 (3 g, 26 umol/g loading).

GalNAc Synthon (9)

Synthesis of the GalNAc synthon 9 was performed as described in Nair et al. J. Am. Chem. Soc., 2014, 136 (49), pp 16958-16961, in 46% yield over two steps.

The characterising data matched the published data.

Synthesis of Oligonucleotides

All single stranded oligonucleotides were synthesised according to the reaction conditions described above and in FIGS. 13 and 14, and are outlined in Tables 10 and 11.

All final single stranded products were analysed by AEX-HPLC to prove their purity. Purity is given in % FLP (% full length product) which is the percentage of the UV-area under the assigned product signal in the UV-trace of the AEX-HPLC analysis of the final product. Identity of the respective single stranded products (non-modified, amino-modified precursors or GalNAc conjugated oligonucleotides) was proved by LC-MS analysis.

TABLE 10

Single stranded un-conjugated oligonucleotides

| Product (11) | Name | MW calc. | MW (ESI−) found | % FLP (AEX-HPLC) |
|---|---|---|---|---|
| A0002 | STS16001A | 6943.3 Da | 6943.0 Da | 86.6% |
| A0006 | STS16001BL4 | 8387.5 Da | 8387.5 Da | 94.1% |
| A0114 | STS22006A | 6143.8 Da | 6143.7 Da | 94.3% |
| A0115 | STS22006BL1 | 7855.1 Da | 7855.1 Da | 92.8% |
| A0122 | STS22009A | 6260.9 Da | 6260.6 Da | 92.8% |
| A0123 | STS22009BL1 | 7783.0 Da | 7782.9 Da | 87.1% |
| A0130 | STS18001A | 6259.9 Da | 6259.8 Da | 76.5% |
| A0131 | STS18001BL4 | 7813.2 Da | 7813.1 Da | 74.3% |
| A0220 | STS16001B-5'1xNH2 | 6982.2 Da | 6982.1 Da | 95.7% |
| A0237 | STS16001A | 6943.3 Da | 6943.3 Da | 95.6% |
| A0244 | STS16001BV1 | 6845.2 Da | 6844.9 Da | 98.2% |
| A0264 | STS16001AV4-3'1xNH2 | 7112.4 Da | 7112.2 Da | 95.4% |
| A0329 | STS16001BV6-3'5'1xNH2 | 7183.3 Da | 7183.2 Da | 88.8% |
| A0560 | STS16001A | 6943.3 Da | 6943.3 Da | 96.7% |
| A0541 | STS16001BV1-3'5'NH2 | 7151.3 Da | 7151.0 Da | 85.6% |
| A0547 | STS16001BV16-3'5'NH2 | 7119.3 Da | 7119.1 Da | 89.9% |
| A0617 | STS16001BV20-3'5'NH2 | 7087.3 Da | 7086.7 Da | 90.1% |
| A0619 | STS16001BV1-3'5'2xNH2 | 7521.3 Da | 7521.3 Da | 93.4% |
| A0680 | STS16001A | 6943.3 Da | 6942.9 Da | 91.2% |
| A0514 | STS22006A | 6143.8 Da | 6143.7 Da | 94.6% |
| A0516 | STS22009BV11-3'5'NH2 | 6665.0 Da | 6664.8 Da | 87.0% |
| A0517 | STS22009BV11-3'5'NH2 | 6593.0 Da | 6593.0 Da | 86.0% |
| A0521 | STS12009BV1-3'5'NH2 | 6437.7 Da | 6437.8 Da | 91.1% |
| A0303 | STS12209BL4 | 7665.0 Da | 7664.9 Da | 90.4% |
| A0304 | STS12209A | 6393.1 Da | 6392.9 Da | 77.6% |
| A0319 | STS22009A | 6260.9 Da | 6260.5 Da | 86.9% |
| A0353 | STS12009A | 6416.1 Da | 6416.1 Da | 94.1% |
| A0216 | STS17001A | 6178.8 Da | 6178.7 Da | 87.2% |
| A0217 | STS17001BL6 | 7937.2 Da | 7937.2 Da | 78.3% |

5'1×NH2 means refers to the position (5' end) and number (1×NH2) of free serinol derived amino groups which are available for conjugation. For example, 1×3'NH2 on A0264 means there is free amino group which can be reacted with GalNAc synthon 9 at the 3' end of the strand A0264. 3'5'1×NH2 means there is one serinol-derived free amino group which can be reacted with GalNAc linker 9 at the 3' end and the 5' end of the strand.

Similarly, 3'5'1×NH2 refers to the position (3' and 5' end) and number (1×NH2 each) of free amino groups which are available for conjugation. For example, 3'5'1×NH2 on A0561 means there are 2 free amino group (1 at the 3' AND 1 at the 5' end) which can be reacted with GalNAc synthon 9 at the 3' end of the strand A0561.

Synthesis of Certain Conjugates of the Invention and Reference Conjugates 1-2

Conjugation of the GalNac synthon (9) was achieved by coupling to the serinol-amino function of the respective oligonucleotide strand 11 using a peptide coupling reagent. Therefore, the respective amino-modified precursor molecule 11 was dissolved in $H_2O$ (500 OD/mL) and DMSO (DMSO/$H_2O$, 2/1, v/v) was added, followed by DIPEA (2.5% of total volume). In a separate reaction vessel pre-activation of the GalN(Ac4)-C4-acid (9) was performed by reacting 2 eq. (per amino function in the amino-modified precursor oligonucleotide 11) of the carboxylic acid component with 2 eq. of HBTU in presence of 8 eq. DIPEA in DMSO. After 2 min the pre-activated compound 9 was added to the solution of the respective amino-modified precursor molecule. After 30 min the reaction progress was monitored by LCMS or AEX-HPLC. Upon completion of the conjugation reaction the crude product was precipitated by addition of 10× iPrOH and 0.1×2M NaCl and harvested by centrifugation and decantation. To set free the acetylated hydroxyl groups in the GalNAc moieties the resulting pellet was dissolved in 40% MeNH2 (1 mL per 500 OD) and after 15 min at RT diluted in $H_2O$ (1:10) and finally purified again by anion exchange and size exclusion chromatography and lyophilised to yield the final product 12 (Table 12).

TABLE 11

Single stranded oligonucleotides with 5' and 3' modifications

| Product | Name | 5'mod | 3'mod | MW calc. | MW (ESI−) found | % FLP (AEX-HPLC) |
|---|---|---|---|---|---|---|
| A0561 | STS16001BV1-3'5'1xNH2 | C6Am | GlyC3Am | 7267.5 Da | 7267.5 Da | 66.7% |
| A0563 | STS16001BV1-3'5'1xNH2 | C3Am | C3Am | 7183.4 Da | 7183.1 Da | 75.1% |
| A0651 | STS16001BV1-3'5'1xNH2 | C6Am | C7Am | 7265.6 Da | 7265.2 Da | 99.6% |
| A0653 | STS16001BV1-3'5'1xNH2 | GlyC3Am | GlyC3Am | 7299.5 Da | 7299.3 Da | 88.1% |
| A0655 | STS16001BV1-3'5'1xNH2 | PipAm | PipAm | 7517.7 Da | 7517.5 Da | 89.8% |

TABLE 12

Single stranded GalNAc-conjugated oligonucleotides

| Product (12) | Starting Material | Name | MW calc. | MW (ESI−) found | % FLP (AEX-HPLC) |
|---|---|---|---|---|---|
| A0241 | A0220 | STS16001BL20 | 7285.5 Da | 7285.3 Da | 91.8% |
| A0268 | A0264 | STS16001AV4L33 | 7415.7 Da | 7415.4 Da | 96.9% |
| A0330 | A0329 | STS16001BV6L42 | 7789.8 Da | 7789.8 Da | 95.5% |
| A0544 | A0541 | STS16001BV1L75 | 7757.9 Da | 7757.7 Da | 93.3% |
| A0550 | A0547 | STS16001BV16L42 | 7725.9 Da | 7725.7 Da | 88.5% |
| A0620 | A0617 | STS16001BV20L75 | 7693.91 Da | 7693.2 Da | 90.9% |
| A0622 | A0619 | STS16001BV1L94 | 8734.3 Da | 8734.6 Da | 82.9% |
| A0519 | A0516 | STS22006BV11L42 | 7271.7 Da | 7271.7 Da | 90.0% |
| A0520 | A0517 | STS22009BV11L42 | 7199.6 Da | 7199.7 Da | 92.9% |
| A0522 | A0521 | STS12009BV1L42 | 7044.4 Da | 7044.4 Da | 96.0% |
| A0603 | A0602 | STS20041BV1L42 | 7280.7 Da | 7280.4 Da | 93.4% |

Synthesis of Certain Conjugates of the Invention

Conjugation of the GalNac synthon (9) was achieved by coupling to the amino function of the respective oligonucleotide strand 14 using a peptide coupling reagent. Therefore, the respective amino-modified precursor molecule 14 was dissolved in $H_2O$ (500 OD/mL) and DMSO (DMSO/$H_2O$, 2/1, v/v) was added, followed by DIPEA (2.5% of total volume). In a separate reaction vessel pre-activation of the GalN(Ac4)-C4-acid (9) was performed by reacting 2 eq. (per amino function in the amino-modified precursor oligonucleotide 14) of the carboxylic acid component with 2 eq. of HBTU in presence of 8 eq. DIPEA in DMSO. After 2 min the pre-activated compound 9 was added to the solution of the respective amino-modified precursor molecule. After 30 min the reaction progress was monitored by LCMS or AEX-HPLC. Upon completion of the conjugation reaction the crude product was precipitated by addition of 10× iPrOH and 0.1×2M NaCl and harvested by centrifugation and decantation. To set free the acetylated hydroxyl groups in the GalNAc moieties the resulting pellet was dissolved in 40% MeNH2 (1 mL per 500 OD) and after 15 min at RT diluted in $H_2O$ (1:10) and finally purified again by anion exchange and size exclusion chromatography and lyophilised to yield the final product 15 (Table 13).

TABLE 13

Single stranded GalNAc-conjugated oligonucleotides

| Product (15) | Starting Material | Name | MW calc. | MW (ESI−) found | % FLP (AEX-HPLC) |
|---|---|---|---|---|---|
| A0562 | A0561 | STS16001BV1L87 | 7874.2 Da | 7874.0 Da | 82.7% |
| A0564 | A0563 | STS16001BV1L88 | 7790.0 Da | 7789.4 Da | 90.4% |
| A0652 | A0651 | STS16001BV1L96 | 7872.2 Da | 7871.8 Da | 94.6% |
| A0654 | A0653 | STS16001BV1L97 | 7906.2 Da | 7905.6 Da | 89.9% |
| A0656 | A0655 | STS16001BV1L98 | 8124.3 Da | 8124.0 Da | 93.6% |

Double Strand Formation

Double strand formation was performed according to the methods described above.

The double strand purity is given in % double strand which is the percentage of the UV-area under the assigned product signal in the UV-trace of the IP-RP-HPLC analysis (Table 14).

TABLE 14

Nucleic acid conjugates

| | Starting Materials | | | % |
|---|---|---|---|---|
| Product | First Strand | Second Strand | Name | double strand |
| Ref. Conj. 1 | A0237 | A0241 | STS16001L20 | 97.7% |
| Ref. Conj. 2 | A0268 | A0244 | STS16001L33 | 97.8% |
| Ref. Conj. 3 | A0130 | A0131 | STS18001L4 | 96.8% |
| Ref. Conj. 4 | A0002 | A0006 | STS16001L4 | 90.1% |
| Ref. Conj. 5 | A0216 | A0217 | STS17001L6 | 88.4% |
| Conjugate 1 | A0268 | A0241 | STS16001L24 | 96.0% |
| Conjugate 2 | A0237 | A0330 | STS16001V1L42 | 98.5% |
| Conjugate 3 | A0268 | A0330 | STS16001V1L43 | 98.2% |
| Conjugate 4 | A0560 | A0544 | STS16001V1L75 | 92.5% |
| Conjugate 5 | A0560 | A0550 | STS16001V16L42 | 95.3% |
| Conjugate 6 | A0237 | A0620 | STS16001V20L75 | 97.8% |
| Conjugate 7 | A0237 | A0622 | STS16001V1L94 | 93.7% |
| Conjugate 8 | A0680 | A0652 | STS16001V1L96 | 98.4% |
| Conjugate 9 | A0680 | A0654 | STS16001V1L97 | 95.8% |
| Conjugate 10 | A0680 | A0656 | STS16001V1L98 | 97.6% |
| Conjugate 11 | A0560 | A0564 | STS16001V1L88 | 95.0% |
| Conjugate 12 | A0237 | A0562 | STS16001V1L87 | 96.8% |
| Conjugate 13 | A0114 | A0115 | STS22006L1 | 85.6% |
| Conjugate 14 | A0122 | A0123 | STS22009L1 | 96.4% |
| Conjugate 15 | A0514 | A0519 | STS22006V11L42 | 98.6% |
| Conjugate 16 | A0319 | A0520 | STS22009V11L42 | 97.0% |
| Conjugate 17 | A0304 | A0303 | STS12209L4 | 93.0% |
| Conjugate 18 | A0353 | A0522 | STS12009V1L42 | 98.0% |
| Conjugate 19 | A0601 | A0603 | STS20041BL42 | 97.6% |

Sequences

Modifications key for the following sequences:

f denotes 2' Fluoro 2' deoxyribonucleotide or 2'-fluoro ribonucleotide (the terms are interchangeable)

m denotes 2'O Methyl ribonucleotide (ps) denotes phosphorothioate linkage

FAM=6-Carboxyfluorescein

BHQ=Black Hole Quencher 1

YY=Yakima Yellow

Definitions

Ser(GN) is a GalNAc-C4 building block attached to serinol derived linker moiety:

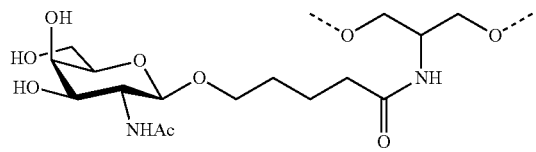

wherein the O— is the linkage between the oxygen atom and e.g. H, phosphodiester linkage or phosphorothioate linkage.

GN is:

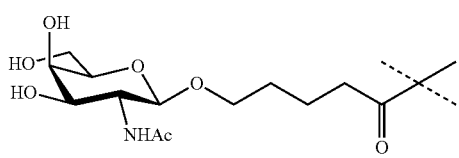

C4XLT (also known as ST41) is:

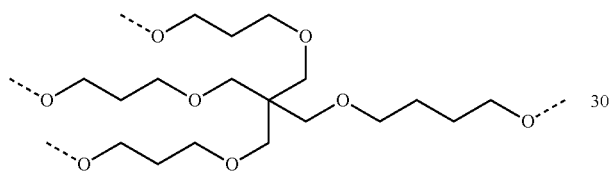

ST23 is:

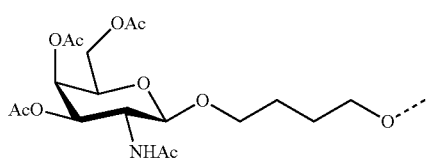

Synthesis of the phosphoramidite derivatives of C4XLT (C4XLT-phos) as well as ST23 (ST23-phos) can be performed as described in WO2017/174657.

C4XLT-phos:

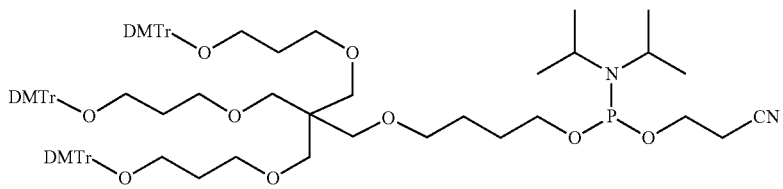

ST23-phos:

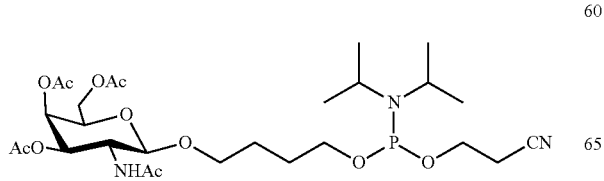

C3Am is:

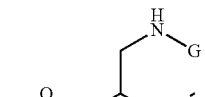

Itrb is:

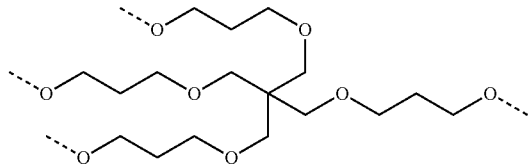

GlyC3Am is:

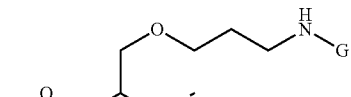

C6Am is:

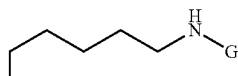

Pip Am is:

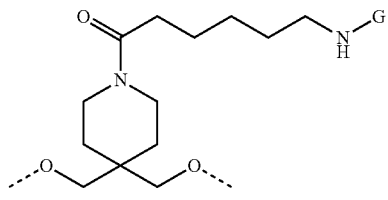

C7Am is:

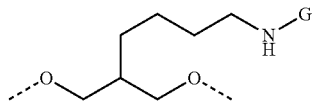

wherein G=H (pre conjugation) or G=GN (post conjugation).

Conjugate 1

```
Antisense strand - STS16001AL33
                                   (SEQ ID NO: 127)
5' mU (ps) fU (ps) mA fU mA fG mA fG mC fA mA fG mA fA mC fA mC fU mG (ps) fU (ps) mU (ps)

Ser(GN) 3'
```

Sense strand - STS16001BL20
(SEQ ID NO: 128)
5' Ser(GN) (ps) fA mA fC mA fG mU fG mU fU mC
fU mU fG mC fU mC fU mA fU (ps) mA (ps) fA 3'

Conjugate 2

Antisense strand - STS16001A
(SEQ ID NO: 129)
mU (ps) fU (ps) mA fU mA fG mA fG mC fA mA fG
mA fA mC fA mC fU mG (ps) fU (ps) mU
Sense strand - STS16001BV1L42
(SEQ ID NO: 130)
Ser(GN) (ps) fA (ps) mA (ps) fC mA fG mU fG mU
fU mC fU mU fG mC fU mC fU mA fU (ps) mA (ps)
fA (ps) Ser(GN)

Conjugate 3

Antisense strand - STS16001AL33
(SEQ ID NO: 127)
5' mU (ps) fU (ps) mA fU mA fG mA fG mC fA mA
fG mA fA mC fA mC fU mG (ps) fU (ps)
mU (ps) Ser(GN) 3'
Sense strand - STS16001BV1L42
(SEQ ID NO: 130)
5' Ser(GN) (ps) fA (ps) mA (ps) fC mA fG mU
fG mU fU mC fU mU fG mC fU mC fU mA fU (ps) mA
(ps) fA (ps) Ser(GN) 3'

Conjugate 4

Antisense strand - STS16001A
(SEQ ID NO: 129)
mU (ps) fU (ps) mA fU mA fG mA fG mC fA mA fG
mA fA mC fA mC fU mG (ps) fU (ps) mU
Sense strand - STS16001BV1L75
(SEQ ID NO: 142)
5' Ser(GN) fA (ps) mA (ps) fC mA fG mU fG mU
fU mC fU mU fG mC fU mC fU mA fU (ps) mA (ps)
fA Ser(GN) 3'

Conjugate 5

Antisense strand - STS16001A
(SEQ ID NO: 129)
mU (ps) fU (ps) mA fU mA fG mA fG mC fA mA fG
mA fA mC fA mC fU mG (ps) fU (ps) mU Sense strand - STS16001BV16L42
(SEQ ID NO: 143)
5' Ser(GN) (ps) fA mA fC mA fG mU fG mU fU mC
fU mU fG mC fU mC fU mA fU mA fA (ps) Ser(GN)
3'

Conjugate 6

Antisense strand - STS16001A
(SEQ ID NO: 129)
mU (ps) fU (ps) mA fU mA fG mA fG mC fA mA fG
mA fA mC fA mC fU mG (ps) fU (ps) mU
Sense strand - STS16001BV20L75
(SEQ ID NO: 144)
5' Ser(GN) fA mA fC mA fG mU fG mU fU mC fU mU
fG mC fU mC fU mA fU mA fA Ser(GN) 3'

Conjugate 7

Antisense strand -
(SEQ ID NO: 129)
mU (ps) fU (ps) mA fU mA fG mA fG mC fA mA fG
mA fA mC fA mC fU mG (ps) fU (ps) mU
Sense strand - STS16001BV1L94
(SEQ ID NO: 145)
5' Ser(GN) (ps) Ser(GN) (ps) fA (ps) mA
(ps) fC mA fG mU fG mU fU mC fU mU fG mC fU
mC fU mA fU (ps) mA (ps) fA (ps) Ser(GN) (ps)
Ser(GN) 3'

Conjugate 8

Antisense strand - STS16001A
(SEQ ID NO: 129)
5' mU (ps) fU (ps) mA fU mA fG mA fG mC fA
mA fG mA fA mC fA mC fU mG (ps) fU (ps) mU 3'
Sense strand - STS16001V1BL96
(SEQ ID NO: 146)
5' C6Am(GN) (ps) fA (ps) mA (ps) fC mA fG
mU fG mU fU mC fU mU fG mC fU mC fU mA fU (ps)
mA (ps) fA (ps) C7Am(GN) 3'

Conjugate 9

Antisense strand - STS16001A
(SEQ ID NO: 129)
5' mU (ps) fU (ps) mA fU mA fG mA fG mC fA
mA fG mA fA mC fA mC fU mG (ps) fU (ps) mU 3'

```
Sense strand - STS16001V1BL97
                                (SEQ ID NO: 147)
5' GlyC3Am(GN) (ps) fA (ps) mA (ps) fC mA fG mU fG mU fU mC fU mU fG mC fU mC fU mA fU (ps)

mA (ps) fA (ps) GlyC3Am(GN) 3'
```

Conjugate 10

```
Antisense strand - STS16001A
                                (SEQ ID NO: 129)
5' mU (ps) fU (ps) mA fU mA fG mA fG mC fA mA fG mA fA mC fA mC fU mG (ps) fU (ps)

mU 3'

Sense strand
                                (SEQ ID NO: 148)
5' PipAm(GN) (ps)fA (ps) mA (ps) fC mA fG mU fG mU fU mC fU mU fG mC fU mC fU mA fU (ps) mA (ps) fA (ps) PipAm(GN) 3'
```

Conjugate 11

```
Antisense strand - STS16001A
                                (SEQ ID NO: 129)
5' mU (ps) fU (ps) mA fU mA fG mA fG mC fA mA fG mA fA mC fA mC fU mG (ps) fU (ps)

mU 3'

Sense strand - STS16001V1BL88
                                (SEQ ID NO: 149)
5' C3Am(GN) (ps) fA (ps) mA (ps) fC mA fG mU fG mU fU mC fU mU fG mC fU mC fU mA fU (ps) mA (ps) fA (ps) C3Am(GN) 3'
```

Conjugate 12

```
Antisense strand - STS16001A
                                (SEQ ID NO: 129)
5' mU (ps) fU (ps) mA fU mA fG mA fG mC fA mA fG mA fA mC fA mC fU mG (ps) fU (ps)

mU 3'

Sense strand - STS16001V1BL87
                                (SEQ ID NO: 150)
5' C6Am(GN) (ps) fA (ps) mA (ps) fC mA fG mU fG mU fU mC fU mU fG mC fU mC fU mA fU (ps) mA (ps) fA (ps) GlyC3Am(GN) 3'
```

Conjugate 15

```
Antisense strand
                                (SEQ ID NO: 151)
mU (ps) fC (ps) mU fU mC fU mU fA mA fA mC fU mG fA mG fU mU (ps) fU (ps) mC
```

```
Sense strand
                                (SEQ ID NO: 152)
Ser(GN) (ps) fG (ps) mA (ps) fA mA fC mU fC mA fG mU fU mU fA mA fG mA fA (ps) mG (ps)

fA (ps) Ser(GN)
```

Conjugate 16

```
Antisense strand
                                (SEQ ID NO: 153)
mA (ps) fU (ps) mG fU mA fG mC fC mG fA mG mA fU mC fU mU (ps) fC (ps) mU Sense strand
                                (SEQ ID NO: 154)
Ser(GN) (ps) fA (ps) mG (ps) fA mA fG mA fU mC fC mU fC mG fG mC mA fC (ps) mA (ps)

fU (ps) Ser(GN)
```

Conjugate 18

```
Antisense strand
                                (SEQ ID NO: 155)
mA (ps) fA (ps) mC fC mA fG mA fA mG fA mA fG mC fA mG fG mU (ps) fG (ps) mA Sense strand
                                (SEQ ID NO: 156)
Ser(GN) (ps) fU (ps) mC (ps) fA mC fC mU fG mC fU mU fC mU fU mC fU mG fG (ps) mU (ps) fU (ps)

Ser(GN)
```

Conjugate 19

```
Antisense strand
                                (SEQ ID NO: 135)
mA (ps) fU (ps) mA fA mC fU mC fU mG fU mC fA fU mU fA mC (ps) fC (ps) mG Sense strand
                                (SEQ ID NO: 136)
Ser(GN) (ps) fC (ps) mG (ps) fG mU fA mA fU mG mA fC mA fG mA fG mU fU (ps) mA (ps) fU (ps)

Ser(GN)
```

Reference Conjugate 1

```
Antisense strand - STS16001A
                                (SEQ ID NO: 129)
mU (ps) fU (ps) mA fU mA fG mA fG mC fA mA fG mA fA mC fA mC fU mG (ps) fU (ps) mU
```

-continued

Sense strand - STS16001BL20
(SEQ ID NO: 128)
Ser(GN) (ps) fA mA fC mA fG mU fG mU fU mC fU mU fG mC fU mC fU mA fU (ps) mA (ps) fA

Reference Conjugate 2

Antisense strand - STS16001AL33
(SEQ ID NO: 127)
mU (ps) fU (ps) mA fU mA fG mA fG mC fA mA fG mA fA mC fA mC fU mG (ps) fU (ps) mU (ps) Ser(GN)

Sense strand - STS16001BV1
(SEQ ID NO: 157)
fA (ps) mA (ps) fC mA fG mU fG mU fU mC fU mU fG mC fU mC fU mA fU (ps) mA (ps) fA

Reference Conjugate 3—"Luc"

Antisense strand - STS18001A
(A0130, SEQ ID NO: 132)
mU (ps) fC (ps) mG fA mA fG mU fA mU fU mC fC mG fC mG fU mA (ps) fC (ps) mG Sense strand - STS18001BL4
(A0131, SEQ ID NO: 133)
[(sT23) (ps)]₃ C4XLT (ps) fC mG fU mA fC mG fC mG fG mA fA mU fA mC fU mU fC (ps) mG (ps) fA

Reference Conjugate 4

Antisense strand - STS16001AL33
(SEQ ID NO: 127)
mU (ps) fU (ps) mA fU mA fG mA fG mC fA mA fG mA fA mC fA mC fU mG (ps) fU (ps) mU Sense strand - STS16001BL4
(SEQ ID NO: 134)
5'[(ST23) (pS)]₃ C4XLT(ps) fA (ps) mA (ps) fC mA fG mU fG mU fU mC fU mU fG mC fU mC fU mA fU (ps) mA (ps) fA

Reference Conjugate 5—"Ctr"

Antisense strand
(SEQ ID NO: 138)
mC (ps) fU (ps) mU fA mC fU mC fU mC fG mC fC mC fA mA fG mC (ps) fG (ps) mA Sense strand
(SEQ ID NO: 139)
[(ST23) (ps)]₃ (C6XLT) (ps) fU mC fG mC fU mU fG mG fG mC fG mA fG mA fG mU fA (ps) mA (ps) fG

Reference Conjugate 6

Antisense strand
(SEQ ID NO: 151)
mU (ps) fC (ps) mU fU mC fU mU fA mA fA mC fU mG fA mG fU mU (ps) fU (ps) mC Sense strand
(SEQ ID NO: 158)
[ST23 (ps)]₃ ltrb (ps) fG mA fA mA fC mU fC mA fG mU fU mU fA mA fG mA fA (ps) mG (ps) fA

Reference Conjugate 7

Antisense strand
(SEQ ID NO: 153)
mA (ps) fU (ps) mG fU mA fG mC fC mG fA mG fG mA fU mC fU mU (ps) fC (ps) mU Sense strand
(SEQ ID NO: 159)
[ST23 (ps)]₃ ltrb (ps) fA mG fA mA fG mA fU mC fC mU fC mG fG mC fU mA fC (ps) mA (ps) fU

Reference Conjugate 8

Antisense strand
(SEQ ID NO: 160)
mU (ps) fA (ps) mC fC mA fG mA fA mG fA mA fG mC fA mG fG mU (ps) fG (ps) mA Sense strand
(SEQ ID NO: 161)
[ST23 (ps)]₃ ST41 (ps)fU mC fA mC fC mU fG mC fU mU fC mU fU mC fU mG fG (ps) mU (ps) fA

Reference Conjugate 9

Antisense strand
(SEQ ID NO: 135)
mA (ps) fU (ps) mA fA mC fU mC fU mG fU mC fC mA fU mU fA mC (ps) fC (ps) mG Sense strand
(SEQ ID NO: 162)
[ST23 (ps)]₃ C6XLT (ps) fC mG fG mU fA mA fU mG fG mA fC mA fG mA fG mU fU (ps) mA (ps) fU

Example 12—In Vitro Determination of TTR Knockdown of Various TTR siRNA GalNAc Conjugates

Conjugates 1 to 3

Murine primary hepatocytes were seeded into collagen pre-coated 96 well plates (Thermo Fisher Scientific, #A1142803) at a cell density of 30,000 cells per well and treated with siRNA-conjugates at concentrations ranging from 10 nM to 0.0001 nM. 24 h post treatment cells were lysed and RNA extracted with InviTrap® RNA Cell HTS 96 Kit/C24×96 preps (Stratec #7061300400) according to the manufactures protocol. Transcripts levels of TTR and housekeeping mRNA (PtenII) were quantified by TaqMan analysis.

Target gene expression in primary murine hepatocytes 24 h following treatment at 0.01 nM, 0.1 nM, 0.5 nM, 1 nM and 10 nM with the conjugates of the invention, Conjugates 1-3, showed that target gene expression decreases as the dose of the conjugate increased compared to the negative controls (see "UT" column and Reference Conjugate 3), as shown in FIG. 15. This indicates that the first strand is binding to the target gene, thus lowering gene expression. FIG. 15 also shows the target gene expression levels of Reference Conjugates 1 and 2 which act as comparator conjugates. As can be seen from a comparison between the data presented in FIGS. 15A and 15C, and 15B and 15C, the conjugates of the invention (Conjugates 1-3) decrease the target gene expression compared to Reference Conjugates 1 and 2. The most effective conjugate at 0.01 nM appears to be Conjugate 2. The most effective conjugate at 0.1 nM, 0.5 nM, 1 nM and 10 nM appears to be Conjugate 3.

Conjugates 4 to 7

The method described above under "In vitro experiments" in the General Method section was followed.

Target gene expression in primary murine hepatocytes 24 h following treatment at 0.01 nM, 0.1 nM, 0.5 nM, 1 nM and 10 nM with the conjugates of the invention, Conjugates 4-7, showed that target gene expression decreases as the dose of the conjugate increased compared to the negative controls (see "UT" column and Luc [Reference Conjugate 3]), as shown in FIG. 31. This indicates that the first strand is binding to the target gene, thus lowering gene expression.

The in vitro data show that in the context of one or two serinol-derived linker moieties being provided at 5' and 3' ends of the sense strand in Conjugates 4-7, the number of phosphorothioate (PS) bonds between the terminal nucleotide and the linker, and/or between the terminal three nucleotides in the sense strand, can be varied whilst maintaining efficacy for decreasing target gene expression.

Conjugates 8 to 12 and 19

The method described above under "In vitro experiments" in the General Method section was followed.

Target gene expression in primary murine hepatocytes 24 h following treatment at 0.01 nM, 0.1 nM, 0.5 nM, 1 nM and 10 nM with the conjugates of the invention, Conjugates 8-12, showed that target gene expression decreases as the dose of the conjugate increased compared to the negative controls (see "UT" column and Luc [Reference Conjugate 3]), as shown in FIG. 32. This indicates that the first strand is binding to the target gene, thus lowering gene expression. In particular, Conjugates 8, 9, 10 and 11 appear to be comparable to or better than Conjugate 2 which was previously shown to be the most effective conjugate at 0.01 nM.

Conjugate 19 was also shown to decrease target gene expression compared to the negative controls (see "UT" column and Ctr which is a non-targeting siRNA and also referred to as Reference Conjugate 5), as shown in FIG. 33. This indicates that the first strand is binding to the target gene, thus lowering gene expression.

The in vitro data for Conjugates 8-12 and 19 show that a number of linkers which are structurally diverse and which are conjugated at both termini of the sense strand are effective at decreasing target gene expression. Conjugates 8-12 and 19 decrease target gene expression more effectively than "Luc" which is Reference Conjugate 3 (for Conjugates 8-12), "Ctr" which is Reference Conjugate 5 (for Conjugate 19) and untreated control.

Example 13—In Vivo Time Course of Serum Ttr, Aldh2 and Tmprss6 in Mice

Conjugates 1 to 3

C57BL/6 mice were treated s.c. with 1 mg/kg siRNA-conjugates at day 0. Serum samples were taken at day 7, 14, and 27 by orbital sinus bleeding and stored at −20° C. until analysis. Serum TTR quantification was performed with a Mouse Prealbumin ELISA (ALPCO, 41-PALMS/lot 22, 2008003B) according to the manufacturers protocol (sample dilution 1:8000 or 1:800).

The results of the time course of serum TTR in c57BL/6 mice cohorts of n=4 at 7, 14, and 27 days post s.c. treatment with 1 mg/kg Conjugates 1-3, Reference Conjugates 1, 2 and 4, and mock treated (PBS) individuals is shown in FIG. 16. As indicated by the data in FIG. 16, the conjugates of the invention are particularly effective at reducing target gene expression compared to the negative control (PBS) and Reference Conjugates 1, 2, and in particular to Reference Conjugate 4. Conjugates 2 and 3 are also more effective than Reference Conjugates 1, 2 and 4. The most effective conjugate is Conjugate 2. Thus, it may be expected that the dosing level of Conjugate 2 would be about three times lower to achieve the same initial knock down and would also result in longer duration of knock down as compared to Reference Conjugate 4.

More specifically, Conjugate 2 resulted in 3-fold lower target protein level in serum at day seven and 4-fold lower target protein level in serum at day 27 compared to Reference Conjugate 4 at equimolar dose in wild type mice. Furthermore, Conjugate 2 resulted in 85% reduction of target serum protein level at day 27 after single injection, compared to 36% reduction by equimolar amount of Reference Conjugate 4.

Conjugates 15 to 18

The method described above under "In vivo experiments" in the General Method section was followed.

The results of the time course of serum Aldh2 in c57BL/6 mice cohorts of n=6 at 14, 28 and 42 days post s.c. treatment with 1 mg/kg Conjugates 15 and 16, Reference Conjugates 6 and 7, and mock treated (PBS) individuals is shown in FIGS. 34 and 35. As indicated by the data in FIGS. 34 and 35, the conjugates of the invention are particularly effective at reducing target gene expression compared to the negative control (PBS) and Reference Conjugates 6 and 7 respectively.

The results of the time course of serum Tmprss6 in c57BL/6 mice cohorts of n=6 at 14, 28 and 42 days post s.c. treatment with 1 mg/kg Conjugate 18, Reference Conjugate 8, and mock treated (PBS) individuals is shown in FIG. 36. As indicated by the data in FIG. 36, the conjugates of the invention are particularly effective at reducing target gene expression compared to the negative control (PBS) and Reference Conjugate 8.

Overall, the in vivo data show that a variety of example linkers which are conjugated at both termini of the second strand are effective at decreasing target gene expression in vivo. The positioning of the linker improves in vivo potency conjugates, as compared to a triantennary GalNAc-linker control at the 5' terminus of the second strand (Reference Conjugates 6, 7 and 8).

Example 14—Serum Stability Studies

The method described above under "Tritosome stability assay" in the General Method section was followed.

FIG. 37 shows the results from the serum stability studies in respect of Conjugates 2, 4, 5, 6 and 7. FIG. 38 shows the serum stability of Conjugates 2, 8, 9, 10, 11 and 12.

All conjugates of the invention that were tested are more stable in serum compared to control.

All tested conjugates contain each one GalNAc linker unit at the 5' end and another at the 3' end of the second strand. The siRNAs are modified with alternating 2'-OMe/2'-F and contain each two phosphorothioate (PS) internucleotide linkages at their 5' and 3' terminal two internucleotide linkages, unless stated differently.

In Conjugate 4 the serinol-GalNAc units are attached via a phosphodiester bond. In Conjugate 5 the serinol-GalNAc units are conjugated via PS, whereas all internucleotide linkage in the second strand are phosphodiesters. In Conjugate 6 the second strand contains no PS. In Conjugate 7 two serinol-GalNAc units are attached to each second strand terminus and to each other via a PS-bonds at the respective ends. In Conjugate 8 a C6-amino-modifier at 5' and a C7-amino-modifier at the 3' end of the second strand were applied for ligand attachment. In Conjugate 9 Gly-C3-amino-modifiers, in Conjugate 10 piperidyl-amino-modifiers, in Conjugate 11 C3-amino-modifiers and in Conjugate 2 serinol-GalNAc units were used as linkers for conjugation to both ends of the second strand. In Conjugate 2 both terminal internucleotides as well as the nucleotide-serinol bonds are PS. In Conjugate 12 a C6-amino-modifier at the 5' and a GlyC3-amino-modifier at the 3' end of second strand were applied for ligand attachment. "ut" indicates an untreated sample which the other samples were normalised to. "Luc" indicates an siRNA targeting Luciferase (Reference Conjugate 3), which was used as non-targeting control and does not reduce target mRNA levels.

The data show that in context of a serinol-derived linker moiety being provided at 5' and 3' ends of the sense strand, the number of phosphorothioate (PS) bonds between the terminal nucleotide and the linker, and/or between the terminal three nucleotides in the sense strand, can be varied whilst maintaining stability in serum.

Example 15

Knockdown of LPA-mRNA in human primary hepatocytes by the different indicated L6-GalNAc conjugated siRNAs in primary human hepatocytes upon receptor-mediated delivery.

TABLE 15

Table 15: Further conjugated nucleic acid sequences tested for inhibition of LPA mRNA expression. Sequences and applied modification pattern are indicated

| SEQ ID NO: | siRNA ID | strand | Sequence | Modifications |
|---|---|---|---|---|
| 63 | LPA-1301 | first strand | 5'uuaacucuguccauuaccg 3' | 5162717181736152738 |
| 64 | | second strand | 5'cgguaauggacagaguuaa 3' | 3845261846364645162 |
| 65 | LPA-1302 | first strand | 5'uuaacucuguccauuaccc 3' | 5162717181736152737 |
| 66 | | second strand | 5'ggguaauggacagaguuaa 3' | 4845261846364645162 |
| 67 | LPA-1303 | first strand | 5'uuaacucuguccauuaccu 3' | 5162717181736152735 |
| 68 | | second strand | 5'agguaauggacagaguuaa 3' | 2845261846364645162 |
| 69 | LPA-1304 | first strand | 5'auaacucuguccauuaccc 3' | 6162717181736152737 |
| 70 | | second strand | 5'ggguaauggacagaguuau 3' | 4845261846364645161 |
| 71 | LPA-1305 | first strand | 5'auaacucuguccauuaccu 3' | 6162717181736152735 |
| 72 | | second strand | 5'agguaauggacagaguuau 3' | 2845261846364645161 |
| 73 | LPA-1306 | first strand | 5'uuaacucuguccauuacca 3' | 5162717181736152736 |
| 74 | | second strand | 5'ugguaauggacagaguuaa 3' | 1845261846364645162 |

Table 15: Nucleotides modifications are depicted by the following numbers (column 4), 1 = 2'F-dU, 2 = 2'F-dA, 3 = 2'F-dC, 4 = 2'F-dG, 5 = 2'-OMe-rU; 6 = 2'-OMe-rA; 7 = 2'-OMe-rC; 8 = 2'-OMe-rG.

Primary human hepatocytes (ThermoFisher) were plated on collagen-coated 96-well plates at 30,000 cells per well (96 well format). GalNAc-L6-conjugated siRNAs were added immediately after cell plating at the indicated concentrations. 24 hours after treatment with siRNAs, total RNA was isolated using the InviTrap RNA cell HTS 96 well kit (Stratec). LPA mRNA expression levels were determined by qRT-PCR relative to APOB mRNA as housekeeping transcript. Values were normalized to LPA mRNA expression in untreated cells. Means and SD of normalized triplicate values are shown in FIG. 39. $IC_{50}$-values and maximum inhibition were estimated using four-parameter non-linear regression curve fit.

STATEMENTS OF INVENTION

1. A nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of RNA transcribed from the LPA gene, wherein said first strand comprises a nucleotide sequence selected from the following sequences: SEQ ID NOs: 9, 1, 3, 5, 7, 11, 13, 15, 17, 19, 21, 23, 25, 27, 29, 31, 33, 35, 37, 39, 41, 43, 63, 65, 67, 69, 71 or 73 or any sequence disclosed herein.
2. A nucleic acid of statement 1, wherein the second strand comprises a nucleotide sequence of SEQ ID NO: 10, 2, 4, 6, 8, 12, 14, 16, 18, 20, 22, 24, 26, 28, 30, 32, 34, 36, 38, 40, 42, 44, 64, 66, 68, 70, 72 or 74 or any sequence disclosed herein.
3. A nucleic acid of statement 1 or statement 2, wherein said first strand comprises a nucleotide sequence of SEQ ID NO:9 or SEQ ID NO:5.
4. A nucleic acid of any one of statements 1 to 3, wherein said second strand comprises the nucleotide sequence of SEQ ID NO:10 or SEQ ID NO:6.
5. A nucleic acid according to any one of statements 1 to 4, wherein said first strand and/or said second strand are each from 17-35 nucleotides in length.
6. A nucleic acid of any one of statements 1 to 5, wherein the at least one duplex region consists of 19-25 consecutive nucleotide base pairs.
7. A nucleic acid of any preceding statement, which
   a) is blunt ended at both ends; or
   b) has an overhang at one end and a blunt end at the other; or
   c) has an overhang at both ends.
8. A nucleic acid according to any preceding statement, wherein one or more nucleotides on the first and/or second strand are modified, to form modified nucleotides.
9. A nucleic acid of statement 8, wherein one or more of the odd numbered nucleotides of the first strand are modified.
10. A nucleic acid according to statement 9, wherein one or more of the even numbered nucleotides of the first strand are modified by at least a second modification, wherein the at least second modification is different from the modification of statement 9.
11. A nucleic acid of statement 10, wherein at least one of the one or more modified even numbered nucleotides is adjacent to at least one of the one or more modified odd numbered nucleotides.
12. A nucleic acid of any one of statements 9 to 11, wherein a plurality of odd numbered nucleotides are modified.
13. A nucleic acid of statement 10 to 12, wherein a plurality of even numbered nucleotides are modified by a second modification.
14. A nucleic acid of any of statements 8 to 13, wherein the first strand comprises adjacent nucleotides that are modified by a common modification.
15. A nucleic acid of any of statements 9 to 14, wherein the first strand comprises adjacent nucleotides that are modified by a second modification that is different to the modification of statement 9.
16. A nucleic acid of any of statements 9 to 15, wherein one or more of the odd numbered nucleotides of the second strand are modified by a modification that is different to the modification of statement 9.
17. A nucleic acid according to any of statements 9 to 15, wherein one or more of the even numbered nucleotides of the second strand are modified by the modification of statement 9.
18. A nucleic acid of statement 16 or 17, wherein at least one of the one or more modified even numbered nucleotides of the second strand is adjacent to the one or more modified odd numbered nucleotides of the second strand.
19. A nucleic acid of any of statements 16 to 18, wherein a plurality of odd numbered nucleotides of the second strand are modified by a common modification.
20. A nucleic acid of any of statements 16 to 19, wherein a plurality of even numbered nucleotides are modified by a modification according to statement 9.
21. A nucleic acid of any of statements 16 to 20, wherein a plurality of odd numbered nucleotides on the second strand are modified by a second modification, wherein the second modification is different from the modification of statement 9.
22. A nucleic acid of any of statements 16 to 21, wherein the second strand comprises adjacent nucleotides that are modified by a common modification.
23. A nucleic acid of any of statements 16 to 22, wherein the second strand comprises adjacent nucleotides that are modified by a second modification that is different from the modification of statement 9.
24. A nucleic acid according to any one of statements 8 to 23, wherein each of the odd numbered nucleotides in the first strand and each of the even numbered nucleotides in the second strand are modified with a common modification.
25. A nucleic acid of statement 24, wherein each of the even numbered nucleotides are modified in the first strand with a second modification and each of the odd numbered nucleotides are modified in the second strand with a second modification.
26. A nucleic acid according to any one of statements 8 to 25, wherein the modified nucleotides of the first strand are shifted by at least one nucleotide relative to the unmodified or differently modified nucleotides of the second strand.
27. A nucleic acid according to any one of statements 8 to 26, wherein the modification and/or modifications are each and individually selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification.

28. A nucleic acid according to any one of statements 8 to 27, wherein the modification is any one of a locked nucleotide, an abasic nucleotide or a non-natural base comprising nucleotide.

29. A nucleic acid according to any one of statements 8 to 28, wherein at least one modification is 2'-O-methyl.

30. A nucleic acid according to any one of statements 8 to 29, wherein at least one modification is 2'-F.

31. A nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of a RNA transcribed from the LPA gene, wherein said first strand comprises a nucleotide sequence selected from the following sequences: SEQ ID NOs: 9, 1, 3, 5, 7, 11, 13, 15, 17, 19, 21, 23, 25, 27, 29, 31, 33, 35, 37, 39, 41, 43, 63, 65, 67, 69, 71 or 73, wherein the nucleotides of first strand are modified by first modification on the odd numbered nucleotides, and modified by a second modification on the even numbered nucleotides, and nucleotides of the second strand are modified by a third modification on the even numbered nucleotides and modified by a fourth modification on the odd numbered nucleotides, wherein at least the first modification is different to the second modification and the third modification is different to the fourth modification.

32. A nucleic acid of statement 31, wherein second sequence comprises a nucleotide sequence of SEQ ID NO: 10, 2, 4, 6, 8, 12, 14, 16, 18, 20, 22, 24, 26, 28, 30, 32, 34, 36, 38, 40, 42, 44, 64, 66, 68, 70, 72 or 74.

33. A nucleic acid of statement 31 or 32, wherein the fourth modification and the second modification are the same.

34. A nucleic acid of any one of statements 31 to 33, wherein the first modification and the third modification are the same.

35. A nucleic acid of any one of statements 31 to 34, wherein the first modification is 2'O-Me and the second modification is 2'F.

36. A nucleic acid of any one of statements 31 to 35, wherein the first strand comprises the nucleotide sequence of SEQ ID NO:9 or SEQ ID NO:5 and the second strand comprises the nucleotide sequence of SEQ ID NO:10 or SEQ ID NO:6.

37. A nucleic acid of any one of statements 31 to 36, comprising a sequence and modifications as shown below:

```
SEQ ID  5'  auaacucuguccauuacca  3' 6162717181736152736
NO: 5
SEQ ID  5'  ugguaauggacagaguuau  3' 1845261846364645161
NO: 6
SEQ ID  5'  auaacucuguccauuaccg  3' 6162717181736152738
NO: 9
SEQ ID  5'  cgguaauggacagaguuau  3' 3845261846364645161
NO: 10
``` wherein, the specific modifications are depicted by numbers
1=2'F-dU,
2=2'F-dA,
3=2'F-dC,
4=2'F-dG,
5=2'-OMe-rU;
6=2'-OMe-rA;
7=2'-OMe-rC;
8=2'-OMe-rG.

38. A nucleic acid according to any one of statements 1 to 37, conjugated to a ligand.

39. A nucleic acid according to any one of statements 1 to 38, comprising a phosphorothioate linkage between the terminal one, two or three 3' nucleotides and/or 5' nucleotides of the first and/or the second strand.

40. A nucleic acid according to any one of statements 1 to 39 comprising two phosphorothioate linkage between each of the three terminal 3' and between each of the three terminal 5' nucleotides on the first strand, and two phosphorothioate linkages between the three terminal nucleotides of the 3' end of the second strand.

41. A nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of a RNA transcribed from the LPA gene, wherein said first strand comprises a nucleotide sequence selected from the following sequences: SEQ ID NOs: 9, 1, 3, 5, 7, 11, 13, 15, 17, 19, 21, 23, 25, 27, 29 31, 33, 35, 37, 39, 41, 43, 63, 65, 67, 69, 71 or 73, and wherein the nucleic acid is conjugated to a ligand.

42. A nucleic acid according to statement 41, wherein the ligand comprises (i) one or more N-acetyl galactosamine (GalNac) moieties and derivatives thereof, and (ii) a linker, wherein the linker conjugates the GalNac moieties to a nucleic acid as defined in statement 41.

43. A nucleic acid according to any of statements 41 or 42, wherein linker may be a bivalent or trivalent or tetravalent branched structure.

44. A nucleic acid of any of statements 41 to 43, wherein the nucleotides are modified as defined in any preceding statements.

45. A nucleic acid of any preceding statement, which is conjugated to a ligand comprising the formula I:

$$[S-X^1-P-X^2]_3-A-X^3- \qquad (I)$$

wherein:
S represents a saccharide, wherein the saccharide is N-acetyl galactosamine;
$X^1$ represents $C_3$-$C_6$ alkylene or $(-CH_2-CH_2-O)_m(-CH_2)_2-$ wherein m is 1, 2, or 3;
P is a phosphate or modified phosphate (preferably a thiophosphate);
$X^2$ is alkylene or an alkylene ether of the formula $(-CH_2)_n-O-CH_2-$ where n=1-6;
A is a branching unit;
$X^3$ represents a bridging unit;
wherein a nucleic acid as defined in any of statements 1 to 40 is conjugated to $X^3$ via a phosphate or modified phosphate (preferably a thiophosphate).

46. A conjugated nucleic acid having one of the following structures
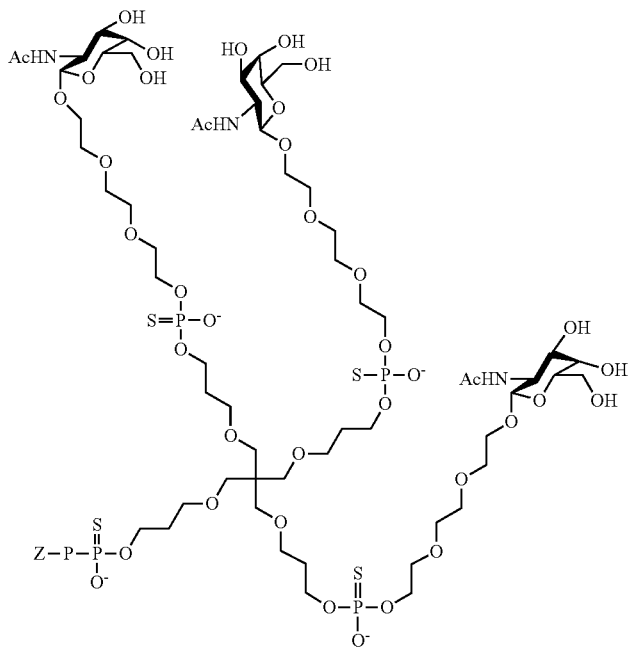
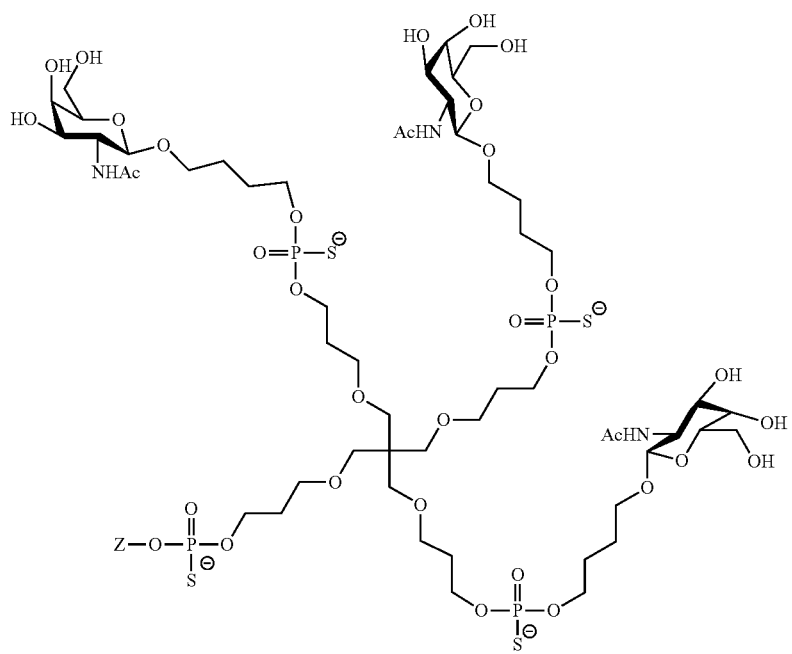

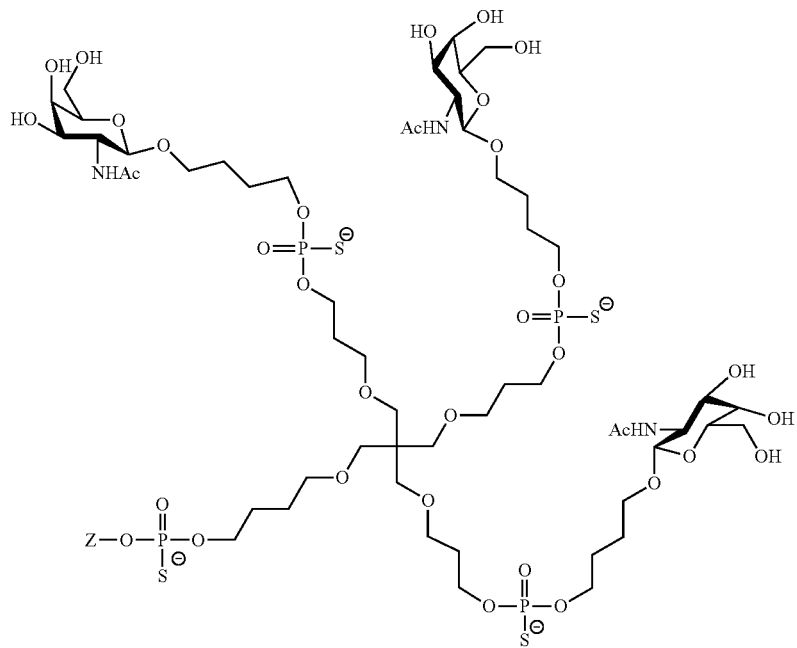
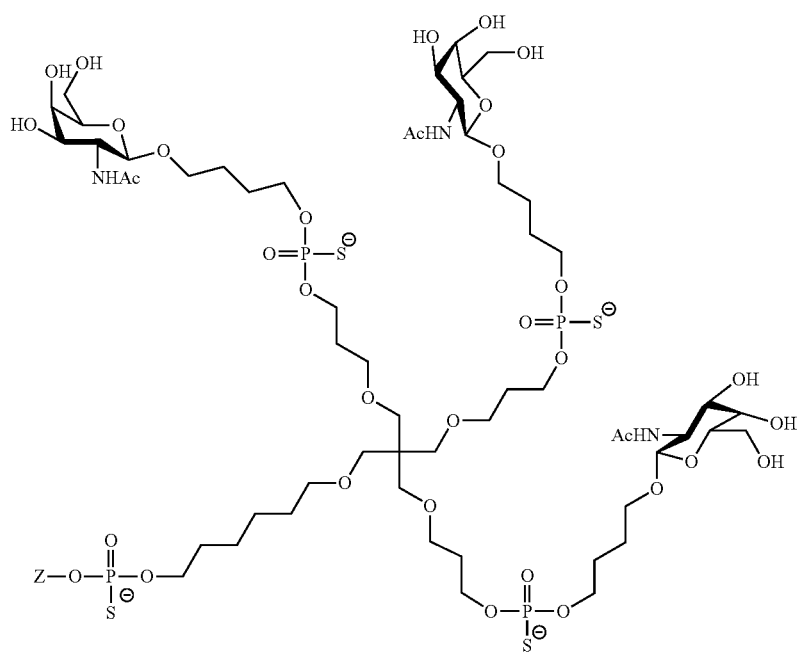

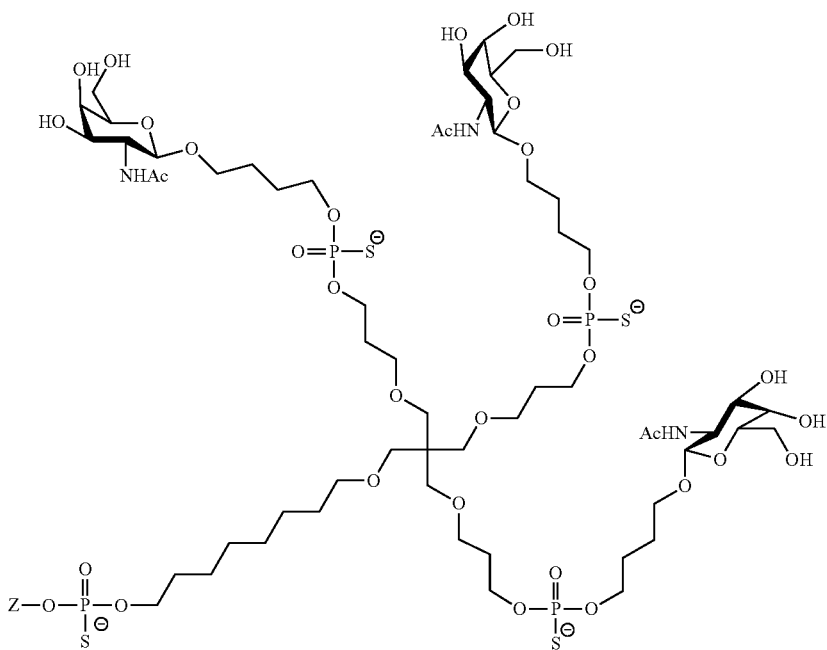
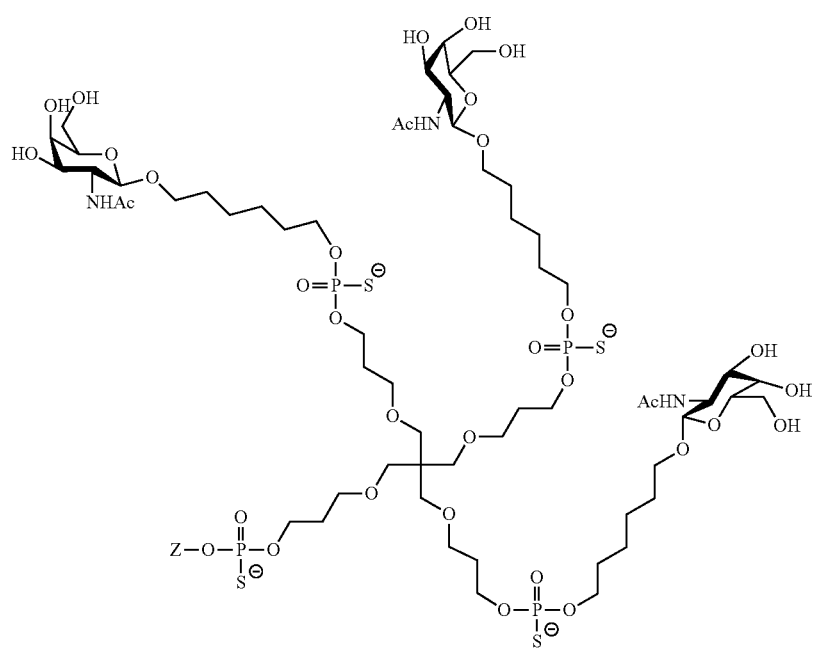

-continued
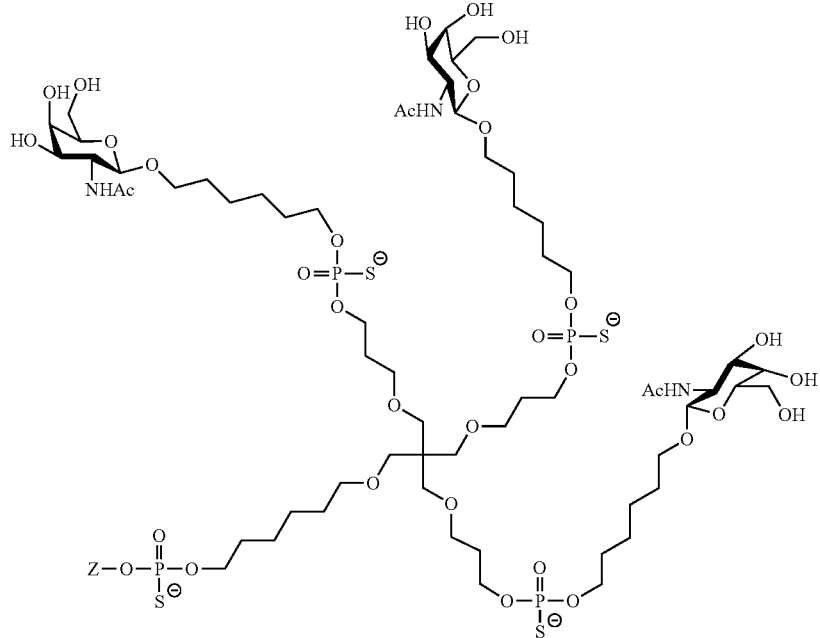
wherein Z is a nucleic acid according to any of statements 1 to 40.
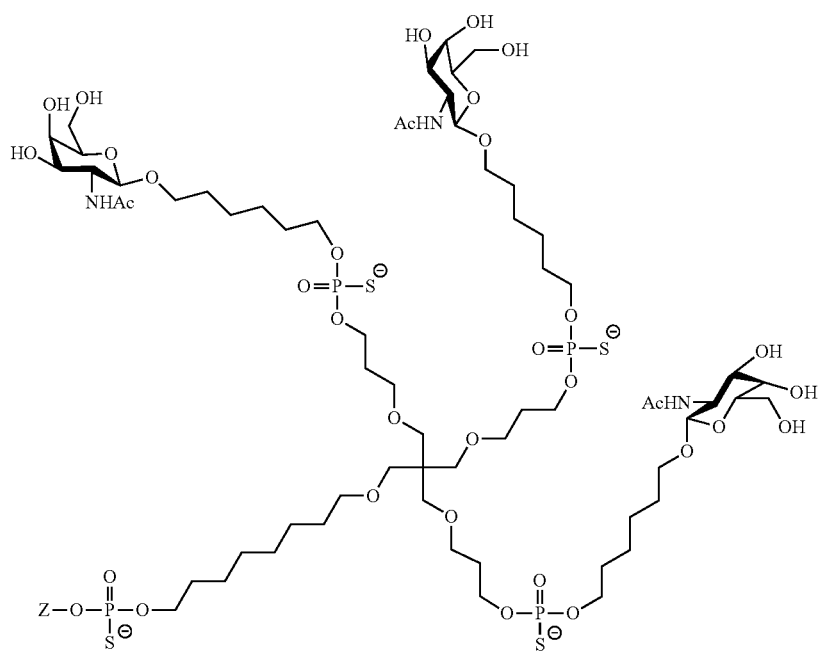
47. A nucleic acid according to an of statements 1 to 40, which is conjugated to a ligand of the following structure

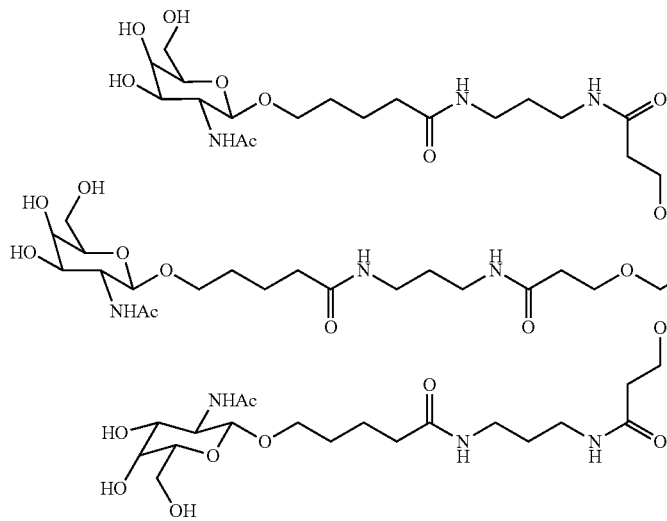
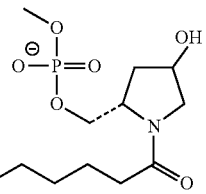

48. A nucleic acid or conjugated nucleic acid of any preceding statement, wherein the duplex comprises separate strands.
49. A nucleic acid or conjugated nucleic acid of any preceding statement, wherein the duplex comprises a single strand comprising a first strand and a second strand.
50. A composition comprising a nucleic acid or conjugated nucleic acid of any preceding statement and a physiologically acceptable excipient.
51. A nucleic acid or conjugated nucleic acid according to any preceding statement for use in the prevention or treatment or reduction of risk of a disease or pathology.
52. Use of a nucleic acid or conjugated nucleic acid according to any preceding statement in the manufacture of a medicament for preventing or treating a disease, disorder or syndrome.
53. A method of preventing or treating a disease, disorder or syndrome comprising administration of a composition comprising a nucleic acid or conjugated nucleic acid according to any preceding statement to an individual in need of treatment.
54. The method of statement 53, wherein the nucleic acid or conjugated nucleic acid is administered to the subject subcutaneously, intravenously or using any other application routes such as oral, rectal or intraperitoneal.
55. A use or method according to statements 52 to 54, wherein said disease or pathology is a cardiovascular disease, a stroke, atherosclerosis, thrombosis or cardiovascular diseases such as coronary heart disease or aortic stenosis and any other disease or pathology associated to elevated levels Lp(a)-containing particles.
56. A use or method according to statement 55, wherein the cardiovascular disease is a stroke, atherosclerosis, thrombosis, a coronary heart disease or aortic stenosis and any other disease or pathology associated to elevated levels of Lp(a)-containing particles.
57. A process for making a nucleic acid or conjugated nucleic acid of any one of statements 1 to 49.
58. A nucleic acid for inhibiting expression of LPA, comprising at least one duplex region that comprises at least a portion of a first strand and at least a portion of a second strand that is at least partially complementary to the first strand, wherein said first strand is at least partially complementary to at least a portion of RNA transcribed from the LPA gene, wherein the expression of LPA is reduced to levels which are at least 15% lower than expression levels observed in same test conditions but in the absence of the nucleic acid or conjugated nucleic acid or in the presence of a non-silencing control.
59. A nucleic acid for inhibiting expression of LPA, comprising at least one duplex region that comprises at least a portion of a first strand and at least a portion of a second strand that is at least partially complementary to the first strand, wherein said first strand is at least partially complementary to at least a portion of a RNA transcribed from the LPA gene, wherein said first strand comprises a nucleotide sequence selected from the following sequences: SEQ ID NOs: 9, 1, 3, 5, 7, 11, 13, 15, 17, 19, 21, 23, 25, 27, 29 31, 33, 35, 37, 39, 41, 43, 63, 65, 67, 69, 71 or 73, wherein the expression of LPA is reduced to levels which are at least 15% lower than expression levels observed in same test conditions but in the absence of the nucleic acid or conjugated nucleic acid or in the presence of a non-silencing control.
60. A nucleic acid for inhibiting expression of LPA in a cell, comprising at least one duplex region that comprises at least a portion of a first strand and at least a portion of a second strand that is at least partially complementary to the first strand, wherein said first strand is at least partially complementary to at least a portion of RNA transcribed from the LPA gene, wherein said first strand comprises a nucleotide sequence selected from the following sequences: SEQ ID NO: 63, 65, 67 and 73, wherein the first RNA strand has a terminal 5' (E)-vinylphosphonate nucleotide.
Other clauses of the invention include:
1. A conjugate for inhibiting expression of a LPA gene in a cell, said conjugate comprising a nucleic acid portion and ligand portions, said nucleic acid portion comprising at least one duplex region that comprises at least a portion of a first RNA strand and at least a portion of a second RNA strand that is at least partially complementary to the first strand, wherein said first strand is at least partially complementary to at least a portion of RNA transcribed from said LPA gene, said ligand portions comprising a serinol-derived linker moiety and a targeting ligand for in vivo targeting of cells and being conjugated exclusively to the 3' and/or 5' ends of one or both RNA strands, wherein the 5' end of the first RNA strand is not conjugated, wherein:

(i) the second RNA strand is conjugated at the 5' end to the targeting ligand, and wherein (a) the second RNA strand is also conjugated at the 3' end to the targeting ligand and the 3' end of the first RNA strand is not conjugated; or (b) the first RNA strand is conjugated at the 3' end to the targeting ligand and the 3' end of the second RNA strand is not conjugated; or (c) both the second RNA strand and the first RNA strand are also conjugated at the 3' ends to the targeting ligand; or (ii) both the second RNA strand and the first RNA strand are conjugated at the 3' ends to the targeting ligand and the 5' end of the second RNA strand is not conjugated, or a conjugate for inhibiting expression of a LPA gene in a cell, said conjugate comprising a nucleic acid portion and ligand portions, said nucleic acid portion comprising at least one duplex region that comprises at least a portion of a first RNA strand and at least a portion of a second RNA strand that is at least partially complementary to the first strand, wherein said first strand is at least partially complementary to at least a portion of RNA transcribed from said LPA gene, said ligand portions comprising a linker moiety and a targeting ligand for in vivo targeting of cells and being conjugated exclusively to the 3' and/or 5' ends of one or both RNA strands, wherein the 5' end of the first RNA strand is not conjugated, wherein:

(i) the second RNA strand is conjugated at the 5' end to the targeting ligand, and wherein (a) the second RNA strand is also conjugated at the 3' end to the targeting ligand and the 3' end of the first RNA strand is not conjugated; or (b) the first RNA strand is conjugated at the 3' end to the targeting ligand and the 3' end of the second RNA strand is not conjugated; or (c) both the second RNA strand and the first RNA strand are also conjugated at the 3' ends to the targeting ligand; or (ii) both the second RNA strand and the first RNA strand are conjugated at the 3' ends to the targeting ligand and the 5' end of the second RNA strand is not conjugated, optionally wherein the linker moiety is a serinol-derived linker moiety or one of the other linker types described herein.

2. The conjugate according to clause 1 wherein the second RNA strand is conjugated at the 5' end to the targeting ligand, the second RNA strand is also conjugated at the 3' end to the targeting ligand and the 3' end of the first RNA strand is not conjugated.

3. The conjugate according to clause 1 wherein the second RNA strand is conjugated at the 5' end to the targeting ligand, the first RNA strand is conjugated at the 3' end to the targeting ligand and the 3' end of the second RNA strand is not conjugated.

4. The conjugate according to clause 1 wherein the second RNA strand is conjugated at the 5' end to the targeting ligand and both the second RNA strand and the first RNA strand are also conjugated at the 3' ends to the targeting ligand.

5. The conjugate according to clause 1 wherein both the second RNA strand and the first RNA strand are conjugated at the 3' ends to the targeting ligand and the 5' end of the second RNA strand is not conjugated.

6. The conjugate according to any one of clauses 1 to 5 wherein the ligands are monomeric ligands.

7. The conjugate according to any one of clauses 1 to 6 wherein the ligands are selected from GalNAc and galactose moieties, especially GalNAc moieties.

8. The conjugate according to any one of clauses 1 to 7 wherein the conjugated RNA strands are conjugated to a targeting ligand via a serinol-derived linker moiety including a further linker wherein the further linker is or comprises a saturated, unbranched or branched $C_{1-15}$ alkyl chain, wherein optionally one or more carbons (for example 1, 2 or 3 carbons, suitably 1 or 2, in particular 1) is/are replaced by a heteroatom selected from O, N, S(O)$_p$ wherein p is 0, 1 or 2, (for example a $CH_2$ group is replaced with O, or with NH, or with S, or with $SO_2$ or a —$CH_3$ group at the terminus of the chain or on a branch is replaced with OH or with $NH_2$) wherein said chain is optionally substituted by one or more oxo groups (for example 1 to 3, such as 1 group).

9. The conjugate according to clause 8 wherein the further linker comprises a saturated, unbranched $C_{1-15}$ alkyl chain wherein one or more carbons (for example 1, 2 or 3 carbons, suitably 1 or 2, in particular 1) is/are replaced by an oxygen atom.

10. The conjugate according to clause 9 wherein the further linker comprises a PEG-chain.

11. The conjugate according to clause 8 wherein the further linker comprises a saturated, unbranched $C_{1-15}$ alkyl chain.

12. The conjugate according to clause 11 wherein the further linker comprises a saturated, unbranched $C_{1-6}$ alkyl chain.

13. The conjugate according to clause 12 wherein the further linker comprises a saturated, unbranched $C_4$ or $C_6$ alkyl chain, e.g. a $C_4$ alkyl chain.

14. The conjugate according to clause 1 or statement 1 wherein the first RNA strand is a compound of formula (XV):

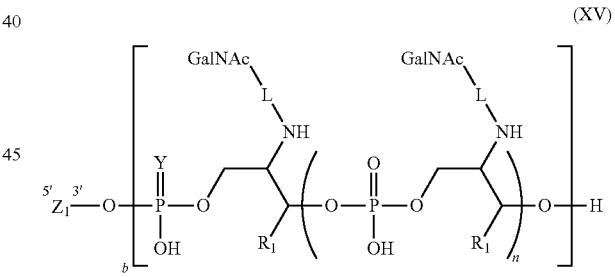

(XV)

wherein b is 0 or 1; and
the second RNA strand is a compound of formula (XVI):

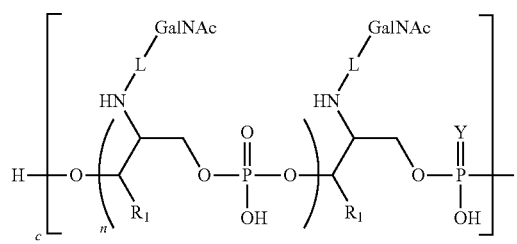 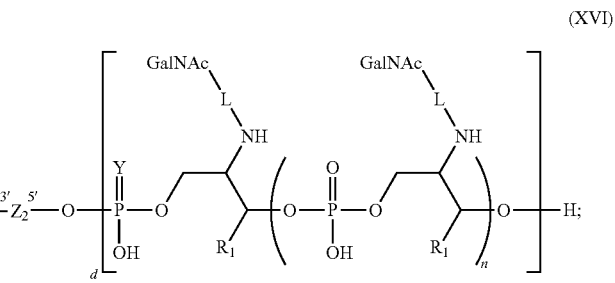

(XVI)

wherein c and d are independently 0 or 1;

wherein:
- $Z_1$ and $Z_2$ are the RNA portions of the first and second RNA strands respectively;
- Y is O or S;
- $R_1$ is H or methyl;
- n is 0, 1, 2 or 3; and
- L is the same or different in formulae (XV) and (XVI) and is selected from the group consisting of:
  - $-(CH_2)_q-$, wherein q=2-12;
  - $-(CH_2)_r-C(O)-$, wherein r=2-12;
  - $-(CH_2-CH_2-O)_s-CH_2-C(O)-$, wherein s=1-5;
  - $-(CH_2)_t-CO-NH-(CH_2)_t-NH-C(O)-$, wherein t is independently 1-5;
  - $-(CH_2)_u-CO-NH-(CH_2)_u-C(O)-$, wherein u is independently 1-5; and
  - $-(CH_2)NH-C(O)-$, wherein v is 2-12; and wherein the terminal C(O) (if present) is attached to the NH group;

and wherein b+c+d is 2 or 3.

15. The conjugate according to clause 14 wherein b is 0, c is 1 and d is 1.
16. The conjugate according to clause 14 wherein b is 1, c is 0 and d is 1.
17. The conjugate according to clause 14 wherein b is 1, c is 1 and d is 0.
18. The conjugate according to clause 14 wherein b is 1, c is 1 and d is 1.
19. The conjugate according to any one of clauses 14-18 wherein Y is O.
20. The conjugate according to any one of clauses 14-18 wherein Y is S.
21. The conjugate according to any one of clauses 14-20 wherein $R_1$ is H.
22. The conjugate according to any one of clauses 14-20 wherein $R_1$ is methyl.
23. The conjugate according to any one of clauses 14-22 wherein n is 0.
24. The conjugate according to any one of clauses 14-23 wherein L is $-(CH_2)_r-C(O)-$, wherein r=2-12.
25. The conjugate according to clause 24 wherein r=2-6.
26. The conjugate according to clause 25 wherein r=4 or 6 e.g. 4.
27. The conjugate according to any preceding clause, with any feature or combination of features disclosed herein.

| SEQ ID NO | Name | Sequence (5'-3') | Unmodified Sequence counterpart (5'-3') |
|---|---|---|---|
| 1 | LPA-1014 first strand | UCGUAUAACAAUAAGGGGC | UCGUAUAACAAUAAGGGGC |
| 2 | LPA-1014 second strand | GCCCCUUAUUGUUAUACGA | GCCCCUUAUUGUUAUACGA |
| 3 | LPA-1024 first strand | GAUAACUCUGUCCAUUACC | GAUAACUCUGUCCAUUACC |
| 4 | LPA-1024 second strand | GGUAAUGGACAGAGUUAUC | GGUAAUGGACAGAGUUAUC |
| 5 | LPA-1038 first strand | AUAACUCUGUCCAUUACCA | AUAACUCUGUCCAUUACCA |
| 6 | LPA-1038 second strand | UGGUAAUGGACAGAGUUAU | UGGUAAUGGACAGAGUUAU |
| 7 | LPA-1040 first strand | UAACUCUGUCCAUUACCGU | UAACUCUGUCCAUUACCGU |
| 8 | LPA-1040 second strand | ACGGUAAUGGACAGAGUUA | ACGGUAAUGGACAGAGUUA |
| 9 | LPA-1041 first strand | AUAACUCUGUCCAUUACCG | AUAACUCUGUCCAUUACCG |
| 10 | LPA-1041 second strand | CGGUAAUGGACAGAGUUAU | CGGUAAUGGACAGAGUUAU |
| 11 | LPA-1055 first strand | AGAAUGUGCCUCGAUAACU | AGAAUGUGCCUCGAUAACU |
| 12 | LPA-1055 second strand | AGUUAUCGAGGCACAUUCU | AGUUAUCGAGGCACAUUCU |
| 13 | LPA-1057 first strand | AUAACUCUGUCCAUCACCA | AUAACUCUGUCCAUCACCA |
| 14 | LPA-1057 second strand | UGGUGAUGGACAGAGUUAU | UGGUGAUGGACAGAGUUAU |
| 15 | LPA-1058 first strand | AUAACUCUGUCCAUCACCU | AUAACUCUGUCCAUCACCU |
| 16 | LPA-1058 second strand | AGGUGAUGGACAGAGUUAU | AGGUGAUGGACAGAGUUAU |
| 17 | LPA-1061 first strand | UAACUCUGUCCAUUACCAU | UAACUCUGUCCAUUACCAU |
| 18 | LPA-1061 second strand | AUGGUAAUGGACAGAGUUA | AUGGUAAUGGACAGAGUUA |
| 19 | LPA-1086 first strand | AUGUGCCUUGAUAACUCUG | AUGUGCCUUGAUAACUCUG |
| 20 | LPA-1086 second strand | CAGAGUUAUCAAGGCACAU | CAGAGUUAUCAAGGCACAU |
| 21 | LPA-1099 first strand | AGUUGGUGCUGCUUCAGAA | AGUUGGUGCUGCUUCAGAA |
| 22 | LPA-1099 second strand | UUCUGAAGCAGCACCAACU | UUCUGAAGCAGCACCAACU |
| 23 | LPA-1102 first strand | AAUAAGGGGCUGCCACAGG | AAUAAGGGGCUGCCACAGG |
| 24 | LPA-1102 second strand | CCUGUGGCAGCCCCUUAUU | CCUGUGGCAGCCCCUUAUU |
| 25 | LPA-1116 first strand | UAACUCUGUCCAUCACCAU | UAACUCUGUCCAUCACCAU |

| SEQ ID NO | Name | Sequence (5'-3') | Unmodified Sequence counterpart (5'-3') |
|---|---|---|---|
| 26 | LPA-1116 second strand | AUGGUGAUGGACAGAGUUA | AUGGUGAUGGACAGAGUUA |
| 27 | LPA-1127 first strand | AUGAGCCUCGAUAACUCUG | AUGAGCCUCGAUAACUCUG |
| 28 | LPA-1127 second strand | CAGAGUUAUCGAGGCUCAU | CAGAGUUAUCGAGGCUCAU |
| 29 | LPA-1128 first strand | AAUGAGCCUCGAUAACUCU | AAUGAGCCUCGAUAACUCU |
| 30 | LPA-1128 second strand | AGAGUUAUCGAGGCUCAUU | AGAGUUAUCGAGGCUCAUU |
| 31 | LPA-1141 first strand | AAUGCUUCCAGGACAUUUC | AAUGCUUCCAGGACAUUUC |
| 32 | LPA-1141 second strand | GAAAUGUCCUGGAAGCAUU | GAAAUGUCCUGGAAGCAUU |
| 33 | LPA-1151 first strand | ACAGUGGUGGAGAAUGUGC | ACAGUGGUGGAGAAUGUGC |
| 34 | LPA-1151 second strand | GCACAUUCUCCACCACUGU | GCACAUUCUCCACCACUGU |
| 35 | LPA-1171 first strand | GUAUGUGCCUCGAUAACUC | GUAUGUGCCUCGAUAACUC |
| 36 | LPA-1171 second strand | GAGUUAUCGAGGCACAUAC | GAGUUAUCGAGGCACAUAC |
| 37 | LPA-1177 first strand | UCGAUAACUCUGUCCAUCA | UCGAUAACUCUGUCCAUCA |
| 38 | LPA-1177 second strand | UGAUGGACAGAGUUAUCGA | UGAUGGACAGAGUUAUCGA |
| 39 | LPA-1189 first strand | UGUCACUGGACAUUGUGUC | UGUCACUGGACAUUGUGUC |
| 40 | LPA-1189 second strand | GACACAAUGUCCAGUGACA | GACACAAUGUCCAGUGACA |
| 41 | LPA-1244 first strand | CUGGGAUCCAUGGUGUAAC | CUGGGAUCCAUGGUGUAAC |
| 42 | LPA-1244 second strand | GUUACACCAUGGAUCCCAG | GUUACACCAUGGAUCCCAG |
| 43 | LPA-1248 first strand | AGAUGACCAAGCUUGGCAG | AGAUGACCAAGCUUGGCAG |
| 44 | LPA-1248 second strand | CUGCCAAGCUUGGUCAUCU | CUGCCAAGCUUGGUCAUCU |
| 45 | LPA: (upper) human | AAGTGTCCTTGCGACGTCC | AAGTGTCCTTGCGACGTCC |
| 46 | LPA: (lower) human | CCTGGACTGTGGGCTTT | CCTGGACTGTGGGCTTT |
| 47 | LPA: (probe) human | CTGTTTCTGAACAAGCACCAACGGAGC | CTGTTTCTGAACAAGCACCAACGGAGC |
| 48 | LPA (upper) cynomolgus | GTGTCCTCGCAACGTCCA | GTGTCCTCGCAACGTCCA |
| 49 | LPA (lower) cynomolgus | GACCCCGGGGCTTTG | GACCCCGGGGCTTTG |
| 50 | LPA (probe) cynomolgus | TGGCTGTTTCTGAACAAGCACCAATGG | TGGCTGTTTCTGAACAAGCACCAATGG |
| 51 | APOB (upper) human | TCATTCCTTCCCCAAAGAGACC | TCATTCCTTCCCCAAAGAGACC |
| 52 | APOB (lower) human | CACCTCCGTTTTGGTGGTAGAG | CACCTCCGTTTTGGTGGTAGAG |
| 53 | APOB (probe) human | CAAGCTGCTCAGTGGAGGCAACACATTA | CAAGCTGCTCAGTGGAGGCAACACATTA |
| 54 | beta-Actin (upper) human | GCATGGGTCAGAAGGATTCCTAT | GCATGGGTCAGAAGGATTCCTAT |
| 55 | beta-Actin (lower) human | TGTAGAAGGTGTGGTGCCAGATT | TGTAGAAGGTGTGGTGCCAGATT |
| 56 | beta-Actin (probe) human | TCGAGCACGGCATCGTCACCAA | TCGAGCACGGCATCGTCACCAA |
| 57 | beta-Actin (upper) cynomolgus | AAGGCCAACCGCGAGAAG | AAGGCCAACCGCGAGAAG |
| 58 | beta-Actin (lower) cynomolgus | AGAGGCGTACAGGGACAGCA | AGAGGCGTACAGGGACAGCA |
| 59 | beta-Actin (probe) cynomolgus | TGAGACCTTCAACACCCCAGCCATGTAC | TGAGACCTTCAACACCCCAGCCATGTAC |
| 60 | PPIB (upper) human | AGATGTAGGCCGGGTGATCTTT | AGATGTAGGCCGGGTGATCTTT |

| SEQ ID NO | Name | Sequence (5'-3') | Unmodified Sequence counterpart (5'-3') |
|---|---|---|---|
| 61 | PPIB (lower) human | GTAGCCAAATCCTTTCTCTCCTGT | GTAGCCAAATCCTTTCTCTCCTGT |
| 62 | PPIB (probe) human | TGTTCCAAAAACAGTGGATAATTTTGTGGCC | TGTTCCAAAAACAGTGGATAATTTTGTGGCC |
| 63 | LPA-1301 first strand | UUAACUCUGUCCAUUACCG | UUAACUCUGUCCAUUACCG |
| 64 | LPA-1301 second strand | CGGUAAUGGACAGAGUUAA | CGGUAAUGGACAGAGUUAA |
| 65 | LPA-1302 first strand | UUAACUCUGUCCAUUACCC | UUAACUCUGUCCAUUACCC |
| 66 | LPA-1302 second strand | GGGUAAUGGACAGAGUUAA | GGGUAAUGGACAGAGUUAA |
| 67 | LPA-1303 first strand | UUAACUCUGUCCAUUACCU | UUAACUCUGUCCAUUACCU |
| 68 | LPA-1303 second strand | AGGUAAUGGACAGAGUUAA | AGGUAAUGGACAGAGUUAA |
| 69 | LPA-1304 first strand | AUAACUCUGUCCAUUACCC | AUAACUCUGUCCAUUACCC |
| 70 | LPA-1304 second strand | GGGUAAUGGACAGAGUUAU | GGGUAAUGGACAGAGUUAU |
| 71 | LPA-1305 first strand | AUAACUCUGUCCAUUACCU | AUAACUCUGUCCAUUACCU |
| 72 | LPA-1305 second strand | AGGUAAUGGACAGAGUUAU | AGGUAAUGGACAGAGUUAU |
| 73 | LPA-1306 first strand | UUAACUCUGUCCAUUACCA | UUAACUCUGUCCAUUACCA |
| 74 | LPA-1306 second strand | UGGUAAUGGACAGAGUUAA | UGGUAAUGGACAGAGUUAA |
| 75 | Modified SEQ ID NO: 1 | 5381616272616284847 | UCGUAUAACAAUAAGGGC |
| 76 | Modified SEQ ID NO: 2 | 4737351615451616382 | GCCCCUUAUUGUUAUACGA |
| 77 | Modified SEQ ID NO: 3 | 8252635354537251637 | GAUAACUCUGUCCAUUACC |
| 78 | Modified SEQ ID NO: 4 | 4816254827282815253 | GGUAAUGGACAGAGUUAUC |
| 79 | Modified SEQ ID NO: 5 | 6162717181736152736 | AUAACUCUGUCCAUUACCA |
| 80 | Modified SEQ ID NO: 6 | 1845261846364645161 | UGGUAAUGGACAGAGUUAU |
| 81 | Modified SEQ ID NO: 7 | 5263535453725163745 | UAACUCUGUCCAUUACCGU |
| 82 | Modified SEQ ID NO: 8 | 2748162548272828152 | ACGGUAAUGGACAGAGUUA |
| 83 | Modified SEQ ID NO: 9 | 6162717181736152738 | AUAACUCUGUCCAUUACCG |
| 84 | Modified SEQ ID NO: 10 | 3845261846364645161 | CGGUAAUGGACAGAGUUAU |
| 85 | Modified SEQ ID NO: 11 | 6462545473538252635 | AGAAUGUGCCUCGAUAACU |
| 86 | Modified SEQ ID NO: 12 | 2815253828472725171 | AGUUAUCGAGGCACAUUCU |
| 87 | Modified SEQ ID NO: 13 | 6162717181736172736 | AUAACUCUGUCCAUCACCA |
| 88 | Modified SEQ ID NO: 14 | 1845461846364645161 | UGGUGAUGGACAGAGUUAU |
| 89 | Modified SEQ ID NO: 15 | 6162717181736172735 | AUAACUCUGUCCAUCACCU |
| 90 | Modified SEQ ID NO: 16 | 2845461846364645161 | AGGUGAUGGACAGAGUUAU |
| 91 | Modified SEQ ID NO: 17 | 5263535453725163725 | UAACUCUGUCCAUUACCAU |
| 92 | Modified SEQ ID NO: 18 | 2548162548272828152 | AUGGUAAUGGACAGAGUUA |
| 93 | Modified SEQ ID NO: 19 | 6181837154616271718 | AUGUGCCUUGAUAACUCUG |
| 94 | Modified SEQ ID NO: 20 | 3646451617264836361 | CAGAGUUAUCAAGGCACAU |
| 95 | Modified SEQ ID NO: 21 | 6451845471835172826 | AGUUGGUGCUGCUUCAGAA |
| 96 | Modified SEQ ID NO: 22 | 1535462836472736271 | UUCUGAAGCAGCACCAACU |
| 97 | Modified SEQ ID NO: 23 | 6252648483547363648 | AAUAAGGGCUGCCACAGG |
| 98 | Modified SEQ ID NO: 24 | 3718184728373715251 | CCUGUGGCAGCCCUUAUU |

-continued

| SEQ ID NO | Name | Sequence (5'-3') | Unmodified Sequence counterpart (5'-3') |
|---|---|---|---|
| 99 | Modified SEQ ID NO: 25 | 5263535453725363725 | UAACUCUGUCCAUCACCAU |
| 100 | Modified SEQ ID NO: 26 | 2548182548272828152 | AUGGUGAUGGACAGAGUUA |
| 101 | Modified SEQ ID NO: 27 | 6182837174616271718 | AUGAGCCUCGAUAACUCUG |
| 102 | Modified SEQ ID NO: 28 | 3646451617464835361 | CAGAGUUAUCGAGGCUCAU |
| 103 | Modified SEQ ID NO: 29 | 6254647353825263535 | AAUGAGCCUCGAUAACUCU |
| 104 | Modified SEQ ID NO: 30 | 2828152538284717251 | AGAGUUAUCGAGGCUCAUU |
| 105 | Modified SEQ ID NO: 31 | 6254715372846361517 | AAUGCUUCCAGGACAUUUC |
| 106 | Modified SEQ ID NO: 32 | 4626181735482647251 | GAAAUGUCCUGGAAGCAUU |
| 107 | Modified SEQ ID NO: 33 | 6364548184646254547 | ACAGUGGUGGAGAAUGUGC |
| 108 | Modified SEQ ID NO: 34 | 4727251717363727181 | GCACAUUCUCCACCACUGU |
| 109 | Modified SEQ ID NO: 35 | 8161818371746162717 | GUAUGUGCCUCGAUAACUC |
| 110 | Modified SEQ ID NO: 36 | 4645161746483636163 | GAGUUAUCGAGGCACAUAC |
| 111 | Modified SEQ ID NO: 37 | 5382526353545372536 | UCGAUAACUCUGUCCAUCA |
| 112 | Modified SEQ ID NO: 38 | 1825482728281525382 | UGAUGGACAGAGUUAUCGA |
| 113 | Modified SEQ ID NO: 39 | 5453635482725181817 | UGUCACUGGACAUUGUGUC |
| 114 | Modified SEQ ID NO: 40 | 4636362545372818272 | GACACAAUGUCCAGUGACA |
| 115 | Modified SEQ ID NO: 41 | 7184825372548181627 | CUGGGAUCCAUGGUGUAAC |
| 116 | Modified SEQ ID NO: 42 | 4516363725482537364 | GUUACACCAUGGAUCCCAG |
| 117 | Modified SEQ ID NO: 43 | 6461827362835184728 | AGAUGACCAAGCUUGGCAG |
| 118 | Modified SEQ ID NO: 44 | 3547362835184536171 | CUGCCAAGCUUGGUCAUCU |
| 119 | GalNAc-LPA-1038-L1 first strand | OMeA-(ps)-FU-(ps)-OMeA-FA-OMeC-FU-OMeC-FU-OMeG-FU-OMeC-FC-OMeA-FU-OMeU-FA-OMeC-(ps)-FC-(ps)-OMeA | AUAACUCUGUCCAUUACCA |
| 120 | GalNAc-LPA-1038-L1 second strand | [ST23 (ps)]3 long trebler (ps)FU-OMeG-FG-OMeU-FA-OMeA-FU-OMeG-FG-OMeA-FC-OMeA-FG-OMeA-FG-OMeU-FU-(ps)-OMeA-(ps)-FU | UGGUAAUGGACAGAGUUAU |
| 121 | GalNAc-LPA-1038-L6 first strand | OMeA-(ps)-FU-(ps)-OMeA-FA-OMeC-FU-OMeC-FU-OMeG-FU-OMeC-FC-OMeA-FU-OMeU-FA-OMeC-(ps)-FC-(ps)-OMeA | AUAACUCUGUCCAUUACCA |
| 122 | GalNAc-LPA-1038-L6 second strand | [ST23 (ps)]3 ST43 (ps)FU-OMeG-FG-OMeU-FA-OMeA-FU-OMeG-FG-OMeA-FC-OMeA-FG-OMeA-FG-OMeU-FU-(ps)-OMeA-(ps)-FU | UGGUAAUGGACAGAGUUAU |
| 123 | GalNAc-LPA-1041-L1 first strand | OMeA-(ps)-FU-(ps)-OMeA-FA-OMeC-FU-OMeC-FU-OMeG-FU-OMeC-FC-OMeA-FU-OMeU-FA-OMeC-(ps)-FC-(ps)-OMeG | AUAACUCUGUCCAUUACCG |
| 124 | GalNAc-LPA-1041-L1 second strand | [ST23 (ps)]3 long trebler (ps) FC-OMeG-FG-OMeU-FA-OMeA-FU-OMeG-FG-OMeA-FC-OMeA-FG-OMeA-FG-OMeU-FU-(ps)-OMeA-(ps)-FU | CGGUAAUGGACAGAGUUAU |
| 125 | GalNAc-LPA-1041-L6 first strand | OMeA-(ps)-FU-(ps)-OMeA-FA-OMeC-FU-OMeC-FU-OMeG-FU-OMeC-FC-OMeA-FU-OMeU-FA-OMeC-(ps)-FC-(ps)-OMeG | AUAACUCUGUCCAUUACCG |
| 126 | GalNAc-LPA-1041-L6 second strand | [ST23 (ps)]3 ST43 (ps) FC-OMeG-FG-OMeU-FA-OMeA-FU-OMeG-FG-OMeA-FC-OMeA-FG-OMeA-FG-OMeU-FU-(ps)-OMeA-(ps)-FU | CGGUAAUGGACAGAGUUAU |
| 127 | STS16001AL33 | mU (ps) fU (ps) mA fU mA fG mA fG mC fA mA fG mA fA mC fA mC fU mG (ps) fU (ps) mU (ps) Ser(GN) | UUAUAGAGCAAGAACACUGUU |

-continued

| SEQ ID NO | Name | Sequence (5'-3') | Unmodified Sequence counterpart (5'-3') |
|---|---|---|---|
| 128 | STS16001BL20 | Ser(GN) (ps) fA mA fC mA fG mU fG mU fU mC fU mU fG mC fU mC fU mA fU (ps) mA (ps) fA | AACAGUGUUCUUGCUCUAUAA |
| 129 | STS16001A | mU (ps) fU (ps) mA fU mA fG mA fG mC fA mA fG mA fA mC fA mC fU mG (ps) fU (ps) mU | UUAUAGAGCAAGAACACUGUU |
| 130 | STS16001BV1L42 | Ser(GN) (ps) fA (ps) mA (ps) fC mA fG mU fG mU fU mC fU mU fG mC fU mC fU mA fU (ps) mA (ps) fA (ps) Ser(GN) | AACAGUGUUCUUGCUCUAUAA |
| 131 | STS16001V1B | fA (ps) mA (ps) fC mA fG mU fG mU fU mC fU mU fG mC fU mC fU mA fU (ps) mA (ps) fA | AACAGUGUUCUUGCUCUAUAA |
| 132 | STS18001A | mU (ps) fC (ps) mG fA mA fG mU fA mU fU mC fC mG fC mG fU mA (ps) fC (ps) mG | UCGAAGUAUUCCGCGUACG |
| 133 | STS18001BL4 | [(ST23) (ps)]₃ C4XLT (ps) fC mG fU mA fC mG fC mG fG mA fA mU fA mC fU mU fC (ps) mG (ps) fA | CGUACGCGGAAUACUUCGA |
| 134 | STS16001BL4 | [(ST23) (ps)]3 C4XLT(ps) fA (ps) mA (ps) fC mA fG mU fG mU fU mC fU mU fG mC fU mC fU mA fU (ps) mA (ps) fA | AACAGUGUUCUUGCUCUAUAA |
| 135 | X0373A | mA (ps) fU (ps) mA fA mC fU mC fU mG fU mC fC mA fU mU fA mC (ps) fC (ps) mG | AUAACUCUGUCCAUUACCG |
| 136 | X0373B | Ser(GN) (ps) fC (ps) mG (ps) fG mU fA mA fU mG fG mA fC mA fG mA fG mU fU (ps) mA (ps) fU (ps) Ser(GN) | CGGUAAUGGACAGAGUUAU |
| 137 | STS2041B | ST23 (ps) ST23 (ps) ST23 (ps) C6XLT (ps) fC mG fG mU fA mA fU mG fG mA fC mA fG mA fG mU fU (ps) mA (ps) fU | CGGUAAUGGACAGAGUUAU |
| 138 | X0125A | mC (ps) fU (ps) mU fA mC fU mC fU mG fC mC fC mA fA mG fC (ps) fG (ps) mA | CUUACUCUCGCCCAAGCGA |
| 139 | X0125B | [(ST23) (ps)]₃ (C6XLT) (ps) fU mC fG mC fU mU fG mG fG mC fG mA fG mA fG mU fA (ps) mA (ps) fG | UCGCUUGGGCGAGAGUAAG |
| 140 | Probe based on SEQ ID NO: 50 | BHQ1-TGGCTGTTTCTGAACAAGCACCAATGG-FAM | TGGCTGTTTCTGAACAAGCACCAATGG |
| 141 | Probe based on SEQ ID NO: 56 | BHQ1-TCGAGCACGGCATCGTCACCAA-VIC | TCGAGCACGGCATCGTCACCAA |
| 142 | STS16001BV1L75 | Ser(GN) fA (ps) mA (ps) fC mA fG mU fG mU fU mC fU mU fG mC fU mC fU mA fU (ps) mA (ps) fA Ser(GN) | AACAGUGUUCUUGCUCUAUAA |
| 143 | STS16001BV16L42 | Ser(GN) (ps) fA mA fC mA fG mU fG mU fU mC fU mU fG mC fU mC fU mA fU mA fA (ps) Ser(GN) | AACAGUGUUCUUGCUCUAUAA |
| 144 | ST516001BV20L75 | Ser(GN) fA mA fC mA fG mU fG mU fU mC fU mU fG mC fU mC fU mA fU mA fA Ser(GN) | AACAGUGUUCUUGCUCUAUAA |
| 145 | STS16001BV1L94 | Ser(GN) (ps) Ser(GN) (ps) fA (ps) mA (ps) fC mA fG mU fG mU fU mC fU mU fG mC fU mC fU mA fU (ps) mA (ps) fA (ps) Ser(GN) (ps) Ser(GN) | AACAGUGUUCUUGCUCUAUAA |
| 146 | STS16001V1BL96 | C6Am(GN) (ps) fA (ps) mA (ps) fC mA fG mU fG mU fU mC fU mU fG mC fU mC fU mA fU (ps) mA (ps) fA (ps) C7Am(GN) | AACAGUGUUCUUGCUCUAUAA |
| 147 | STS16001V1BL97 | GlyC3Am(GN) (ps) fA (ps) mA (ps) fC mA fG mU fG mU fU mC fU mU fG mC fU mC fU mA fU (ps) mA (ps) fA (ps) GlyC3Am(GN) | AACAGUGUUCUUGCUCUAUAA |
| 148 | Conjugate 10 second strand | PipAm(GN) (ps) fA (ps) mA (ps) fC mA fG mU fG mU fU mC fU mU fG mC fU mC fU mA fU (ps) mA (ps) fA (ps) PipAm(GN) | AACAGUGUUCUUGCUCUAUAA |
| 149 | STS16001V1BL88 | C3Am(GN) (ps) fA (ps) mA (ps) fC mA fG mU fG mU fU mC fU mU fG mC fU mC fU mA fU (ps) mA (ps) fA (ps) C3Am(GN) | AACAGUGUUCUUGCUCUAUAA |

-continued

| SEQ ID NO | Name | Sequence (5'-3') | Unmodified Sequence counterpart (5'-3') |
|---|---|---|---|
| 150 | STS16001V1BL87 | C6Am(GN) (ps) fA (ps) mA (ps) fC mA fG mU fG mU fU mC fU mU fG mC fU mC fU mA fU (ps) mA (ps) fA (ps) GlyC3Am(GN) | AACAGUGUUCUUGCUCUAUAA |
| 151 | Conjugate 15 antisense strand | mU (ps) fC (ps) mU fU mC fU mU fA mA fA mC fU mG fA mG fU mU (ps) fU (ps) mC | UCUUCUUAAACUGAGUUUC |
| 152 | Conjugate 15 sense strand | Ser(GN) (ps) fG (ps) mA (ps) fA mA fC mU fC mA fG mU fU mU fA mA fG mA fA (ps) mG (ps) fA (ps) Ser(GN) | GAAACUCAGUUUAAGAAGA |
| 153 | Conjugate 16 antisense strand | mA (ps) fU (ps) mG fU mA fG mC fC mG fA mG fG mA fU mC fU mU (ps) fC (ps) mU | AUGUAGCCGAGGAUCUUCU |
| 154 | Conjugate 16 antisense strand | Ser(GN) (ps) fA (ps) mG (ps) fA mA fG mA fU mC fC mU fC mG fC fU mA fC (ps) mA (ps) fU (ps) Ser(GN) | AGAAGAUCCUCGGCUACAU |
| 155 | Conjugate 18 antisense strand | mA (ps) fA (ps) mC fC mA fG mA fA mG fA mA fG mC fA mG fG mU (ps) fG (ps) mA | AACCAGAAGAAGCAGGUGA |
| 156 | Conjugate 18 sense strand | Ser(GN) (ps) fU (ps) mC (ps) fA mC fC mU fG mC fU mU fC mU fU mG fG (ps) mU (ps) fU (ps) Ser(GN) | UCACCUGCUUCUUCUGGUU |
| 157 | STS16001BV1 | fA (ps) mA (ps) fC mA fG mU fG mU fU mC fU mU fG mC fU mC fU mA fU (ps) mA (ps) fA | AACAGUGUUCUUGCUCUAUAA |
| 158 | Reference Conjugate 6 sense strand | [ST23 (ps)]3 ltrb (ps) fG mA fA mA fC mU fC mA fG mU fU mU fA mA fG mA fA (ps) mG (ps) fA | GAAACUCAGUUUAAGAAGA |
| 159 | Reference Conjugate 7 sense strand | [ST23 (ps)]3 ltrb (ps) fA mG fA mA fG mA fU mC fC mU fC mG fC fU mA fC (ps) mA (ps) fU | AGAAGAUCCUCGGCUACAU |
| 160 | Reference Conjugate 8 antisense strand | mU (ps) fA (ps) mC fC mA fG mA fA mG fA mA fG mC fA mG fG (ps) mU (ps) fG (ps) mA | UACCAGAAGAAGCAGGUGA |
| 161 | Reference Conjugate 8 sense strand | [ST23 (ps)]3 ST41 (ps)fU mC fA mC fC mU fG mC fU mU fC mU fU mC fU mG fG (ps) mU (ps) fA | UCACCUGCUUCUUCUGGUA |
| 162 | Reference Conjugate 9 sense strand | [ST23 (ps)]3 C6XLT (ps) fC mG fG mU fA mA fU mG fG mA fC mA fG mA fG mU fU (ps) mA (ps) fU | CGGUAAUGGACAGAGUUAU |

```
Key
1 = 2'F-dU
2 = 2'F-dA
3 = 2'F-dC
4 = 2'F-dG
5 = 2'OMe-rU
6 = 2'OMe-rA
7 = 2'OMe-rC
8 = 2'OMe-rG
mA, mU, mC, mG, OMeA, OMeU, OMeC, OMe - 2'-OMe RNA
fA, fU, fC, fG, FA, FU, FG, FC - 2'deoxy-2'-F RNA
(ps) - phosphorothioate
(vp) - Vinyl-(E)-phosphonate
ivA, ivC, ivU, ivG - inverted RNA (3'-3')
```

A single sequence may have more than one name. In those cases, one of those names is given in the summary sequence table.

Where specific linkers and or modified linkages are taught within an RNA sequence, such as PS and [ST23 (ps)]3 ST41 (ps) etc, these are optional parts of the sequence, but are a preferred embodiment of that sequence.

The following abbreviations may be used:

FAM    6-Carboxyfluorescein

BHQ    Black Hole Quencher 1

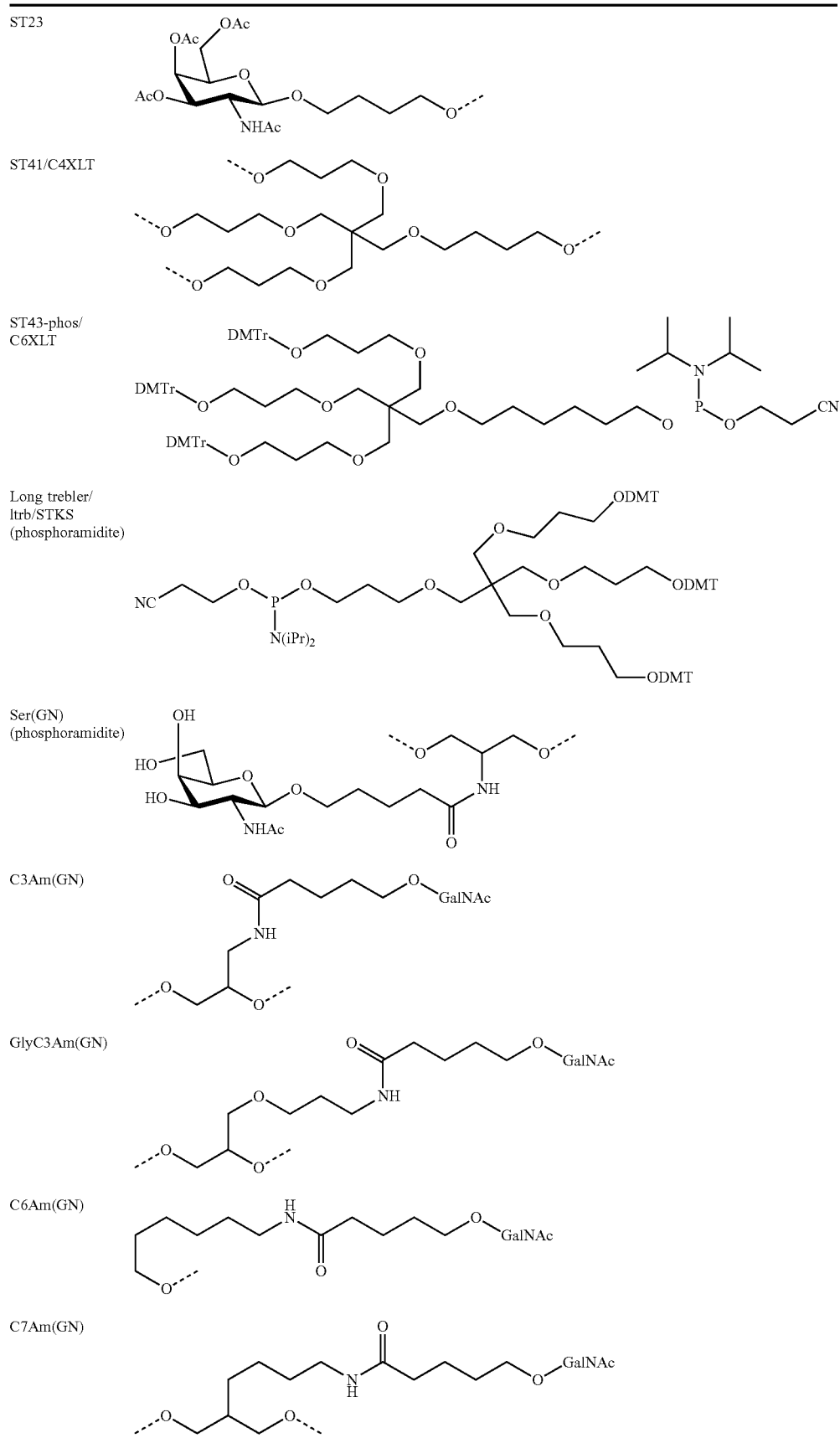

PipAm(GN)

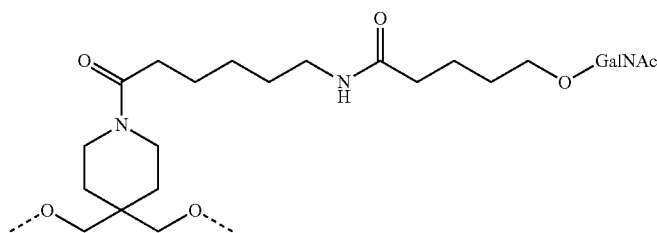

The invention claimed is:

1. A nucleic acid for inhibiting expression of the apolipoprotein(a) (LPA) gene in a cell, comprising at least one duplex region that comprises at least a portion of a first strand and at least a portion of a second strand that is at least partially complementary to the first strand, wherein said first strand is at least partially complementary to at least a portion of RNA transcribed from the LPA gene, wherein
said first strand is 19-35 nucleotides in length and comprises a nucleotide sequence of SEQ ID NO: 9;
said second strand is 17-35 nucleotides in length and optionally comprises a nucleotide sequence of SEQ ID NO: 10;
and wherein the at least one duplex region consists of 17-25 consecutive nucleotide base pairs.

2. The nucleic acid of claim 1, wherein said second strand comprises a nucleotide sequence of SEQ ID NO: 10.

3. The nucleic acid of claim 1, wherein the at least one duplex region consists of 19-25 consecutive nucleotide base pairs.

4. The nucleic acid of claim 1, wherein the nucleic acid is blunt ended at both ends.

5. The nucleic acid of claim 1, wherein one or more nucleotides on the first and/or second strand are modified, to form modified nucleotides.

6. The nucleic acid of claim 1, wherein the nucleic acid is conjugated to a ligand.

7. The nucleic acid of claim 6, wherein the ligand comprises (i) one or more N-acetyl galactosamine (GalNAc) moieties or derivatives thereof, and (ii) a linker, wherein the linker conjugates the at least one GalNAc moiety or derivative thereof to the nucleic acid.

8. The nucleic acid of claim 6, wherein the nucleic acid is conjugated to a ligand comprising a compound of formula (I):

wherein:
S represents a saccharide, preferably wherein the saccharide is N-acetyl galactosamine;
$X^1$ represents $C_3$-$C_6$ alkylene or $(-CH_2-CH_2-O)_m$ $(-CH_2)_2-$ wherein m is 1, 2, or 3;
P is a phosphate or modified phosphate, preferably a thiophosphate;
$X^2$ is alkylene or an alkylene ether of the formula $(-CH_2)_n-O-CH_2-$ where n=1-6;
A is a branching unit;
$X^3$ represents a bridging unit;
wherein the nucleic acid as defined in claim 1 is conjugated to $X^3$ via a phosphate or modified phosphate, preferably a thiophosphate.

9. The nucleic acid of claim 6, wherein the first RNA strand is a compound of formula (X):

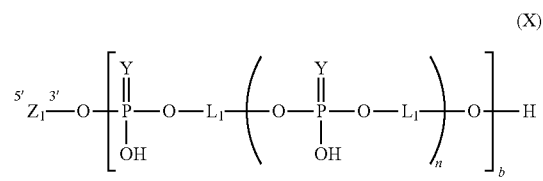

wherein b is 0 or 1; and
the second RNA strand is a compound of formula (XI):

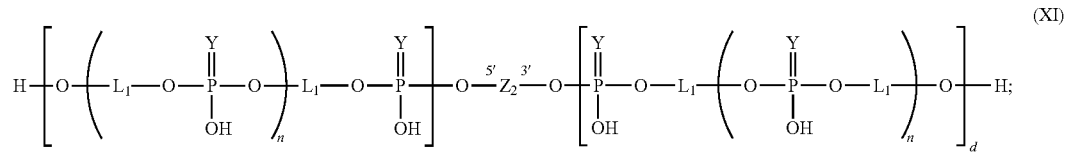

wherein:

c and d are independently 0 or 1;

$Z_1$ and $Z_2$ are the RNA portions of the first and second RNA strands respectively;

Y is O or S;

n is 0, 1, 2 or 3; and $L_1$ is a linker to which a ligand is attached; and wherein b+c+d is 2 or 3.

10. The nucleic acid of claim 1, wherein said first strand consists of the nucleotide sequence of SEQ ID NO: 9 and/or wherein said second strand comprises or consists of the nucleotide sequence of SEQ ID NO: 10.

11. The nucleic acid of claim 10, wherein the nucleic acid is conjugated to a ligand, wherein the first RNA strand is a compound of formula (XV):

(XV)

wherein b is 0 or 1; and
the second RNA strand is a compound of formula (XVI):

(XVI)

wherein c and d are independently 0 or 1;
wherein:
$Z_1$ and $Z_2$ are the RNA portions of the first and second RNA strands respectively;
Y is O or S;
$R_1$ is H or methyl;
n is 0, 1, 2 or 3; and
L is the same or different in formulae (XV) and (XVI) and is selected from the group consisting of:
—$(CH_2)_q$—, wherein q=2-12;
—$(CH_2)_r$—C(O)—, wherein r=2-12;
—$(CH_2)$—$CH_2$—$O)_s$—$CH_2$—C(O)—, wherein s=1-5;
—$(CH_2)_t$—CO—NH—$(CH_2)_t$—NH—C(O)—, wherein t is independently 1-5;
—$(CH_2)_u$—CO—NH—$(CH_2)_u$—C(O)—, wherein u is independently s 1-5; and
—$(CH_2)_v$—NH—C(O)—, wherein v is 2-12; and
wherein the terminal C(O), if present, is attached to the NH group;
and wherein b+c+d is 2 or 3.

12. A pharmaceutical composition comprising a nucleic acid of claim 1 and further comprising a delivery vehicle and/or liposomes and/or a physiologically acceptable excipient and/or a carrier and/or a diluent.

13. The nucleic acid of claim 1 wherein said first strand is 19-25 nucleotides in length.

14. The nucleic acid of claim 1 wherein said second strand is 17-25 nucleotides in length, optionally 19-25 nucleotides in length.

15. The nucleic acid of claim 10, wherein said first strand consists of the nucleotide sequence of SEQ ID NO: 9 having modifications as shown below:

| SEQ ID NO: | sequence | modifications |
|---|---|---|
| 9 | 5' AUAACUCUGUCCAUUACCG 3' | 6162717181736152738 | wherein the specific modifications are depicted by numbers:
1=2'F-dU,
2=2'F-dA,
3=2'F-dC,
4=2'F-dG,
5=2'-OMe-rU;
6=2'-OMe-rA;
7=2'-OMe-rC; and
8=2'-OMe-rG.

* * * * *